(12) United States Patent
Flexner et al.

(10) Patent No.: US 10,570,413 B2
(45) Date of Patent: Feb. 25, 2020

(54) MANAGEMENT OF CORN ROOTWORM AND OTHER INSECT PESTS

(71) Applicants:PURDUE RESEARCH FOUNDATION, West Lafayette, IN (US); E.I. du Pont de Nemours and Company, Wilmington, DE (US); PIONEER HI-BRED INTERNATIONAL, INC., Johnston, IA (US)

(72) Inventors: John Lindsey Flexner, Landenberg, PA (US); Gurmukh S. Johal, West Lafayette, IN (US); Dilbag S. Multani, Urbandale, IA (US); James K. Presnail, Des Moines, IA (US); Scott V. Tingey, Rockdale, TX (US)

(73) Assignees: Purdue Research Foundation, West Lafayette, IN (US); E.I. du Pont de Nemours and Company, Wilmington, DE (US); Pioneer Hi-Bred International, INC., Johnston, IA (US)

( * ) Notice: Subject to any disclaimer, the term of this patent is extended or adjusted under 35 U.S.C. 154(b) by 715 days.

(21) Appl. No.: 14/430,029

(22) PCT Filed: Sep. 20, 2013

(86) PCT No.: PCT/US2013/061037
§ 371 (c)(1),
(2) Date: Mar. 20, 2015

(87) PCT Pub. No.: WO2014/047511
PCT Pub. Date: Mar. 27, 2014

(65) Prior Publication Data
US 2015/0337330 A1    Nov. 26, 2015

Related U.S. Application Data

(60) Provisional application No. 61/781,124, filed on Mar. 14, 2013, provisional application No. 61/782,116, filed on Mar. 14, 2013, provisional application No. 61/781,057, filed on Mar. 14, 2013, provisional application No. 61/703,414, filed on Sep. 20, 2012, provisional application No. 61/703,396, filed on Sep. 20, 2012.

(51) Int. Cl.
*C12N 15/82* (2006.01)
*A01B 79/02* (2006.01)

(52) U.S. Cl.
CPC .......... *C12N 15/8286* (2013.01); *A01B 79/02* (2013.01)

(58) Field of Classification Search
CPC ................................................ C12N 15/8286
See application file for complete search history.

(56) References Cited

U.S. PATENT DOCUMENTS

| | | |
|---|---|---|
| 2006/0150283 A1 | 7/2006 | Alexandrov et al. |
| 2007/0011773 A1 | 1/2007 | Clough et al. |
| 2008/0214443 A1 | 9/2008 | Baum et al. |
| 2008/0313777 A1* | 12/2008 | Dhugga .............. C07K 14/415 800/287 |
| 2009/0249510 A1 | 10/2009 | van der Reijden |
| 2010/0083407 A1 | 4/2010 | Feldmann et al. |
| 2010/0257621 A1 | 10/2010 | Ketkar et al. |
| 2011/0239329 A1* | 9/2011 | Dhugga .............. C07K 14/415 800/290 |
| 2012/0017338 A1 | 1/2012 | Wu et al. |
| 2012/0159672 A1 | 6/2012 | Alexandrov et al. |
| 2012/0210462 A1 | 8/2012 | Bermudez et al. |

FOREIGN PATENT DOCUMENTS

| | | |
|---|---|---|
| WO | WO-2006/107293 A1 | 10/2006 |
| WO | WO-2010/075143 A1 | 7/2010 |
| WO | WO-2011/044254 A1 | 4/2011 |
| WO | WO-2012/058223 A1 | 5/2012 |

OTHER PUBLICATIONS

Venkata et al 2013, PLOS ONE 8(8): e71296 11 pages.*
Ooka et al 2003, DNA Research 10: 239-247.*
Dhillon et al 2007, 49th Annual Maize Genetics Conference Program & Abstracts, Mar. 22-25, 2007.*
MBS Genetics, LLC 2011 Genetic Handbook.*
Zukoff et al 2012 Jounal of Economic Entomology 105(4): 1248-1260.*
Shelton, et al., "Concepts and applications of trap cropping in pest management," Annual Review of Entomology, vol. 51 (2006) (pp. 285-308).
Extended European Search Report dated Apr. 18, 2016 for application EP 1839524.9, filed on Sep. 20, 2013 and published as EP 2897453 on Jul. 29, 2015 (Applicant—E.I. Du Pont de Nemours and Company, et al. // Inventor—Li, et al.) (7 pages).
Barros-Rios et al., "Cell wall composition as a maize defense mechanism against corn borers" (2011), Phytochem. 72:365-371.
Christensen et al., "Maize polyubiquitin genes: structure, thermal perturbation of expression and transcript splicing, and promoter activity following transfer to protoplasts by electroporation" (1992), Plant Mol. Biol. 18: 675-689.
Guo et al., "Protein Tolerance to random amino acid change" (2004), Proc. Natl. Acad. Sci. USA 101: 9205-9210.
Kjaersgaard et al., "Senescence-associated Barley NAC (NAM, ATAF 1 ,2, CUC) Transcription Factor Interacts with Radical-induced Cell Death 1 through a Disordered Regulatory Domain" (2011), J. Biol. Chem 286:35418-35429.

(Continued)

*Primary Examiner* — David H Kruse
(74) *Attorney, Agent, or Firm* — Ballard Spahr LLP

(57) ABSTRACT

Trap and/or refuge crops and methods of use in managing corn rootworm and other insect pests of maize are provided. Some methods involve using trap crops comprising plants with enhanced susceptibility to one or more insect pests to lure and kill insect pests. Other methods involve using refuge crops comprising plants with enhanced susceptibility to one or more insect pests to monitor insect pest populations in an area or to promote mating between insecticide resistant and insecticide non-resistant insects.

6 Claims, 57 Drawing Sheets

Specification includes a Sequence Listing.

(56) References Cited

OTHER PUBLICATIONS

Welner et al, "NAC transcription factors: from structure to function in stress-associated networks" Plant Transcription Factors, (2016) Chapter 13; 199-212.
Non Final Rejection dated Feb. 14, 2017 by the USPTO for U.S. Appl. No. 14/430,002, filed Mar. 20, 2015 and published as 2015-0275228 A1 on Oct. 1, 2015 (Applicant—Pioneer Hi-Bred International Inc.) (16 pages).
Non Final Rejection dated Feb. 15, 2017 by the USPTO for U.S. Appl. No. 14/430,017, filed Mar. 20, 2015 and published as 2015-0240257 A1 on Aug. 27, 2015 (Applicant—E.I. Dupont De Nemours and Company) (15 pages).
Alexander, et al., "Determinants of Corn Rootworm Resistant Corn Adoption in Indiana", AgBioForum, 2005, 8(4), pp. 197-204.
Alston et al., "An Ex Ante Analysis of the Benefits from the Adoption of Corn Rootworm Resistant Transgenic Corn Technology", AgBioForum. 2002, 5(3), pp. 71-84.
International Search Report and Written Opinion issued by the International Searching Authority dated Apr. 22, 2014 for international application PCT/US2013/61037, filed on Sep. 20, 2013, and published as WO 2014/047511 on Mar. 27, 2014 (Applicant—E.I. DuPont de Nemours and Company // Inventor—Flexner, et al.) (13 pages).
International Preliminary Report on Patentability dated Apr. 2, 2015 for international application PCT/US2013/61037, filed on Sep. 20, 2013, and published as WO 2014/047511 on Mar. 27, 2014 (Applicant—E.I. DuPont de Nemours and Company // Inventor—Flexner, et al.) (8 pages).
Zhong, et al., "Transcriptional Activation of Secondary Wall Biosynthesis by Rice and Maize NAC and MYB Transcription Factors", Plant Cell Physiol. 52(10): 1856-1871 (2011).
Dhillon B, Moose SP; and Johal GS. (2007). crw1—A novel maize mutant exceptionally susceptible to Western Corn Rootworm. Maize Genetics Conference Abstracts. Mar. 22-25, St. Charles, Illinois, available at maizegdb.org/data_center/reference?id=1079616 (2 pages).
UniProt G3M8D2 (2011) (5 pages).
UniProt Q9SNM6 (2000) (7 pages).
UniProt C5YM23 (2009) (6 pages).
UniProt Q5NKS7 (2005) (6 pages).
UniProt I1MKD6 (2012) (1 page).
UniProt I1KHQ4 (2012) (6 pages).
UniProt Q84WP6 (2006) (9 pages).
UniProt Q9LPI7 (2008) (9 pages).
UniProt Q9M274 (2006) (9 pages).
UniProt B4FPS5 (2008) (7 pages).
UniProt Q5NKQ3 (2005) (6 pages).
UniProt F6HU82 (2011) (6 pages).
UniProt G4V2G0 (2011) (5 pages).
UniProt D9ZJ90 (2010) (5 pages).
UniProt F2DV83 (2011) (5 pages).
UniProt C0PDR7 (2009) (5 pages).
UniProt C4J6G0 (2009) (5 pages).
UniProt Q5Z8T7 (2004) (7 pages).
UniProt Q6Z0Z4 (2004) (7 pages).
UniProt C5Z9B2 (2009) (5 pages).
UniProt C5XTX5 (2009) (5 pages).
UniProt I1K5F9 (2012) (6 pages).
UniProt I1KQG2 (2012) (6 pages).
UniProt Q9LV23 (2000) (6 pages).
UniProt Q9LV22 (2000) (7 pages).
UniProt F2DBB4 (2011) (5 pages).
UniProt I1GWV1 (2012) (5 pages).
NCBI GI No. 356511269 (2 pages).
Purdue University, "Corn Rootworms", (2009), [Last retrieved Sep. 15, 2017] extension.entm.purdue.edu/fieldcropsipm/insects/corn-rootworms.php (pp. 1-6).
Chiang, H.C., Bionomics of the Northern and Western Corn Rootworms. Annu Rev Entomol. 1973; 18:47-72.
Elliott, N. C. et al., Influence of Adult Diet on the Reproductive Biology and Survival of the Western Corn Rootworm, *Diabrotica virgifera virgifera*. Entomol Exp Appl. 1990; 56:15-21.
Hein, G.L. and Tollefson, J.J., Seasonal Oviposition of Northern and Western Corn Rootworms (Coleoptera: Chrysomelidae) in Continuous Cornfields. J Econ Entomol. 1985; 78:1238-41.
Hill, R.E. and Mayo, Z.B., Trap-Corn to Control Corn Rootworms. J Econ Entomol. 1974; 67(6):748-50.
Jackson, J.J. and Elliot, N. C., Temperature-Dependent Development of Immature Stages of the Western Corn Rootworm, *Diabrotica virgifera virgifera* (Coleoptera: Chryaomelidae). Environ Entomol. 1988; 17(2):166-71.
Quiring, D.T. and Timmins, P.R., Influence of Reproductive Ecology on Feasibility of mass Trapping *Diabrotica virgifera virgifera* (Coleoptera: Chrysomelidae). J Appl Ecol. 1990; 27(3):965-82.
Ruppel, R.F. et al., Indices for Projecting Emergence of Corn Rootworm Adults in Michigan. J Econ Entomol. 1978; 71:947-9.
Short, D.E. and Hill, R.E., Adult Emergence, Ovarian Development, and Oviposition Sequence of the Western Corn Rootworm in Nebraska. J Econ Entomol. 1972; 65(3):685-9.

\* cited by examiner

FIG. 6A

```
                 1..........11..........21..........31..........41..........51..........60
ZmCiwi-WT       ATGAGCATCTCGGTGAACGTGCAGGGCAGTCGTGCGTGCCGGGTTCCGCTTCCACCCCACG
Zmciwi-AC       ATGAGCATCTCGGTGAACGGGCAGGGCAGTCGTGCGTGCCGGGTTCCGCTTCCACCCCACG
                ************************************************************

61.........71..........81..........91.........101.........111........120
ZmCiwi-WT       GAGGAGGAGCTGCTCAACTACTA------CCTCCGCAAGAAGGTGGCCTCCCAGGAGA
Zmciwi-AC       GAGGAGGAGCTGCTCAACTACTA[ACTACTA]CCTCCGCAAGAAGGTGGCCTCCCAGGAGA
                ***********************       *****************************

121........131.........141.........151.........161.........171........180
ZmCiwi-WT       TCGACCTCGAGTCATCCGGACGTCGACCTCAACAAGAGCTGAGCCATGGACATCCAAG
Zmciwi-AC       TCGACCTCGAGTCATCCGGACGTCGACCTCAACAAGAGCTGAGCCATGGACATCCAAG
                ***********************************************************

181........191.........201.........211.........221.........231........240
ZmCiwi-WT       AGAAATGCAAGATCGGGTCGGGTCCCAGAACGACGACTGGTACTTCTCAGCCACAAGGACA
Zmciwi-AC       AGAAATGCAAGATCGGGTCGGGTCCCAGAACGACGACTGGTACTTCTCAGCCACAAGGACA
                ************************************************************

241........251.........261.........271.........281.........291........300
ZmCiwi-WT       AGAAGTACCCGACGGGGACGGCGCACCAAGCGCGCCAACGGCGGCCCGGGTTCTGGAAGGCCA
Zmciwi-AC       AGAAGTACCCGACGGGGACGGCGCACCAAGCGCGCCAACGGCGGCCCGGGTTCTGGAAGGCCA
                ************************************************************

301........311.........321.........331.........341.........351........360
ZmCiwi-WT       CCGGCCCGGCGGACAAGGCCATCTACAACGCCGGTCAAGGCCATGGCAAGCGCAAGAGCGCTCG
Zmciwi-AC       CCGGCCCGGCGGACAAGGCCATCTACAACGCCGGTCAAGGCCATGGCAAGCGCAAGAGCGCTCG
                ************************************************************

361........371.........381.........391.........401.........411........420
ZmCiwi-WT       TCTTCTACAAGGACGCGGCCGCGCCGCACGGGCCAGAAGTCCGACTGGATCATGCACGAGTACC
Zmciwi-AC       TCTTCTACAAGGACGCGGCCGCGCCGCACGGGCCAGAAGTCCGACTGGATCATGCACGAGTACC
                ************************************************************
```

FIG. 6B

```
ZmCrw1-WT    421........431........441........451........461........471........480
ZmCrw1-AC    GCCTCGACGACCCGGCTCGCTGCTGCTGCTGCTGGATCCGGTGAATGCCGTGGCCAACGACG
             GCCTCGACGACCCGGCTCGCTGCTGCTGCTGCTGGATCCGGTGAATGCCGTGGCCAACGACG
             ************************************************************

ZmCrw1-WT    481........491........501........511........521........531........540
ZmCrw1-AC    ACGGCAGCCCGGCCAACGGCGCTGCTGCCTGCTGCCCGGCCGTCGTCGGACCGGGGCAGGAGGACG
             ACGGCAGCCCGGCCAACGGCGCTGCTGCCTGCTGCCCGGCCGTCGTCGGACCGGGGCAGGAGGACG
             ************************************************************

ZmCrw1-WT    541........551........561........571........581........591........600
ZmCrw1-AC    GCTCGGTGGTGTGCAGGGTGTTCAAGAAGAAGCACCACCACCAAGGAGTCAGGTGGGGGCG
             GCTCGGTGGTGTGCAGGGTGTTCAAGAAGAAGCACCACCACCAAGGAGTCAGGTGGGGGCG
             ************************************************************

ZmCrw1-WT    601........611........621........631........641........651........660
ZmCrw1-AC    GGGCAACAAGCAAGGCCTGCGGCCAGCAGCAGTAACAACAGCAGCGGAGCATGGGCGGGCACGGCGAGCCGGGCAAGGCAT
             GGGCAACAAGCAAGGCCTGCGGCCAGCAGCAGTAACAACAGCAGCGGAGCATGGGCGGGCACGGCGAGCCGGGCAAGGCAT
             ************************************************************

ZmCrw1-WT    661........671........681........691........701........711........720
ZmCrw1-AC    CGGCTGCGGCTGCGGCTGCGGCGCAGCAGCAGCCAGCACCAGCACCAGCCATGGAGGCCTGCAGCCTGCAGGTACTCCT
             CGGCTGCGGCTGCGGCTGCGGCGCAGCAGCAGCCAGCACCAGCACCAGCCATGGAGGCCTGCAGCCTGCAGGTACTCCT
             ************************************************************

ZmCrw1-WT    721........731........741........751........761........771........780
ZmCrw1-AC    CCAGCGACGAGGAGGCCGGCCGTGGACCAGATCCTGCAGTACATGGGCAGGTCGGTCCAAGCAGGAGC
             CCAGCGACGAGGAGGCCGGCCGTGGACCAGATCCTGCAGTACATGGGCAGGTCGGTCCAAGCAGGAGC
             ************************************************************

ZmCrw1-WT    781........791........801........811........821........831........840
ZmCrw1-AC    ACGAGCTGGTGTCGGCGGCGGCCGCCCGGGACCGGCCGGTCCAGGTACTCC
             ACGAGCTGGTGTCGGCGGCGGCCGCCCGGGACCGGCCGGTCCAGGTACTCC
             ************************************************************
```

FIG. 6C

```
                   841........851........861........871........881........891........900
ZmCrw1-WT          GGCCCATCGAGACCGTTCTGGGGGCGGCACGGCGTTCATGAAGCTTCCGGCTCGAGAGC
ZmCrw1-AC          GGCCCATCGAGACCGTTCTGGGGGCGGCACGGCGTTCATGAAGCTTCCGGCTCGAGAGC
                   ************************************************************

901........911........921........931........941........951........960
ZmCrw1-WT          CGTCCGCGGCCGGTCCGCATCGCTGCTGACACAGCGGCGCAGCGACGACGAGCTCTACCGCG
ZmCrw1-AC          CGTCCGCGGCCGGTCCGCATCGCTGCTGACACAGCGGCGCAGCGACGACGAGCTCTACCGCG
                   ************************************************************

961........971........981........991........1001.......1011.......1020
ZmCrw1-WT          CCGCCGGGAACGGGATCACGGATCGGGCCATGATGGCCGGCTGGTCGGTCGGCACCTGA
ZmCrw1-AC          CCGCCGGGAACGGGATCACGGATCGGGCCATGATGGCCGGCTGGTCGGTCGGCACCTGA
                   ************************************************************

1021.......1031.......1041.......1051.......1061.......1071.......1080
ZmCrw1-WT          ACGGGCAGCAGAGCGCGGAAGACGCGGACGCGGAGCCAGCTCGGCCGGCTCGGCCTGGAGCGG
ZmCrw1-AC          ACGGGCAGCAGAGCGCGGAAGACGCGGACGCGGAGCCAGCTCGGCCGGCTCGGCCTGGAGCGG
                   ************************************************************

1081.......1091.......1101.......1111.......1121.......1131.......1140
ZmCrw1-WT          ACGGCGGCGGCGAGAGCAGGCGCGGACGCGGAGCGCGGGCCTCGCCTTCTACTCCGCCGCCAGCCGGC
ZmCrw1-AC          ACGGCGGCGGCGAGAGCAGGCGCGGACGCGGAGCGCGGGCCTCGCCTTCTACTCCGCCGCCAGCCGGC
                   ************************************************************

1141.......1151.......1161.......1171.......1181.......1191.......1200
ZmCrw1-WT          TGCTCGGCTCCGGCGGCGGCGGCGGCCGGCCAGCGACGACGACCTGTGGAGCTTCACGCGGTCGT
ZmCrw1-AC          TGCTCGGCTCCGGCGGCGGCGGCGGCCGGCCAGCGACGACGACCTGTGGAGCTTCACGCGGTCGT
                   ************************************************************

1201.......1211.......1221.......1231.......1241.......1251.......1260
ZmCrw1-WT          CGGTTCGTCAACGGCGGCGGCCGGCCGCACGTCCACGGCTCCAGCGGTCCAGCCACGTGTCAC
ZmCrw1-AC          CGGTTCGTCAACGGCGGCGGCCGGCCGCACGTCCACGGCTCCAGCGGTCCAGCCACGTGTCAC
                   ************************************************************

1261 1265
ZmCrw1-WT          TGTAG
ZmCrw1-AC          TGTAG
                   *****
```

```
ZmCrw1-WT    421........431........441........451........461........471........480
ZmCrw1-CO109 CGACCCCGGCTGCTGCTGCTGCTGCTGGATCCGGTGATGCCGTGGCCAACGACGACGCAGC
             CGACCCCGGCTGCTGCTGCTGCTGCTGGATCCGGTGATGCCGTGGCCAACGACGACGCAGC
             ************************************************************

ZmCrw1-WT    481........491........501........511........521........531........540
ZmCrw1-CO109 CGCCACGGCTGCTGCTGCTGCTGCCCGCCGGCGTCGTCGGACGGCGGGCAGGAGGACGGCTGGGT
             CGCCACGGCTGCTGCTGCTGCTGCCCGCCGGCGTCGTCGGACGGCGGGCAGGAGGACGGCTGGGT
             ************************************************************

ZmCrw1-WT    541........551........561........571........581........591........600
ZmCrw1-CO109 GGTGTGCCAGGGTGTTCAAGAGAAGCACCACCACCAAGGAGTCAGGTGGGCGGGGGGCAA
             GGTGTGCCAGGGTGTTCAAGAGAAGCACCACCACCAAGGAGTCAGGTGGGCGGGGGGCAA
             ************************************************************

ZmCrw1-WT    601........611........621........631........641........651........660
ZmCrw1-CO109 CAAGCACGGCAGCAGTAACAGCAGCGAGCAGCATGGGCACGGCGGCGCCGGCAAGGCATCGGCTGC
             CAAGCACGGCAGCAGTAACAGCAGCGAGCAGCATGGGCACGGCGGCGCCGGCAAGGCATCGGCTGC
             ************************************************************

ZmCrw1-WT    661........671........681........691........701........711........720
ZmCrw1-CO109 GGCTGCGGCTGCGGCGCACGATCCTGCAGCCAGCCAGCACCATGGGAGGCCTGCAGTACTCCTCCAGCGA
             GGCTGCGGCTGCGGCGCACGATCCTGCAGCCAGCCAGCACCATGGGAGGCCTGCAGTACTCCTCCAGCGA
             ************************************************************

ZmCrw1-WT    721........731........741........751........761........771........780
ZmCrw1-CO109 CGAGGCGCTGGACCAGATCCTGCAGTACATGGGCAGGTCGTGCAAGCAGGAGCAGGAGCACGGAGCT
             CGAGGCGCTGGACCAGATCCTGCAGTACATGGGCAGGTCGTGCAAGCAGGAGCAGGAGCACGGAGCT
             ************************************************************

ZmCrw1-WT    781........791........801........811........821........831........840
ZmCrw1-CO109 GGTGTCGCCGGCGCCGGCGCCGGCGCCGGGACGGCCGGCGGTCCAGGTCCAGGTACCTCCGGCCCAT
             GGTGTCGCCGGCGCCGGCGCCGGCGCCGGGACGGCCGGCGGTCCAGGTCCAGGTACCTCCGGCCCAT
             ************************************************************
```

FIG. 7C

```
                 841......851.......861.......871.......881.......891.......900
ZmCrw1-WT        CGAGACCGTTCTGGACGGGCACGCGTTCGACGCGCACGCGTTCATGAAGCTTCCCGGCTCGAGAGCCGGTCCGC
ZmCrw1-CO109     CGAGACCGTTCTGGACGGGCACGCGTTCGACGCGCACGCGTTCATGAAGCTTCCCGGCTCGAGAGCCGGTCCGC
                 ************************************************************************

901......911.......921.......931.......941.......951.......960
ZmCrw1-WT        GGCCGGTCCGCATCGGACACAGCCGGCGCCAGCACCGAGACGAGCTCTACCGCCGCCGCCGG
ZmCrw1-CO109     GGCCGGTCCGCATCGGACACAGCCGGCGCCAGCACCGAGACGAGCTCTACCGCCGCCGCCGG
                 ************************************************************************

961......971.......981.......991.......1001......1011......1020
ZmCrw1-WT        GAACGGGATCACGGACTGGGCCATGATGGACCGGGCTGGTGGCGTCGGCACCTGAACGGGCA
ZmCrw1-CO109     GAACGGGATCACGGACTGGGCCATGATGGACCGGGCTGGTGGCGTCGGCACCTGAACGGGCA
                 ************************************************************************

1021......1031.......1041.......1051.......1061.......1071......1080
ZmCrw1-WT        GCAGGCGCCCGGCCGGCGCCGCCGGCGGACCAGTCCGGCGGGCTGGCTTCGACGCGGAACGCGG
ZmCrw1-CO109     GCAGGCGCCCGGCCGGCGCCGCCGGCGGACCAGTCCGGCGGGCTGGCTTCGACGCGGAACGCGG
                 ************************************************************************

1081......1091.......1101.......1111.......1121.......1131......1140
ZmCrw1-WT        CGCCGAAGAGCGGACGGCGCCGCCGGCCTCGCCTTCTACTCCGCCGGCGCCAGCGGCTGCTCGG
ZmCrw1-CO109     CGCCGAAGAGCGGACGGCGCCGCCGGCCTCGCCTTCTACTCCGCCGGCGCCAGCGGCTGCTCGG
                 ************************************************************************

1141......1151.......1161.......1171.......1181.......1191......1200
ZmCrw1-WT        CTCCGGCGGCGCGGCCGGCGGCGAGCGACCTGTGAGCTTCACGCGGTCGTCGGTTC
ZmCrw1-CO109     CTCCGGCGGCGCGGCCGGCGGCGAGCGACCTGTGAGCTTCACGCGGTCGTCGGTTC
                 ************************************************************************

1201......1211.......1221.......1231.......1241.......1251......1258
ZmCrw1-WT        GTCAACGGCGGCGCCGGCGGCGGCCACGTCCACGGAGCGGCTCAGCCACGTGTCACTGTAG
ZmCrw1-CO109     GTCAACGGCGGCGCCGGCGGCGGCCACGTCCACGGAGCGGCTCAGCCACGTGTCACTGTAG
                 ************************************************************************
```

```
WT    GCCGGGACGGGCGGCGGCGCGTTCCAGTACCTCCGGCCCATCGAGACCGTTCTGGCGGGCA  848
NC316 GCCGGGACGGGCGGCGGCGCGTTCCAGTACCTCCGGCCCATCGAGACCGTTCTGGCGGGCA  900
      ************************************************************

WT    CGCGTTCATGAAGCTGCCCGCGCTCGAGAGCCCGTCGCACCTCGCGCCGGCCATCGCTGAC  908
NC316 CGCGTTCATGAAGCTGCCCGCGCTCGAGAGCCCGTCGCACCTCGCGCCGGCCATCGCTGAC  960
      ************************************************************

WT    ACAGCCGGCGCGCAGCACGAGCTCTACCGCGCCGCCGGGAACGGGATCACGGACTGGGC    968
NC316 ACAGCCGGCGCGCAGCACGAGCTCTACCGCGCCGCCGGGAACGGGATCACGGACTGGGC   1020
      **********************************************************

WT    CATGATGGACCGGCTGGTGGCGTCGCACCTGAACGGGCAGGCCCCGCCGCCGCGGCGGA   1028
NC316 CATGATGGACCGGCTGGTGGCGTCGCACCTGAACGGGCAGGCCCCGCCGCCGCGGCGGA   1080
      **********************************************************

WT    CCAGCTCGGCGGCGGCGCTGCGGGCCTTCGACGCGGAGCGCCCGAAGACGCGGACGCCGG  1088
NC316 CCAGCTCGGCGGCGGCGCTGCGGGCCTTCGACGCGGAGCGCCCGAAGACGCGGACGCCGG  1140
      ************************************************************

WT    CCTCGCCCTTCTACTCCGCGCCGCCCAGCCGCCTGCTGCTCCGGCTCCGGCCGGCCGCAG  1148
NC316 CCTCGCCCTTCTACTCCGCGCCGCCCAGCCGCCTGCTGCTCCGGCTCCGGCCGGCCGCAG  1200
      ************************************************************

WT    CGACGACGACCTGTGGAGCTTGGAGCTTCACGCGGTCGTCGGTTTCGTCAACGGGCGGC   1208
NC316 CGACGACGACCTGTGGAGCTTGGAGCTTCACGCGGTCGTCGGTTTCGTCAACGGGCGGC   1260
      **********************************************************

WT    CACGTCCACGGAGCGGCTCAGCCACGTGTCACTGTAG 1245
NC316 CACGTCCACGGAGCGGCTCAGCCACGTGTCACTGTAG 1297
      *************************************
```

FIG. 9B

```
     70         80         90         100        110        120
DIQE.C.IG..PQN.WY..SHKDKKYPTGTRTNRAT..GFWKATGRDK.I..........G Consensus #1
DIQEKCKIGSTPQNDWYFFSHKDKKYPTGTRTNRATAAGFWKATGRDKAIYSX--XRRIG Majority 55  DIQEKCKIGSGPQNDWYFFSHKDKKYPTGTRTNRATAAGFWKATGRDKAIYNA--VKRIG Zm(SEQIDNO3)
55  DIQERCKIGSGPQNDWYFFSHKDKKYPTGTRTNRATAAGFWKATGRDKAIYNA--VHRIG Os(SEQIDNO10)
55  DIQERCRIGSTPQNDWYFFSHKDKKYPTGTRTNRATAAGFWKATGRDKAIYSS--SNRIG Os(SEQIDNO11)
55  DIQEKCKIGSGPQNDWYFFSHKDKKYPTGTRTNRATAAGFWKATGRDKAIYNA--VKRIG Sb(SEQIDNO12)
55  DIQEKCRIGSGPQNDWYFFSHKDKKYPTGTRTNRATAAGFWKATGRDKAIYAS-GARRIG Sb(SEQIDNO13)
59  DIQEKCKIGTTPQNDWYFFSHKDKKYPTGTRTNRATAAGFWKATGRDKVIYSN--GKRIG Gm(SEQIDNO14)
59  DIQEKCKIGTTPQNDWYFFSHKDKKYPTGTRTNRATAAGFWKATGRDKAIYSN--GKRIG Gm(SEQIDNO15)
60  DIQEMCKIGTTPQNDWYFFSHKDKKYPTGTRTNRATAAGFWKATGRDKIIYSN--GRRIG At(SEQIDNO16)
60  DIQECRIGSTPQNDWYFFSHKDKKYPTGTRTNRATVAGFWKATGRDKICSC--VRRIG At(SEQIDNO17)
55  DIQEMCKIGTTPQNDWYFFSHKDKKYPTGTRTNRATAAGFWKATGRDKIIYTN--GDRIG At(SEQIDNO18)
55  DIQERCKIGSGPQNDWYFYSHKDKKYPTGTRTNRATTVGFWKATGRDKAIYSA--VRRMG Zm(SEQIDNO19)
55  DIQEKCKIGSGPQNDWYFFSHKDKKYPTGTRTNRATAAGFWKATGRDKAIYASPGARRIG Zm(SEQIDNO20)
59  DIQEKCRIGSGPQNDWYFFSHKDKKYPTGTRTNRATAAGFWKATGRDKAIYNA--VSRIG Bd(SEQIDNO21)
59  DIQEKCKIGSGPQNDWYFFSHKDKKYPTGTRTNRATAAGFWKATGRDKVIYSS--FRRIG Vv(SEQIDNO22)
55  DIQEKCRIGTTPQNDWYFFSHKDKKYPTGTRTNRATAAGFWKATGRDKIIYSN--GKRIG Gm(SEQIDNO23)
55  DIQEKCRIGSTPQNEWYFFSHKDKKYPTGTRTNRATAAGFWKATGRDKIIYSG--FRRIG Gh(SEQIDNO24)
60  DIQEKCRIGSTPQNDWYFFSHKDKKYPTGTRTNRATAAGFWKATGRDKIIYSG--FKRIG Pm(SEQIDNO25)
55  DIQECCRIGTGPQNDWYLFSHKDKKYPTGTRTNRATTVGFWKATGRDKAIYPAAGYGHIG Hv(SEQIDNO26)
59  DIQEMCKIGTTPQNDWYFFSHKDKKYPTGTRTNRATAAGFWKATGRDKIIYSN--GRRIG At(SEQIDNO27)
```

FIG. 9C

```
        .RKTLVFY.GRAPHG.KSDWIMHEYRL................------PYTADX  Consensus #1
        MRKTLVFYKGRAPHGQKSDWIMHEYRLDDP-------------------PYTADX  Majority 130       140       150       160       170       180
    113 MRKTLVFYKGRAPHGQKSDWIMHEYRLDDPAAAAAAGSG----------DAVANDDAAATA  Zm(SEQIDNO3)
    113 MRKTLVFYKGRAPHGQKSDWIMHEYRLDDPATDTAAAT-----------PTVTSAAAA    Os(SEQIDNO10)
    113 MRKTLVFYKGRAPHGQKSDWIMHEYRLDDP--SSASAS-----------VSVNLPSYYSSS Os(SEQIDNO11)
    113 MRKTLVFYKGRAPHGQKSDWIMHEYRLDDPAASGDAAA-----------AATAAAAAT    Sb(SEQIDNO12)
    114 MRKTLVFYKGRAPHGQKSDWIMHEYRLEPALDVDAAAGSASAHHAAAGAAADHHPYTSS   Sb(SEQIDNO13)
    117 MRKTLVFYKGRAPHGQKSDWIMHEYRLDD--------------------NNTSDI      Gm(SEQIDNO14)
    117 MRKTLVFYKGRAPHGQKSDWIMHEYRLDD--------------------NNTADT      Gm(SEQIDNO15)
    118 MRKTLVFYKGRAPHGQKSDWIMHEYRLDDNIIS----------------PEDVTV      At(SEQIDNO16)
    118 LRKTLVFYKGRAPHGQKSDWIMHEYRLDDT-------------------PMSNGY      At(SEQIDNO17)
    113 MRKTLVFYKGRAPHGQKSDWIMHEYRLDESVLI----------------SSCGDH      At(SEQIDNO18)
    113 MRKTLVFYRGRAPHGHKSDWIMHEYRLDDPD-------A----------AAVAAT      Zm(SEQIDNO19)
    115 MRKTLVFYKGRAPHGQKSDWIMHEYRLEAP--VDAGAG--AAHHLLL--PAAEHPPYTSP  Zm(SEQIDNO20)
    113 MRKTLVFYKGRAPHGLKSDWIMHEYRLIDADDSSSAAT-----------AAMVRVSVTASS Bd(SEQIDNO21)
    117 MRKTLVFYKGRAPHGQKSDWIMHEYRLEEN-------------------TPVHD-      Vv(SEQIDNO22)
    117 MRKTLVFYKGRAPHGQKSDWIMHEYRLDD--------------------NNTADT      Gm(SEQIDNO23)
    113 LRKTLVFYKGRAPHGQKSDWIMHEYRLDDN-------------------TTTHD-      Gh(SEQIDNO24)
    118 LRKTLVFYKGRAPHGQKSDWIMHEYRLEES-------------------NSTHD-      Pm(SEQIDNO25)
    115 MRKTLVFYQGRAPHGQKSDWIMHEYRLDDA--TTPGNN--PAN------QAIGNAPYYPGS Hv(SEQIDNO26)
    117 MRKTLVFYKGRAPHGQKSDWIMHEYRLDDNIIS----------------PEDVTV      At(SEQIDNO27)
```

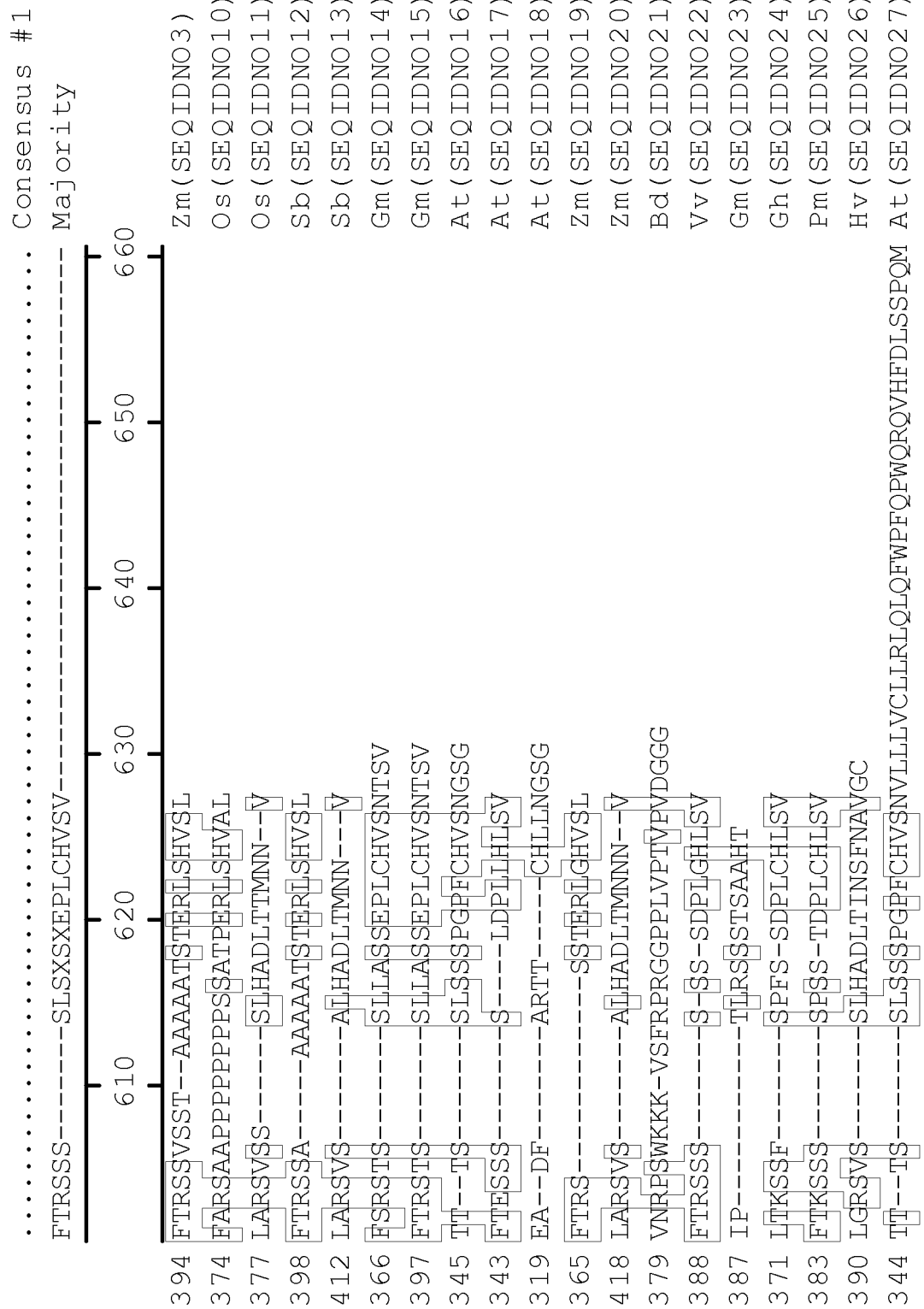

FIG. 9L

```
                  Consensus #1
                  Majority

418               Zm(SEQIDNO3)
400               Os(SEQIDNO10)
395               Os(SEQIDNO11)
419               Sb(SEQIDNO12)
428               Sb(SEQIDNO13)
388               Gm(SEQIDNO14)
419               Gm(SEQIDNO15)
365               At(SEQIDNO16)
358               At(SEQIDNO17)
334               At(SEQIDNO18)
379               Zm(SEQIDNO19)
435               Zm(SEQIDNO20)
408               Bd(SEQIDNO21)
405               Vv(SEQIDNO22)
400               Gm(SEQIDNO23)
389               Gh(SEQIDNO24)
401               Pm(SEQIDNO25)
411               Hv(SEQIDNO26)
395 QISLH         At(SEQIDNO27)
```

FIG. 10

Percent Identity

| | 1 | 2 | 3 | 4 | 5 | 6 | 7 | 8 | 9 | 10 | 11 | 12 | 13 | 14 | 15 | 16 | 17 | 18 | 19 | |
|---|---|---|---|---|---|---|---|---|---|---|---|---|---|---|---|---|---|---|---|---|
| 1 | | 76.2 | 55.4 | 85.8 | 52.0 | 58.6 | 59.1 | 56.2 | 52.3 | 52.7 | 80.3 | 52.3 | 63.5 | 56.1 | 58.6 | 53.4 | 54.8 | 50.0 | 56.2 | Zm(SEQIDNO3) |
| 2 | 28.6 | | 60.4 | 76.6 | 55.2 | 58.1 | 56.6 | 56.4 | 52.1 | 52.5 | 74.9 | 56.1 | 65.4 | 55.4 | 56.3 | 51.4 | 54.5 | 52.4 | 56.4 | Os(SEQIDNO10) |
| 3 | 66.4 | 55.8 | | 54.8 | 71.6 | 58.1 | 56.6 | 55.1 | 51.4 | 52.1 | 56.2 | 71.5 | 53.6 | 54.9 | 57.4 | 52.9 | 54.7 | 61.9 | 55.1 | Os(SEQIDNO11) |
| 4 | 15.8 | 28.1 | 67.9 | | 52.4 | 58.1 | 58.4 | 54.9 | 50.3 | 51.1 | 85.3 | 52.2 | 65.1 | 55.9 | 57.9 | 53.4 | 53.3 | 49.7 | 54.9 | Sb(SEQIDNO12) |
| 5 | 74.8 | 67.0 | 35.6 | 73.7 | | 54.9 | 53.9 | 53.5 | 51.7 | 51.0 | 52.4 | 81.4 | 50.9 | 52.6 | 54.8 | 50.4 | 54.2 | 61.5 | 53.5 | Sb(SEQIDNO13) |
| 6 | 59.5 | 60.4 | 60.5 | 60.4 | 67.7 | | 93.0 | 65.9 | 55.8 | 57.5 | 55.3 | 55.9 | 53.7 | 63.6 | 89.1 | 59.8 | 60.3 | 51.2 | 65.6 | Gm(SEQIDNO14) |
| 7 | 58.4 | 63.8 | 63.7 | 59.9 | 69.9 | 7.3 | | 66.1 | 56.3 | 57.8 | 55.8 | 54.9 | 54.5 | 63.0 | 96.0 | 59.5 | 59.8 | 51.2 | 65.8 | Gm(SEQIDNO15) |
| 8 | 64.7 | 64.3 | 67.2 | 67.6 | 71.0 | 45.4 | 45.0 | | 53.9 | 68.2 | 55.4 | 53.6 | 54.4 | 58.8 | 64.9 | 55.9 | 58.0 | 52.2 | 99.2 | At(SEQIDNO16) |
| 9 | 74.0 | 74.4 | 76.2 | 79.1 | 75.4 | 65.6 | 64.4 | 70.0 | | 51.1 | 50.3 | 52.0 | 51.1 | 57.3 | 55.3 | 56.6 | 57.2 | 50.5 | 53.9 | At(SEQIDNO17) |
| 10 | 73.0 | 73.5 | 74.4 | 77.0 | 77.3 | 61.8 | 61.1 | 41.3 | 76.9 | | 49.7 | 50.8 | 50.3 | 55.1 | 57.9 | 51.9 | 55.3 | 48.5 | 67.3 | At(SEQIDNO18) |
| 11 | 22.9 | 30.7 | 64.6 | 16.5 | 73.7 | 66.8 | 65.6 | 66.5 | 79.1 | 80.7 | | 52.3 | 64.4 | 55.7 | 55.4 | 52.8 | 53.6 | 50.0 | 55.4 | Zm(SEQIDNO19) |
| 12 | 73.9 | 65.0 | 35.8 | 74.2 | 21.5 | 65.5 | 67.7 | 70.7 | 74.6 | 77.7 | 73.9 | | 51.8 | 53.4 | 55.5 | 50.3 | 53.7 | 60.9 | 53.6 | Zm(SEQIDNO20) |
| 13 | 49.7 | 46.1 | 70.7 | 46.8 | 77.4 | 70.6 | 68.6 | 68.9 | 77.0 | 79.0 | 48.0 | 75.1 | | 54.9 | 56.7 | 51.7 | 53.5 | 48.1 | 53.9 | Bd(SEQIDNO21) |
| 14 | 64.9 | 66.6 | 67.7 | 65.4 | 73.2 | 49.5 | 50.6 | 59.1 | 62.3 | 67.3 | 65.8 | 71.2 | 67.7 | | 61.4 | 73.5 | 75.5 | 48.5 | 58.8 | Vv(SEQIDNO22) |
| 15 | 59.4 | 64.5 | 62.1 | 61.0 | 67.8 | 11.8 | 4.1 | 47.1 | 66.8 | 60.9 | 66.5 | 66.2 | 63.5 | 53.7 | | 59.6 | 59.4 | 52.0 | 64.9 | Gm(SEQIDNO23) |
| 16 | 71.1 | 76.3 | 72.4 | 71.2 | 78.7 | 56.9 | 57.6 | 65.3 | 63.7 | 75.0 | 72.7 | 79.1 | 75.5 | 32.8 | 57.3 | | 72.4 | 48.3 | 55.9 | Gh(SEQIDNO24) |
| 17 | 67.9 | 68.5 | 68.0 | 71.5 | 69.2 | 56.0 | 56.9 | 60.6 | 62.5 | 66.7 | 70.9 | 70.4 | 71.1 | 29.7 | 57.8 | 34.5 | | 51.4 | 58.0 | Pm(SEQIDNO25) |
| 18 | 79.9 | 73.7 | 52.8 | 80.6 | 53.6 | 76.7 | 76.7 | 74.3 | 78.6 | 83.8 | 79.9 | 54.7 | 85.1 | 83.9 | 74.6 | 84.6 | 76.2 | | 51.9 | Hv(SEQIDNO26) |
| 19 | 64.7 | 64.3 | 67.2 | 67.6 | 71.0 | 45.9 | 45.5 | 0.8 | 70.0 | 42.9 | 66.5 | 70.7 | 70.0 | 59.1 | 47.1 | 65.3 | 60.6 | 75.0 | | At(SEQIDNO27) |
| | 1 | 2 | 3 | 4 | 5 | 6 | 7 | 8 | 9 | 10 | 11 | 12 | 13 | 14 | 15 | 16 | 17 | 18 | 19 | |

FIG. 11A

```
              1.....11.....21.....31.....41.....51.....60
Crw2          ATGAAGCAGCCGAGGGGCCGGCCGGAGCCGGGCAACGCCCGCCATGGTCGTC
crw2-Mutag    ATGAAGCAGCCGAGGGGCCGGCCGGAGCCGGGCAACGCCCGCCATGGTCGTC
              ************************************************************

61.....71.....81.....91.....101.....111.....120
Crw2          ACCATGGTCGTCCTCCCTCTGCGTCCTCGGTCCCTCACGTACATCAAGGCGGATACTGCTCCAACCCT
crw2-Mutag    ACCATGGTCGTCCTCCCTCTGCGTCCTCGGTCCCTCACGTACATCAAGGCGGATACTGCTCCAACCCT
              ************************************************************

121.....131.....141.....151.....161.....171.....180
Crw2          TTCCCCAAGGCGGTGGCGAGGAGGTGGAGGACTACGACAGCACGCGGTACAAG
crw2-Mutag    TTCCCCAAGGCGGTGGCGAGGAGGTGGAGGACTACGACAGCACGCGGTACAAG
              ************************************************************

181.....191.....201.....211.....221.....231.....240
Crw2          CTGACGGGGCCCCGTGGGCGAGGAGGAGGACTTCGACCCGTCCCGCCCACCTGCTACAACACC
crw2-Mutag    CTGACGGGGCCCCGTGGGCGAGGAGGAGGACTTCGACCCGTCCCGCCCACCTGCTACAACACC
              ************************************************************

241.....251.....261.....271.....281.....291.....300
Crw2          AGCAAGCGGTCGGAGCGGTGCGCCGCCGTGGGCGACATCCGCGTGGACGGCAACGGCAACCACTCG
crw2-Mutag    AGCAAGCGGTCGGAGCGGTGCGCCGCCGTGGGCGACATCCGCGTGGACGGCAACGGCAACCACTCG
              ************************************************************
```

FIG. 11B

```
crw2        301.......311.......321.......331.......341.......351.......360
            CGGATCTACATCAGCCGCTGTCCCGGCGAGTGGCGGACCAAGCCGTAGCCGTACGCGGCGGCAC
crw2-Mutag  CGGATCTACATCAGCCGCTGTCCCGGCGAGTGGCGGACCAAGCCGTAGCCGTACGCGGCGGCAC
            **************************************************************** crw2        361.......371.......381.......391.......401.......411.......420
            GACGCCGTGGCCATGGACGACGTGCGCGAGTTCACGCTGGTCCCCCTTCGGCGGCCCCAAC
crw2-Mutag  GACGCCGTGGCCATGGACGACGTGCGCGAGTTCACGCTGGTCCCCTTCGGCGGCCCCAAC
            **************************************************************** crw2        421.......431.......441.......451.......461.......471.......480
            GACACGGCCGTGCCGTGCCGCGCTCTGCACGCGCACCCCACTCCGTCCGGGCTTCCTCTTCTCC
crw2-Mutag  GACACGGCCGTGCCGTGCCGCGCTCTGCACGCGCACCCCACTCCGTCCGGGCTTCCTCTTCTCC
            **************************************************************** crw2        481.......491.......501.......511.......521.......531.......540
            AGCGGGCGGGTTCGCGGGCAACCTGTACCACGACTACGCGGACGTGCTGGTGCCGGCTCTTC
crw2-Mutag  AGCGGGCGGGTTCGCGGGCAACCTGTACCACGACTACGCGGACGTGCTGGTGCCGGCTCTTC
            **************************************************************** crw2        541.......551.......561.......571.......581.......591.......600
            GCCAGCGGCACCACCACCTGGGCGGGGAGGTCCAGTTCCTGCTGGCCGACATCAAGGACTGG
crw2-Mutag  GCCAGCGGCACCACCACCTGGGCGGGGAGGTCCAGTTCCTGCTGGCCGACATCAAGGACTGG
            ****************************************************************
```

FIG. 11C

```
             601.......611.......621.......631.......641.......651.......660
Crw2         TGGGCCGACAAGTTCCGCCCGCTCTCCGCCAGTCTCCGCTACGACGTCATCGACGTG
crw2-Mutag   TGGGCCGACAAGTTCCGCCCGCTCTCCGCCAGTCTCCGCTACGACGTCATCGACGTG
             ************************************************************

661.......671.......681.......691.......701.......711.......720
Crw2         AACAACGACCGCGAGGTGCACTGCTTCCGCGATCATCATCGGCTCCACCTTCCACCGC
crw2-Mutag   AACAACGACCGCGAGGTGCACTGCTTCCGCGATCATCATCGGCTCCACCTTCCACCGC
             ************************************************************

721.......731.......741.......751.......761.......771.......780
Crw2         GCCATGGGCATCGACCCCTCGCGCTCGCCGGTCACGGTGGCCGACTTCAAGCGC
crw2-Mutag   GCCATGGGCATCGACCCCTCGCGCTCGCCGGTCACGGTGGCCGACTTCAAGCGC
             ************************************************************

781.......791.......801.......811.......821.......831.......840
Crw2         CTGCTCCGGCGGCCGTTCCGGCTGGAGCGCCGTCGCGTCGGGGTCGGGGGCCCGG
crw2-Mutag   CTGCTCCGGCGGCCGTTCCGGCTGGAGCGCCGTCGCGTCGGGGTCGGGGGCCCGG
             ************************************************************

841.......851.......861.......871.......881.......891.......900
Crw2         CGCCGGGACCGGCCCCGCCCCTCCTCATCATCTCCGGCAAGAGCTCCGCCGCTTCGTCAAC
crw2-Mutag   CGCCGGGACCGGCCCCGCCCCTCCTCATCATCTCCGGCAAGAGCTCCGCCGCTTCGTCAAC
             ************************************************************
```

FIG. 11D

```
            901.......911.......921.......931.......941.......951.......960
Crw2        GAGCGCGGCCATGGGCGGCGGCCGGCGGCGGCCCGGTTCGACGTGCGGATCGCCGAGCCC
crw2-Mutag  GAGCGCGGCCATGGCGCGCGGCCGGCGGCGGCCCGGTTCGACGTGCGGATCGCCGAGCCC
            ************ **** *****************************************

961.......971.......981.......991......1001......1011....1020
Crw2        GACAACCACACGGACATGCCCAACTTCGCGAGGTGAACTCGGCGTGAACGTGATGATG
crw2-Mutag  GACAACCACACGGACATGCCCAACTTCGCGAGGTGAACTCGGCGTGAACGTGATGATG
            ************************************************************

1021......1031......1041......1051......1061......1071....1080
Crw2        GGCGTGCACGGCGCCGGACTCACCAACATGGTGTTCCTGCCCAGCCGCGCCGTGCTGGTG
crw2-Mutag  GGCGTGCACGGCGCCGGACTCACCAACATGGTGTTCCTGCCCAGCCGCGCCGTGCTGGTG
            ************************************************************

1081......1091......1101......1111......1121......1131....1140
Crw2        CAGGTGGTGCCGTTCGGCGGGGCTGGAGTGGCTCACCCGGTCACCTTCAAGGACCCCGCA
crw2-Mutag  CAGGTGGTGCCGTTCGGCGGGGCTGGAGTGGCTCACCCGGTCACCTTCAAGGACCCCGCA
            ************************************************************

1141......1151......1161......1171......1181......1191....1200
Crw2        AGGGAC------------------------------------------------------
crw2-Mutag  AGGGACGAGATAATTGCCATTATGGACGGAAGAGGAAGGGGATTCGACGAAATGGAGGCG
            ******
```

FIG. 11E

```
           1201........1211........1221........1231........1241........1251........1260
Crw2       |         |         |         |         |         |         |
crw2-Mutag TTGGCGTTGGCTTCTCTGTTTTGGAGACGCACGCGACAGCCAAACTCCAAAACGGATACG 1261........1271........1281........1291........1301........1311........1320
Crw2                                    ----------ATGGACGTCACGTACACATGGAGTACAACGT
crw2-Mutag AGACAGCTCTTGGGGCTGCGTAAACAGGACATGGACGTCACGTACATGGAGTACAACGT
                                         ************************************

1321........1331........1341........1351........1361........1371........1380
Crw2       GTCGCTGGAGGAGAGCTCGCTCAGGGACCTCAGGGAGGACCACTTCTACCTGAAGCA
crw2-Mutag GTCGCTGGAGGAGAGCTCGCTCAGGGACCTCAGGGAGGACCACTTCTACCTGAAGCA
           ************************************************************

1381........1391........1401........1411........1421........1431........1440
Crw2       CCCCTACGACGAGCTGCACAAGAAGAAGGGGTGGACGCCATCAAGACGGTGTACCTGGACAAGCA
crw2-Mutag CCCCTACGACGAGCTGCACAAGAAGAAGGGGTGGGACGCCATCAAGACGGTGTACCTGGACAAGCA
           ************************************************************

1441........1451........1461........1471........1481........1491........1500
Crw2       GAACGTCAGGCTCAACCTCACCAGGTTCACCAGGACGCTGGAGCAGGCGCGAGATCTCTT
crw2-Mutag GAACGTCAGGCTCAACCTCACCAGGTTCACCAGGACGCTGGAGCAGGCGCGAGATCTCTT
           ************************************************************
```

FIG. 11F

```
Crw2         1501......1511......1521......1531......1541......1551......1560
             GCCGACGCCATGACTGACTGATGATGACCTCCCCCTCTTCCTCTGCTCTGCTGCAGGTTTCAT
crw2-Mutag   GCCGACGCCATGACTGACTGATGATGACCTCCCCCTCTTCCTCTGCTCTGCTGCAGGTTTCAT
             ****************************************************************

Crw2         1561......1571......1581......1591......1601......1611......1620
             TCACTTCAGATCAGCTGCTCACTTCACTTCACGCCGTGTCTCTCTCTTTTTTTTTTTCT
crw2-Mutag   TCACTTCAGATCAGCTGCTCACTTCACTTCACGCCGTGTCTCTCTCTTTTTTTTTTTCT
             ****************************************************************

Crw2         1621......1631......1641......1651......1661......1671......1680
             GTTGTTGTTCTATACATATACTTGTTCCTCTTCCCCTCTCCTTTCCCCTCTCCTCTAGTCTCT
crw2-Mutag   GTTGTTGTTCTATACATATACTTGTTCCTCTTCCCCTCTCCTTTCCCCTCTCCTCTAGTCTCT
             ****************************************************************

Crw2         1681......1691......1701......1711......1721......1731......1740
             CCCTCTCCACTCTTGTGGTGGCAAGATTCATTTCTTCATTCATTTCTTCATTGTTTTTGTTG
crw2-Mutag   CCCTCTCCACTCTTGTGGTGGCAAGATTCATTTCTTCATTCATTTCTTCATTGTTTTTGTTG
             ****************************************************************

Crw2         1741......1751......1761......1771......1781......1791......1800
             TTGTTGAGGAAGGATAGGAACAAAAACAAGGTATTGTCGTGTCCAAGGTTAATCTACACA
crw2-Mutag   TTGTTGAGGAAGGATAGGAACAAAAACAAGGTATTGTCGTGTCCAAGGTTAATCTACACA
             ****************************************************************
```

FIG. 11G

```
             1801......1811......1821......1831......1841......1851....1860
Crw2         AACACACACTGTAAATGATTGATTGATTGCTGTCAGTAGAGGCGAACACAAGGAATAGGT
crw2-Mutag   AACACACACTGTAAATGATTGATTGATTGCTGTCAGTAGAGGCGAACACAAGGAATAGGT
             ************************************************************

1861......1870
Crw2         AAAAAAAAAA
crw2-Mutag   AAAAAAAAAA
             **********
```

FIG. 12A

```
          1.....11.....21.....31.....41.....51.....60
crw2      ATGAAGCAGCAGCCGAGGGGCCGGCAGGAGCCCGCGGGTGGGCAACGCCCCATGGTCGTC
crw2-EMS  ATGAAGCAGCAGCCGAGGGGCCGGCAGGAGCCCGCGGGTGGGCAACGCCCCATGGTCGTC
          ************************************************************

61.....71.....81.....91.....101....111....120
crw2      ACCATGGTCGTCTCCCCTCTGGTCCTCACGTACATCAAGGCGGATACTGCTCCAACCCT
crw2-EMS  ACCATGGTCGTCTCCCCTCTGGTCCTCACGTACATCAAGGCGGATACTGCTCCAACCCT
          ************************************************************

121....131....141....151....161....171....180
crw2      TTCCCCAAGGCGGTGGCGGTGGAGGTGGACGAGGAGGACTACGACAGCACGCGGTACAAG
crw2-EMS  TTCCCCAAGGCGGTGGCGGTGGAGGTGGACGAGGAGGACTACGACAGCACGCGGTACAAG
          ************************************************************

181....191....201....211....221....231....240
crw2      CTGACGGGCCCCGTGGGCGGAGGAGGACTTCGACCCGTCCCACCCTGCTACAACACC
crw2-EMS  CTGACGGGCCCCGTGGGCGGAGGAGGACTTCGACCCGTCCCACCCTGCTACAACACC
          ************************************************************

241....251....261....271....281....291....300
crw2      AGCAAGCGGTCGGAGCCGGTGCGCCCGTGGGCGACATCCGCGTGGACGGCAACCACTCG
crw2-EMS  AGCAAGCGGTCGGAGCCGGTGCGCCCGTGGGCGACATCCGCGTGGACGGCAACCACTCG
          ************************************************************
```

FIG. 12B

```
         301.......311.......321.......331.......341.......351.......360
Crw2     CGGATCTACATCAGCCCGTGTCCCGGGAGTGGGGGGACCAAGCCGTACGCGGGGCAC
Crw2-EMS CGGATCTACATCAGCCCGTGTCCCGGGAGTGGGGGGACCAAGCCGTACGCGGGGCAC
         **********************************************************

361.......371.......381.......391.......401.......411.......420
Crw2     GACGCCGTGGCCATGGACGACGAGTTCACGCTGGTCTCCCCTTCGGGCCCCAAC
Crw2-EMS GACGCCGTGGCCATGGACGACGAGTTCACGCTGGTCTCCCCTTCGGGCCCCAAC
         **********************************************************

421.......431.......441.......451.......461.......471.......480
Crw2     GACACGGCCGTGCCGTGCCGCTCTGCACGCGCACCCCGTCCCACTCCGGGCTTCCTCTCTCC
Crw2-EMS GACACGGCCGTGCCGTGCCGCTCTGCACGCGCACCCCGTCCCACTCCGGGCTTCCTCTCTCC
         **********************************************************

481.......491.......501.......511.......521.......531.......540
Crw2     AGCGGGCGGTTCGGGGGCAACCTGTACCACGACTACGCCGAGCGTGCTGGTGCCGCTCTTC
Crw2-EMS AGCGGGCGGTTCGGGGGCAACCTGTACCACGACTACGCCGAGCGTGCTGGTGCCGCTCTTC
         **********************************************************

541.......551.......561.......571.......581.......591.......600
Crw2     GCCAGCACCAACCACCTGGGCGGGGAGGTCCAGTTCCTGGCCGACATCAAGGACTGG
Crw2-EMS GCCAGCACCAACCACCTGGGCGGGGAGGTCCAGTTCCTGGCCGACATCAAGGACTGG
         **********************************************************
```

FIG. 12C

```
         601.......611.......621.......631.......641.......651.......660
Crw2     TGGGCCGGACAAGTTCCGCCCGCTCTTCCGCCAAGCTCTCCGGCTACGACGTCATCGACGTG
crw2-EMS TGGGCCGGACAAGTTCCGCCCGCTCTTCCGCCAAGCTCTCCGGCTACGACGTCATCGACGTG
         ************************************************************

661.......671.......681.......691.......701.......711.......720
Crw2     AACAACGACCGGCGAGGTGCACTGCTTCCCGGGATCATCATCGGCTCCACCTTCCACCGC
crw2-EMS AACAACGACCGGCGAGGTGCACTGCTTCCCGGGATCATCATCGGCTCCACCTTCCACCGC
         ************************************************************

721.......731.......741.......751.......761.......771.......780
Crw2     GCCATGGGCATCGACCCCCTCGGCGCCGGCGTCACGGTGGCTCGACTTCAAGCGC
crw2-EMS GCCATGGGCATCGACCCCCTCGGCGCCGGCGTCACGGTGGCTCGACTTCAAGCGC
         ************************************************************

781.......791.......801.......811.......821.......831.......840
Crw2     CTGCTCCGCCGGCGTTCCGGAGCGCGCCGTCGGCCGGTCGTCGGGGGCGCCCCGG
crw2-EMS CTGCTCCGCCGGCGTTCCGGAGCGCGCCGTCGGCCGGTCGTCGGGGGCGCCCCGG
         ************************************************************

841.......851.......861.......871.......881.......891.......900
Crw2     CGCCGGGACCGGCCCCCGCCTCCTCATCATCTCGCGAAGAGCTCGCGCCGCTTCGTCAAC
crw2-EMS CGCCGGGACCGGCCCCCGCCTCCTCATCATCTCGTGCAAGAGCTCGCGCCGCTTCGTCAAC
         **********************************←*************************
```

FIG. 12D

```
        901.......911.......921.......931.......941.......951.......960
crw2     GAGCGCGCCATGGCGCGCGCGGCGCGCGGCCGGTTCGAGTCGGATCGCCGAGCCC
crw2-EMS GAGCGCGCCATGGCGCGGCGCCGGCGCGGGCCGGTTCGAGTCGGATCGCCGAGCCC
         ************************************************************

961.......971.......981.......991......1001......1011....1020
crw2     GACAACCACACGGACATGCCCAACTTCGCGGAGGCTGGTGAACTCGGCGGTGATGATG
crw2-EMS GACAACCACACGGACATGCCCAACTTCGCGGAGGCTGGTGAACTCGGCGGTGATGATG
         ************************************************************

1021......1031......1041......1051......1061......1071....1080
crw2     GGCGTGCACGGCGCGCGGGCTCACCAACATGGTGTTCCTGCCCAGCCGCGTGCTGGTG
crw2-EMS GGCGTGCACGGCGCGCGGGCTCACCAACATGGTGTTCCTGCCCAGCCGCGTGCTGGTG
         ************************************************************

1081......1091......1101......1111......1121......1131....1140
crw2     CAGGTGGTGCCGTTCGGCCGGGCTGGAGTGGGCTCACCGCGTCACCCGGTCAAGGACCCCGCA
crw2-EMS CAGGTGGTGCCGTTCGGCCGGGCTGGAGTGGGCTCACCGCGTCACCCGGTCAAGGACCCCGCA
         ************************************************************

1141......1151......1161......1171......1181......1191....1200
crw2     AGGGACATGGACGTCACGTACATGGAGTACAACGTGTCGCTGGAGGAGAGCTCGCTCAGG
crw2-EMS AGGGACATGGACGTCACGTACATGGAGTACAACGTGTCGCTGGAGGAGAGCTCGCTCAGG
         ************************************************************
```

FIG. 12E

```
              1201.....1211.....1221.....1231.....1241.....1251.....1260
Crw2          GACCCTCTACCGGAGGACCACTTCCTACCTGAAGCACCCTGAAGCACGACGTGCACAAGAAGGGG
crw2-EMS      GACCCTCTACCGGAGGACCACTTCCTACCTGAAGCACCCTGAAGCACGACGTGCACAAGAAGGGG
              ****************************************************************

1261.....1271.....1281.....1291.....1301.....1311.....1320
Crw2          TGGGACGGCCATCAAGACGGTGTACCTGGACAAGCAGAACGTCAGGCTCAACCTCACCAGG
crw2-EMS      TGGGACGGCCATCAAGACGGTGTACCTGGACAAGCAGAACGTCAGGCTCAACCTCACCAGG
              *************************************************************

1321.....1331.....1341.....1351.....1361.....1371.....1380
Crw2          TTCACCAGGACGCTGGAGCAGGCGGCGAGATCTCTTGCCGACGCCATGACTGACTGATGACC
crw2-EMS      TTCACCAGGACGCTGGAGCAGGCGGCGAGATCTCTTGCCGACGCCATGACTGACTGATGACC
              *************************************************************

1381.....1391.....1401.....1411.....1421.....1431.....1440
Crw2          TCCCCCTCTTTCCTCTGCTCTGCTGCAGGTTTCATTCACTTCAGATCAGCTGCTCACCTC
crw2-EMS      TCCCCCTCTTTCCTCTGCTCTGCTGCAGGTTTCATTCACTTCAGATCAGCTGCTCACCTC
              *************************************************************

1441.....1451.....1461.....1471.....1481.....1491.....1500
Crw2          ACTTCACGCCGTCTCTCTCTCTTTTTTTTTTCTGTTGTTGTTCTATACATATACTTGT
crw2-EMS      ACTTCACGCCGTCTCTCTCTCTTTTTTTTTTTCTGTTGTTGTTCTATACATATACTTGT
              *************************************************************
```

FIG. 12F

```
         1501.....1511.....1521.....1531.....1541.....1551.....1560
crw2     TTCCTCTTCTCCTTTCCCTCTCTCTAGTCTCTCCCTCTCCACTCTTGTGGTGGCAAG
crw2-EMS TTCCTCTTCTCCTTTCCCTCTCTCTAGTCTCTCCCTCTCCACTCTTGTGGTGGCAAG
         *********************************************************

1561.....1571.....1581.....1591.....1601.....1611.....1620
crw2     ATTCATTTCTTTCATTGTTTTGTTTTTGTTGTTGTGTTGAGGAAGGATAGGAACAAAA
crw2-EMS ATTCATTTCTTTCATTGTTTTGTTTTTGTTGTTGTGTTGAGGAAGGATAGGAACAAAA
         *********************************************************

1621.....1631.....1641.....1651.....1661.....1671.....1680
crw2     ACAAGGTATTGTCGTGTCCAAGGTTAATCTACACAAACACTGTAAATGATTGATTG
crw2-EMS ACAAGGTATTGTCGTGTCCAAGGTTAATCTACACAAACACTGTAAATGATTGATTG
         *********************************************************

1681.....1691.....1701.....1711.....17211725
crw2     ATTGCTCAGTAGAGGCGAACACAAGGAATAGGTAAAAAAAAA
crw2-EMS ATTGCTCAGTAGAGGCGAACACAAGGAATAGGTAAAAAAAAA
         ******************************************
```

FIG. 14D

```
    ..PYAR.....AM..VRE..............C...H......FS.GG....N..H Consensus #1
    TKPYARRHDAVAMDDVREFTLKPFG---XXTAVPPLCTRNHSVPAFLFSXGGFAGNLYH Majority
              |         |         |         |         |         |
             190       200       210       220       230       240

113 TKPYARRHDAVAMDDVREFTLVPFG--GPNDTAVPPLCTRTHSVPGFLFSSGGFAGNLYH Zm(SEQIDNO29)
149 TKPYARYHDPVAMAHVREYTLKPLP--E--AAPAPACTRNHSVPGFLFSNGGFSGNLYH Zm(SEQIDNO34)
148 TKPYARYHDPVAMAHVREYTLKALP----EPGAAAAPACTRNHSVPGFLFSNGGFSGNLYH Zm(SEQIDNO35)
119 TKPYARLHDAVAMDDVREFTLVPFG--GANHTAVPPLCTRNHSVPGFLFSSGGFAGNLYH Os(SEQIDNO36)
149 TKPYARYHDPVAMAVVREFTLKPVT--E---S-SPACTRNHSVPAFVFSNGGFSGNLYH Os(SEQIDNO37)
118 TKPYARLHDPVAMDDVREFTLVPFGPGSPNGTVVPPLCTRNHSVPGFLFSSGGFAGNLYH Sb(SEQIDNO38)
162 TKPYARYHDPVAMAHVREYTLKPLP------AAEAPACTRNHSVPGFLFSNGGFSGNLYH Sb(SEQIDNO39)
116 LKPYARRDDVDAMIRVREWSVKAVN-----VSQKAPQCTQYHNIPAVLFSTGGYAGNHFH Gm(SEQIDNO40)
126 LKPYARRGDIDAMNRVREWSVKAVN-----ASQKAPQCTQSHNITAVLFSTGYSGNHFH Gm(SEQIDNO41)
45  IRPYARKGDTVAMKRVREWTVKLEQNADQLENANFSRCVRNHSVPAMIFSLGGYSMNNFH At(SEQIDNO42)
136 MRPYARKDQVPAMKRVREWTVKLVQ------NASLSRCVRNHSVPAILFSLGGFSLNNFH At(SEQIDNO43)
118 TKPYARRHDAVAMDDVREFALLPFG--GGNDSAVPPLCTRNHSVPAFLFSSGGFAGNLYH Hv(SEQIDNO44)
119 TKPYARRHDAVAMDDVREFTLLPFDTESSNTTVVPPLCTRNHSVPAFLFSSGGFAGNLYH Bd(SEQIDNO45)
118 TKPYARLHDAVAMDDVREYTLVPFG--GANDTAVPPLCTRNHSAPAFLFSNGGFAGNLYH Pn(SEQIDNO47)
116 TKPYARRHDAVAMDDVREFTLLPFG--GANDTAVPPLCTRNHSVPGFLFSIGGFAGNLYH En(SEQIDNO49)
126 LKPYARRDDVDAMIRVREWSVKAVN-----VSQKAPQCTQYHNIPAVLFSTGGYAGNHFH Gm(SEQIDNO50)
```

FIG. 14F

```
    .HCF......G..................DF..LR.....L....A........... Consensus #1
    VHCFPRIVVGAT----FHXAMGIDPSRSPGGVSVADFKRLLRRAFRLERXVASRTG---A Majority
             |         |         |         |         |         |
            310       320       330       340       350       360

226 VHCFPRTIIGST----FHRAMGIDPSRSPGGVTVADFKRLLRRAFRLERAVASRSG---A Zm(SEQIDNO29)
259 VHCFPRIVVGAT----FHKDMGVDPRRSPGHVSVVDFKRALRRAFGLPREAASRGG---A Zm(SEQIDNO34)
260 VHCFPRIVVGAT----FHRDMGVDPRRAPGHVSAVDFKRALRAAFGLKREAASRGGGGA Zm(SEQIDNO35)
232 VHCFPRIFIGAT----FHRAMGIDPARSPGGVTVADFKRLLRRTFRLERAVASRTG---A Os(SEQIDNO36)
257 VHCFPRIVVGAT----FHKDMGVDPKRSPGHVSVVDFKRALRRAFGLERVAASRGG---A Os(SEQIDNO37)
233 VHCFPRIVIGST----FHRAMGIDASRSPGGETVADFKVLRRAFKLERAVASRSG---A Sb(SEQIDNO38)
271 VHCFPRIVAGAT----FHKDMGVDPRRSPGHVSVVDFKRALRRAFGLEREAASRGG---A Sb(SEQIDNO39)
226 VHCFPRVTVGLKR---YQKELSIEPQKYS---YSMKDFRDLLRSSYALKRVEAIKTR---D Gm(SEQIDNO40)
236 VHCFPSVTVGLKR---YQKELSIDPQKYS---YSMKDFRDLLRSSYALKRVEAMKIR---D Gm(SEQIDNO41)
160 THCFSSVTVGLTRHREYFKELTIDPSNSE---YSMSDFRSFLRDTYSLR-NDAVATR---Q At(SEQIDNO42)
245 THCFSSVIVGLNRHRDYDKELTTDPSNSE---YSMSDFRKFLRDTYSLR-NSAVTT---- At(SEQIDNO43)
231 VHCFPRIVIGST----FHRPMGIDGTRSPGGETVADFKRLLRRAFRLDRVVASHDG---S Hv(SEQIDNO44)
234 VHCFRRIIIGAT----FHRAMGIDPKRSPGGETVADFKRLLRHAFHLTRPVASRD----- Bd(SEQIDNO45)
231 VHCFHRIVIGAT----FHRAMGIDPTRSPGGITVADFKRTLRRAFRLERAVASRTG---A Pn(SEQIDNO47)
234 VHCFPRIVIGPT----FHRAMGIDPTRSPGGINIADFKRLLRRTFRLERAVASRTG---A En(SEQIDNO49)
236 VHCFPRVTVGLKR---YQKELSIEPQKYS---YSMKDFRDLLRSSYALKRVEAIKTR---D Gm(SEQIDNO50)
```

FIG. 14G

```
........PR..I..R..SR.F.N....A..A.....F.V...E..........FA..VNS.D.  Consensus #1
PRR-GKPRLLIISRKSSRRFLNERAMARAAAAXAGFDVRIAEPDNHTDMPNFARLVNSADV     Majority
                 |         |         |         |         |
                370       380       390       400       410       420
279 PRRRDRPRLLIISRKSSRRFVNERAMARAAAAARFDVRIAEPDNHTDMPNFARLVNSADV  Zm(SEQIDNO29)
312 TGR-GKPRLLIISRRGSRRFLNEREMARAAAAGAGFEVRVAEPDQHTDTAAFAALVNSADV Zm(SEQIDNO34)
316 TGD-GKPRLLIISRRGSRRFLNSREMAVAAGDAGFEVRVAEPDQRTDMAAFAALVNSADA  Zm(SEQIDNO35)
285 PRR-DKPRLLIISRKSSRRFLNERAMAHAAALARFDVRIAEPDNHTDMPNFARLVNSADV  Os(SEQIDNO36)
310 TGN-GKPRLLIISRKNSRRFLNEREMAQAAAAVGFEVRIAEPDQHTDMSTFAQLVNSADV  Os(SEQIDNO37)
286 PRRKDRPRLLIISRKSSRRFVNERAMARAAAAAKFDVRIAEPDNHTDMPNFARLVNSADV  Sb(SEQIDNO38)
324 TGH-GKPRLLIISRRGSRRFLNEREMARAAADAGFEVRVAEPDQHTDMATFAALVNSADV  Sb(SEQIDNO39)
278 GLR-GKPRLMILSRKRSRFFTNTDEIAKMAESLGFDVIIKEAG--WSMWGFANVVNSCDV  Gm(SEQIDNO40)
288 GLR-GKPRLMILSRKRSRSFTNTDEIAKMAASLGFDVIVKEAG--WSMWGFANVVNSCDV  Gm(SEQIDNO41)
214 IRR-RRPRILILARGRSRAFVNTGEIARAARQIGFKVVVAEAN--IGIAKFAQTVNSCDV  At(SEQIDNO42)
297 --R-RKPRLLIISRKSSRRFLNERAMAHAAALAQFDVRIAEPDNHTDMPNFARLVNSADV  At(SEQIDNO43)
284 ASL-GKPRLLIISRKSSRRFLNERAMAHAAALAKFDVRIAEPDNHTDMPNFARLVNSADV  Hv(SEQIDNO44)
285 -----NPRLLIISRKSSRRFLNERAMAHAAAAARFDVRIAEPDNHTDMPNFARLVNSADI  Bd(SEQIDNO45)
284 PRR-DRPRLLIISRRSSRRFLNERAMAHAAAAARFDVRIAEPDNHTDMPNFARLVNSADV  Pn(SEQIDNO47)
287 PRR-DKPRLLIISRKSSRRFLNERAVAHAAALAKFDVRIAEPDNHTDMPNFARLVNSADV  En(SEQIDNO49)
288 GLR-GKPRLMILSRKRSRFFTNTDEIAKMAESLGFDVIIKEAG--WSMWGFANVVNSCDV  Gm(SEQIDNO50)
```

FIG. 14I

```
       S.L...Y...H......P........GW...K..YL..Q.............L......L.....  Consensus #1
       SSLRDQYPRDHFYLKDPYDVHKKGWDAIKTVYLDKQNVRLDDRFXPTLEKARDLLPSP-           Majority 490         500         510         520         530         540
                |           |           |           |           |           |
   397 SSLRDLYPEDHFYLKHPYDVHKKGWDAIKTVYLDKQNVRLNLTRFTRTLEQARDLLPTP           Zm(SEQIDNO29)
   429 SSLIDQYPRNHQVLTDPYAVHKQGWDALKAAYLDKQNIRMDLDRFRATLREAMSRLPPAP          Zm(SEQIDNO34)
   433 SSLVDQYPRGHQVLTDPYAVHRQGWDALKTAYLDRFRATLREVMARLPSP                    Zm(SEQIDNO35)
   402 SSLRELYPRDHFYIQHPYDVHKKGWDAIKTVYLDKQNVELNLTKLTNTLERARDFLPEP           Os(SEQIDNO36)
   427 SSLIDQYPRNHQVLTDPYAVHKQGWDALKTAYLDKQNIKMDMDRFKKTLQEALDRLPPA           Os(SEQIDNO37)
   404 SSLRDLYPEDHFYLKHPYDVHKKGWDAIKTVYLDKQNVRLNLTRFTRTLEQARDLLPSP           Sb(SEQIDNO38)
   441 SSLLDQYPRNHQVLTDPYAVHKQGWDALKTAYLDKQNIRMDLDRFRATLREAMSRLPSP           Sb(SEQIDNO39)
   395 STLIQQYPLDHMFIKDPPLIEKIGWEEFKSVYLDKQNVKLDVDRFRPTLQKALELLHQ            Gm(SEQIDNO40)
   405 STLIQQYPLDHIFIKDPPLVEKIGWEEFKSVYLDKQNVKLDVDRFRPTLQKAFELLHQ            Gm(SEQIDNO41)
   329 STLVKKYGRDHEIVRDPSAVAKHGWEMFKSVYLVQQNVSIDINRFKPVLVKALELL              At(SEQIDNO42)
   410 STLVKQYGRDHEFVRDPLAVAKRGWGTFKSVYLVQQNVSVDINRFKLVLVKALELLHNQS          At(SEQIDNO43)
   401 SSLKNLYPKDHFYLQHPYDVHKKGWNAIKTVYLDKQSVRLDLAKLTRTLEHARSLLPSSS          Hv(SEQIDNO44)
   398 SSLRNLYPEGHFYLKHPYDVHKKGWDAIKTVYLDKQSVRLNLTKFVQTLELARSRLPA            Bd(SEQIDNO45)
   401 SSLRDLYPEGHFYLKHPYDVHKKGWDAIKTVYLDKQNVRLNLTRFTETLEQARDLLPLP           Pn(SEQIDNO47)
   404 SSLRDLYPEDHFYLKHPYDVHKKGWDAIKTTYLDKQNVRLNLTRFTKTLQQARDLLPSP           En(SEQIDNO49)
   405 STLIQQYPLDHMFIKDPPLIEKIGWEEFKSVYLDKQNVKLDVDRFRPTLQKALELLHQ            Gm(SEQIDNO50)
```

FIG. 14J

```
Consensus #1
Majority

Zm(SEQIDNO29)    455
Zm(SEQIDNO34)    488
Zm(SEQIDNO35)    491
Os(SEQIDNO36)    460
Os(SEQIDNO37)    485
Sb(SEQIDNO38)    462
Sb(SEQIDNO39)    499
Gm(SEQIDNO40)    452
Gm(SEQIDNO41)    462
At(SEQIDNO42)    384
At(SEQIDNO43)    470 V
Hv(SEQIDNO44)    461 SH
Bd(SEQIDNO45)    455
Pn(SEQIDNO47)    459
En(SEQIDNO49)    462
Gm(SEQIDNO50)    462
```

FIG. 15

Percent Identity

| | 1 | 2 | 3 | 4 | 5 | 6 | 7 | 8 | 9 | 10 | 11 | 12 | 13 | 14 | 15 | 16 | |
|---|---|---|---|---|---|---|---|---|---|---|---|---|---|---|---|---|---|
| 1 | ■ | 64.5 | 60.7 | 86.3 | 63.5 | 93.8 | 64.7 | 40.5 | 38.6 | 41.9 | 36.7 | 83.0 | 82.4 | 89.4 | 86.8 | 40.0 | 1 | Zm(SEQIDNO29) |
| 2 | 47.8 | ■ | 87.2 | 64.8 | 80.1 | 65.0 | 94.0 | 40.1 | 39.9 | 44.4 | 40.0 | 64.1 | 64.1 | 65.4 | 65.0 | 40.8 | 2 | Zm(SEQIDNO34) |
| 3 | 55.1 | 14.1 | ■ | 61.1 | 74.0 | 61.2 | 86.4 | 38.9 | 38.7 | 42.6 | 38.6 | 60.7 | 60.9 | 62.0 | 61.4 | 39.6 | 3 | Zm(SEQIDNO35) |
| 4 | 15.1 | 47.2 | 54.4 | ■ | 64.7 | 86.2 | 66.1 | 39.9 | 38.6 | 42.7 | 38.0 | 84.4 | 85.9 | 87.5 | 88.8 | 39.5 | 4 | Os(SEQIDNO36) |
| 5 | 49.7 | 23.2 | 32.0 | 47.5 | ■ | 64.4 | 80.6 | 42.2 | 41.2 | 44.7 | 39.9 | 63.7 | 64.2 | 64.1 | 65.5 | 41.9 | 5 | Os(SEQIDNO37) |
| 6 | 6.4 | 47.0 | 54.2 | 15.3 | 48.1 | ■ | 65.3 | 40.2 | 38.2 | 42.2 | 36.9 | 84.2 | 83.1 | 89.3 | 88.0 | 39.8 | 6 | Sb(SEQIDNO38) |
| 7 | 47.5 | 6.2 | 15.1 | 45.0 | 22.5 | 46.3 | ■ | 39.0 | 39.2 | 44.0 | 39.2 | 64.6 | 64.9 | 66.2 | 66.7 | 39.7 | 7 | Sb(SEQIDNO39) |
| 8 | 109.7 | 111.0 | 115.7 | 111.8 | 103.6 | 110.6 | 115.4 | ■ | 85.8 | 55.6 | 50.9 | 41.8 | 40.7 | 39.8 | 42.0 | 92.7 | 8 | Gm(SEQIDNO40) |
| 9 | 116.8 | 111.8 | 116.5 | 117.1 | 107.0 | 118.5 | 114.4 | 15.7 | ■ | 56.4 | 52.0 | 40.4 | 39.5 | 38.2 | 40.2 | 92.2 | 9 | Gm(SEQIDNO41) |
| 10 | 104.4 | 96.0 | 102.2 | 101.7 | 95.3 | 103.4 | 97.4 | 66.1 | 64.3 | ■ | 83.4 | 41.4 | 41.0 | 42.2 | 42.2 | 55.6 | 10 | At(SEQIDNO42) |
| 11 | 125.0 | 111.3 | 117.1 | 119.5 | 112.0 | 123.8 | 114.4 | 77.5 | 74.7 | 18.8 | ■ | 37.4 | 37.1 | 36.7 | 38.5 | 52.7 | 11 | At(SEQIDNO43) |
| 12 | 19.3 | 48.6 | 55.1 | 17.5 | 49.4 | 17.8 | 47.6 | 104.8 | 109.8 | 106.3 | 121.7 | ■ | 87.1 | 82.8 | 85.1 | 42.0 | 12 | Hv(SEQIDNO44) |
| 13 | 20.1 | 48.5 | 54.7 | 15.7 | 48.4 | 19.1 | 47.0 | 108.9 | 113.2 | 107.7 | 123.1 | 14.2 | ■ | 83.1 | 85.7 | 40.5 | 13 | Bd(SEQIDNO45) |
| 14 | 11.4 | 46.3 | 52.6 | 13.7 | 48.6 | 11.6 | 44.8 | 112.3 | 118.5 | 103.5 | 124.8 | 19.7 | 19.2 | ■ | 88.0 | 39.6 | 14 | Pn(SEQIDNO47) |
| 15 | 14.6 | 47.0 | 53.7 | 12.1 | 46.0 | 13.2 | 43.9 | 104.1 | 110.8 | 103.5 | 117.5 | 16.7 | 15.9 | 13.2 | ■ | 41.5 | 15 | En(SEQIDNO49) |
| 16 | 111.5 | 108.5 | 113.0 | 113.5 | 104.6 | 112.3 | 112.7 | 7.7 | 8.2 | 66.1 | 73.0 | 104.1 | 109.8 | 113.2 | 105.8 | ■ | 16 | Gm(SEQIDNO50) |
| | 1 | 2 | 3 | 4 | 5 | 6 | 7 | 8 | 9 | 10 | 11 | 12 | 13 | 14 | 15 | 16 | | |

MANAGEMENT OF CORN ROOTWORM AND OTHER INSECT PESTS

CROSS REFERENCE TO RELATED APPLICATIONS

The application is a National Phase Under 35 U.S.C. § 371 of PCT/US2013/061037 filed in the Patent Cooperation Treaty U.S. Receiving Office on Sep. 20, 2013, which claims the benefit of U.S. Provisional Application No. 61/703,396, filed Sep. 20, 2012, U.S. Provisional Application No. 61/781,057, filed Mar. 14, 2013, U.S. Provisional Application No. 61/703,414, filed Sep. 20, 2012; U.S. Provisional Application No. 61/781,124, filed Mar. 14, 2013; and U.S. Provisional Application No. 61/782,116, filed Mar. 14, 2013; the entire contents of which are herein incorporated by reference.

REFERENCE TO SEQUENCE LISTING

The Sequence Listing submitted Mar. 19, 2015 as a text file named "36446_0197U1_Sequence_Listing.txt," created on Mar. 19, 2015, and having a size of 167,936 bytes is hereby incorporated by reference pursuant to 37 C.F.R. § 1.52(e)(5).

FIELD

The field relates to trap crops and/or refuge crops comprising plants with enhanced susceptibility to herbivory by one or more insect pests and their use as part of an insect pest management plan.

BACKGROUND

Insects, nematodes, and related arthropods annually destroy an estimated 15% of agricultural crops in the United States and even more than that in developing countries. Some of this damage occurs in the soil when plant pathogens, insects and other such soil borne pests attack the seed after planting. In the production of corn, for example, much of the rest of the damage is caused by rootworms—insect pests that feed upon or otherwise damage the plant roots; by cutworms, European corn borers (ECB), and by other pests that feed upon or damage the above ground parts of the plant. General descriptions of the type and mechanisms of attack of pests on agricultural crops are provided by, for example, Metcalf (1962) in *Destructive and Useful Insects: Their Habits and Control,* Fourth Edition. (Earlier editions by C. L. Metcalf and W. P. Flint) McGraw-Hill Book Company; New York, San Francisco, Toronto, London; and Agrios, (1988) in *Plant Pathology,* 3$^{rd}$ Ed., Academic Press.

Traditionally, crop rotation and use of insecticides were the primary management strategies for corn rootworm [Western corn rootworm (*Diabrotica virgifera virgifera* LeConte), Northern corn rootworm (*Diabrotica barberi* Smith and *Diabrotica barberi* Lawrence), and Southern corn rootworm (*Diabrotica undecimpunctata howardi* Barber)] in North America. However, the adaptation of a biotype of Western corn rootworm (WCR) to preferentially lay eggs on soybean plants; the adaptation of a biotype of Northern corn rootworm (NCR) resulting in extended diapause in eggs; counter-resistance of corn rootworms to soil and foliar insecticides; and an increased demand for continuous corn have resulted in significant range expansion of this insect pest in recent years. The commercial availability of rootworm-protected transgenic insecticidal corn hybrids (Bt) has provided an effective alternative, resulting in a rapid increase in acreage of transgenic corn for WCR control. Insect resistance management approaches need to be considered with respect to widespread use of Bt insecticidal proteins. Similar issues and concerns exist with control plans for other insect pests such as European corn borer.

There is a need for additional methods of control that can be used in conjunction with other methods or processes towards a cost-effective and sustainable insect pest management program. There is also a need for methods to reduce the probability of development of resistance towards the Bt toxin in insect pests.

SUMMARY

Plants with enhanced susceptibility to herbivory by an insect pest due to a reduction in endogenous expression of Crw1 and/or Crw2 are provided herein. Also provided are methods for making such plants. The plants may be maize, soybean, sunflower, sorghum, canola, wheat, alfalfa, cotton, rice, barley, millet, or sugarcane. Maize is of particular interest. The insect pest may be Coleopteran or Lepidopteran. Corn rootworm, European corn borer, Japanese beetle, fall webworm, and cattail caterpillar are of particular interest.

Trap crops comprising such plants are also provided. The trap crop may be comprised of plants selected from the group consisting of: maize, soybean, sunflower, sorghum, canola, wheat, alfalfa, cotton, rice, barley, millet, and sugar cane. Maize is of particular interest.

Methods of using trap crops to control one or more insect pests are provided.

Refuge crops comprising such plants are also provided. The refuge crop may be comprised of plants selected from the group consisting of: maize, soybean, sunflower, sorghum, canola, wheat, alfalfa, cotton, rice, barley, millet, and sugar cane. Maize is of particular interest.

Methods of using refuge crops to reduce an insect pest's development of resistance to insecticides or to a toxin provided by insect resistant transgenic plants are provided herein.

BRIEF DESCRIPTION OF THE DRAWINGS AND SEQUENCE LISTING

The disclosure can be more fully understood from the following detailed description and the accompanying drawings and Sequence Listing which form a part of this application.

Figure 3:
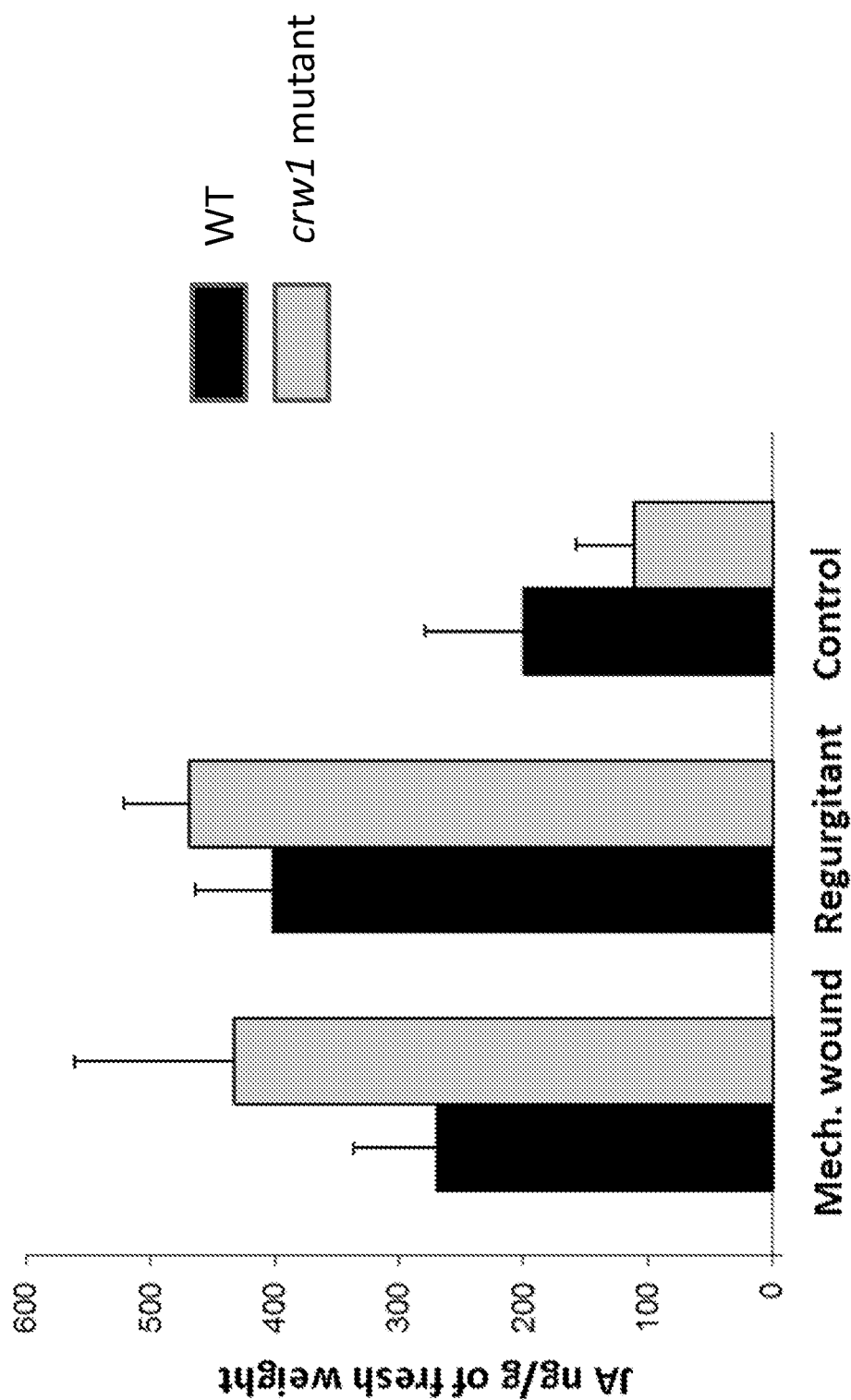

FIG. 3 depicts the quantification of Jasmonic Acid (JA) from the Crw1 mutant (MT) and wild type (WT) plants in response to mechanical wounding ("Mech. Wound") and Fall Armyworm caterpillar regurgitant ("Regurgitant"). Crw1 mutant plants accumulate higher levels of JA but only in response to applied stress.

Figure 4:
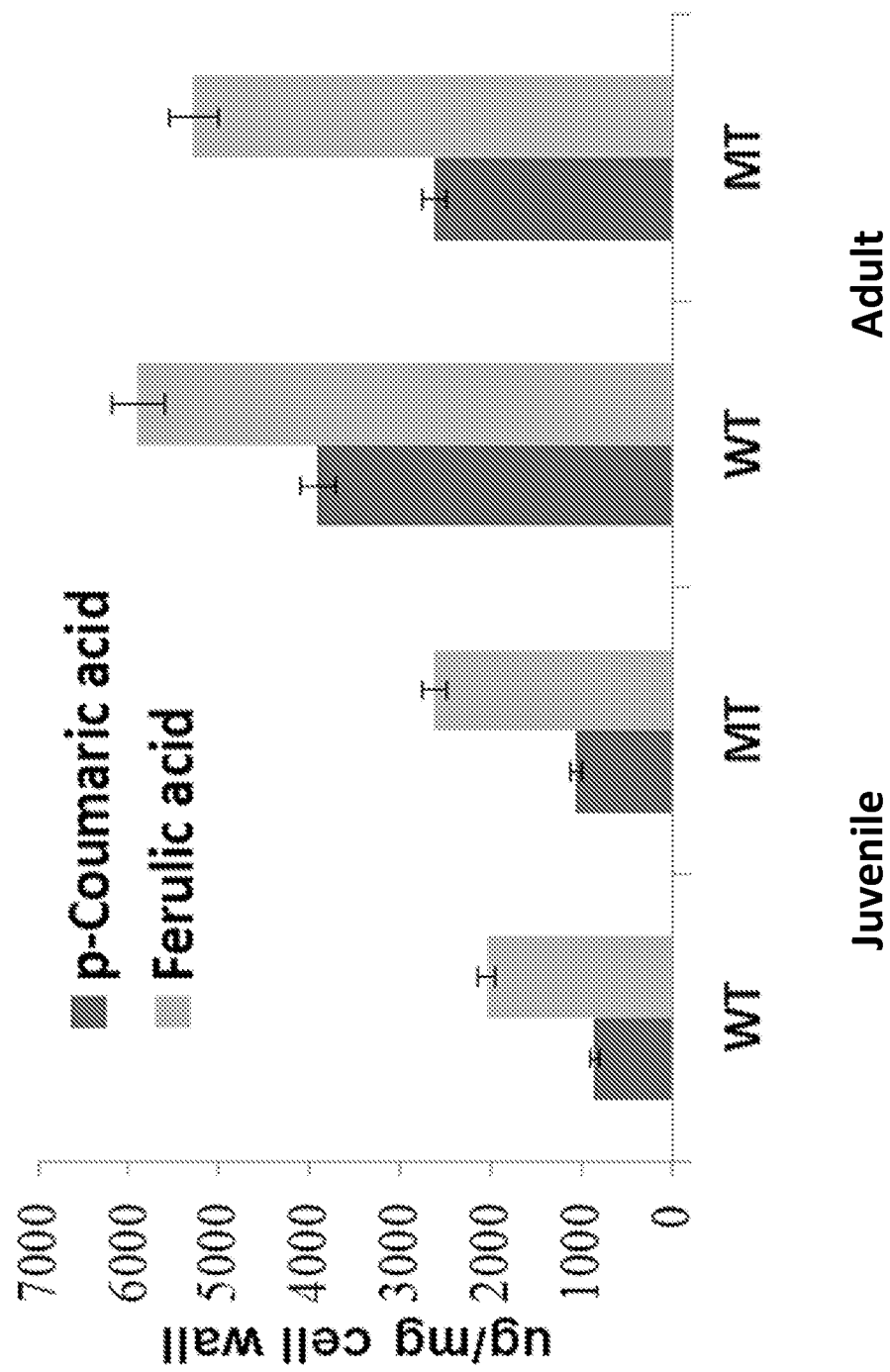

FIG. 4 depicts the differences in p-coumaric and ferulic acid levels from juvenile and adult leaves of Crw1 MT (mutant) and WT (wild-type) plants.

Figure 5:
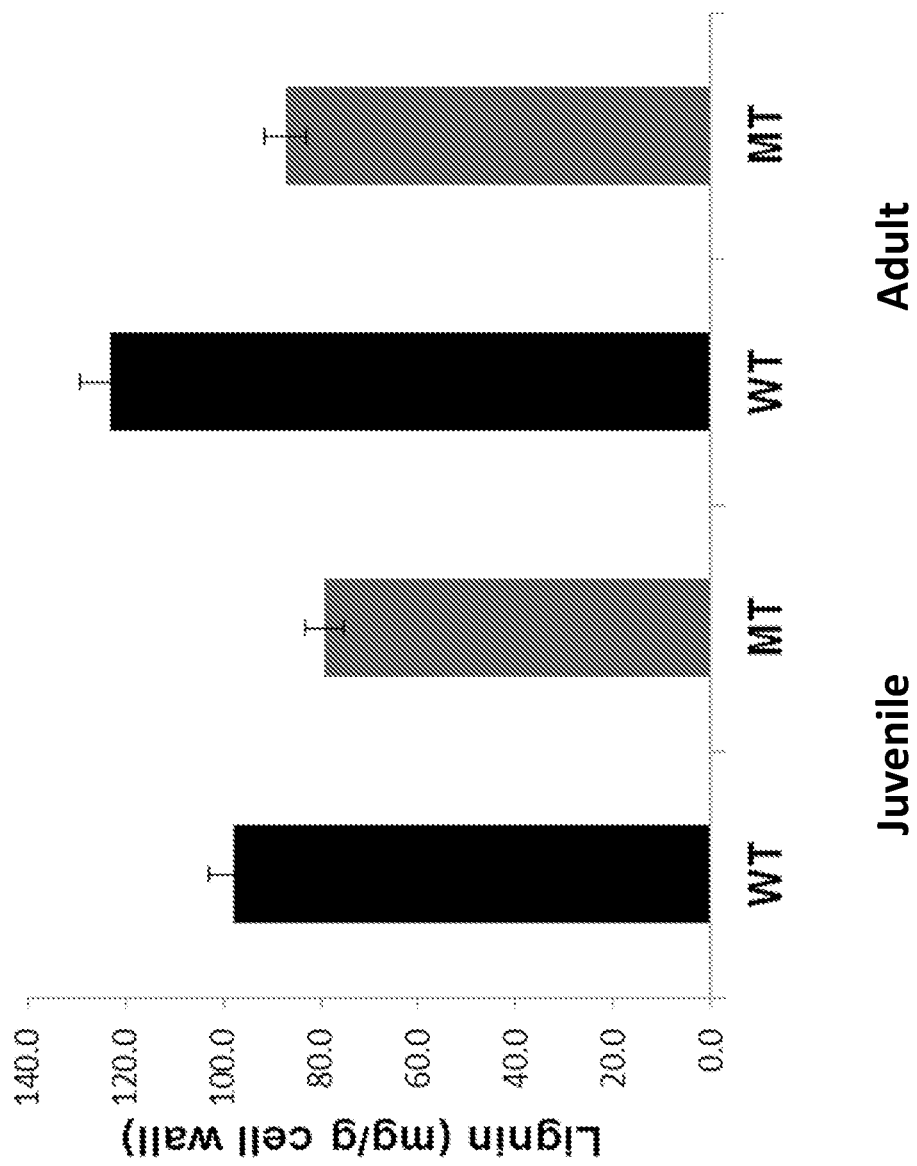
Figure 9A:
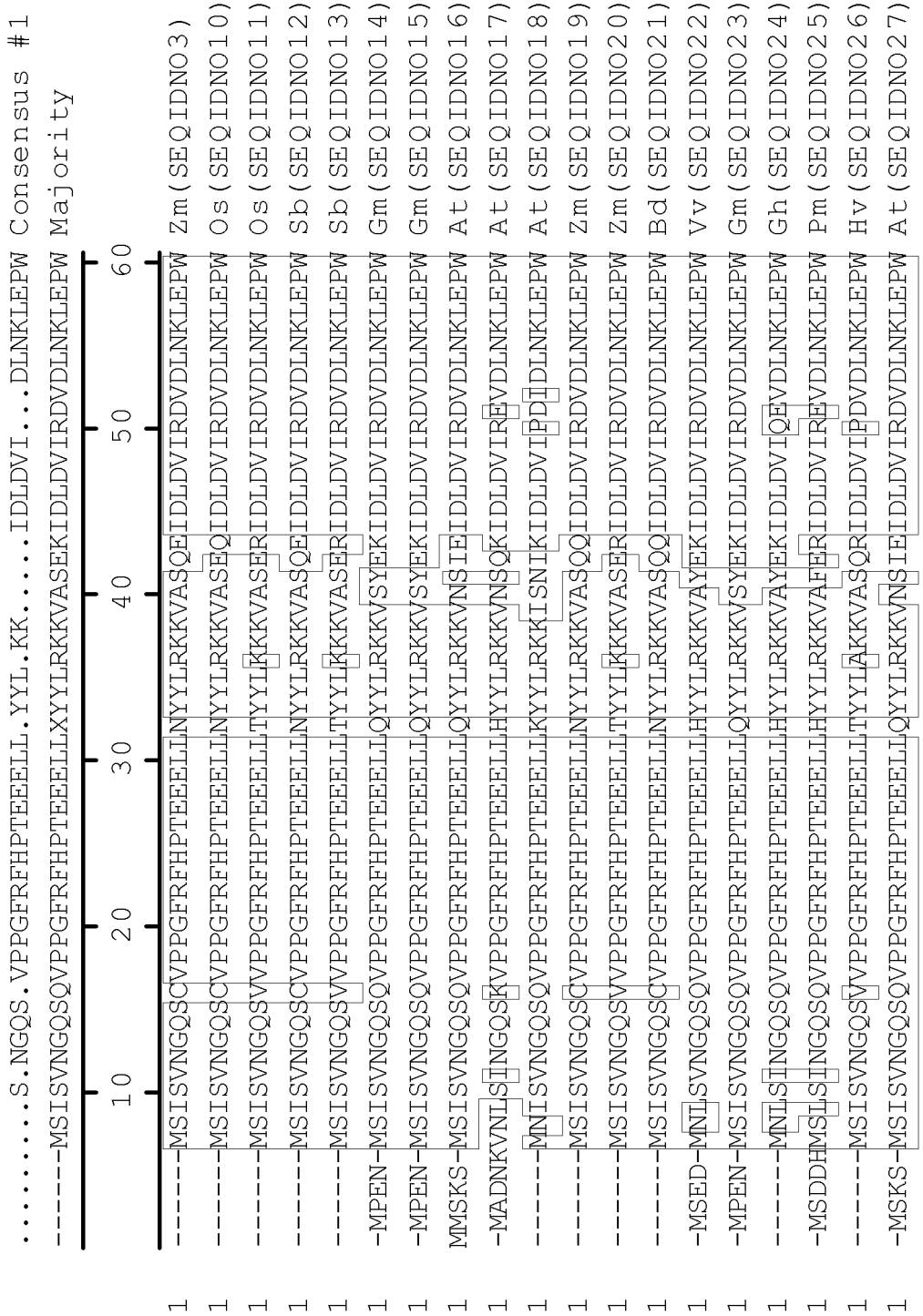
Figure 9D:
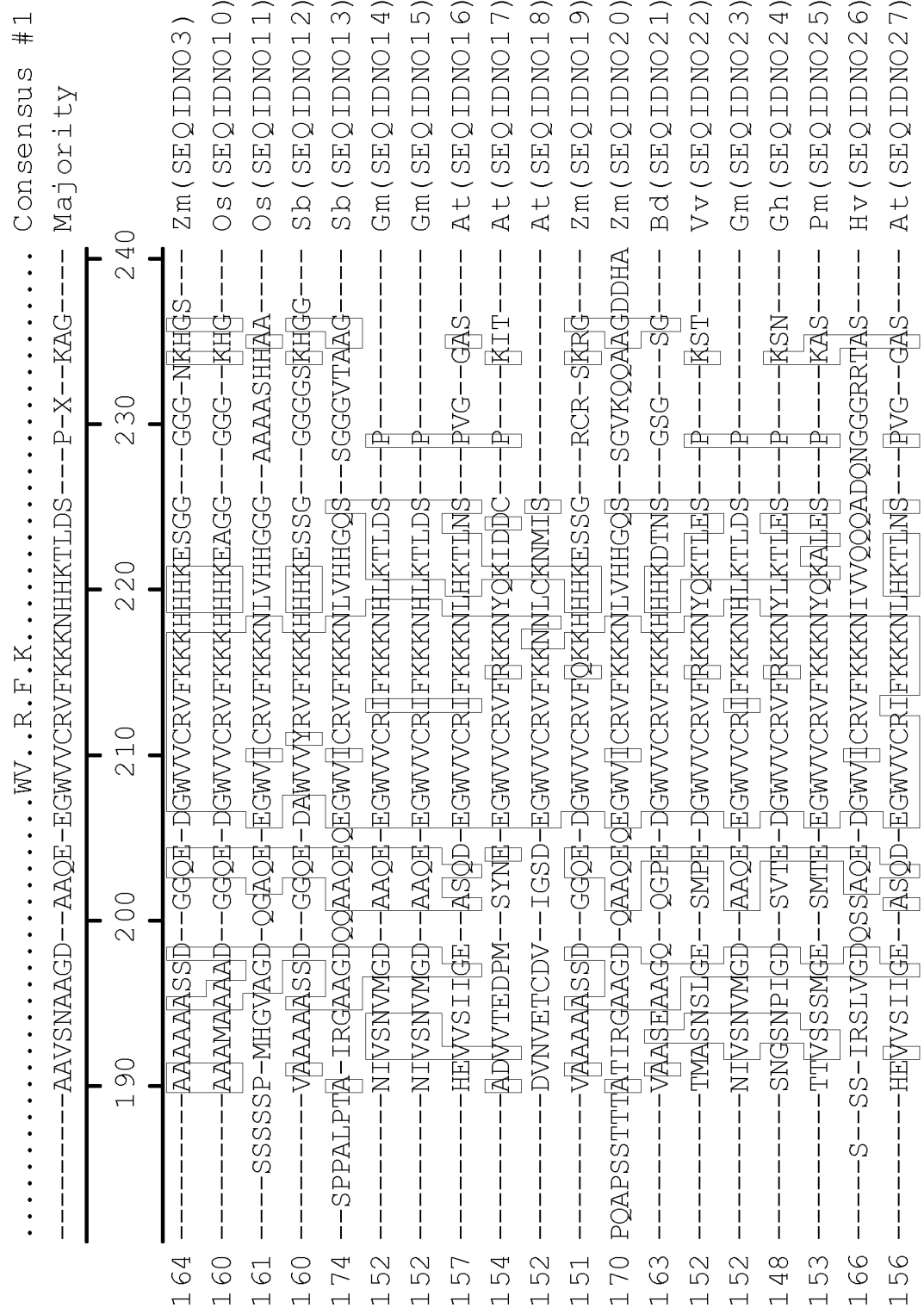
Figure 9E:
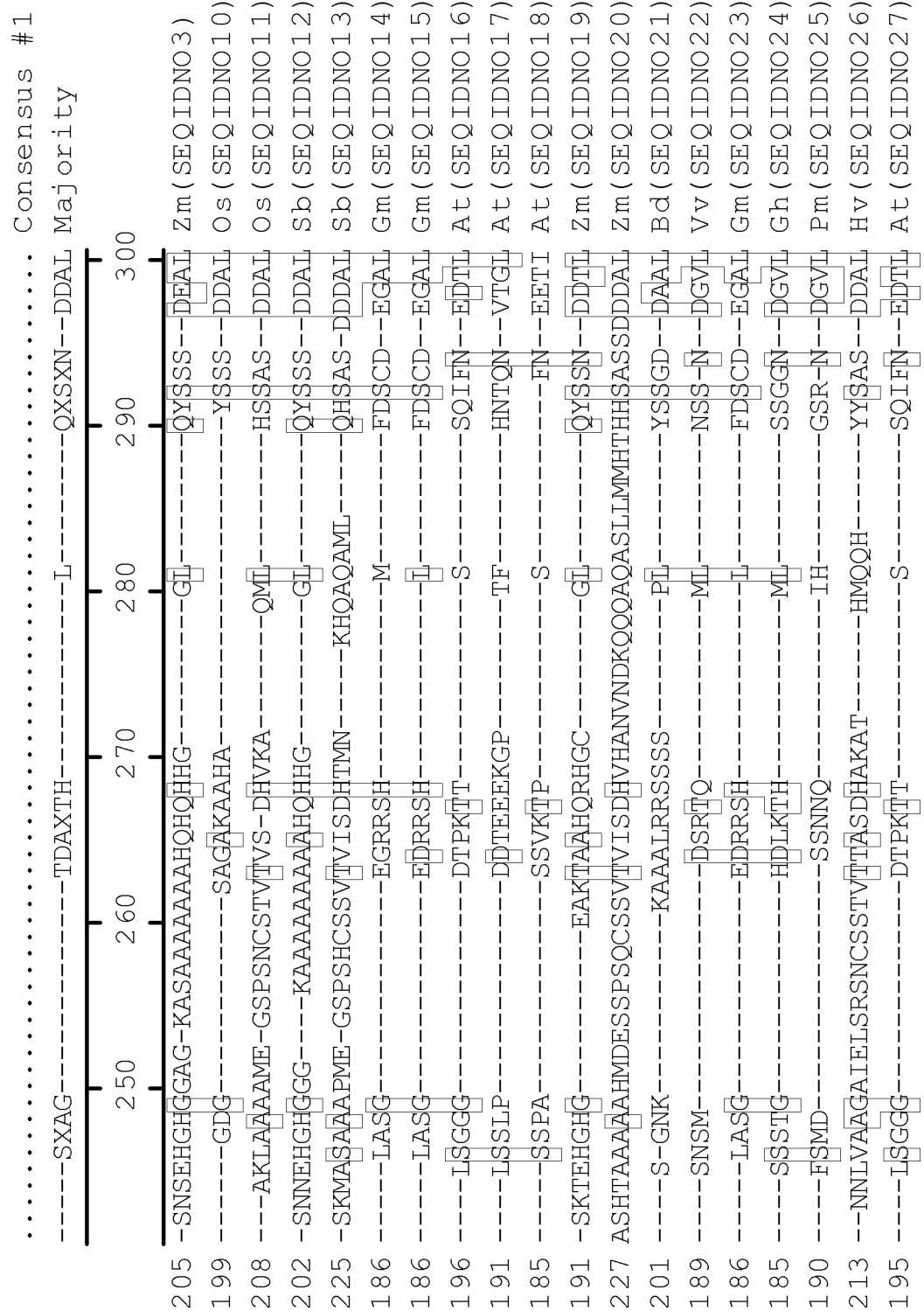
Figure 9F:
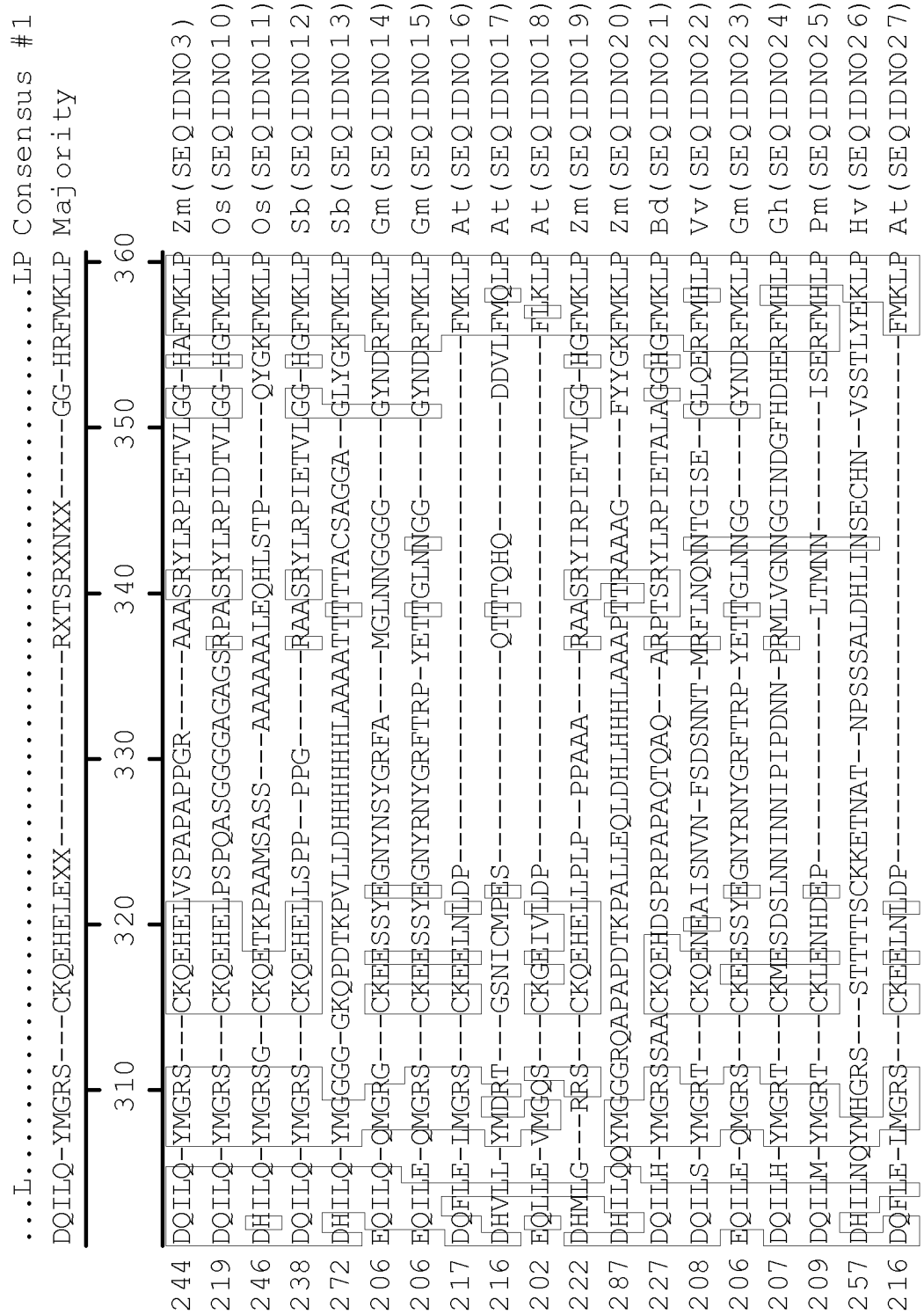
Figure 9G:
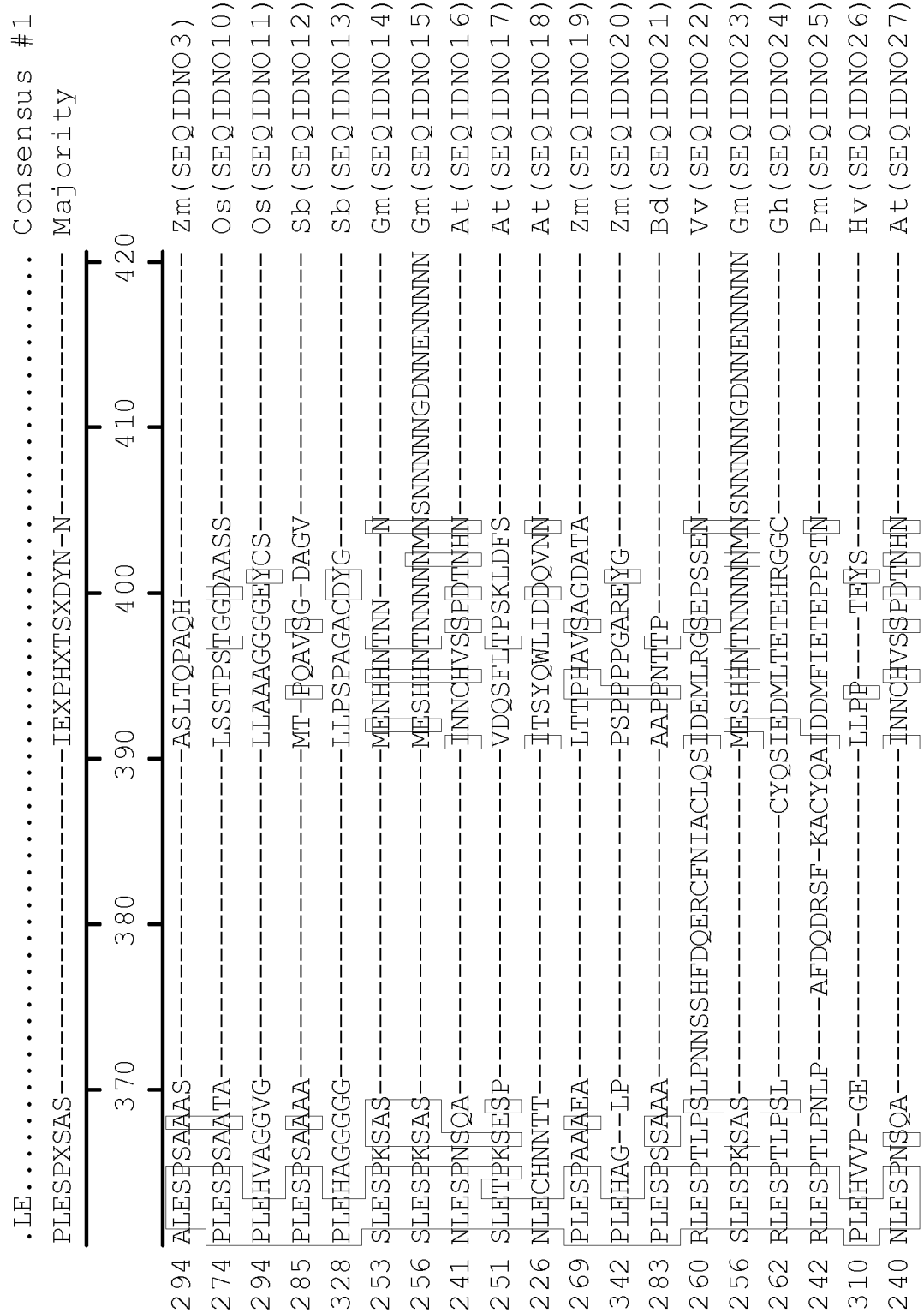
Figure 9H:
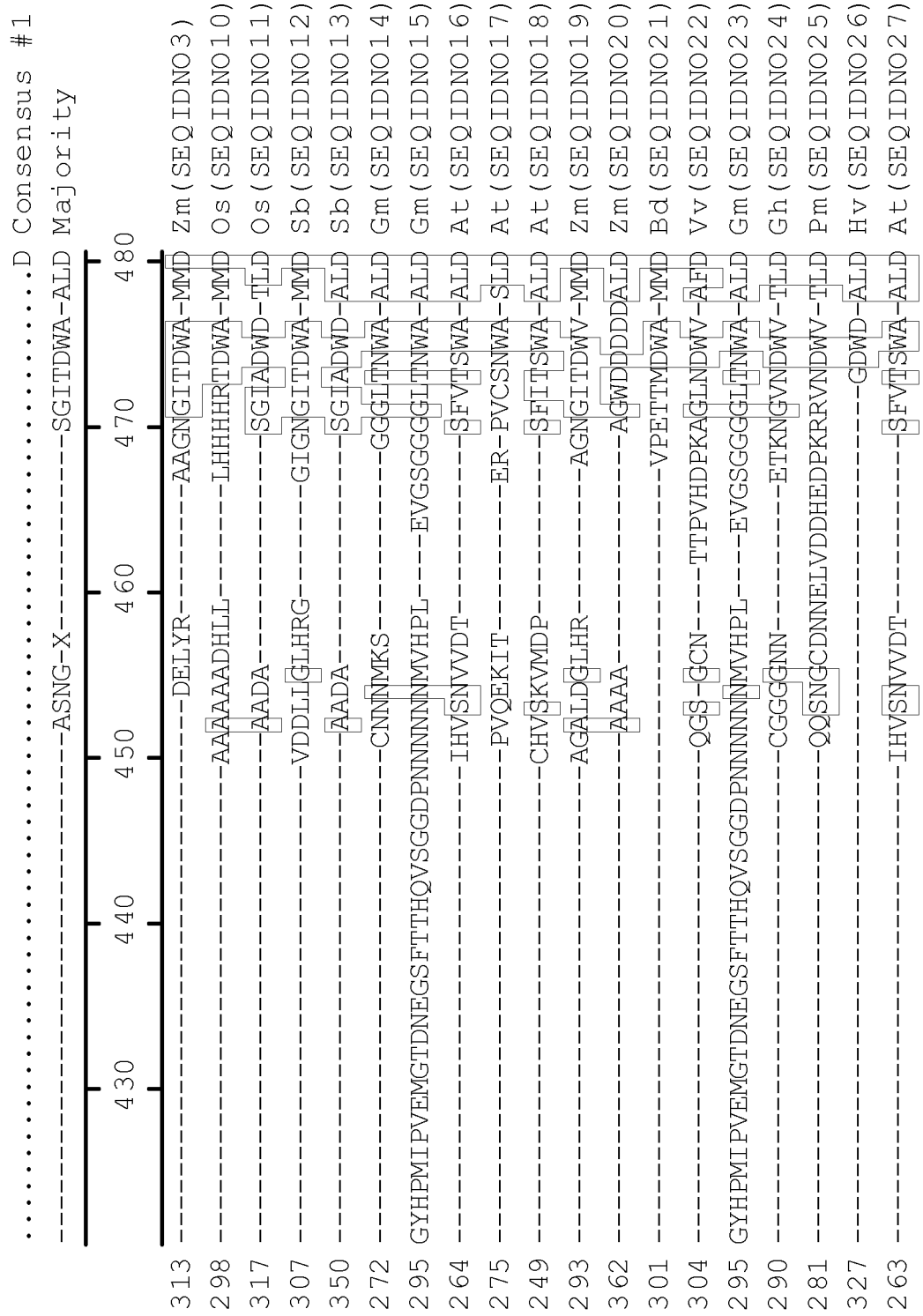
Figure 9I:
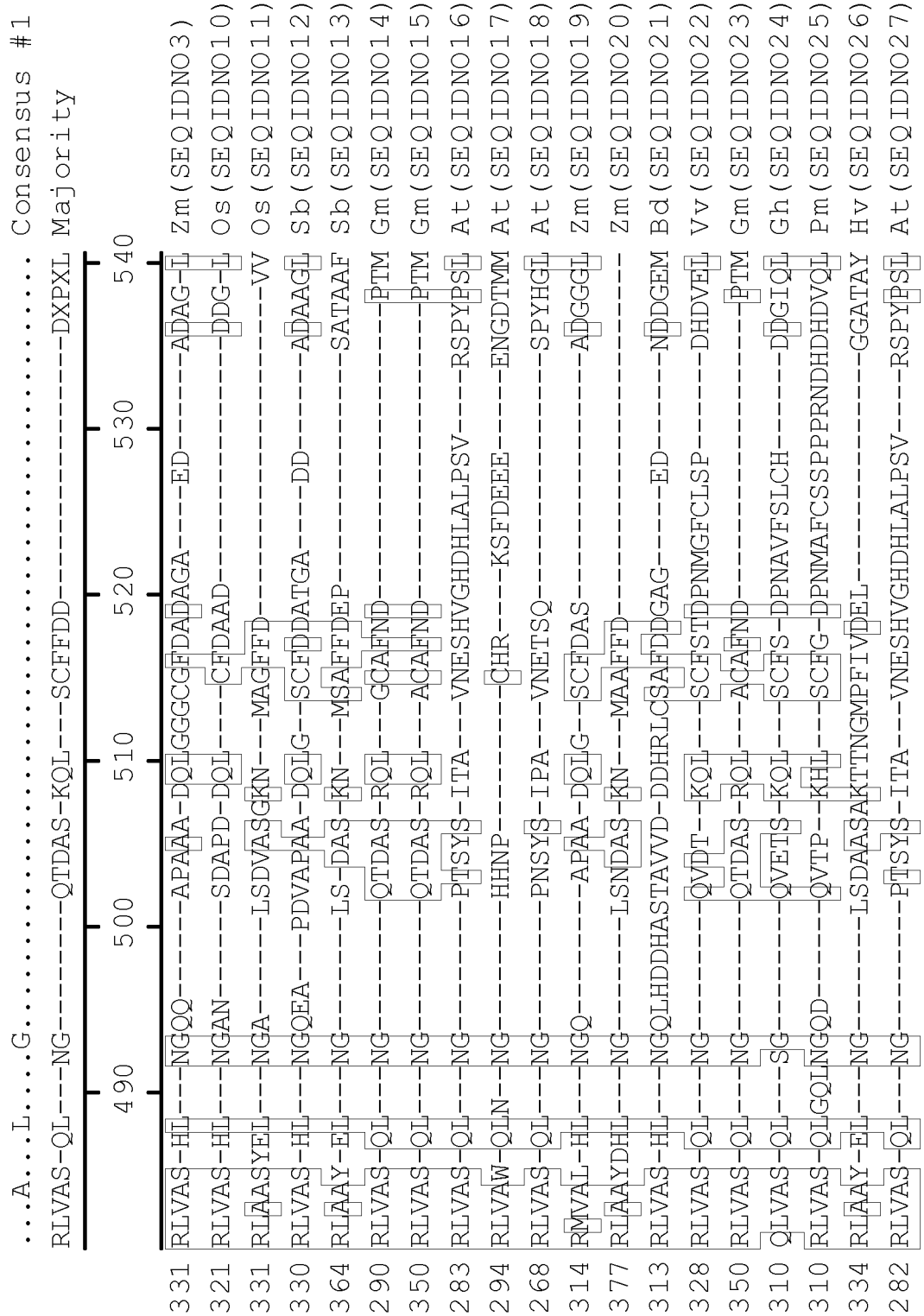
Figure 9J:
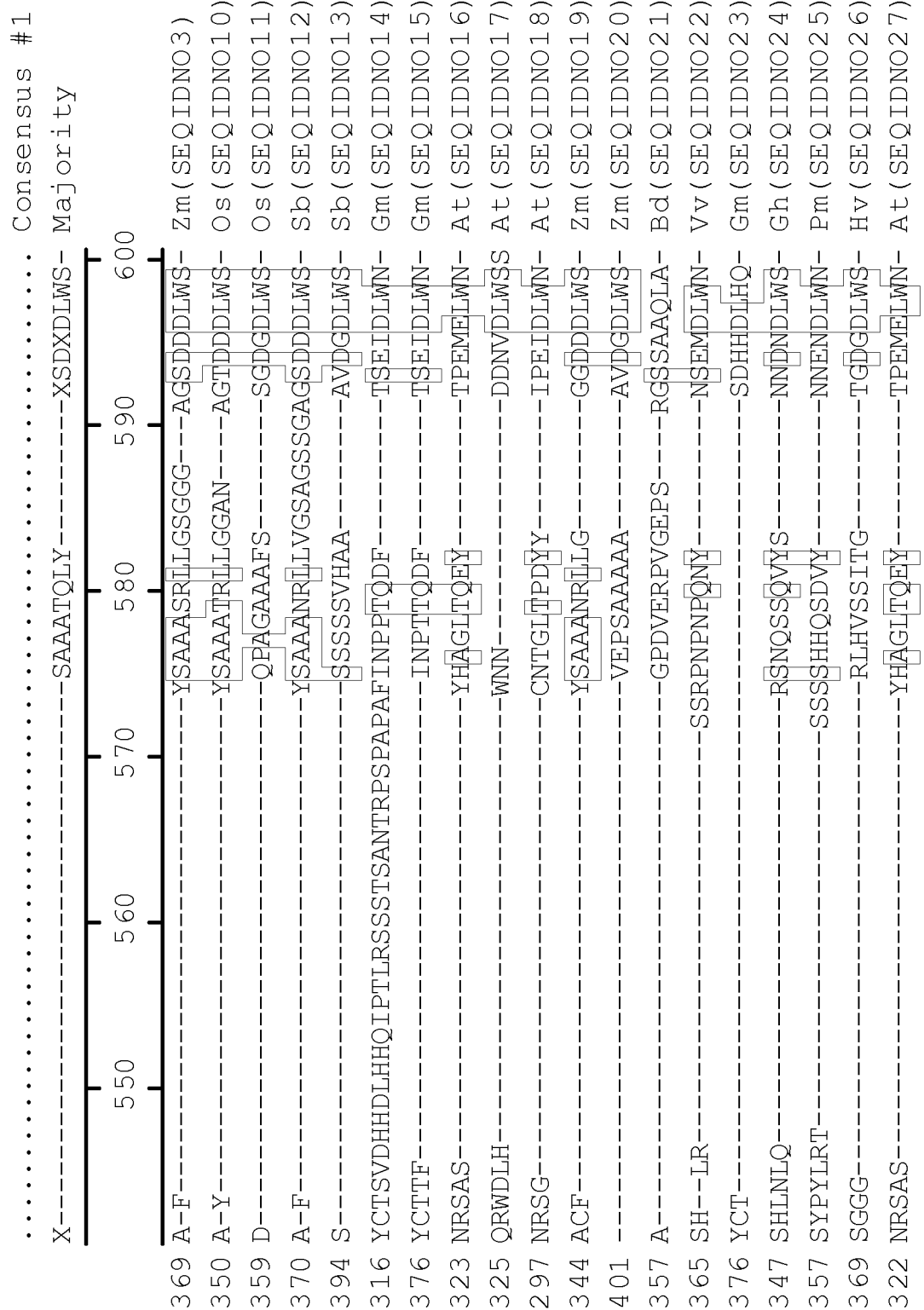

FIG. 5 depicts differences in the foliar lignin contents of Crw1 mutant (MT) and wild-type (WT) plants.

FIGS. 6A-6C show an alignment of the cDNA-sequences of Crw1 (SEQ ID NO:2) from a WT-Sib and the crw1-Ac mutant allele (SEQ ID NO:4), which is the result of excision of the autonomous Ac transposon present in the original allele. The 8 bp insertion (boxed) in exon 1 leads to a premature termination in the predicted peptide chain at the site of insertion.

Figure 7A:
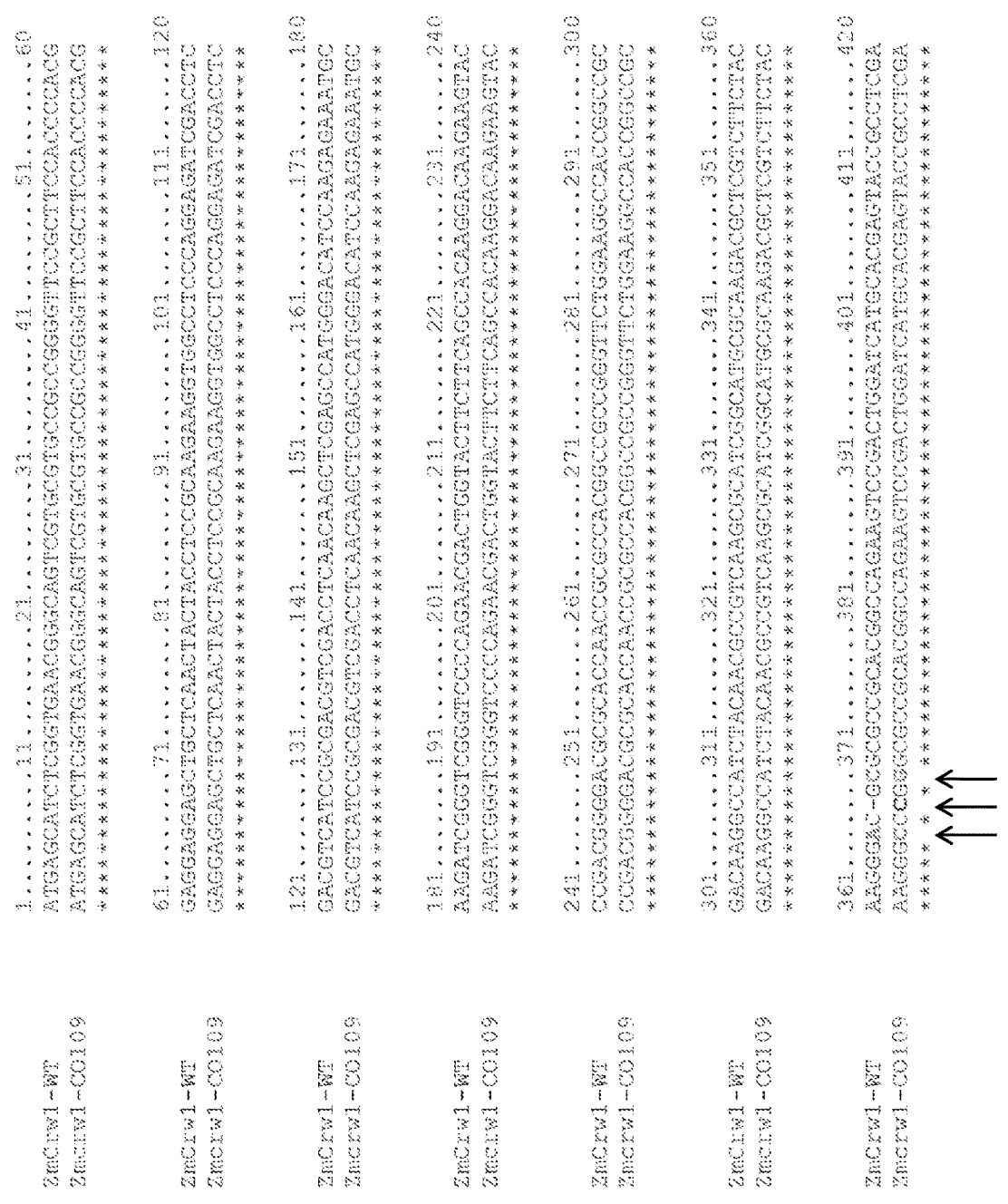

FIGS. 7A-7C show an alignment of cDNA-sequences of Crw1 (SEQ ID NO:2) from a WT-Sib and the crw1-C0109 allele (SEQ ID NO:6). The crw1-C0109 allele has an addition of 1 bp insertion and two other bp changes in exon 2 as compared to its WT-sib (see the arrows in FIG. 7 A indicating the positions of the insertion and bp changes). The insertion of 1 bp in exon 2 results in premature termination of the CRW1 peptide.

Figure 8B:
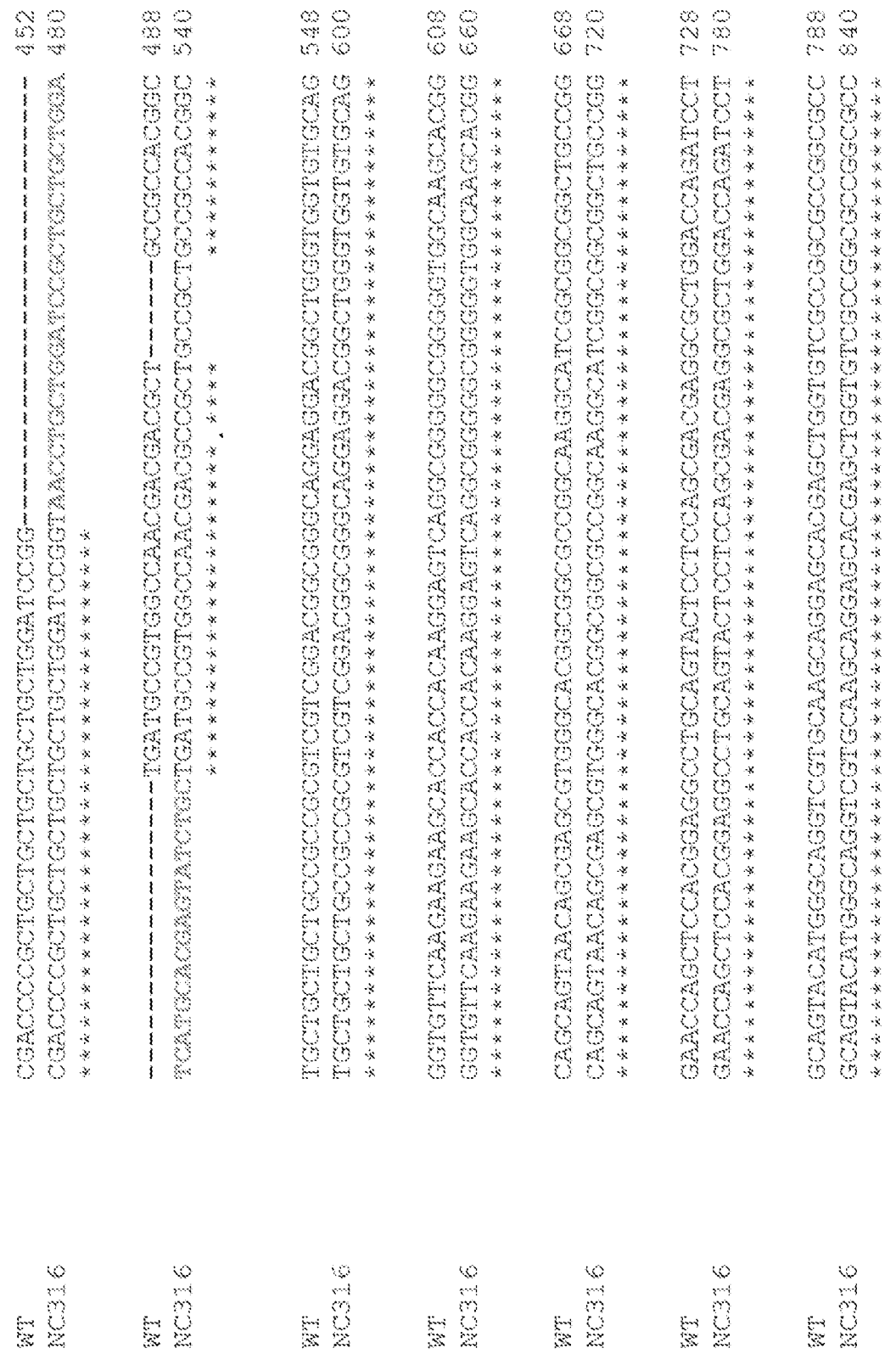

FIGS. 8A-8C show an alignment of the eDNA-sequences of Crw1 (SEQ ID NO:2) from a WT-Sib and the crw1-NC316 allele (SEQ ID NO:8). The crw1-NC316 allele has a 1 bp insertion (see arrow in FIG. 8A) and a 45 bp insertion in the second exon. The presence of the 1 bp insertion results in a premature termination codon at the site of the 45 bp insertion.

FIGS. 9A-9L show the multiple alignment of the amino acid sequences of the polypeptides of SEQ ID NOs:3, 10, 11, 12, 13, 14, 15, 16, 17, 18, 19, 20, 21, 22, 23, 24, 25, 26, and 27. When all residues at a position match the residue of the consensus sequence, the residue is shown; otherwise a "." is shown. In addition, residues that match the consensus exactly are boxed.

FIG. 10 shows the percent sequence identity and the divergence values for each pair of amino acids sequences of the polypeptides displayed in FIGS. 9A-9L.

FIGS. 11A-11G show the alignment between ZmCrw2 (SEQ ID NO:28) and the crw2-Mutag (SEQ ID NO:30) mutant allele.

FIGS. 12A-12F show the alignment between ZmCrw2 (SEQ ID NO:28) and the crw2-EMS (SEQ ID NO:32) mutant allele.

Figure 13:
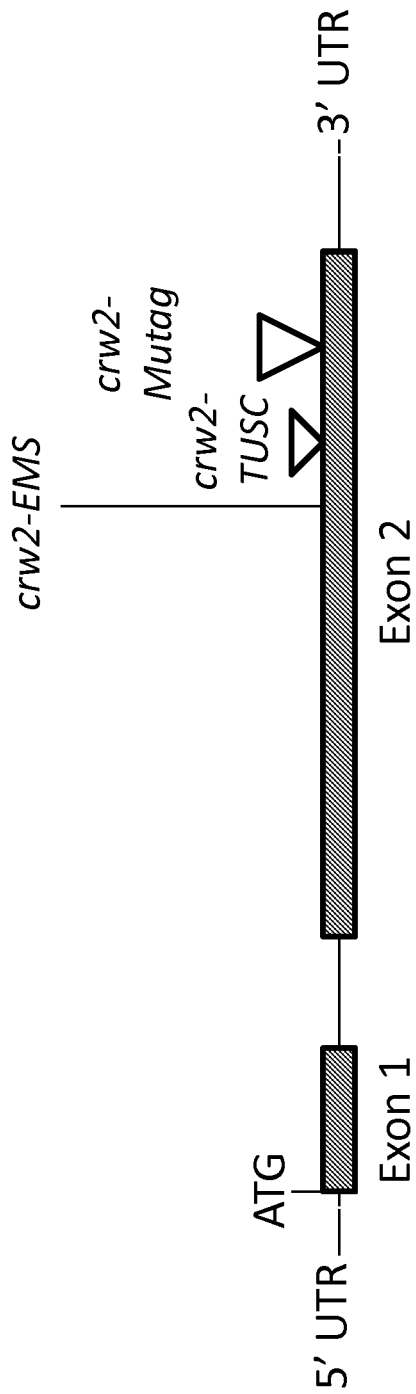
Figure 14A:
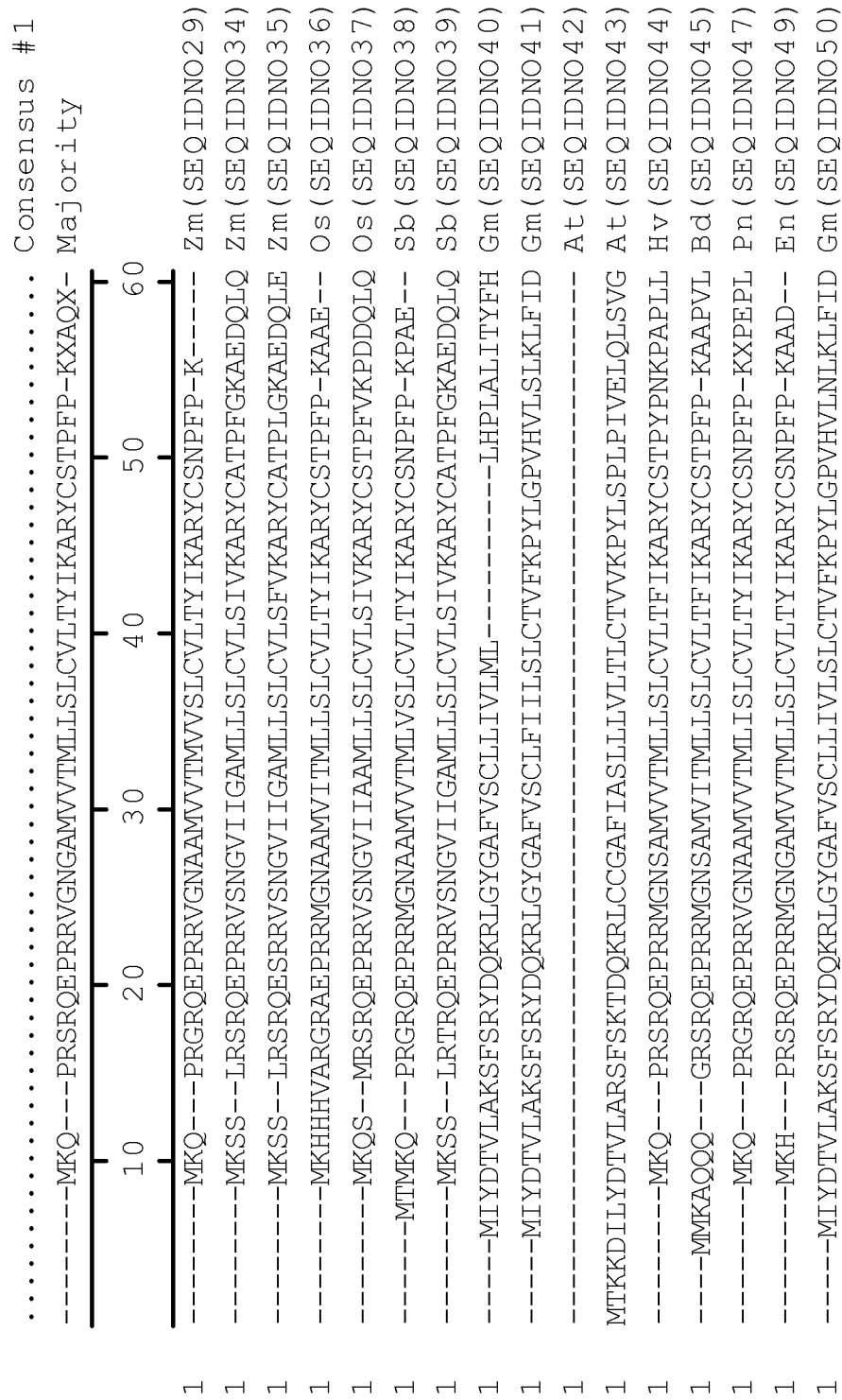
Figure 14B:
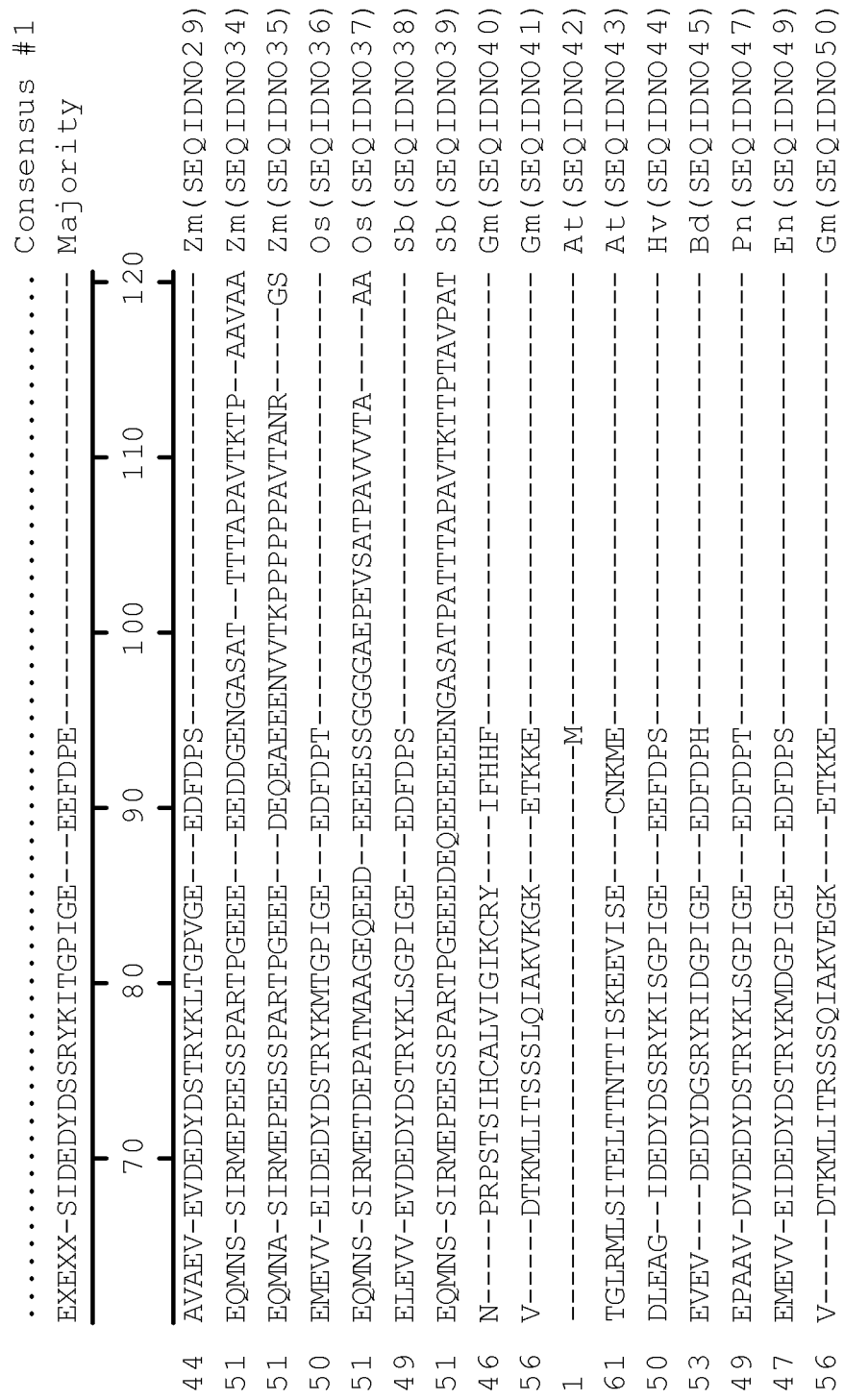
Figure 14C:
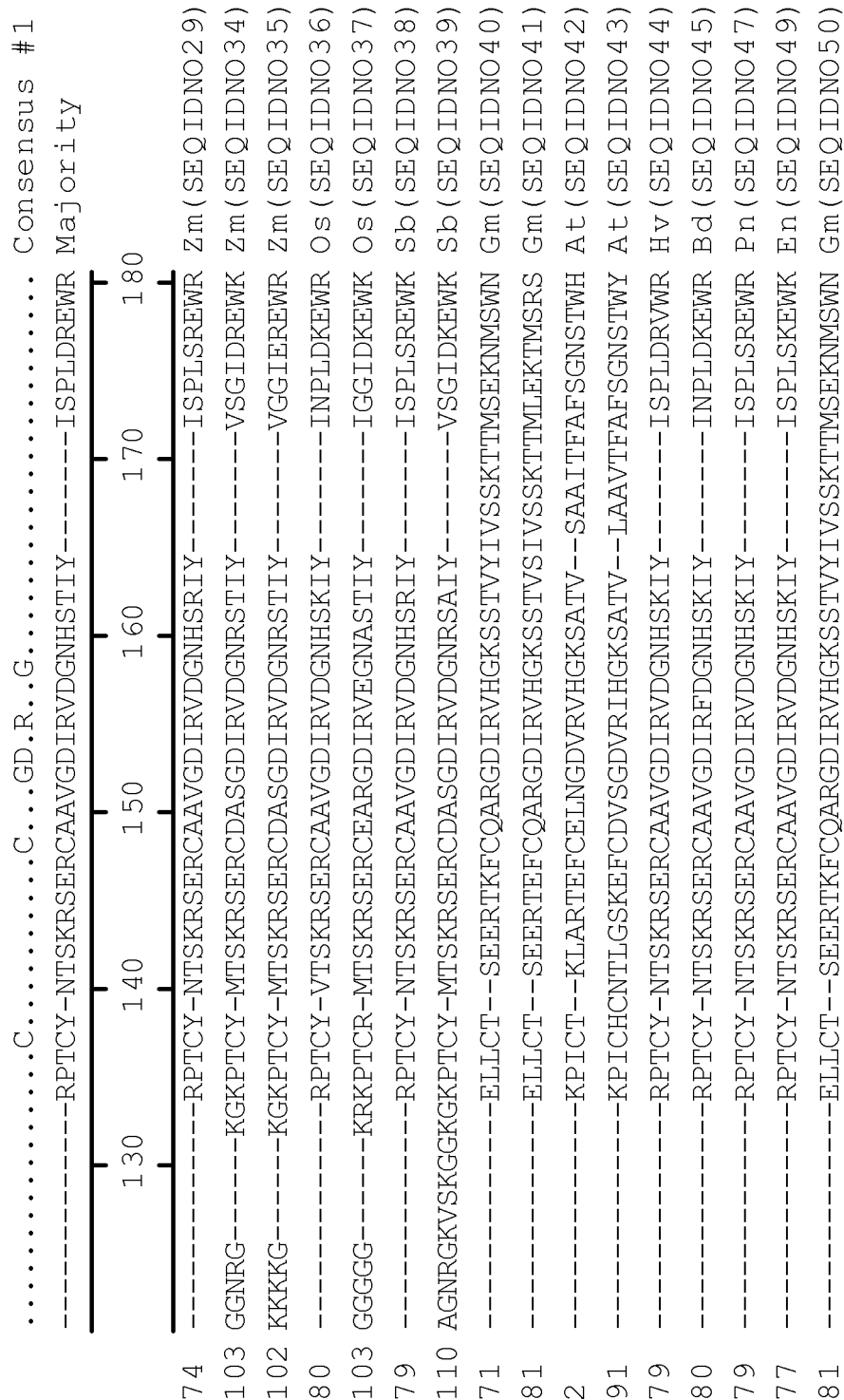
Figure 14E:
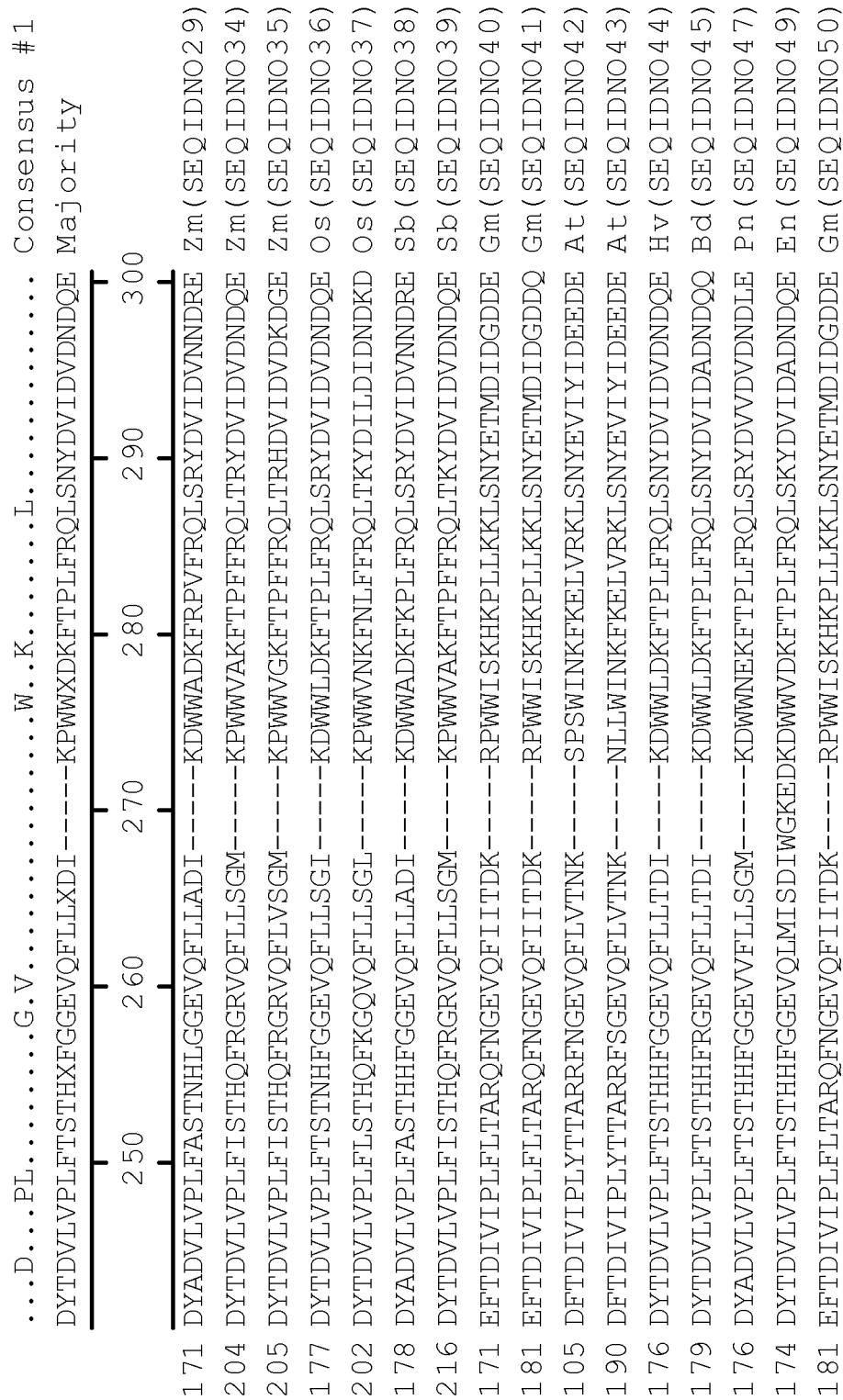
Figure 14H:
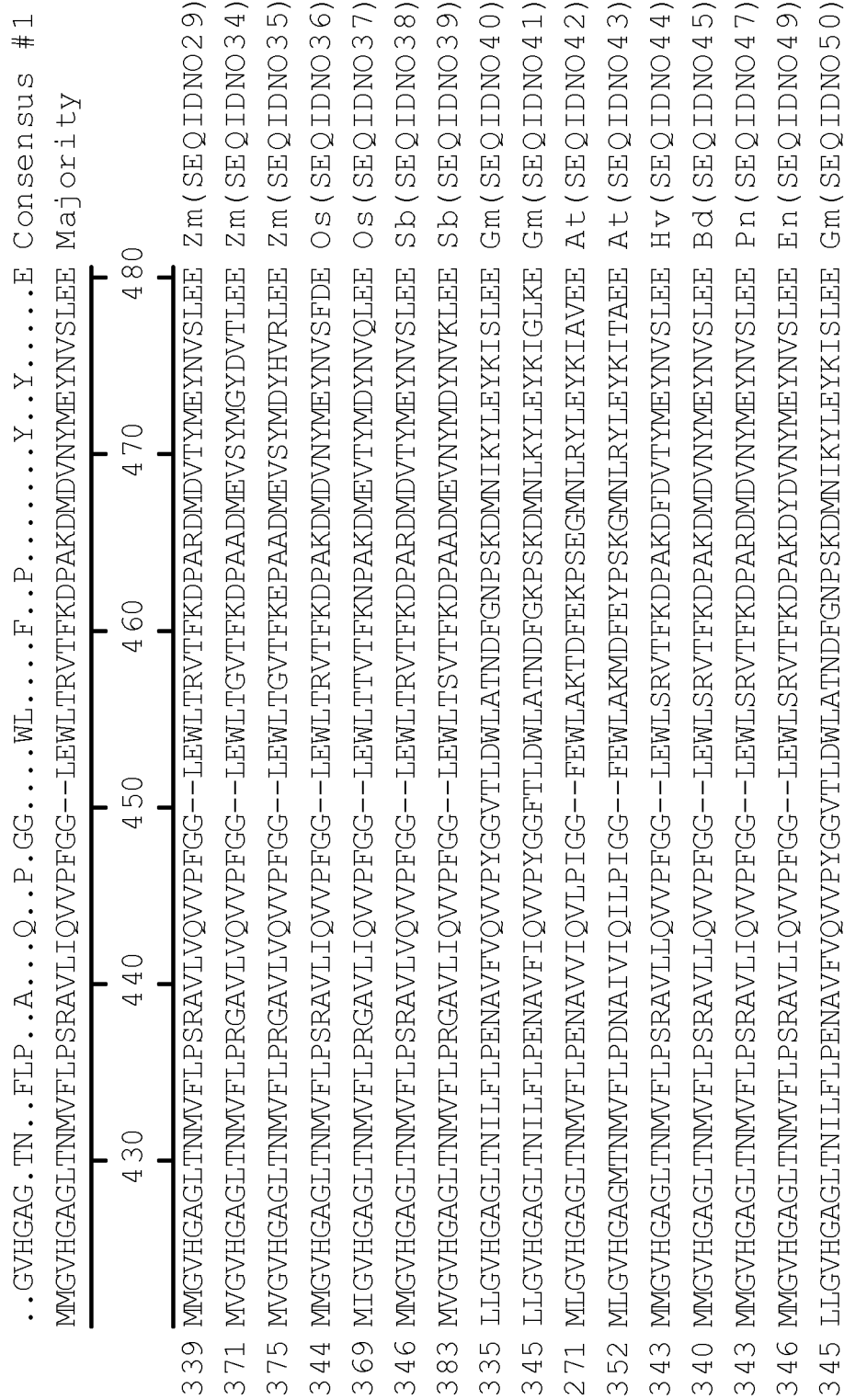

FIG. 13 shows the structure of the maize Homogalacturonan1 (HGA1) gene (also referred to as glycosyltransferase AER61 or Crw2). The positions of the two Mutator insertions and the EMS allele are shown.

FIGS. 14A-14J show an alignment of the ZmCrw2 protein (SEQ ID NO:29) and its homologs (SEQ ID NOs: 34, 35, 36, 37, 38, 39, 40, 41, 42, 43, 44, 45, 47, 49, and 50).

FIG. 15 shows the percent sequence identity and the divergence values for each pair of amino acids sequences of the polypeptides displayed in FIGS. 14A-14J.

Figure 16:
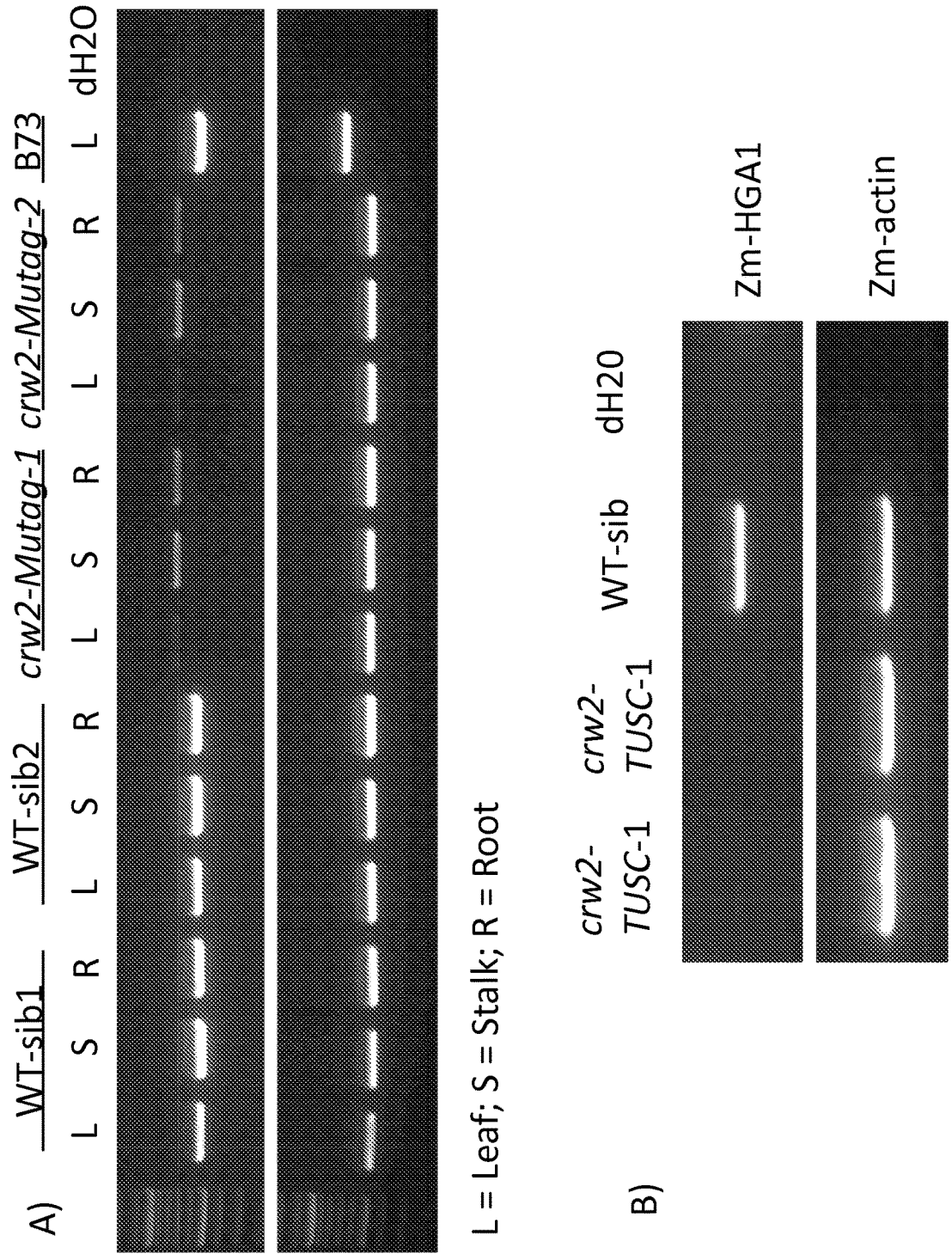

FIG. 16 (A) shows gene expression of crw2-Mutag mutant allele in 10 day old seedlings. Total RNA samples were collected from leaf, stalk, and root tissues, and RT-PCR analysis was performed using gene specific primers. The crw2-Mutag mutant showed differential expression in three tissues and has a transcript that is 145 bp longer than in the WT-sibs. FIG. 16 (B) shows RT-PCR analysis of the crw2-TUSC mutant as compared to its WT-sibs.

Figure 17:
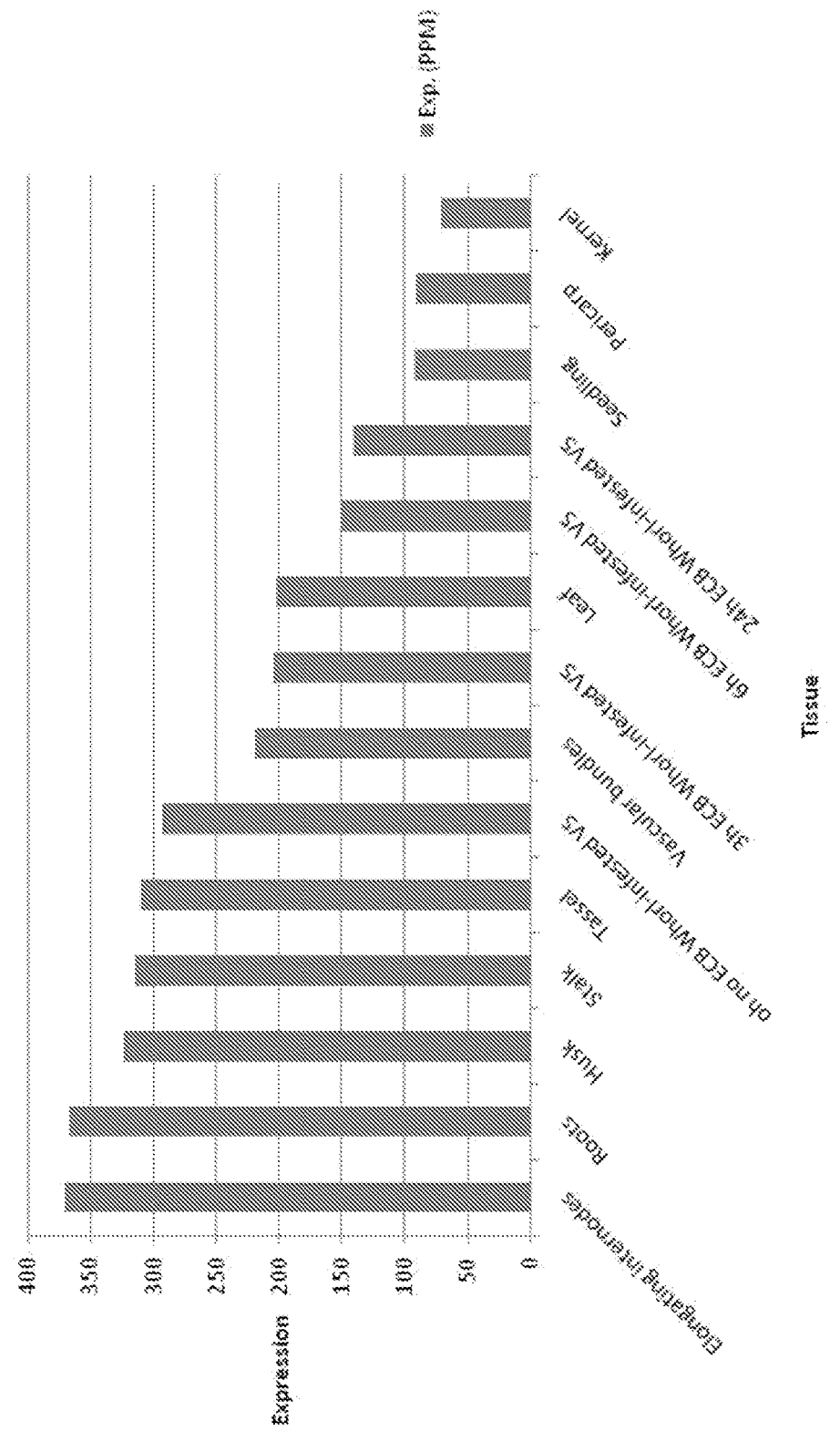

FIG. 17 shows expression of the ZmCrw2 gene in different plant tissues compiled from the Lynx database.

Figure 18:
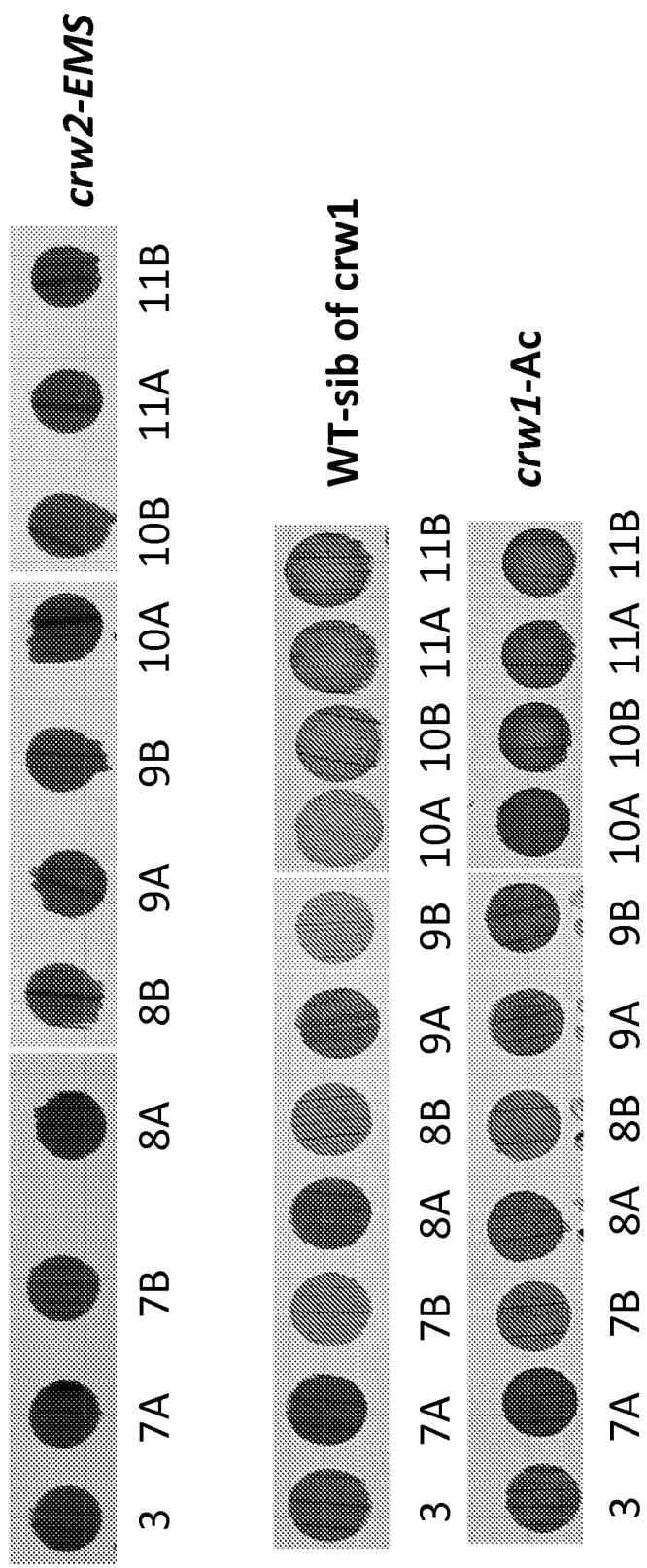

FIG. 18 shows the TBO staining pattern of leaf discs from the crw2-EMS mutant in comparison with the crw1-Ac mutant and its WT-sib. The leaf position numbers are indicated below each panel, and the "A" or "B" following each number represents the apical or basal portion of the leaf, respectively. The crw2-EMS mutant leaf discs exhibit uniform dark staining throughout development in contrast to the normal WT leaf discs that show dark staining until transition (leaf number 7) followed by lighter staining. The crw2-EMS mutant TBO staining pattern resembles that of the crw1-Ac mutant.

Figure 19:
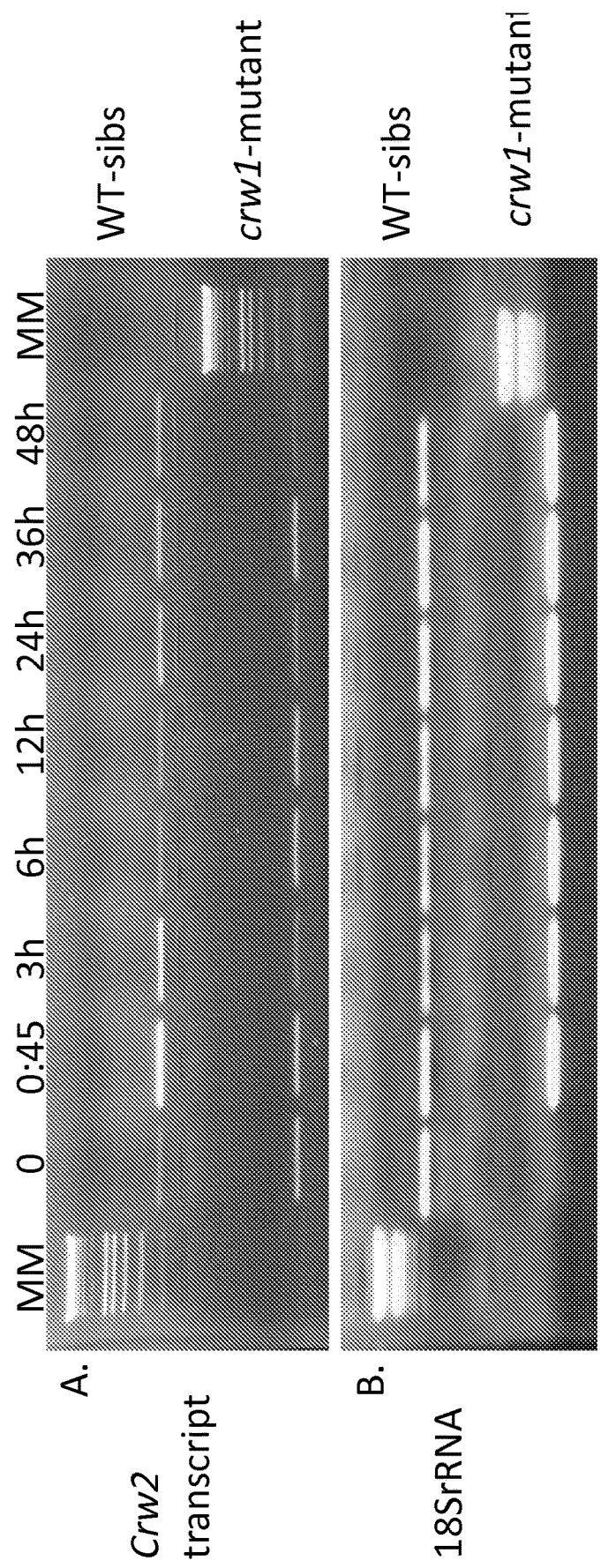

FIG. 19 shows Crw2 transcript levels in Crw1 mutant in comparison to its WT at various time points after WCR beetle feeding. There is a rapid up-regulation in the levels of the Crw2 transcript in WT plants within 45 minutes of WCR feeding (A, upper panel). Such up-regulation is not observed in the Crw1 mutant upon WCR feeding (A, lower panel). The 18S rRNA control with the same loading scheme is represented in B.

Figure 20:
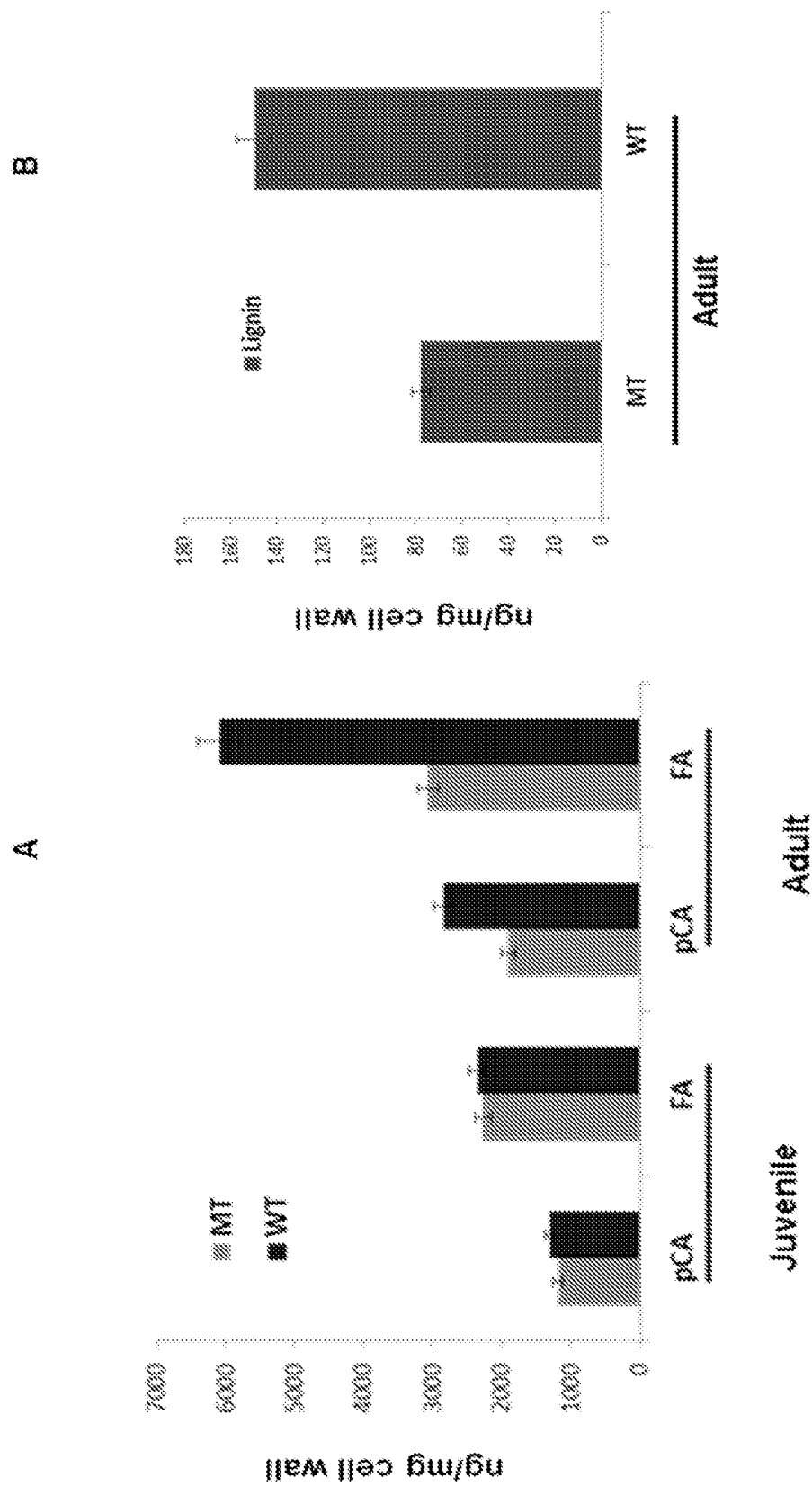

FIG. 20 (A) shows that a Crw2 mutant ("MT") has lower levels of cell wall bound p-coumaric acid (pCA) and ferulic acid (FA) as well as (B) lower levels of lignin, in comparison to wild-type ("WT") during adult stages (p<0.05; unpaired t test).

The sequence descriptions and Sequence Listing attached hereto comply with the rules governing nucleotide and/or amino acid sequence disclosures in patent applications as set forth in 37 C.F.R. § 1.821 1.825.

The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (No. 2):345 373 (1984) which are herein incorporated by reference. The symbols and format used for nucleotide and amino acid sequence data comply with the rules set forth in 37 C.F.R. § 1.822.

SEQ ID NO:1 is the nucleotide sequence of the genomic wild-type *Zea mays* Crw1.

SEQ ID NO:2 is the nucleotide sequence of the coding region of the wild-type *Zea mays* Crw1 (ZmCrw1) cDNA.

SEQ ID NO:3 is the amino acid sequence of the wild-type *Zea mays* CRW1 (ZmCRW1) protein.

SEQ ID NO:4 is the nucleotide sequence of the cDNA of the mutant crw1-Ac allele.

SEQ ID NO:5 is the amino acid sequence of the polypeptide encoded by the mutant crw1-Ac allele.

SEQ ID NO:6 is the nucleotide sequence of the Crw1 cDNA from maize inbred line CO109.

SEQ ID NO:7 is the amino acid sequence of the polypeptide encoded by SEQ ID NO:6.

SEQ ID NO:8 is the nucleotide sequence of the Crw1 cDNA from maize inbred line NC316.

SEQ ID NO:9 is the amino acid sequence of the polypeptide encoded by SEQ ID NO:8.

SEQ ID NO:10 is the amino acid sequence of a secondary wall NAC transcription factor 2 from *Oryza sativa* (UniProt entry G3M8D2).

SEQ ID NO:11 is the amino acid sequence of a putative NAM protein (OsNAC7) from *Oryza sativa* (Identifier Os06g04090.1; UniProt entry Q9SNM6).

SEQ ID NO:12 is the amino acid sequence of a putative uncharacterized protein from *Sorghum bicolor* (Identifier Sb07g001550.1; UniProt entry C5YM23).

SEQ ID NO:13 is the amino acid sequence of a putative NAM protein from *Sorghum bicolor* (Identifier Sb10g002120.1; UniProt entry Q5NKS7).

SEQ ID NO:14 is the amino acid sequence of an uncharacterized protein from *Glycine max* (Identifier Glyma16g02200.1; UniProt entry I1MKD6).

SEQ ID NO:15 is the amino acid sequence of an uncharacterized protein from *Glycine max* (Identifier Glyma07g05660.1; UniProt entry I1 KHQ4).

SEQ ID NO:16 is the amino acid sequence of a NAC domain-containing protein 43 from *Arabidopsis thaliana* (Identifier At2g46770.1; UniProt entry Q84WP6).

SEQ ID NO:17 is the amino acid sequence of a NAC domain-containing protein 12 from *Arabidopsis thaliana* (At1g32770.1; UniProt entry Q9LPI7).

SEQ ID NO:18 is the amino acid sequence of a NAC domain-containing protein 66 from *Arabidopsis thaliana* (Identifier At3g61910.1; UniProt entry Q9M274).

SEQ ID NO:19 is the amino acid sequence of a secondary wall NAC transcription factor 2 from *Zea mays* (UniProt entry B4FPS5)

SEQ ID NO:20 is the amino acid sequence of a putative NAM protein from *Zea mays* (UniProt entry Q5NKQ3).

SEQ ID NO:21 is the amino acid sequence of a NAC domain-containing protein 43-like from *Brachypodium distachyon* (NCBI GI No. 357139497 and herein referred to as BdCRW1).

SEQ ID NO:22 is the amino acid sequence of a putative uncharacterized protein from *Vitis vinifera* (UniProt entry F6HU82).

SEQ ID NO:23 is the amino acid sequence of a NAC domain-containing protein 43-like from *Glycine max* (NCBI GI No. 356522480 and herein referred to as GmCRW1).

SEQ ID NO:24 is the amino acid sequence of a NAC domain-containing protein from *Gossypium hirsutum* (UniProt entry G4V2G0).

SEQ ID NO:25 is the amino acid sequence of a NAC domain class transcription factor (NAC12) from *Pyrus malus* (UniProt entry D9ZJ90). SEQ ID NO:26 is the amino acid sequence of a predicted protein from *Hordeum vulgare* (UniProt entry F2DV83).

SEQ ID NO:27 is the amino acid sequence of a NAM-like protein from *Arabidopsis thaliana* (NCBI GI No. 3510262; UniProt entry Q84WP6).

SEQ ID NO:28 is the nucleotide sequence of the coding region of the wild-type *Zea mays* Crw2 (ZmCrw2) cDNA.

SEQ ID NO:29 is the amino acid sequence of the wild-type *Zea mays* CRW2 (ZmCRW2) protein, which is also referred to as a glycosyltransferase (UniProt entry B6TY42; 455 aa).

SEQ ID NO:30 is the nucleotide sequence of the cDNA of the mutant crw2-Mutag allele.

SEQ ID NO:31 is the amino acid sequence of the polypeptide encoded by the mutant crw2-Mutag allele.

SEQ ID NO:32 is the nucleotide sequence of the cDNA of the mutant crw2-EMS allele.

SEQ ID NO:33 is the amino acid sequence of the polypeptide encoded by the mutant crw2-EMS allele.

SEQ ID NO:34 is the amino acid sequence of the *Zea mays* putative uncharacterized protein (UniProt entry C0PDR7; 488 aa).

SEQ ID NO:35 is the amino acid sequence of the *Zea mays* putative uncharacterized protein (UniProt entry C4J6G0; 491 aa).

SEQ ID NO:36 is the amino acid sequence of the *Oryza sativa* putative HGA1 (Identifier Os06g49320; UniProt entry Q5Z8T7; 460 aa).

SEQ ID NO:37 is the amino acid sequence of the *Oryza sativa* putative HGA1 (Identifier Os02g0135500; UniProt entry Q6Z0Z4; 485 aa).

SEQ ID NO:38 is the amino acid sequence of the *Sorghum bicolor* putative uncharacterized protein Sb10g029380 (UniProt entry C5Z9B2; 462 aa).

SEQ ID NO:39 is the amino acid sequence of the *Sorghum bicolor* putative uncharacterized protein Sb04g002850 (UniProt entry C5XTX5; 499 aa).

SEQ ID NO:40 is the amino acid sequence of the *Glycine max* uncharacterized protein (Identifier Glyma05g34170; UniProt entry I1K5F9; 452 aa).

SEQ ID NO:41 is the amino acid sequence of the *Glycine max* uncharacterized protein (Identifier Glyma08g05490; UniProt entry 11 KQG2; 462 aa).

SEQ ID NO:42 is the amino acid sequence of the *Arabidopsis thaliana* At3g18170 (UniProt entry Q9LV23; 535 aa).

SEQ ID NO:43 is the amino acid sequence of the *Arabidopsis thaliana* At3g18180 locus also referred to as glycosyltransferase family 61 protein (UniProt entry Q9LV22; 470 aa).

SEQ ID NO:44 is the amino acid sequence of the *Hordeum vulgare* predicted protein (UniProt entry F2DBB4; 462 aa).

SEQ ID NO:45 is the amino acid sequence of the *Brachypodium distachyon* uncharacterized protein also known as BRADI1G34670 (UniProt entry I1GWV1; 455 aa).

SEQ ID NO:46 is the nucleotide sequence of a homolog of ZmCrw2 from *Paspalum notatum* (identified in an internal proprietary database and referred to herein as PnCrw2).

SEQ ID NO:47 is the amino acid sequence of the polypeptide encoded by SEQ ID NO:46. The polypeptide is herein referred to as PnCRW2.

SEQ ID NO:48 is the nucleotide sequence of a homolog of ZmCrw2 from *Eragrostis nindensis* (identified in an internal proprietary database and referred to herein as EnCrw2).

SEQ ID NO:49 is the amino acid sequence of the polypeptide encoded by SEQ ID NO:48. The polypeptide is referred to herein as EnCRW2.

SEQ ID NO:50 is the amino acid sequence of an uncharacterized glycosyltransferase AGO61-like from *Glycine max* (NCBI GI No. 356511269).

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot includes the Gramineae.

The terms "dicot" and "dicotyledonous plant" are used interchangeably herein. A dicot includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

A "trait" refers to a physiological, morphological, biochemical, or physical characteristic of a plant or particular plant material or cell. "Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to a polynucleotide sequence that when transcribed, processed, and/or translated results in the production of a polypeptide sequence.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

Promoters that cause a gene to be expressed in most cell types at most times are commonly referred to as "constitutive promoters."

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches. Silencing may be targeted to coding regions or non-coding regions, e.g., introns, 5'-UTRs and 3'-UTRs, or both.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)). Cosuppression constructs may contain sequences from coding regions or non-coding regions, e.g., introns, 5'-UTRs and 3'-UTRs, or both.

Another variation describes the use of plant viral sequences to direct the suppression of proximal mRNA encoding sequences (PCT Publication No. WO 98/36083 published on Aug. 20, 1998).

RNA interference (RNAi) refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

The term "locus" generally refers to a genetically defined region of a chromosome carrying a gene or, possibly, two or more genes so closely linked that genetically they behave as a single locus responsible for a phenotype.

A "gene" shall refer to a specific genetic coding region within a locus, including its associated regulatory sequences. One of ordinary skill in the art would understand that the associated regulatory sequences will be within a distance of about 4 kb from the coding sequence, with the promoter located upstream.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

The terms "gene shuffling" and "directed evolution" are used interchangeably herein. The method of "gene shuffling" consists of iterations of DNA shuffling followed by appropriate screening and/or selection to generate variants of Crw1 and/or Crw2 nucleic acids or portions thereof having a modified biological activity (Castle et al., (2004) Science 304(5674): 1151-4; U.S. Pat. Nos. 5,811,238 and 6,395,547).

"TILLING" or "Targeting Induced Local Lesions IN Genomics" refers to a mutagenesis technology useful to generate and/or identify, and to eventually isolate mutagenized variants of a particular nucleic acid with modulated expression and/or activity (McCallum et al., (2000), *Plant Physiology* 123:439-442; McCallum et al., (2000) *Nature Biotechnology* 18:455-457; and, Colbert et al., (2001) *Plant Physiology* 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

TILLING also allows selection of plants carrying mutant variants. These mutant variants may exhibit modified expression, either in strength or in location or in timing (if the mutations affect the promoter for example). TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (U.S. Pat. No. 8,071,840).

Other mutagenic methods can also be employed to introduce mutations in the Crw1 and/or Crw2 genes. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Other detection methods for detecting mutations in the Crw1 and/or Crw2 gene can be employed, e.g., capillary electrophoresis (e.g., constant denaturant capillary electrophoresis and single-stranded conformational polymorphism). In another example, heteroduplexes can be detected by using mismatch repair enzymology (e.g., CELI endonuclease from celery). CELI recognizes a mismatch and cleaves exactly at the 3' side of the mismatch. The precise base position of the mismatch can be determined by cutting with the mismatch repair enzyme followed by, e.g., denaturing gel electrophoresis. See, e.g., Oleykowski et al., (1998) "Mutation detection using a novel plant endonuclease" *Nucleic Acid Res.* 26:4597-4602; and, Colbert et al., (2001) "High-Throughput Screening for Induced Point Mutations" *Plant Physiology* 126:480-484.

The plant containing the mutated Crw1 and/or Crw2 genes can be crossed with other plants to introduce the mutation into another plant. This can be done using standard breeding techniques.

Homologous recombination allows introduction in a genome of a selected nucleic acid at a defined selected position. Homologous recombination has been demonstrated in plants. See, e.g., Puchta et al. (1994), *Experientia* 50: 277-284; Swoboda et al. (1994), *EMBO J.* 13: 484-489; Offringa et al. (1993), *Proc. Natl. Acad. Sci. USA* 90: 7346-7350; Kempin et al. (1997) *Nature* 389:802-803; and, Terada et al., (2002) *Nature Biotechnology,* 20(10):1030-1034).

Methods for performing homologous recombination in plants have been described not only for model plants (Offringa et al. (1990) *EMBO J.* October; 9(10):3077-84) but also for crop plants, for example rice (Terada R, Urawa H, Inagaki Y, Tsugane K, Iida S. *Nat Biotechnol.* 2002; Iida and Terada: *Curr Opin Biotechnol.* 2004 April; 15(2):1328). The nucleic acid to be targeted (which may be Crw1 and/or Crw2 or a variant thereof as hereinbefore defined) need not be targeted to the locus of Crw1 and/or Crw2 genes, respectively, but may be introduced in, for example, regions of high expression.

Transposable elements can be categorized into two broad classes based on their mode of transposition. These are designated Class I and Class II; both have applications as mutagens and as delivery vectors. Class I transposable elements transpose by an RNA intermediate and use reverse transcriptases, i.e., they are retroelements. There are at least three types of Class I transposable elements, e.g., retrotransposons, retroposons, SINE-like elements. Retrotransposons typically contain LTRs, and genes encoding viral coat proteins (gag) and reverse transcriptase, RnaseH, integrase and polymerase (pol) genes. Numerous retrotransposons have been described in plant species. Such retrotransposons mobilize and translocate via a RNA intermediate in a reaction catalyzed by reverse transcriptase and RNase H encoded by the transposon. Examples fall into the Ty1-copia and Ty3-gypsy groups as well as into the SINE-like and LINE-like classifications (Kumar and Bennetzen (1999) *Annual Review of Genetics* 33:479). In addition, DNA transposable elements such as Ac, Tam1 and En/Spm are also found in a wide variety of plant species, and can be utilized. Transposons (and IS elements) are common tools for introducing mutations in plant cells.

"Insect" and "insect pest" are used interchangeably herein.

"Susceptibility" refers to the inability of a plant variety to restrict the growth and development of a specified pest.

"Resistance" refers to the ability of a plant variety to restrict the growth and development of a specified pest and/or the damage they cause when compared to susceptible plant varieties under similar environmental conditions and pest pressure.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal W method of alignment.

The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB.

After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner.

Mutations in two corn genes, Crw1 and Crw2, result in maize plants with enhanced susceptibility to one or more insect pests. These plants and similar plants with reduced endogenous expression of Crw1 and/or Crw2 can be used as part of an insect pest management program to control for such pests.

CRW1

A maize mutant (corn rootworm 1) whose leaves are devoured by the Western corn rootworm (WCR) beetle (Dhillon B, Moose S P; and Johal G S. (2007). crw1—A novel maize mutant exceptionally susceptible to Western Corn Rootworm. *Maize Genetics Conference*. March 22-25, St. Charles, Ill. Abstract and Presentation available online) was identified using a forward genetics approach. The phenotype of the mutant is unusual because the WCR beetle normally feeds on maize pollen and silks and not leaves. Thus, it appears that a mechanism that normally renders maize leaves unpalatable to the WCR beetle is compromised in the mutant. The Crw1 gene (SEQ ID NO:2) encodes a NAC transcription factor. The gene is located on chromosome 6 and is inherited in a recessive fashion.

Figure 1:
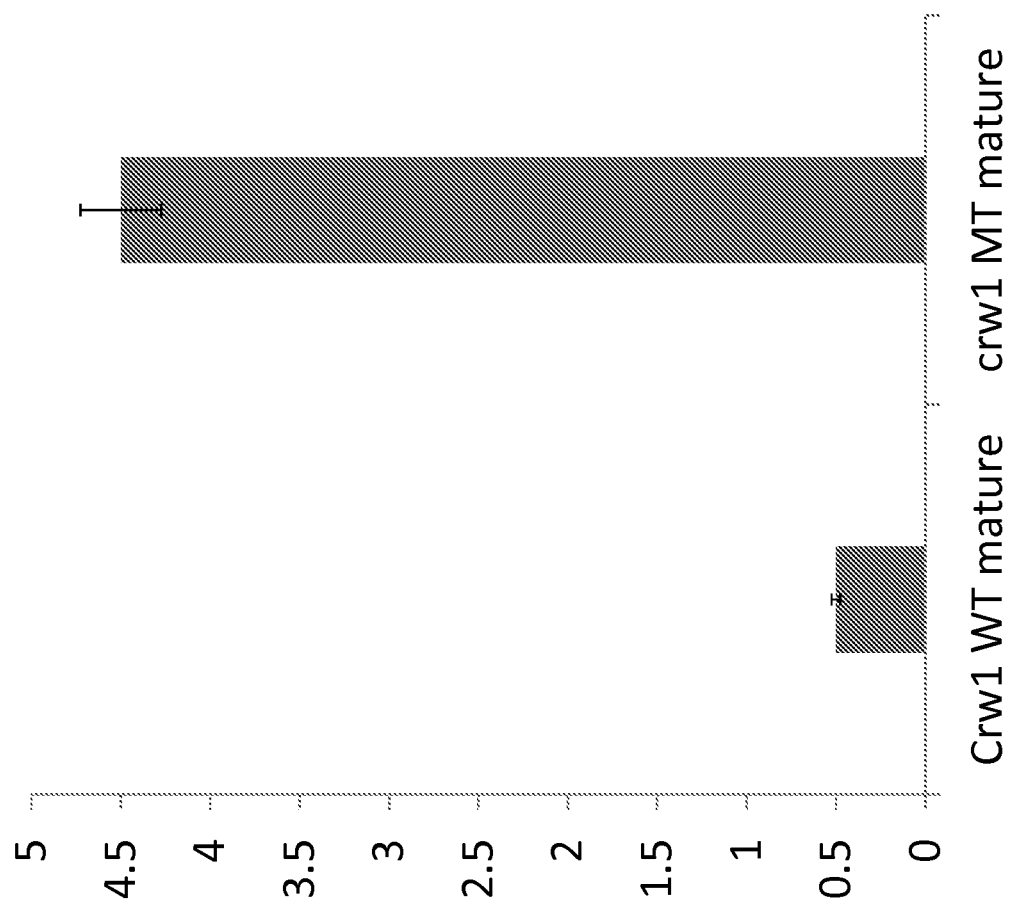
FIG. 1 shows results obtained from a foliar feeding choice assay in which Western corn rootworm (WCR) beetles were placed in a box with leaves from the maize crw1-Ac mutant and leaves from their wild-type SIBs. The results represent the average mean of 9 biological samples.
Figure 2:
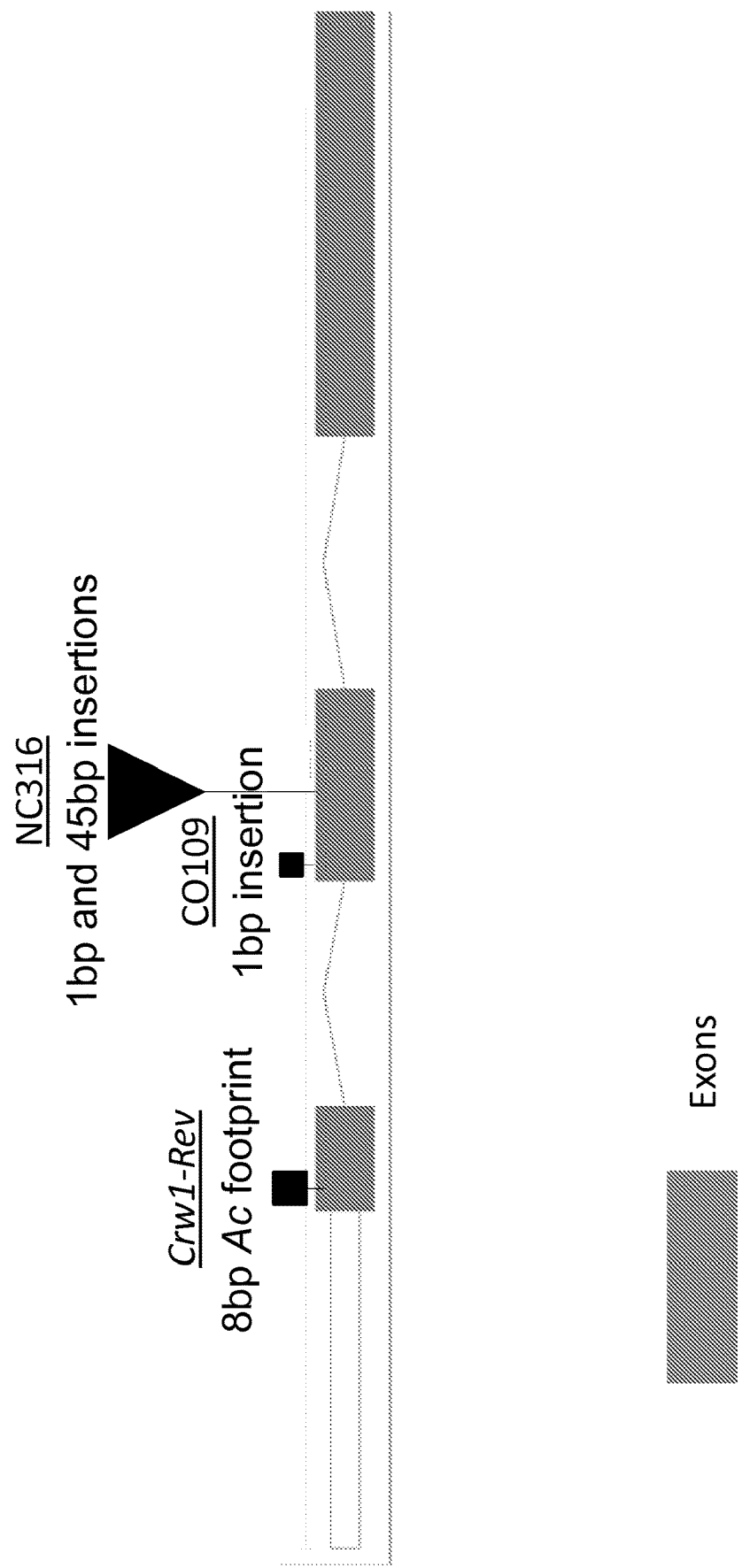
FIG. 2 shows a schematic representation of the maize Crw1 gene; the position of the mutation in the crw1-Ac mutant line; and the positions of the insertions in the public diversity lines CO109 and NC316.

At least three alleles of Crw1 that confer enhanced susceptibility to herbivory by the corn rootworm beetle were subsequently identified, one mutant and two naturally occurring. One is a stably mutant but revertant allele of Crw1 containing an 8-bp direct duplication at the site of insertion ('footprint' of Ac excision), thereby causing premature termination of CRW1. The other two are in public maize inbred lines. The Crw1 gene in CO109 contains a 1 bp insertion in exon 2, whereas the Crw1 gene in NC316 contains a 1 bp insertion and a 45 bp insertion at separate positions in exon 2. Premature termination codons result in both instances. FIG. 2 shows the position of the artificially induced mutation in crw1-Ac and the positions of the naturally occurring mutations in the CO109 and NC316 lines.

The terms "wild-type crw1 gene", "crw1 wt gene", "Crw1 gene" and "CRW1 gene" are used interchangeably herein.

The present disclosure includes the following isolated polynucleotides, cDNAs and polypeptides:

An isolated polynucleotide or cDNA comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:3, 10, 11, 12, 13, 14, 15, 16, 17, 18, 19, 20, 21, 22, 23, 24, 25, 26, or 27; or (ii) a full complement of the nucleic acid sequence of (i), wherein the full complement and the nucleic acid sequence of (i) consist of the same number of nucleotides and are 100% complementary. Any of the foregoing isolated polynucleotides or cDNA may be utilized in any recombinant DNA constructs (including suppression DNA constructs) of the present disclosure. The polypeptide is preferably a CRW1 polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO: 3, 10, 11, 12, 13, 14, 15, 16, 17, 18, 19, 20, 21, 22, 23, 24, 25, 26, or 27. The polypeptide is preferably a CRW1 polypeptide.

An isolated polynucleotide or cDNA comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:2; or (ii) a full complement of the nucleic acid sequence of (i). Any of the foregoing isolated polynucleotides or cDNAs may be utilized in any recombinant DNA constructs (including suppression constructs) of the present disclosure.

An isolated polynucleotide or cDNA comprising a nucleotide sequence, wherein the nucleotide sequence is hybridizable under stringent conditions with a DNA molecule comprising the full complement of SEQ ID NO:2.

An isolated polynucleotide or cDNA comprising a nucleotide sequence, wherein the nucleotide sequence is derived from SEQ ID NO:2 by alteration of one or more nucleotides by at least one method selected from the group consisting of: deletion, substitution, addition and insertion.

An isolated polynucleotide or cDNA comprising a nucleotide sequence, wherein the nucleotide sequence corresponds to an allele of SEQ ID NO:2.

CRW2

A maize mutant showing enhanced susceptibility to WCR adults was isolated from an EMS population and named crw2-EMS. Independently, another WCR-susceptible mutant named crw2-Mutag was identified in an F2 population derived from a Mu-active line. The Crw2 mutants showed enhanced susceptibility to WCR adults as well as to Japanese beetles and European Corn Borer (ECB) when evaluated in field testing. Both crw2-EMS and crw2-Mutag segregated as monogenic recessive, mapped to the same region of chromosome 5, and were allelic to each other in reciprocal crosses. The Crw2 gene (SEQ ID NO:28) was cloned and was determined to encode a putative Homogalacturonan (HGA1), which is also annotated as "Glycosyltransferase AER61" or a "putative uncharacterized protein" (SEQ ID NO:29). Glycosyltransferases are members of a large superfamily that can transfer single or multiple activated sugars to a wide range of small molecular acceptors in plants. Recent studies have shown that glycosyltransferases in plants may have roles in numerous processes of plant growth, development, and response to the environment (Wang, J. and Hou, B. (2009) *Front. Biol. China* 4:39-46).

At least two mutant alleles of Crw2 have shown to confer enhanced susceptibility to herbivory by the corn rootworm beetle: an allele known as crw2-Mutag that has a Mu-element insertion in exon 2 and the crw2-EMS allele that has a single amino acid change R292C in a conserved region of HGA1, and an independent TUSC allele that also has an insertion in exon 2. FIG. 13 shows a diagram of the maize Crw2 gene structure and the positions of each of the identified Crw2 mutations.

The terms "wild-type crw2 gene", "crw2 wt gene", "Crw2 gene" and "CRW2 gene" are used interchangeably herein.

The present disclosure includes the following isolated polynucleotides, cDNAs and polypeptides:

An isolated polynucleotide or cDNA comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:29, 34, 35, 36, 37, 38, 39, 40, 41, 42, 43, 44, 45, 46, 47, 48, 49, or 50; or (ii) a full complement of the nucleic acid sequence of (i), wherein the full complement and the nucleic acid sequence of (i) consist of the same number of nucleotides and are 100% complementary. Any of the foregoing isolated polynucleotides or cDNAs may be utilized in any recombinant DNA constructs (including suppression DNA constructs) of the present disclosure. The polypeptide is preferably a CRW2 polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:29, 34, 35, 36, 37, 38, 39, 40, 41, 42, 43, 44, 45, 46, 47, 48, 49, or 50. The polypeptide is preferably a CRW2 polypeptide.

An isolated polynucleotide or cDNA comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:28; or (ii) a full complement of the nucleic acid sequence of (i). Any of the foregoing isolated polynucleotides or cDNAs may be utilized in any recombinant DNA constructs (including suppression constructs) of the present disclosure. The polypeptide is preferably a CRW2 polypeptide.

An isolated polynucleotide or cDNA comprising a nucleotide sequence, wherein the nucleotide sequence is hybridizable under stringent conditions with a DNA molecule comprising the full complement of SEQ ID NO:28. The polypeptide is preferably a CRW2 polypeptide.

An isolated polynucleotide or cDNA comprising a nucleotide sequence, wherein the nucleotide sequence is derived from SEQ ID NO:28 by alteration of one or more nucleotides by at least one method selected from the group consisting of: deletion, substitution, addition and insertion.

An isolated polynucleotide or cDNA comprising a nucleotide sequence, wherein the nucleotide sequence corresponds to an allele of SEQ ID NO:28.

Plants with Enhanced Susceptibility to Herbivory by an Insect Pest and Methods for Making Same.

Plants with enhanced susceptibility to herbivory by an insect pest due to a reduction in endogenous expression of Crw1 can include any variant of the Crw1 gene such as: (i) a portion of a Crw1 nucleic acid sequence (SEQ ID NO: 2); (ii) a nucleic acid sequence capable of hybridizing with a Crw1 nucleic acid sequence (SEQ ID NO: 2); (iii) a splice variant of a Crw1 nucleic acid sequence (SEQ ID NO: 2); (iv) a naturally occuring allelic variant of a Crw1 nucleic acid sequence (SEQ ID NO: 2); (v) a Crw1 nucleic acid sequence obtained by gene shuffling; (vi) a Crw1 nucleic acid sequence obtained by site-directed mutagenesis; (vii) a Crw1 variant obtained and identified by the method of TILLING.

Similarly, plants with enhanced susceptibility to herbivory by an insect pest due to a reduction in endogenous expression of Crw2 can include any variant of the Crw2 gene such as: (i) a portion of a Crw2 nucleic acid sequence (SEQ ID NO:28); (ii) a nucleic acid sequence capable of hybridizing with a Crw2 nucleic acid sequence (SEQ ID NO:28); (iii) a splice variant of a Crw2 nucleic acid sequence (SEQ ID NO:28); (iv) a naturally occuring allelic variant of a Crw2 nucleic acid sequence (SEQ ID NO:28); (v) a Crw2 nucleic acid sequence obtained by gene shuffling; (vi) a Crw2 nucleic acid sequence obtained by site-directed mutagenesis; (vii) a Crw2 variant obtained and identified by the method of TILLING.

The levels of endogenous Crw1 and/or Crw2 expression can be reduced in a plant cell by antisense constructs, sense constructs, RNA silencing constructs, RNA interference, artificial microRNAs, and genomic disruptions such as but not limited to, disruptions induced by transposons, tilling, and homologous recombination.

In one aspect, a modified plant miRNA precursor may be used, wherein the precursor has been modified to replace the miRNA encoding region with a sequence designed to produce a miRNA directed to the target gene (Crw1 or Crw2). The precursor is also modified in the star strand sequence to correspond to changes in the miRNA encoding region.

In another aspect, a nucleic acid variant of Crw1 and/or Crw2 useful in the methods of the disclosure is obtained by gene shuffling.

In another aspect, a genetic modification may also be introduced in the locus of a maize Crw1 or Crw2 gene using the technique of TILLING (Targeted Induced Local Lesions In Genomes).

In another aspect, site-directed mutagenesis may be used to generate variants of Crw1 and/or Crw2 nucleic acids. Several methods are available to achieve site-directed mutagenesis; the most common being PCR based methods (U.S. Pat. No. 7,956,240).

In another aspect, homologous recombination can also be used to inactivate, or reduce the expression of endogenous Crw1 and/or Crw2 in a plant.

Homologous recombination can be used to induce targeted gene modifications by specifically targeting the Crw1 and/or Crw2 genes in vivo. Mutations in selected portions of the genes (including 5' upstream, 3' downstream, and intragenic regions) such as those provided herein are made in vitro and introduced into the desired plant using standard techniques. Homologous recombination between the introduced mutated genes and the target endogenous genes would lead to targeted replacement of the wild-type gene in transgenic plants, resulting in suppression of gene expression.

In another aspect, catalytic RNA molecules or ribozymes can also be used to inhibit expression of a gene of interest (Crw1 or Crw2). It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the constructs. A number of classes of ribozymes have been identified. For example, one class of ribozymes is derived from a number of small circular RNAs that are capable of self-cleavage and replication in plants. The RNAs can replicate either alone (viroid RNAs) or with a helper virus (satellite RNAs). Examples of RNAs include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes has been described. See, e.g., Haseloff et al. (1988) *Nature*, 334:585-591.

In another aspect, the gene of interest (Crw1 or Crw2) can be inactivated by inhibiting expression via sense suppression. Introduction of expression cassettes in which a nucleic acid is configured in the sense orientation with respect to the promoter has been shown to be an effective means by which to block the transcription of a desired target gene. (Napoli et al. (1990), *The Plant Cell* 2:279-289; and U.S. Pat. Nos. 5,034,323, 5,231,020, and 5,283,184).

In another aspect, the Crw1 and/or Crw2 genes can also be inactivated by, e.g., transposon based gene inactivation.

In another aspect, the inactivating step comprises producing one or more mutations in the gene of interest (Crw1 or Crw2), where the one or more mutations in the gene sequence comprise one or more transposon insertions, thereby inactivating the gene compared to a corresponding control plant. For example, the mutation may comprise a homozygous disruption in the gene or the one or more mutations comprise a heterozygous disruption in the gene.

These mobile genetic elements are delivered to cells, e.g., through a sexual cross, transposition is selected for and the resulting insertion mutants are screened, e.g., for a phenotype of interest. Plants comprising disrupted Crw1 and/or Crw2 genes can be crossed with a wild-type plant. Any of a number of standard breeding techniques can be used, depending upon the species to be crossed. The location of a TN (transposon) within a genome of an isolated or recombinant plant can be determined by known methods, e.g., sequencing of flanking regions as described herein. For example, a PCR reaction from the plant can be used to amplify the sequence, which can then be diagnostically sequenced to confirm its origin. Optionally, the insertion mutants are screened for a desired phenotype, such as the inhibition of expression of Crw1 and/or Crw2 or enhanced susceptibility to herbivory by an insect pest.

Any plant identified herein as having reduced expression of Crw1 and/or Crw2 thereby having enhanced susceptibility to herbivory by an insect pest could be used in the methods described below.

A reduction in expression of Crw1 may confer enhanced susceptibility to herbivory by an insect pest, wherein the insect pest may be coleopteran. Examples of coleopteran pests include, without limitation, the western corn rootworm (WCR, *Diabrotica virgifera virgifera* LeConte), the northern corn rootworm (NCR; *Diabrotica barberi* Smith and Lawrence), the Mexican corn rootworm (MCR, *Diabrotica virgifera zeae* Krysan and Smith), the southern corn rootworm (SCR, *Diabrotica undecimpunctata howardi*), the Colorado potato beetle (CPB, *Leptinotarsa decemlineata*), and the Japanese beetle (*Popiffia japonica*). The corn rootworm is of particular interest.

A reduction in expression of Crw2 may confer enhanced susceptibility to herbivory by an insect pest, wherein the insect pest may be coleopteran or lepidopteran.

Examples of coleopteran pests include, without limitation, the western corn rootworm (WCR, *Diabrotica virgifera virgifera* LeConte), the northern corn rootworm (NCR; *Diabrotica barberi* Smith and Lawrence), the Mexican corn rootworm (MCR, *Diabrotica virgifera zeae* Krysan and Smith), the southern corn rootworm (SCR, *Diabrotica undecimpunctata howardi*), the Colorado potato beetle (CPB, *Leptinotarsa decemlineata*), and the Japanese beetle (*Popiffia japonica*). The corn rootworm and Japanese beetle are of particular interest.

Examples of lepidopteran pests include, without limitation, the European corn borer (ECB) (Order Lepidoptera: Family Crambidae), the southwestern corn borer (SWCB) (Order Lepidoptera: Family Crambidae), the corn earworm (CEW) (Order Lepidoptera: Family Noctuidae), the fall armyworm (FAW) (Order Lepidoptera: Family Noctuidae), the velvetbean caterpillar (VBC) (Order Lepidoptera: Family Noctuidae), the soybean looper (SBL) (Order Lepidoptera: Family Noctuidae), the western bean cutworm (WBCW) (Order Lepidoptera: Family Noctuidae), the black cutworm (BCW) (Order Lepidoptera: Family Noctuidae), the sugar cane borer (SCB) (Order Lepidoptera: Family Crambidae), the fall webworm (*Hyphantria cunea*), and the cattail caterpillar (*Simyra insularis*). The European corn borer is of particular interest.

Trap Crops and Uses Thereof

The unusual susceptibility of the Crw1 and Crw2 mutants to herbivory enables such plants to be used as a "trap" crop. Trap crops can be defined as plant stands that "attract, divert, intercept, and/or retain targeted insects or the pathogens they vector in order to reduce damage to the main crop" (Shelton and Badenes-Perez. 2006. *Annu. Rev. Entomol.* 51:285-308).

A trap crop comprises one or more plants with enhanced susceptibility to herbivory by an insect pest due to a reduction in endogenous expression of Crw1 and/or Crw2. The insect pest may be Coleopteran or Lepidopteran. The insect pest may be corn rootworm, European corn borer, or Japanese beetle. The trap crop and/or main crop may comprise plants selected from the group consisting of: maize, soybean, sunflower, sorghum, canola, wheat, alfalfa, cotton, rice, barley, millet, or sugar cane. Maize is of particular interest.

A trap crop may be planted within, adjacent to, or within 2 kilometers of a main crop. If interspersed "within" the main crop, seed for the trap crop and seed for the main crop may be present in the same bag of seed. The term "mixing" with respect to seeds means, for example, mixing at least two types of seeds in a bag (such as during packaging, production, or sale), mixing at least two types of seeds in a plot, or any other method that results in at least two types of seeds being introduced into the plot. The mixture could result in a random arrangement in the plot, or could be structured (such as, for example, in a block or strip). Seed for the trap crop may constitute 1%, 2%, 3%, 4%, 5%, 6%, 7%, 8%, 9%, 10%, 11%, 12%, 13%, 14%, 15%, 16%, 17%, 18%, 19%, or up to 20% of the total seed in a bag. The size and configuration of the trap crop area usually is not based on the size of the area but rather on the number of insect pests expected.

In one aspect, a trap crop may be used to lure insect pests to the trap crop in an effort to monitor insect pest numbers. Monitoring is a critical component of an insect pest management program and can be performed by direct observation or using a device to sample crops. The use of trap crops would be particularly useful for monitoring populations of colonizing adult beetles early in a growing season in order to estimate insect pest pressure for the remainder of the growing season and to make recommendations for the most cost effective control methods to use. Monitoring is also important for limiting the increase in geographic distribution of an exotic pest (such as *Diabrotica virgifera* in Europe).

In another aspect, a trap crop may be used to attract an insect pest away from a main crop, thus preventing or making less likely the arrival of the insect pest on the main crop. This method thus reduces insect pest numbers on the main crop.

In another aspect, the trap crop may be used to lure insect pests to the trap crop, where action may be taken either to kill the insect pest or to reduce numbers of the pests. This strategy is referred to as an "attract-and-kill" strategy. In this scenario, the "killing" may be performed by any method known to one of ordinary skill in the art. Typically, the method of choice is the application of insecticides, but transgenic insecticidal agents targeting adult insects or entomophagous agents such as entomopathogenic fungi may also be used. "Attract-and-kill" strategies can also be an important and effective region-wide management tool to reduce increased geographic distribution of an exotic pest species (such as *Diabrotica virgifera* in Europe).

One of the most important characteristics of an insect pest that can determine whether an insect may be subject to management by trap crops is the insect stage targeted by the trap crop. For example, adult female Lepidoptera select plants for oviposition, but it is the larvae, which typically have limited mobility, that are the damaging stage.

Another important characteristic is the insect's ability to direct its movement, its migratory behavior, and its host-finding behavior. Larger insects in the order Coleoptera and Lepidoptera generally have an enhanced capacity for directional flight that makes them more amenable for trap cropping.

In the case of corn rootworm, methods for control may include controlling adult insect pests in one growing season and the larvae in the next generation. For example, a trap crop may be used to attract adult beetles to the area of the trap crop where they remain and oviposit. Insecticides may be used to kill the adult insect pests, thereby managing the adult beetle population and reducing damage to corn silks. In addition, if the insects are killed prior to egg laying, the number of insect pest larvae will be reduced in the next generation. Hence, damage to corn roots in the following season will be reduced due to limited numbers of corn rootworm larvae. Sticky traps may also be placed in the area of the trap crop in an effort to reduce numbers of adult insect pests. Alternatively, the trap crop may be destroyed, along with the insect pest eggs.

Combining biological, insecticidal, and/or cultural control methods to supplement the effects of the trap crop can increase the effectiveness of a trap crop and provide other benefits as well.

The application of insecticides on the trap crop only, and not on the main crop, provides the benefit of reducing overall pesticide use, with less negative impact on the environment.

The trap crop may comprise a transgene that interferes with the life cycle of an insect pest when said insect pest feeds on the plants in the trap crop. This may occur through mechanisms involving RNAi. The life cycle disruption could take the form of insecticidal agents that kill or injure the current generation or sterilizing agents that reduce egg viability of the next generation or that interfere with development and viability of the next generation.

Cultural practices such as crop rotation and/or tilling of the soil after harvest may be used with trap cropping to attract adult insect pests in one generation and to kill the next generation of insects. In the methods herein, a trap crop may be planted in one growing season in a small area within or near a main crop. The trap crop attracts adult beetles during that growing season, reducing insect pest pressure on the main crop and increasing egg production and deposition in the trap crop. In the next season, the area where the trap crop was located may be seeded with a non-host plant (i.e. crop rotation) or the soil may be tilled prior to planting, thus reducing next generation insect populations.

In general, a trap crop may be about 1%, 2%, 3%, 4%, 5%, 6%, 7%, 8%, 9%, 10%, 11%, 12%, 13%, 14%, 15%, 16%, 17%, 18%, 19%, or up to 20% of the total area.

The cost of setting aside land for trap cropping can be significant. However, trap crops comprising one or more plants with enhanced susceptibility to herbivory by an insect pest due to a reduction in endogenous expression of Crw1 and/or Crw2 may still be harvested, particularly if the trap crop is interspersed with the main crop. Although yield may not be optimal, harvesting the susceptible plants minimizes the losses associated with the use of land resources for trap cropping.

Refuge Crops and Uses Thereof

A rapid increase in acreage of transgenic Bt corn to control insect pests such as, for example, corn rootworm and European corn borer, has sparked an interest in managing resistance development in insects, e.g., mandated refuge crop in field containing insect resistant crop plants. In an embodiment, an insect refuge constitutes plants that do not contain an in-plant insect resistant trait (e.g., a Bt trait) that controls corn borer and/or corn rootworm. The presence of the refuge allows potentially resistant insects that emerge from fields with the insect resistant trait (s) to mate with susceptible insects from the refuge, diluting resistance genotypes in the insect population and extending the durability of the insect resistant trait (s).

In an embodiment, a refuge crop comprises one or more plants with enhanced susceptibility to herbivory by an insect pest due to a reduction in endogenous expression of Crw1 and/or Crw2. The insect pest may be Coleopteran or Lepidopteran. The insect pest may be corn rootworm, European corn borer, or Japanese beetle. The refuge crop and/or main crop (comprising one or more insect resistant traits) may comprise plants selected from the group consisting of: maize, soybean, sunflower, sorghum, canola, wheat, alfalfa, cotton, rice, barley, millet, or sugar cane. Maize is of particular interest.

The refuge crop may be used to reduce the development of resistance to insect resistant transgenic plants in an insect pest. A method for producing a transgenic plant with reduced expression of endogenous Crw1 is provided herein, in which the method comprises: (a) introducing into a regenerable plant cell a recombinant construct that comprises a polynucleotide or cDNA operably linked to a promoter, wherein the expression of the polynucleotide or cDNA sequence reduces endogenous Crw1 expression; (b) regenerating a transgenic plant from the regenerable plant cell after step (a), wherein the transgenic plant comprises in its genome the recombinant DNA construct; and (c) selecting the transgenic plant of (b), wherein the transgenic plant comprises the recombinant construct and exhibits reduced expression of Crw1, when compared to a control plant not comprising the recombinant DNA construct.

A method for producing a transgenic plant with reduced expression of endogenous Crw1 is provided herein in which the method comprises: (a) introducing into a regenerable plant cell a recombinant DNA construct comprising an isolated polynucleotide or cDNA operably linked, sense or antisense orientation, to a promoter functional in a plant, wherein the polynucleotide or cDNA may comprise (i) the nucleotide sequence of SEQ ID NO:1 or 2; (ii) a nucleotide sequence with at least 90% sequence identity, based on the Clustal W method of alignment, when compared to SEQ ID NO:1 or 2; (iii) a nucleotide sequence of at least 100 contiguous nucleotides of SEQ ID NO:1 or 2; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce an miRNA directed to SEQ ID NO:1 or 2; (b) regenerating a transgenic plant cell after step (a), wherein the transgenic plant comprises in its genome the recombinant DNA construct; and (c) selecting a transgenic plant of (b), wherein the transgenic plant comprises the recombinant DNA construct and exhibits a reduced expression of Crw1, when compared to a control plant not comprising the recombinant DNA construct.

A method for identifying an allele of Crw1 that confers enhanced susceptibility to herbivory by an insect pest is provided herein in which the method comprises: (a) performing a genetic screen on a population of mutant maize plants; (b) identifying one or more mutants that exhibit enhanced susceptibility to herbivory by an insect pest; and (c) identifying the Crw1 allele from the mutant maize plant that confers enhanced susceptibility to herbivory by an insect pest.

A method of identifying an allele of Crw1 that confers enhanced susceptibility to herbivory by an insect pest is provided herein in which the method comprises the steps of: (a) gene shuffling using one or more nucleotide sequences encoding SEQ ID NO:3 or a protein that is at least 70% identical to SEQ ID NO:3, or a fragment thereof; (b) transforming the shuffled sequences from step (a) into a population of regenerable plant cells; (c) regenerating a population of transformed plants from the population of transformed regenerable plant cells of step (b); (d) screening the population of transformed plants from step (c) for enhanced susceptibility to herbivory by an insect pest; and (e) identifying the Crw1 allele from the transformed plant exhibiting enhanced susceptibility to herbivory by an insect pest.

A method for identifying an allele of Crw1 in a maize plant that is associated with enhanced susceptibility to herbivory by an insect pest is provided herein in which the method comprises the steps of: (a) crossing two maize plants with differing levels of resistance to said insect pest; (b) evaluating allelic variations in the progeny plants with respect to the polynucleotide or cDNA sequence encoding a protein comprising SEQ ID NO:3 or in the genomic region that regulates the expression of the polynucleotide or cDNA encoding the protein; (c) phenotyping the progeny plants for susceptibility to herbivory by said insect pest; (d) associating allelic variations with said susceptibility; and (e) identifying the alleles that are associated with enhanced susceptibility to herbivory by an insect pest. The method further comprises introducing identified alleles into other maize plants through plant breeding.

A method of identifying an allegle of Crw1 in a maize plant that is associated with enhanced susceptibility to herbivory by an insect pest is provided herein in which the method comprises the steps of: (a) obtaining a population of maize plants, wherein said maize plants exhibit differing levels of susceptibility to herbivory by said insect pest; (b) evaluating allelic variations with respect to the polynucleotide or cDNA sequence encoding a protein comprising SEQ ID NO:3, or in the genomic region that regulates the expression of the polynucleotide or cDNA encoding the protein; (c) associating allelic variations with said susceptibility; and (d) identifying an allelic variant that is associated with enhanced susceptibility to herbivory by an insect pest. The method further comprising introducing the identified allele into other maize plants through plant breeding.

A method for making a plant that exhibits enhanced susceptibility to herbivory by an insect pest is provided herein in which the method comprises: (a) introducing a mutation into the endogenous Crw1 gene; and (b) detecting the mutation. The steps of (a) and (b) may be done using a Targeting Induced Local Lesions IN Genomics (TILLING) method and the mutation may be effective in reducing the expression of the endogenous Crw1 gene. The mutation may be a site-specific mutation.

A method for making a plant that exhibits enhanced susceptibility to herbivory by an insect pest is provided herein in which the method comprises: (a) introducing a transposon into a germplasm containing an endogenous Crw1 gene (b) obtaining progeny of the germplasm of step (a); and (c) identifying a progeny plant from step (b) in which the transposon inserted into the endogenous Crw1 gene results in reduced expression of Crw1. Step (a) further comprises introduction of the transposon into a regenerable plant cell of the germplasm by transformation and regeneration of a transgenic plant from the regenerable plant cell, wherein the transgenic plant comprises in its genome the transposon. The method further comprises the steps of: (a) introducing into a regenerable plant cell a recombinant construct comprising the identified Crw1 allele; (b) regenerating a transgenic plant from the regenerable plant cell after step (i), wherein the transgenic plant comprises in its genome the recombinant DNA construct; and (c) selecing a transgenic plant of (b), wherein the transgenic plant comprises the recombinant DNA construct and exhibits enhanced susceptibility to herbivory by an insect pest when compared to a control plant not comprising the recombinant DNA construct.

A method for producing a transgenic plant with enhanced susceptibility to herbivory by an insect pest is provided herein in which the method comprises the steps of: (a) introducing into a regenerable plant cell a recombinant DNA construct comprising an isolated polynucleotide or cDNA operably linked, in sense or antisense orientation, to a promoter functional in a plant, wherein the polynucleotide or cDNA comprises: (i) the nucleotide sequence of SEQ ID NO:1 or 2; (ii) a nucleotide sequence with at least 90% sequence identity, based on the Clustal W method of alignment, when compared to SEQ ID NO:1 or 2; (iii) a nucleotide sequence of at least 100 contiguous nucleotides of SEQ ID NO:1 or 2; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce a miRNA directed to SEQ ID NO:1 or 2; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits enhanced susceptibility to herbivory by an insect pest when compared to a control plant not comprising the recombinant DNA construct.

A plant comprising within its genome a polynucleotide or cDNA encoding a polypeptide having the amino acid sequence set forth in SEQ ID NO:5 is provided herein, wherein said plant has enhanced susceptibility to herbivory by an insect pest.

A plant is provided herein wherein said plant comprises in its genome a recombinant DNA construct comprising an isolated polynucleotide or cDNA operably linked, in sense or antisense orientation or both, to a promoter functional in a plant, wherein the polynucleotide or cDNA comprises: (a) the nucleotide sequence of SEQ ID NO:1 or 2; (b) a nucleotide sequence with at least 90% sequence identity, based on the Clustal W method of alignment, when compared to SEQ ID NO:1 or 2; (c) a nucleotide sequence that can hybridize under stringent conditions with the nucleotide sequence of (a); or (d) a modified plant miRNA precursor, wherein the precursor has been modified to replace the miRNA encoding region with a sequence designed to produce a miRNA directed to SEQ ID NO:1 or 2. The plant may exhibit enhanced susceptibility to herbivory by an insect pest when compared to a control plant not comprising the recombinant DNA construct.

In any of the preceding methods of the present disclosure, a plant may be produced. The plant may be maize, soybean, sunflower, sorghum, canola, wheat, alfalfa, cotton, rice, barely, millet, or sugarcane. The insect pest may be Coleopteran. The insect pest may be corn rootworm.

A method for producing a transgenic plant with reduced expression of endogenous Crw2 is provided wherein in which the method comprises: (a) introducing into a regenerable plant cell a recombinant construct comprising a polynucleotide or cDNA operably linked to a promoter, wherein the expression of the polynucleotide or cDNA sequence reduces endogenous Crw2 expression; (b) regenerating a transgenic plant from the regenerable plant cell after step (a), wherein the transgenic plant comprises in its genome the recombinant DNA construct; and (c) selecting the transgenic plant of (b), wherein the transgenic plant comprises the recombinant construct and exhibits reduced expression of Crw2, when compared to a control plant not comprising the recombinant DNA construct.

A method for producing a transgenic plant with reduced expression of endogenous Crw2 is provided herein in which the method comprises: (a) introducing into a regenerable plant cell a recombinant DNA construct comprising an isolated polynucleotide or cDNA operably linked, sense or antisense orientation, to a promoter functional in a plant, wherein the polynucleotide or cDNA comprises: (i) the nucleotide sequence of SEQ ID NO:28; (ii) a nucleotide sequence with at least 90% sequence identity, based on the Clustal W method of alignment, when compared to SEQ ID NO:28; (iii) a nucleotide sequence of at least 100 contiguous nucleotides of SEQ ID NO:28; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce an miRNA directed to SEQ ID NO:28; (b) regenerating a transgenic plant cell after step (a), wherein the transgenic plant comprises in its genome the recombinant DNA construct; and (c) selecting a transgenic plant of (b), wherein the transgenic plant comprises the recombinant DNA construct and exhibits a reduced expression of Crw2, when compared to a control plant not comprising the recombinant DNA construct.

A method for identifying an allele of Crw2 that confers enhanced susceptibility to herbivory by an insect pest is provided in which the method comprises: (a) performing a genetic screen on a population of mutant maize plants; (b) identifying one or more mutants that exhibit enhanced susceptibility to herbivory by an insect pest; and (c) identifying the Crw2 allele from the mutant maize plant that confers enhanced susceptibility to herbivory by an insect pest.

A method for identifying an allele of Crw2 that confers enhanced susceptibility to herbivory by an insect pest is provided in which the method comprises the steps of: (a) gene shuffling using one or more nucleotide sequences encoding SEQ ID NO:29 or a protein that is at least 70% identical to SEQ ID NO:29, or a fragment thereof; (b) transforming the shuffled sequences from step (a) into a population of regenerable plant cells; (c) regenerating a population of transformed plants from the population of transformed regenerable plant cells of step (b); (d) screening the population of transformed plants from step (c) for enhanced susceptibility to herbivory by an insect pest; and (e) identifying the Crw2 allele from the transformed plant exhibiting enhanced susceptibility to herbivory by an insect pest.

A method for identifying an allele of Crw2 in a maize plant that is associated with enhanced susceptibility to herbivory by an insect pest is provided in which the method comprises the steps of: (a) crossing two maize plants with differing levels of resistance to said insect pest; (b) evaluating allelic variations in the progeny plants with respect to the polynucleotide or cDNA sequence encoding a protein comprising SEQ ID NO:29 or in the genomic region that regulates the expression of the polynucleotide or cDNA encoding the protein; (c) phenotyping the progeny plants for susceptibility to herbivory by said insect pest; (d) associating allelic variations with said susceptibility; and (e) identifying the alleles that are associated with enhanced susceptibility to herbivory by an insect pest. The method further comprises introducing the identified allele into other maize plants through plant breeding.

A method for identifying an allele of Crw2 in a maize plant that is associated with enhanced susceptibility to herbivory by an insect pest is provided in which the method comprises the steps of: (a) obtaining a population of maize plants, wherein said maize plants exhibit differing levels of susceptibility to herbivory by said insect pest; (b) evaluating allelic variations with respect to the polynucleotide or cDNA sequence encoding a protein comprising SEQ ID NO:29, or in the genomic region that regulates the expression of the polynucleotide or cDNA encoding the protein; (c) associating allelic variations with said susceptibility; and (d) identifying an allelic variant that is associated with enhanced susceptibility to herbivory by an insect pest. The method further comprises introducing the identified allele into other maize plants through plant breeding.

A method for making a plant that exhibits enhanced susceptibility to herbivory by an insect pest is provided in which the method comprises: (a) introducing a mutation into the endogenous Crw2 gene; and (2) detecting the mutation. Steps (a) and (b) may be done using a Targeting Induced Local Lesions IN Genomics (TILLING) method and wherein the mutation may be effective in reducing the expression of the endogenous Crw2 gene. The mutation may be a site-specific mutation.

A method of making a plant that exhibits enhanced susceptibility to herbivory by an insect pest is provided in which the method comprises: (a) introducing a transposon into a germplasm containing an endogenous Crw2 gene; (b) obtaining progeny of the germplasm of step (a); and (c) identifying a progeny plant from step (b) in which the a transposon inserted into the endogenous Crw2 gene resulting in reduced expression of Crw2. Step (a) further comprises introduction of the transposon into a regenerable plant cell of the germplasm by transformation and regeneration of a transgenic plant from the regenerable plant cell, wherein the transgenic plant comprises in its genome the transposon. The method further comprises the steps of: (a) introducing into a regenerable plant cell a recombinant construct comprising the Crw2 allele identified by the method of claim 34 or 35; (b) regenerating a transgenic plant from the regenerable plant cell after step (a), wherein the transgenic plant comprises in its genome the recombinant DNA construct; and (c) selecing a transgenic plant of (b), wherein the transgenic plant comprises the recombinant DNA construct and exhibits enhanced susceptibility to herbivory by an insect pest when compared to a control plant not comprising the recombinant DNA construct.

A method of producing a transgenic plant with enhanced susceptibility to herbivory by an insect pest is provided herein in which the method comprises the steps of: (a) introducing into a regenerable plant cell a recombinant DNA construct comprising an isolated polynucleotide or cDNA operably linked, in sense or antisense orientation, to a promoter functional in a plant, wherein the polynucleotide or cDNA comprises: (i) the nucleotide sequence of SEQ ID NO:28; (ii) a nucleotide sequence with at least 90% sequence identity, based on the Clustal W method of alignment, when compared to SEQ ID NO:28; (iii) a nucleotide sequence of at least 100 contiguous nucleotides of SEQ ID NO:28; (iv) a nucleotide sequence that can hybridize under stringent conditions with the nucleotide sequence of (i); or (v) a modified plant miRNA precursor, wherein the precursor has been modified to replace the miRNA encoding region with a sequence designed to produce a miRNA directed to SEQ ID NO:28; (b) regenerating a transgenic plant from the regenerable plant cell after step (a), wherein the transgenic plant comprises in its genome the recombinant DNA construct; and (c) selecting a transgenic plant of (b), wherein the transgenic plant comprises the recombinant DNA construct and exhibits enhanced susceptibility to herbivory by an insect pest when compared to a control plant not comprising the recombinant DNA construct.

A plant comprising within its genome a polynucleotide or cDNA encoding a polypeptide having the amino acid sequence set forth in SEQ ID NO:31 or SEQ ID NO:33 is provided herein, wherein said plant has enhanced susceptibility to herbivory by an insect pest.

Further provided herein is a plant comprising in its genome a recombinant DNA construct comprising an isolated polynucleotide or cDNA operably linked, in sense or antisense orientation or both, to a promoter functional in a plant, wherein the polynucleotide or cDNA comprises: (a) the nucleotide sequence of SEQ ID NO:28; (b) a nucleotide sequence with at least 90% sequence identity, based on the Clustal W method of alignment, when compared to SEQ ID NO:28; (c) a nucleotide sequence that can hybridize under stringent conditions with the nucleotide sequence of (a); or (d) a modified plant miRNA precursor, wherein the precursor has been modified to replace the miRNA encoding region with a sequence designed to produce a miRNA directed to SEQ ID NO28; and wherein the plant exhibits enhanced susceptibility to herbivory by an insect pest when compared to a control plant not comprising the recombinant DNA construct.

In any of the preceding methods of the present disclosure, a plant may be produced. The plant may be maize, soybean, sunflower, sorghum, canola, wheat, alfalfa, cotton, rice, barely, millet, or sugar cane. The insect pest may be Coleopteran or Lepidopteran. The insect pest may be corn rootworm, European corn borer, or Japanese beetle.

Further provided herein is a plant comprising within its genome: (a) a polynucleotide or cDNA encoding a polypeptide having the amino acid sequence set forth in: SEQ ID NO:5, SEQ ID NO:7, or SEQ ID NO:9; and (b) a polynucleotide or cDNA encoding a polypeptide having the amino acid sequence set forth in SEQ ID NO:31 or SEQ ID NO:33, wherein said plant has enhanced susceptibility to herbivory by an insect pest. The plant may be maize, soybean, sunflower, sorghum, canola, wheat, alfalfa, cotton, rice, barley, millet, or sugar cane. The insect pest may be Coleopteran or Lepidopteran. The insect pest may be corn rootworm, European corn borer, or Japanese beetle.

A method for reducing the development of resistance to Bt transgenic plants in an insect pest is provided herein in which the method comprises: (a) growing a main crop of Bt transgenic plants in an area; and (b) planting a refuge crop containing plants with enhanced susceptibility to an insect pest within, adjacent to, or within 2 kilometers of the main crop.

In any of the methods presented above, the evaluation of resistance or susceptibility to herbivory by an insect pest can comprise any protocol known to one of ordinary skill in the art. The feeding choice assay presented herein could also be used.

EXAMPLES

The present disclosure is further illustrated in the following Examples, in which parts and percentages are by weight and degrees are Celsius, unless otherwise stated. It should be understood that these Examples, while indicating embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Foliar Feeding Choice Assay

A feeding choice assay was be performed to assess the level of resistance to corn rootworm beetles in plants. A PVC box containing a detachable lid was used, and equal weights of freshly harvested mature leaves from both mutant and wild-type plants were affixed to moist filter paper in a randomized manner. Western corn rootworm beetles and southern corn rootworm beetles, which had been starved overnight, were placed into the box. Previous observations showed that the establishment of feeding preference is usually preceded by random scouting within the first 45 minutes, and that preferential feeding usually continues until the leaves of choice are completely devoured. Leaf feeding was scored on a scale from 0 to 5, with 0 indicating no damage and 5 indicating complete decimation.

Example 2

Cloning and Validation of Maize Crw1 Gene

A Crw1 maize mutant, which is highly susceptible to the adult beetle of Western corn rootworm (WCR), was identified in Ac-active material (and is also referred to herein as the crw1-Ac mutant). WCR beetles had an overwhelming preference for crw1-Ac mutant leaves over wild-type sib (WT-sib) leaves as assessed using the feeding choice assay. The gene was cloned by co-segregation analysis with Ac, and it was determined that the Crw1 gene is on chromosome 6 and that it encodes a polypeptide with high homology to the plant-specific NAC family transcription factors. A stably mutant but revertant allele of Crw1 containing an 8-bp direct duplication at the site of insertion ('footprint' of Ac excision) was identified from the original Ac allele. This 8-bp insertion caused premature termination of CRW1. FIG. 2 shows a schematic representation of the Crw1 gene and the position of the mutation in the crw1-Ac mutant. FIGS. 6A-6C show the alignment between wild-type Crw1 and the crw1-Ac allele. SEQ ID NOs:4 and 5 refer to the crw1-Ac nucleotide coding sequence and CRW1-Ac amino acid sequence, respectively.

To identify additional mutant alleles of Crw1, a public collection of maize diversity lines was first screened for susceptibility to the WCR beetle in the field under natural conditions of infestation before validation by the foliar feeding choice assay described in Example 1. Two public diversity lines, CO109 and NC316, were found to segregate for susceptibility to the WCR beetle. By crossing each of the lines to the crw1-Ac line, it was shown that CO109 and NC316 contained naturally occurring mutant alleles at the Crw1 gene that conferred increased susceptibility to WCR beetles. Sequencing of the Crw1 cDNA in each line showed that CO109 contains a 1 bp insertion (at nucleotide 368) in exon 2 and NC316 contains a 1 bp insertion (at nucleotide 366) and a 45 bp insertion at separate positions in exon 2. Premature termination codons result in both instances. FIG. 2 shows the positions of the mutations in the CO109 and NC316 lines. FIGS. 7A-7C show the alignment between wild-type Crw1 and Crw1 from CO109. SEQ ID NOs:6 and 7 refer to the crw1-CO109 nucleotide coding sequence and CRW1-CO109 amino acid sequence, respectively. FIGS. 8A-8C show the alignment between wild-type Crw1 and Crw1 from NC316. SEQ ID NOs:8 and 9 refer to the crw1-NC316 nucleotide coding sequence and CRW1-NC316 amino acid sequence, respectively.

Example 3

Transcriptional and Biochemical Characteristics of the Maize Crw1 Gene

The transcriptional profile of the maize Crw1 gene has been difficult to establish fully thus far. One possible reason is that the maize Crw1 transcript may lack a polyA tail. This prediction is based on the fact that the maize Crw1 cDNA has not been found in any public EST database. In addition, no reads of the maize Crw1 gene were detected in an RNA seq experiment (transcriptomics) which was conducted on cDNAs generated from RNA samples of adult leaves isolated at different time intervals following beetle damage. Nevertheless, the transcriptomics experiment and subsequent RT-PCR verification of significant hits revealed three important features of the maize Crw1 mutant:

First, there was a significant change in the expression of the lipoxygenase pathway genes that control Jasmonic Acid (JA) and green leaf volatile (GLV, such as diterpenes) production in maize. Both of these compounds play significant, albeit opposing, roles in plants' interaction with insect pests. For instance, JAs are known to mediate host resistance, whereas GLVs aid attraction of pests as well as their predators. While the expression of the JA pathway genes was upregulated in the maize Crw1 mutant compared to its WT counterparts (Table 1), the expression of the GLV genes was diminished. These results were consistent with the higher inducible levels of JA in mutant Crw1 plants compared to their WT counterparts (FIG. 3).

Table 1 is a list of the lipoxygenase pathway genes regulated differentially in the Crw1 mutant compared to WT siblings in response to insect feeding. The positive and negative values indicate the fold change of a particular transcript in the mutant vs. WT. There appears to be an up-regulation of the JA biosynthesis and signalling genes and a concomitant reduction of GLV genes in Crw1 in response to WCR feeding.

| Gene name (ID) | Fold Change(log2) | Presumed Function |
|---|---|---|
| LOX2 (EU971362) | +1.8 | JA biosynthesis |
| AOS (NM001111774) | +1.8 | JA biosynthesis |
| OPR12 (EU970844) | +2.58 | JA biosynthesis |
| ZIM motif family protein (LOC100284979) | −2.58 | JA signaling |
| Skp1-like protein 1a (NM_001136917) | +2.58 | JA signaling |
| ACO31(NM001111764) | +3.16 | JA/ET signalling |
| ERF1 like (NM001111800) | +2 | ET/JA signaling |
| LOX10 (NM001112510) | −2 | GLV biosynthesis |
| Fps (EU961933) | −2 | GLV biosynthesis |
| Mevalonate kinase (EU974298) | −4.16 | Terpenoid biosynthesis |
| HMG-CoA synthase (EU961019) | −2.58 | Terpenoid biosynthesis |
| TPS7 (EU954571) | −2.2 | Terpenoid biosynthesis |
| TPS11 (EU716166) | −1.8 | Terpenoid biosynthesis |
| B6TY42_Glycosyltransferase | −2.8 | Resistance to WCR feeding |

Second, the expression of phenylpropanoid and lignin biosynthetic genes was downgraded in the maize Crw1 mutant (Table 2). Compatible with these results are the findings that the Crw1 mutant accumulated lower levels of p-coumaric and ferulic acids (FIG. 4) and exhibited reduced lignification of adult tissues (FIG. 5). Given that these phenolics carry out cell wall cross-linking, our results agreed with both the compromised tensile strength of Crw1 mutant leaves and their altered staining with toluidine blue 0 (TBO), which reacts with free hydroxyl groups in the cell wall.

Table 2 is a list of differentially regulated transcripts involved in lignin biosynthesis. The positive and negative values indicate the fold change of a particular transcript in the Crw1 mutant in comparison to the WT. There appeared to be an up-regulation of negative regulators of lignin biosynthesis and down-regulation of few key genes of the lignin biosynthetic pathway in Crw1 in response to WCR beetle feeding.

| Gene name (ID) | Fold Change(log2) | Presumed Function |
|---|---|---|
| MYB39 (GRMZM2G127857) | +2 | −ve regulator of lignin biosynthesis |
| MYB42 (GRMZM2G419239) | +2.16 | −ve regulator of lignin biosynthesis |
| MYB1 (GRMZM2G005066) | −3.8 | +ve regulator of lignin biosynthesis |
| MYB59 (GRMZM2G093789) | −4.6 | +ve regulator of lignin biosynthesis |
| Hydroxycinnamoyl shikimate quinate transferase-like (NM001139418) | −4.45 | Key enzyme in the lignin biosynthesis |
| COMT (EU964048) | −1.8 | Key enzyme in lignin biosynthesis |

Third, the expression of many of the amino acid biosynthetic and modification genes was upregulated in the Crw1 mutant (Table 3), which, in turn, caused higher levels of relevant amino acids (Table 4). Prominent among these free amino acids were alanine, asparagine, glycine, and serine, all of which have shown to act as potent phagostimulants for WCR beetles.

Table 3 is a list of amino acid biosynthesis or modification genes differentially induced in the mutant vs. wild type siblings of Crw1 in response to WCR feeding. The positive and negative values indicate the fold change of a particular transcript in the Crw1 mutant in comparison to the WT. Alanine amino transferase is involved in the formation of alanine, while serine family amino acid biosynthesis protein-like and glycine hydroxymethyltransferase are involved in the formation of alanine and glycine.

| Gene name (ID) | Fold Change(log2) | Presumed Function |
|---|---|---|
| Aspartate aminotransferase (EU965394) | +2.3 | Aspartate metabolism |
| Alanine amino transferase-like protein (EL01N0413D07) | +1.8 | Alanine metabolism |
| Hypothetical protein (NM001149740) Serine family amino acid biosynthesis-like | +7.3 | Serine family amino acid biosynthesis |
| Glycine hydroxymethyltransferase EU961022 | −2 | Glycine-Serine interconversion |
| Sad1 (NM_001137318) | +1.8 | Shikimic acid biosynthesis |

Table 4 shows growth stage specific leaf metabolite distribution in the Crw1 mutant. The differential metabolite levels are presented as fold change in the mutant in comparison to wild-type. The negative and positive values indicate lower and higher levels respectively, of a particular metabolite in the mutant in comparison to wild-type at a particular growth stage. A zero value in the table indicates no fold change was detected at is that particular growth stage.

| Metabolite Class | Growth Stage | | |
|---|---|---|---|
| | Juvenile | Transition Fold Change | Mature |
| Amino acids | | | |
| Alanine | 0 | +3.1 | +2.5 |
| Asparagine | −3.5 | +2.7 | +9.7 |
| Aspartic Acid | −2.1 | +2.2 | +2.1 |
| Glycine | −1.8 | +2.1 | +2.9 |
| Serine | 0 | +2.5 | +4.8 |
| Tyramine | −2.6 | 0 | +1.9 |
| Threonine | 0 | +1.9 | +1.9 |
| Glutamic Acid | 0 | 0 | +2.1 |
| Sugars | | | |
| Arabinose | 0 | −1.2 | +1.3 |
| Glucose | −2.2 | +1.8 | +1.6 |
| Ribose | 0 | +1.5 | +1.5 |
| Raffinose | 0 | 0 | +1.2 |
| Inositol | −1.1 | −1.1 | +1.1 |
| Organic acids | | | |
| Aconitic Acid | 0 | 0 | +1.1 |
| Alpha-Ketoglutaric Acid | 0 | 0 | +1.7 |
| Cinnamic Acid | 0 | +2.2 | +2.1 |
| Iso-Citric Acid | 0 | 0 | +1.9 |
| Shikimic Acid | 0 | 0 | +2.5 |

Example 4

Identification of Homologs of the Maize CRW1 Polypeptide

The maize CRW1 polypeptide can be analyzed for similarity to all publicly available amino acid sequences contained in the "nr" database using the BLASTP algorithm provided by the National Center for Biotechnology Information (NCBI) as well as to the DUPONT™ proprietary internal databases.

A BLAST search using the sequence of the maize CRW1 polypeptide revealed similarity of the maize CRW1 polypeptide to NAC transcription factors from various organisms. Shown in Table 5 (non-patent literature) and Table 6 (patent literature) are the BLASTP results for the amino acid sequence of the maize CRW1. Also shown in Tables 5 and 6 are the percent sequence identity values for each pair of amino acid sequences using the Clustal W method of alignment with default parameters:

TABLE 5

BLASTP Results for Maize CRW1 Polypeptide (Non-patent)

| UniProt Identifier | % Seq Identity |
|---|---|
| G3M8D2 (SEQ ID NO: 10) | 76.2 |
| Q9SNM6 (SEQ ID NO: 11) | 55.4 |
| C5YM23 (SEQ ID NO: 12) | 85.8 |
| Q5NKS7 (SEQ ID NO: 13) | 52.0 |
| I1MKD6 (SEQ ID NO: 14) | 58.6 |
| I1KHQ4 (SEQ ID NO: 15) | 59.1 |
| Q84WP6 (SEQ ID NO: 16) | 56.2 |
| Q9LPI7 (SEQ ID NO: 17) | 52.3 |
| Q9M274 (SEQ ID NO: 18) | 52.7 |
| B4FPS5 (SEQ ID NO: 19) | 80.3 |
| Q5NKQ3 (SEQ ID NO: 20) | 52.3 |
| *BdCRW1 (SEQ ID NO: 21) | 63.5 |
| F6HU82 (SEQ ID NO: 22) | 56.1 |

TABLE 5-continued

BLASTP Results for Maize CRW1 Polypeptide (Non-patent)

| UniProt Identifier | % Seq Identity |
|---|---|
| *GmCRW1 (SEQ ID NO: 23) | 58.6 |
| G4V2G0 (SEQ ID NO: 24) | 53.4 |
| D9ZJ90 (SEQ ID NO: 25) | 54.8 |
| F2DV83 (SEQ ID NO: 26) | 50.0 |
| Q84WP6 (SEQ ID NO: 27) | 56.2 |

TABLE 6

BLASTP Results for Maize CRW1 Polypeptide (Patent)

| Sequence (SEQ ID NO) | Reference (SEQ ID NO) | BLASTP E-value | Percent Sequence Identity |
|---|---|---|---|
| ZmCRW1 (SEQ ID NO: 3) | SEQ ID NO: 50 in US20110239329 | 8.36e−246 | 100 |
| | SEQ ID NO: 50215 in US20120017338 | 8.36e−246 | 100 |
| | SEQ ID NO: 2528 in US20110258735 | 8.36e−246 | 100 |
| | SEQ ID NO: 2528 in WO2010075143 | 8.36e−246 | 100 |
| | SEQ ID NO: 50 in U.S. Pat. No. 7,994,398 | 8.36e−246 | 100 |
| | SEQ ID NO: 50 in WO2008157370 | 8.36e−246 | 100 |
| | SEQ ID NO: 50 in US20080313777 | 8.36e−246 | 100 |

*The E-value is representative of only the portion that is aligned.

FIGS. 9A-9L present an alignment of the amino acid sequences of the polypeptides set forth in SEQ ID NOs:3, 10, 11, 12, 13, 14, 15, 16, 17, 18, 19, 20, 21, 22, 23, 24, 25, 26, and 27. FIG. 10 presents the percent sequence identities and divergence values for each sequence pair presented in FIGS. 9A-9L.

Sequence alignments and percent identity calculations were performed using the Megalign® program of the LASERGENE® bioinformatics computing suite (DNASTAR® Inc., Madison, Wis.). Multiple alignment of the sequences was performed using the Clustal W method of alignment (Thompson et al. (1994) Nucleic Acids Research. 22:4673-80) with the default parameters (GAP PENALTY=10, GAP LENGTH PENALTY=0.20). Default parameters for pairwise alignments using the Clustal method were GAP PENALTY=10.00 and GAP LENGTH=0.10. The Protein Weight Matrix used was the Gonnet series.

Example 5

Cloning and Validation of the Crw2 Gene

A maize mutant showing enhanced susceptibility to WCR adults was isolated from an EMS population and named crw2-EMS.

Independently, another WCR-susceptible mutant named crw2-Mutag was identified in an F2 population derived from a Mu-active line. The Crw2 mutants showed enhanced susceptibility to WCR adults as well as to Japanese beetles and European Corn Borer (ECB) when evaluated in field testing. Both crw2-EMS and crw2-Mutag segregated as monogenic recessive, mapped to the same region of chromosome 5, and were allelic to each other in reciprocal crosses. A candidate gene was isolated from the crw2-Mutag mutant using co-segregation analysis, and the gene (SEQ ID NO:28) was found to encode a putative Homogalacturonan (HGA1), which is also annotated as "Glycosyltransferase AER61" or a "putative uncharacterized protein". The candidate gene comprised two exons and one intron and encoded a product 445 amino acids (aa) in length (SEQ ID NO:29) with one transmembrane helix (TMH) of 20aa (from amino acid 13-32 of the peptide). The transmembrane helix is expected to localize the protein to ER/Golgi, with the first 12 amino acids of the peptide facing the organelle interior and the rest (from aa 33-455) hanging outside into the cytoplasm. Cloning and sequence of crw2-Mutag (SEQ ID NO:30 is the nucleotide sequence of the cDNA and SEQ ID NO:31 is the amino acid sequence of the encoded polypeptide) revealed that the Mu-element added 145 bp (See alignment FIGS. 11A-11G).

To validate the candidate gene, a set of nested primers was used to amplify the full length gene from the crw2-EMS mutant allele (SEQ ID NO:32 is the nucleotide sequence of the cDNA and SEQ ID NO:33 is the amino acid sequence of the encoded polypeptide) and its progenitor MO20W, a public maize inbred line. A single amino acid change R292C was detected in the crw2-EMS allele as compared to the MO20W HGA1 gene (FIGS. 12A-12F). This amino acid change is in the conserved region of HGA1 and is likely the causative allele of the crw2-EMS mutation. An independent TUSC allele with a Mutator insertion located between the positions of the EMS allele and the Mu-tag allele was isolated and subjected to phenotypic and molecular analyses. The TUSC allele was found to be allelic to crw2-Mutag allele and showed similar enhanced susceptibility to WCR adults and to Japanese beetles. FIG. 13 shows a diagram of the maize Crw2 gene structure and the positions of each of the Crw2 mutations.

Example 6

Identification of Homologs of the Maize CRW2 Polypeptide

The maize CRW2 polypeptide can be analyzed for similarity to all publicly available amino acid sequences contained in the "nr" database using the BLASTP algorithm provided by the National Center for Biotechnology Information (NCBI) as well as to the DUPONT™ proprietary internal databases.

A BLAST search using the sequence of the maize CRW2 (SEQ ID NO:29) polypeptide revealed similarity of the maize CRW2 polypeptide to homogalacturonans from various organisms. Shown in Table 1 (non-patent literature) and Table 2 (patent literature) are the BLASTP results for the amino acid sequence of the maize CRW2. Also shown in Tables 7 and 8 are the percent sequence identity values for each pair of amino acid sequences using the Clustal W method of alignment with default parameters:

TABLE 7

BLASTP Results for Maize CRW2 Polypeptide (Non-patent)

| UniProt Identifier | % Seq Identity |
|---|---|
| C0PDR7 (SEQ ID NO: 34) | 64.5 |
| C4J6G0 (SEQ ID NO: 35) | 60.7 |

TABLE 7-continued

BLASTP Results for Maize CRW2 Polypeptide (Non-patent)

| UniProt Identifier | % Seq Identity |
|---|---|
| Q5Z8T7 (SEQ ID NO: 36) | 86.3 |
| Q6Z0Z4 (SEQ ID NO: 37) | 63.5 |
| C5Z9B2 (SEQ ID NO: 38) | 93.8 |
| C5XTX5 (SEQ ID NO: 39) | 64.7 |
| I1K5F9 (SEQ ID NO: 40) | 40.5 |
| I1KQG2 (SEQ ID NO: 41) | 38.6 |
| Q9LV23 (SEQ ID NO: 42) | 41.9 |
| Q9LV22 (SEQ ID NO: 43) | 36.7 |
| F2DBB4 (SEQ ID NO: 44) | 83.0 |
| I1GWV1 (SEQ ID NO: 45) | 82.4 |
| PnCRW2* (SEQ ID NO: 47) | 89.4 |
| EnCRW2* (SEQ ID NO: 49) | 86.8 |
| NCBI GI No. 356511269 (SEQ ID NO: 50) | 40.0 |

*indicates that the sequence was discovered in an internal proprietary database

TABLE 8

BLASTP Results for Maize CRW2 Polypeptide (Patent)

| Sequence (SEQ ID NO) | Reference (SEQ ID NO) | BLASTP E-value | Percent Sequence Identity |
|---|---|---|---|
| ZmCrw2 (SEQ ID NO: 29) | SEQ ID NO: 38006 in US20120159672 | 1.23e−268 | 100 |
| ZmCrw2 (SEQ ID NO: 29) | SEQ ID NO: 42102 in US20100083407 and U.S. Pat. No. 7,569,389 | 1.23e−268 | 100 |
| ZmCrw2 (SEQ ID NO: 29) | SEQ ID NO: 16309 in US20070214517 and US20060150283 | 1.23e−268 | 100 |

FIGS. 14A-14J show an alignment of the ZmCRW2 protein (SEQ ID NO:29) and its homologs (SEQ ID NOs: 34, 35, 36, 37, 38, 39, 40, 41, 42, 43, 44, 45, 47, 49, and 50). FIG. 15 presents the percent sequence identities and divergence values for each sequence pair presented in FIGS. 14A-14J.

Sequence alignments and percent identity calculations were performed using the Megalign® program of the LASERGENE® bioinformatics computing suite (DNASTAR® Inc., Madison, Wis.). Multiple alignment of the sequences was performed using the Clustal W method of alignment (Thompson et al. (1994) *Nucleic Acids Research.* 22:4673-80) with the default parameters (GAP PENALTY=10, GAP LENGTH PENALTY=0.20). Default parameters for pairwise alignments using the Clustal method were GAP PENALTY=10.00 and GAP LENGTH=0.10. The Protein Weight Matrix used was the Gonnet series.

Example 7

RT-PCR Analysis of the ZmCrw2 Gene in Mutants and Wild-Type Sibs

Total RNA samples were collected from leaf, stalk, and root tissue of 10-day-old seedlings of crw2-Mutag mutants and their WT siblings, and RT-PCR analysis was completed using gene specific primers (FIG. 16A). The crw2-Mutag mutant showed differential expression in three tissues (more in stalk as compared to leaf and root samples) and had a transcript that was 145 bp longer than in WT-sibs. Cloning and sequencing of the crw2-Mutag transcript revealed an interference of Mu-TIR end in differential splicing of the mature transcript. The Mu-element added 141 bp of the MuTIR (Terminal Inverted Repeat) end and 4 bp from a 9 bp direct duplication. This resulted in the frame shift by changing the last 73 amino acids (as compared to the WT) and making the translational product longer by adding 149 additional amino acids. RT-PCR of the crw2-TUSC mutant showed complete absence of Crw2 transcript in leaves as compared to its WT-sibs (FIG. 16B).

Example 8

Expression of ZmCrw2 Gene in Different Tissues Using Lynx Database

The Lynx database shows that the expression of ZmCrw2 was relatively low in different tissues such as elongating internodes (370 PPM), roots (367 PPM), inner husks at silking stage (324 PPM), tassel (310 PPM), and vascular bundles (220 PPM) (FIG. 17). The expression of the ZmCrw2 gene in leaf tissue was highest in V5 leaves (300 PPM); however, expression in V5 leaf tissue went down significantly in response to European Corn Borer (ECB) infection. When V5 leaf whorls were infested with ECB larvae, the expression of ZmCrw2 was 300, 200, 150, and 137 RPMs at 0 h, 3 h, 6 h, and 24 h, respectively, after infestation.

Example 9

Crw1 and Crw2 Pathway Analysis

TBO staining of crw2-EMS resulted in a pattern that is identical to that of crw1-Ac (FIG. 18), suggesting that both of these mutants have defects in a single genetic pathway or network.

To investigate this link further, differences in the Crw2 transcript levels at various time points post—insect feeding were compared between the Crw1 mutant and WT plants. Seven week old plants of crw1-Ac mutants and their WT-sibs were enclosed in a tent in the field and then infested with adult beetles that had been fasting for 16 hours. RNA was collected at 0 min, 45 min, 1 hr, 6 hr, 12 hr, 24 hr, 36 hr, and 48 hr after infestation. RNA samples were then pooled from different time points for the mutants (pool 1) and WT-sibs (pool 2). Crw2 transcript levels were evaluated in each of the two pools at the various time points. A significant upregulation in Crw2 transcript levels was observed immediately (45 min) in the wild-type sibs ("WT-sibs") as compared to crw1-Ac mutant plants (FIG. 19). These results were also confirmed in RNA Seq experiments where the Crw2 transcript was 2.8 times higher (at log 2 scale) in Crw1 WT-sibs (Table 1). These results indicate that Crw2 is insect-inducible and that responsiveness to insect feeding is dependent on having a functional Crw1 product.

These results also suggest that Crw1 and Crw2 belong to the same genetic or biochemical network and Crw2 may be acting downstream of the Crw1 gene.

Example 10

Further Assessment of crw2 Phenotype

Crw2 mutants and corresponding wild-type (WT) siblings were planted in the field at bi-weekly intervals. Plants were assessed for insect damage by the Western corn rootworm (WCR) beetle in the middle of July when the WCR pressure is at its maximum. Irrespective of the availability of young mutant seedlings, the foliar susceptibility phenotype was not observed until the Crw2 mutant plants reached the age of 5 weeks or more. Thereafter, the foliar damage continued to occur steadily and resulted in complete defoliation of the mutant plant under heavy WCR infestation. In addition, Crw2 mutants fell prey to diverse insect herbivores that included Japanese beetles, European corn borer, fall webworm, and cattail caterpillar.

Example 11

Biochemical Characteristics of the Maize Crw2 Gene

Staining of Crw2 mutant leaves with toluidine blue O (TBO), which reacts with free hydroxyl groups in the cell wall, shows reduced staining in intercostal cells, presumably resulting in compromised tensile strength. To test if this was due to reduction in the levels of cell wall bound p-coumaric acid (pCA) and ferulic acid (FA), quantification of these hydroxycinnamates was performed with the juvenile (V3 stage) and adult (V8 stage) epidermal cell walls of both Crw2 and wild-type leaves. A significant reduction in pCA and FA levels was observed in Crw2 mutants as compared to WT siblings, but only in the adult leaves (FIG. 20A).

To address if the reduced levels of hydroxycinnamates also resulted in reduced lignin levels, lignin was extracted from isolated cell walls of adult (V8 stage) Crw2 mutant and WT-sib leaves as acetyl bromide soluble (ABS) fraction and analyzed by UV spectroscopy. The levels of ABS lignin were significantly lower (p<0.05; unpaired t test) in the adult leaves of Crw2 in comparison to wild-type leaves (FIG. 20B).

What is claimed is:

1. A method for reducing herbivory of a maize crop by corn rootworm, European corn borer, and/or Japanese beetle, the method comprising:
   a. growing the maize crop in an area; and
   b. planting a trap crop comprising one or more maize plants with enhanced susceptibility to herbivory by corn rootworm, European corn borer, and/or Japanese beetle due to a reduction in endogenous expression of Crw1 and/or Crw2, within, adjacent to, or within 2 kilometers of the maize crop;
   wherein Crw1 is a NAC transcription factor gene corresponding to a wild-type Crw1 locus encoding a Crw1 protein having at least 97% sequence identity to the amino acid sequence set forth in SEQ ID NO: 3; and
   further wherein Crw2 is a glycosyltransferase gene corresponding to a wild-type Crw2 locus encoding a Crw2 protein having at least 95% sequence identity to the amino acid sequence set forth in SEQ ID NO: 29.

2. The method of claim 1, further comprising:
   a) destroying said corn rootworm, European corn borer, and/or Japanese beetle present on the trap crop;
   b) rotating the area of the trap crop in the next growing season to control the corn rootworm, European corn borer, and/or Japanese beetle in the next generation; or
   c) tilling the soil prior to planting in the next growing season to control the corn rootworm, European corn borer, and/or Japanese beetle in the next generation.

3. The method of claim 1, wherein said trap crop comprises one or more maize plants that comprise a transgene that interferes with the life cycle of the corn rootworm, European corn borer, and/or Japanese beetle.

4. The method of claim 3, wherein said transgene produces dsRNA that is introduced to the corn rootworm, European corn borer, and/or Japanese beetle upon feeding on plants in the trap crop.

5. The method of claim 1, wherein said trap crop is about 10% of the total area comprising the trap crop and maize crop.

6. The method of claim 1, wherein said trap crop is harvested with the maize crop.

* * * * *

SEQUENCE LISTING

```
<160> NUMBER OF SEQ ID NOS: 50

<210> SEQ ID NO 1
<211> LENGTH: 4695
<212> TYPE: DNA
<213> ORGANISM: Zea mays
```

```
<400> SEQUENCE: 1
tgtcgatttt gtgatccaaa ttctgaagaa gacggctaaa ttgacgagcg aagcggaggc      60
tcccccgtct tcgggaggct tatcttttt ttcctaataa gattttatta tattattact     120
ttgtgtgtgc atgcatgtgc actgtatata tatgtcattt gtactttgat gcgagtgaca     180
ccaacagctg gtccatccat atgggagaag aagaagaagc tagtgccaca catatgcatt     240
gatcagctct gtaccaggct agctagctgc ttcttatgta tgcaggcaga tagtagccag     300
gggtagtaat tataattatt atatgaagca gccagagaag aggacacaaa taaaataata     360
gagacgagat gggatggata tatatatata tatatatata tataaagaac acgaatatta     420
gaccaccatc ctcaaaagat tccaaggcta ggcgtgtcaa tatctatagt taagttgtgt     480
gtgtgtgtat atatataaat tctactaatt ccttatatat acacagacat atgtatatga     540
tactatgtac gtaggtacgt gtatatatat gggtacgtcc gtacgagagc aatataacgc     600
atggagcaag agaaatggaa aaccgttggc tttgtcctct ccctttctct ctcttaattt     660
ctactgctcg tagtacgtac tagcaaggat gcagtgcagc acctttcctc tgtctctctc     720
tctctctctc tctctctctc ctgcgtctct ctcaggagtg ggtggcaaaa ctaacccca     780 ctgctactag cagctaggag ctctgcagca gggctagcta gcctgcagtg cactgaccga     840
cgactcttat ctactagaag atgtggtcgt accagtattg tatttgtag agagagagag     900 aaagagctag cagccagcag cagcagcaga tacgtacagg tacaacaagc agagctatct     960
aggtaggtag caacagagag agagagagag tgaagcaggc agaggcagca gcatggaaat    1020
ggaatggtgg ccatatgatt catggatgat gggtgcatgg tggacgcgat cgaatcgaac    1080
gcgatcccct ccccccctcac ccctaattt cactcggatc catgcctgtg tgtgctagct    1140
gccgtcgtcg gccttgcctc gcaaaagtac ccccaacccc ccactatata taagtgcagc    1200
gcctttcctc ccctgccacc accagcttcc ctcctagctc ttctctttcc tcatcatcgt    1260
cttcctcccc tcacatcctc tggcctctgg tcctccaccg tcctgctagc cagagctgct    1320
cttgtacgcg cagctggcct ctgtgcatat caccagcaca ccgcgcaggg gaagaaatt     1380 aacaagagaa aaggcaagga gagcaggcag gcaaggaagc tgcagaagcc aaggaaggag    1440
aaggaggatc atcaatgagc atctcggtga acggcagtc gtgcgtgccg ccggggttcc    1500
gcttccaccc cacggaggag gagctgctca actactacct ccgcaagaag gtggcctccc    1560
aggagatcga cctcgacgtc atccgcgacg tcgacctcaa caagctcgag ccatgggaca    1620
tccaaggtac gtacgtacgc acggccggtc cggtccgatc cggtaccact gccttcttca    1680
acttcaagtt caagcacgcg cgcgcgcagt agcagagcag ctcgtggtcg tggatcagat    1740
cggatcggag ctggtgcacg accatgagag cacggacatg aacatgaaca gaccttgttg    1800
tgaatgcaac tgccttagct agctaccaag caagtactct cgttcgtaca gcagcatgta    1860
tagcttatgt tcgttgatcg acaaaactag ctagcaaaca atcaaacgcg atcgaattca    1920
tcgcgcgcta actactggct aacaactgct actactacta aagccgctag ctccattcca    1980
tgcatggaaa tcgcgcgcag agaaatgcaa gatcgggtcg ggtccccaga acgactggta    2040
cttcttcagc cacaaggaca agaagtaccc gacgggacg cgcaccaacc gcgccacggc    2100
cgccgggttc tggaaggcca ccggccgcga caaggccatc tacaacgccg tcaagcgcat    2160
cggcatgcgc aagacgctcg tcttctacaa gggccgcgcg ccgcacggcc agaagtccga    2220
ctggatcatg cacgagtacc gcctcgacga ccccgctgct gctgctgctg ctggatccgg    2280
tgatgccgtg gccaacgacg acgcagccgc cacggtaagc aaagcaacga ccctgatcgc    2340
```

-continued

```
cgttaatctc ttctctgcac caccagttca cgtacgccac cattaataat tgcctgccgt    2400
aagataagaa acaattatat ggcggtggtg gtgcaatcat gcgagtacgg cgacccgcct    2460
tgatttgatc cagctccagg ctcaaggctc cggccgtatt tttttccgct ctcttgtttt    2520
gattgattga tgaggaggag agagagagca gtaggcgcta gctactagct agctagggga    2580
aggagggagg gacggacgta gtaataatta ttaaactttg ccatgtgcct catgtgcccc    2640
aaaaggtagc aataattaac actgctgcac tgttttttttt taatctgctt cttgtcgact    2700
tgtcgtcggc ggcgatgtcg cggtggacag gctgctgctg ctgccgccgc gtcgtcggac    2760
ggcgggcagg aggacggctg ggtggtgtgc agggtgttca agaagaagca ccaccacaag    2820
gagtcaggtg ggggcggggg caacaagcac ggcagcagta acagcgagca tgggcacggc    2880
ggcgccggca aggcatcggc tgcggctgcg gctgcggcgc accagcacca gcaccatgga    2940
ggcctgcagt actcctccag cgacgaggcg ctggaccaga tcctgcagta catgggcagg    3000
tcgtgcaagc aggagcacga gctggtgtcg ccggcgccgg cgccgccggg acgggcggcg    3060
gcgtccaggt acctccggcc catcgagacc gttctgggcg gcacgcgtt catgaagctt    3120 cccgcgctcg agagcccgtc cgcggccgcg tccgcatcgc tgacacagcc ggcgcagcac    3180
gacgagctct accgcgccgc cgggaacggg atcacggact gggccatgat ggaccggctg    3240
gtggcgtcgc acctgaacgg gcagcaggcg cccgccgcgg cggaccagct cggcggcggc    3300
tgcggcttcg acgcggacgc cggcgccgaa gacgcggacg ccggcctcgc cttctactcc    3360
gccgccgcca gccggctgct cggctccggc ggcggcgccg gcagcgacga cgacctgtgg    3420
agcttcacgc ggtcgtcggt ttcgtcaacg cggcggcgg cggccacgtc cacggagcgg    3480
ctcagccacg tgtcactgta gacgccgttc ttcgtcgccg tcgccgtcgc cttaactatg    3540
tacgtacgta cgtcgtaagc ccctacgtga tgacatggcc agcatgccct ggtggtacac    3600
gtactagtaa agaagagaca aacaccaaca gcaggagcag agagagagaa agaggaaata    3660
aaagaagggt ctctagagag agagagagtg atttcagagg aggtgattag agtgatgaga    3720
gagactgaaa gtagatcgat ggatcgctga ttcgctgata cgattaaagc tggcagtaag    3780
ttggagtggc actgtcactc ggacgccaca tgcatcatct ctccttctta tagcttcatt    3840
ctctctccat catctcagcc actgtttaat taacccccgg ccaccgattg ttattactat    3900
aatatataac cacagcattt tactagcaga ttgatactac atctaccact gttactatat    3960
attagattgt tcatttcaat ataattagga gagagaggag gggagtaatt aattgacagc    4020
gagcagcatg gcaaaaacag tgtaaggcga ttattattgc tggtttgttt actagtacct    4080
acctacgtac gtgctgtggg cggtgtgtgt gcatggtgtt tgcagtttgc acatgtgcat    4140
cctttatttt taattattcc catgactata tatatagata ttaaatatac atgcaggttg    4200
tatctatcta tctatacata caaattgcat ttctgtctgt ctctccctct gaatatgaat    4260
gatacccgtg cattaatttg tccgtggctg ccagctgcat caatttccac ctgtgtgaga    4320
tatatatagt cctaaccaac acttgaccat gcattctttt tttttcttgg acaatagagc    4380
taatgagcta taggtaccag ccagtagcta atttgtagct agctacagat agcctctaga    4440
gcgtccggcg gccctggcta ggtgtgtcct atcatgcatc acccagccat taactttgaa    4500
ttgcctttat ctgcgttgaa tgcatgcatg tatgtatgcc ctctaacaac agatgccatt    4560
aggccgtctc gtttaattag gacactgaca cgcgcgttct tcaacgtgac actttgacat    4620 gcaatttttcg ttacctccgc cgcgcgtgtg tgccaaagat gatgccacca taagttatgg    4680
tttaaatgga gctat                                                    4695
```

<210> SEQ ID NO 2
<211> LENGTH: 1257
<212> TYPE: DNA
<213> ORGANISM: Zea mays

<400> SEQUENCE: 2

| | | |
|---|---|---|
| atgagcatct cggtgaacgg gcagtcgtgc gtgccgccgg ggttccgctt ccaccccacg | 60 |
| gaggaggagc tgctcaacta ctacctccgc aagaaggtgg cctcccagga gatcgacctc | 120 |
| gacgtcatcc gcgacgtcga cctcaacaag ctcgagccat gggacatcca agagaaatgc | 180 |
| aagatcgggt cgggtcccca gaacgactgg tacttcttca gccacaagga caagaagtac | 240 |
| ccgacgggga cgcgcaccaa ccgcgccacg gccgccgggt tctggaaggc caccggccgc | 300 |
| gacaaggcca tctacaacgc cgtcaagcgc atcggcatgc gcaagacgct cgtcttctac | 360 |
| aagggccgcg cgccgcacgg ccagaagtcc gactggatca tgcacgagta ccgcctcgac | 420 |
| gaccccgctg ctgctgctgc tgctggatcc ggtgatgccg tggccaacga cgacgcagcc | 480 |
| gccacggctg ctgctgctgc cgccgcgtcg tcggacggcg gcaggagga cggctgggtg | 540 |
| gtgtgcaggg tgttcaagaa gaagcaccac acaaggagt caggtggggg cggggcaac | 600 |
| aagcacggca gcagtaacag cgagcatggg cacggcggcg ccggcaaggc atcggctgcg | 660 |
| gctgcggctg cggcgcacca gcaccagcac catggaggcc tgcagtactc ctccagcgac | 720 |
| gaggcgctgg accagatcct gcagtacatg ggcaggtcgt gcaagcagga gcacgagctg | 780 |
| gtgtcgccgg cgccggcgcc gccgggacgg gcggcggcgt ccaggtacct ccggcccatc | 840 |
| gagaccgttc tgggcgggca cgcgttcatg aagcttcccg cgctcgagag cccgtccgcg | 900 |
| gccgcgtccg catcgctgac acagccggcg cagcacgacg agctctaccg cgccgccggg | 960 |
| aacgggatca cggactgggc catgatggac cggctggtgg cgtcgcacct gaacgggcag | 1020 |
| caggcgcccg ccgcggcgga ccagctcggc ggcggctgcg gcttcgacgc ggacgccggc | 1080 |
| gccgaagacg cggacgccgg cctcgccttc tactccgccg ccgccagccg gctgctcggc | 1140 |
| tccggcggcg gcgccggcag cgacgacgac ctgtggagct tcacgcggtc gtcggtttcg | 1200 |
| tcaacggcgg cggcggcggc cacgtccacg gagcggctca gccacgtgtc actgtag | 1257 |

<210> SEQ ID NO 3
<211> LENGTH: 418
<212> TYPE: PRT
<213> ORGANISM: Zea mays

<400> SEQUENCE: 3

Met Ser Ile Ser Val Asn Gly Gln Ser Cys Val Pro Pro Gly Phe Arg
1               5                   10                  15

Phe His Pro Thr Glu Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Asn Ala Val Lys Arg Ile Gly
            100                 105                 110

```
Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Asp Pro Ala Ala
130                 135                 140

Ala Ala Ala Ala Gly Ser Gly Asp Ala Val Ala Asn Asp Asp Ala Ala
145                 150                 155                 160

Ala Thr Ala Ala Ala Ala Ala Ala Ser Ser Asp Gly Gly Gln Glu
                165                 170                 175

Asp Gly Trp Val Val Cys Arg Val Phe Lys Lys His His His Lys
            180                 185                 190

Glu Ser Gly Gly Gly Gly Asn Lys His Gly Ser Ser Asn Ser Glu
        195                 200                 205

His Gly His Gly Gly Ala Gly Lys Ala Ser Ala Ala Ala Ala Ala
        210                 215                 220

Ala His Gln His Gln His His Gly Gly Leu Gln Tyr Ser Ser Ser Asp
225                 230                 235                 240

Glu Ala Leu Asp Gln Ile Leu Gln Tyr Met Gly Arg Ser Cys Lys Gln
                245                 250                 255

Glu His Glu Leu Val Ser Pro Ala Pro Ala Pro Pro Gly Arg Ala Ala
                260                 265                 270

Ala Ser Arg Tyr Leu Arg Pro Ile Glu Thr Val Leu Gly Gly His Ala
            275                 280                 285

Phe Met Lys Leu Pro Ala Leu Glu Ser Pro Ser Ala Ala Ser Ala
        290                 295                 300

Ser Leu Thr Gln Pro Ala Gln His Asp Glu Leu Tyr Arg Ala Gly
305                 310                 315                 320

Asn Gly Ile Thr Asp Trp Ala Met Met Asp Arg Leu Val Ala Ser His
                325                 330                 335

Leu Asn Gly Gln Gln Ala Pro Ala Ala Asp Gln Leu Gly Gly Gly
            340                 345                 350

Cys Gly Phe Asp Ala Asp Ala Gly Ala Glu Asp Ala Asp Ala Gly Leu
        355                 360                 365

Ala Phe Tyr Ser Ala Ala Ala Ser Arg Leu Leu Gly Ser Gly Gly Gly
        370                 375                 380

Ala Gly Ser Asp Asp Asp Leu Trp Ser Phe Thr Arg Ser Ser Val Ser
385                 390                 395                 400

Ser Thr Ala Ala Ala Ala Ala Thr Ser Thr Glu Arg Leu Ser His Val
                405                 410                 415

Ser Leu

<210> SEQ ID NO 4
<211> LENGTH: 1265
<212> TYPE: DNA
<213> ORGANISM: Zea mays

<400> SEQUENCE: 4
atgagcatct cggtgaacgg gcagtcgtgc gtgccgccgg ggttccgctt ccaccccacg      60
gaggaggagc tgctcaacta ctagtctact acctccgcaa gaaggtggcc tcccaggaga    120
tcgacctcga cgtcatccgc gacgtcgacc tcaacaagct cgagccatgg acatccaag     180 agaaatgcaa gatcgggtcg ggtccccaga cgactggta cttcttcagc cacaaggaca    240
agaagtaccc gacggggacg cgcaccaacc gcgccacggc cgccgggttc tggaaggcca   300
ccggccgcga caaggccatc tacaacgccg tcaagcgcat cggcatgcgc aagacgctcg   360
```

```
tcttctacaa gggacgcgcg ccgcacggcc agaagtccga ctggatcatg cacgagtacc    420
gcctcgacga ccccgctgct gctgctgctg ctggatccgg tgatgccgtg gccaacgacg    480
acgcagccgc cacggctgct gctgctgccg ccgcgtcgtc ggacggcggg caggaggacg    540
gctgggtggt gtgcagggtg ttcaagaaga agcaccacca caaggagtca ggtgggggcg    600
ggggcaacaa gcacggcagc agtaacagcg agcatgggca cggcggcgcc ggcaaggcat    660
cggctgcggc tgcggctgcg cgcaccagc accagcacca tggaggcctg cagtactcct    720
ccagcgacga ggcgctggac cagatcctgc agtacatggg caggtcgtgc aagcaggagc    780
acgagctggt gtcgccggcg ccggcgccgc cgggacgggc ggcggcgtcc aggtacctcc    840
ggcccatcga gaccgttctg gcgggcacg cgttcatgaa gcttcccgcg ctcgagagcc    900
cgtccgcggc cgcgtccgca tcgctgacac agccggcgca gcacgacgag ctctaccgcg    960
ccgccgggaa cgggatcacg gactgggcca tgatggaccg gctggtggcg tcgcacctga   1020
acgggcagca ggcgcccgcc gcggcggacc agctcggcgg cggctgcggc ttcgacgcgg   1080
acgccggcgc cgaagacgcg gacgccggcc tcgccttcta ctccgccgcc gccagccggc   1140
tgctcggctc cggcggcggc gccggcagcg acgacgacct gtggagcttc acgcggtcgt   1200
cggtttcgtc aacggcggcg gcggcggcca cgtccacgga gcggctcagc cacgtgtcac   1260
tgtag                                                               1265

<210> SEQ ID NO 5
<211> LENGTH: 27
<212> TYPE: PRT
<213> ORGANISM: Zea mays

<400> SEQUENCE: 5

Met Ser Ile Ser Val Asn Gly Gln Ser Cys Val Pro Pro Gly Phe Arg
1               5                   10                  15

Phe His Pro Thr Glu Glu Glu Leu Leu Asn Tyr
            20                  25

<210> SEQ ID NO 6
<211> LENGTH: 1258
<212> TYPE: DNA
<213> ORGANISM: Zea mays

<400> SEQUENCE: 6
atgagcatct cggtgaacgg gcagtcgtgc gtgccgccgg ggttccgctt ccaccccacg     60
gaggaggagc tgctcaacta ctacctccgc aagaaggtgg cctcccagga gatcgacctc    120
gacgtcatcc gcgacgtcga cctcaacaag ctcgagccat gggacatcca agagaaatgc    180
aagatcgggt cgggtcccca gaacgactgg tacttcttca gccacaagga caagaagtac    240
ccgacgggga cgcgcaccaa ccgcgccacg gccgccgggt ctggaaggc accggccgc     300 gacaaggcca tctacaacgc cgtcaagcgc atcggcatgc gcaagacgct cgtcttctac    360
aagggcccgg gcgccgcacg gccagaagtc cgactggatc atgcacgagt accgcctcga    420
cgaccccgct gctgctgctg ctgctggatc cggtgatgcc gtggccaacg acgacgcagc    480
cgccacggct gctgctgctg ccgccgcgtc gtcggacggc gggcaggagg acggctgggt    540
ggtgtgcagg gtgttcaaga agaagcacca ccacaaggag tcaggtgggg gcggggcaa    600 caagcacggc agcagtaaca gcgagcatgg gcacggcggc gccggcaagg catcggctgc    660
ggctgcggct gcgcgcacc agcaccagca ccatggaggc ctgcagtact cctccagcga    720
cgaggcgctg gaccagatcc tgcagtacat gggcaggtcg tgcaagcagg agcacgagct    780
```

| | |
|---|---:|
| ggtgtcgccg gcgccggcgc cgccgggacg ggcggcggcg tccaggtacc tccggcccat | 840 |
| cgagaccgtt ctgggcgggc acgcgttcat gaagcttccc gcgctcgaga gcccgtccgc | 900 |
| ggccgcgtcc gcatcgctga cacagccggc gcagcacgac gagctctacc gcgccgccgg | 960 |
| gaacgggatc acggactggg ccatgatgga ccggctggtg gcgtcgcacc tgaacgggca | 1020 |
| gcaggcgccc gccgcggcgg accagctcgg cggcggctgc ggcttcgacg cggacgccgg | 1080 |
| cgccgaagac gcggacgccg gcctcgcctt ctactccgcc gccgccagcc ggctgctcgg | 1140 |
| ctccggcggc ggcgccggca gcgacgacga cctgtggagc ttcacgcggt cgtcggtttc | 1200 |
| gtcaacggcg gcggcggcgg ccacgtccac ggagcggctc agccacgtgt cactgtag | 1258 |

```
<210> SEQ ID NO 7
<211> LENGTH: 151
<212> TYPE: PRT
<213> ORGANISM: Zea mays

<400> SEQUENCE: 7

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Asn Ala Val Lys Arg Ile Gly
            100                 105                 110

Met Arg Lys Thr Leu Val Phe Tyr Lys Gly Pro Gly Ala Ala Arg Pro
        115                 120                 125

Glu Val Arg Leu Asp His Ala Arg Val Pro Pro Arg Pro Arg Cys
    130                 135                 140

Cys Cys Cys Cys Trp Ile Arg
145                 150

<210> SEQ ID NO 8
<211> LENGTH: 1297
<212> TYPE: DNA
<213> ORGANISM: Zea mays

<400> SEQUENCE: 8
```

| | |
|---|---:|
| atgagcatct cggtgaacgg gcagtcgtgc gtgccgccgg ggttccgctt ccaccccacg | 60 |
| gaggaggagc tgctcaacta ctacctccgc aagaaggtgg cctcccagga gatcgacctc | 120 |
| gacgtcatcc gcgacgtcga cctcaacaag ctcgagccat gggacatcca agagaaatgc | 180 |
| aagatcgggt cgggtcccca gaacgactgg tacttcttca gccacaagga caagaagtac | 240 |
| ccgacgggga cgcgcaccaa ccgcgccacg gccgccgggt tctggaaggc caccggccgc | 300 |
| gacaaggcca tctacaacgc cgtcaagcgc atcggcatgc gcaagacgct cgtcttctac | 360 |
| aaagggaccgg gcgccgcacg gccagaagtc cgactggatc atgcacgagt accgcctcga | 420 |
| cgaccccgct gctgctgctg ctgctggatc cggtaacctg ctggatccgc tgctgctgga | 480 |
| tcatgcacga gtatctgctg atgccgtggc caacgacgcc gctgccgctg ccgccacggc | 540 |

```
tgctgctgct gccgccgcgt cgtcggacgg cgggcaggag gacggctggg tggtgtgcag      600
ggtgttcaag aagaagcacc accacaagga gtcaggcggg ggcggggggtg gcaagcacgg     660
cagcagtaac agcgagcgtg ggcacggcgg cgccggcaag gcatcggcgg cggctgccgg     720
gaaccagctc cacggaggcc tgcagtactc ctccagcgac gaggcgctgg accagatcct     780
gcagtacatg ggcaggtcgt gcaagcagga gcacgagctg gtgtcgccgg cgccggcgcc     840
gccgggacgg gcggcggcgt ccaggtacct ccggcccatc gagaccgttc tgggcgggca     900
cgcgttcatg aagctgcccg cgctcgagag cccgtccgcg gccgcggccg catcgctgac     960
acagccggcg cagcacgacg agctctaccg cgccgcgggg aacgggatca cggactgggc    1020
catgatggac cggctggtgg cgtcgcacct gaacgggcag caggcgcccg ccgcggcgga    1080
ccagctcggc ggcggctgcg gcttcgacgg ggacgccggc gccgaagacg cggacgccgg    1140
cctcgccttc tactccgccg ccgccagccg gctgctcggc tccggcggcg cgccggcag    1200
cgacgacgac ctgtggagct tcacgcggtc gtcggtttcg tcaacggcgg cggcggcggc    1260
cacgtccacg gagcggctca gccacgtgtc actgtag                            1297
```

<210> SEQ ID NO 9
<211> LENGTH: 151
<212> TYPE: PRT
<213> ORGANISM: Zea mays

<400> SEQUENCE: 9

Met Ser Ile Ser Val Asn Gly Gln Ser Cys Val Pro Pro Gly Phe Arg
1               5                   10                  15

Phe His Pro Thr Glu Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Asn Ala Val Lys Arg Ile Gly
            100                 105                 110

Met Arg Lys Thr Leu Val Phe Tyr Lys Gly Thr Gly Ala Ala Arg Pro
        115                 120                 125

Glu Val Arg Leu Asp His Ala Arg Val Pro Arg Arg Pro Arg Cys
    130                 135                 140

Cys Cys Cys Cys Trp Ile Arg
145                 150

<210> SEQ ID NO 10
<211> LENGTH: 400
<212> TYPE: PRT
<213> ORGANISM: Oryza sativa

<400> SEQUENCE: 10

Met Ser Ile Ser Val Asn Gly Gln Ser Cys Val Pro Pro Gly Phe Arg
1               5                   10                  15

Phe His Pro Thr Glu Glu Glu Leu Leu Asn Tyr Tyr Leu Arg Lys Lys
            20                  25                  30

```
Val Ala Ser Glu Gln Ile Asp Leu Asp Val Ile Arg Asp Val Asp Leu
             35                  40                  45

Asn Lys Leu Glu Pro Trp Asp Ile Gln Glu Arg Cys Lys Ile Gly Ser
 50                  55                  60

Gly Pro Gln Asn Asp Trp Tyr Phe Phe Ser His Lys Asp Lys Lys Tyr
 65                  70                  75                  80

Pro Thr Gly Thr Arg Thr Asn Arg Ala Thr Ala Ala Gly Phe Trp Lys
                 85                  90                  95

Ala Thr Gly Arg Asp Lys Ala Ile Tyr Asn Ala Val His Arg Ile Gly
                100                 105                 110

Met Arg Lys Thr Leu Val Phe Tyr Lys Gly Arg Ala Pro His Gly Gln
                115                 120                 125

Lys Ser Asp Trp Ile Met His Glu Tyr Arg Leu Asp Asp Pro Ala Thr
130                 135                 140

Asp Thr Ala Ala Ala Thr Pro Thr Val Thr Ser Ala Ala Ala Ala Ala
145                 150                 155                 160

Ala Ala Met Ala Ala Ala Asp Gly Gly Gln Glu Asp Gly Trp Val
                165                 170                 175

Val Cys Arg Val Phe Lys Lys Lys His His Lys Glu Ala Gly Gly
                180                 185                 190

Gly Gly Gly Lys His Gly Gly Asp Gly Ser Ala Gly Ala Lys Ala Ala
                195                 200                 205

His Ala Tyr Ser Ser Ser Asp Asp Ala Leu Asp Gln Ile Leu Gln Tyr
                210                 215                 220

Met Gly Arg Ser Cys Lys Gln Glu His Glu Leu Pro Ser Pro Gln Ala
225                 230                 235                 240

Ser Gly Gly Gly Gly Ala Gly Ala Gly Ser Arg Pro Ala Ser Arg Tyr
                245                 250                 255

Leu Arg Pro Ile Asp Thr Val Leu Gly Gly His Gly Phe Met Lys Leu
                260                 265                 270

Pro Pro Leu Glu Ser Pro Ser Ala Ala Thr Ala Leu Ser Ser Thr Pro
                275                 280                 285

Ser Thr Gly Gly Asp Ala Ala Ser Ala Ala Ala Ala Ala Asp
290                 295                 300

His Leu Leu Leu His His His Arg Thr Asp Trp Ala Met Met Asp
305                 310                 315                 320

Arg Leu Val Ala Ser His Leu Asn Gly Ala Asn Ser Asp Ala Pro Asp
                325                 330                 335

Asp Gln Leu Cys Phe Asp Ala Ala Asp Asp Gly Leu Ala Tyr Tyr
                340                 345                 350

Ser Ala Ala Ala Thr Arg Leu Leu Gly Gly Ala Asn Ala Gly Thr Asp
                355                 360                 365

Asp Asp Leu Trp Ser Phe Ala Arg Ser Ala Ala Pro Pro Pro Pro
                370                 375                 380

Pro Pro Pro Ser Ser Ala Thr Pro Glu Arg Leu Ser His Val Ala Leu
385                 390                 395                 400

<210> SEQ ID NO 11
<211> LENGTH: 395
<212> TYPE: PRT
<213> ORGANISM: Oryza sativa
```

```
<400> SEQUENCE: 11

Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
                20                  25                  30

Val Ala Ser Glu Arg Ile Asp Leu Asp Val Ile Arg Asp Val Asp Leu
            35                  40                  45

Asn Lys Leu Glu Pro Trp Asp Ile Gln Glu Arg Cys Arg Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Gly Phe Trp Lys
                85                  90                  95

Ala Thr Gly Arg Asp Lys Ala Ile Tyr Ser Ser Ser Asn Arg Ile Gly
            100                 105                 110

Met Arg Lys Thr Leu Val Phe Tyr Lys Gly Arg Ala Pro His Gly Gln
                115                 120                 125

Lys Ser Asp Trp Ile Met His Glu Tyr Arg Leu Asp Asp Pro Ser Ser
    130                 135                 140

Ala Ser Ala Ser Val Ser Val Asn Leu Pro Ser Tyr Tyr Ser Ser Ser
145                 150                 155                 160

Ser Ser Ser Ser Ser Pro Met His Gly Val Ala Gly Asp Gln Gly Ala
                165                 170                 175

Gln Glu Glu Gly Trp Val Ile Cys Arg Val Phe Lys Lys Lys Asn Leu
            180                 185                 190

Val His His Gly Gly Gly Ala Ala Ala Ala Ser His His Ala Ala Ala
                195                 200                 205

Lys Leu Ala Ala Ala Ala Met Glu Gly Ser Pro Ser Asn Cys Ser Thr
    210                 215                 220

Val Thr Val Ser Asp His Val Lys Ala Gln Met Leu His Ser Ser Ala
225                 230                 235                 240

Ser Asp Asp Ala Leu Asp His Ile Leu Gln Tyr Met Gly Arg Ser Gly
                245                 250                 255

Cys Lys Gln Glu Thr Lys Pro Ala Ala Met Ser Ala Ser Ser Ala Ala
            260                 265                 270

Ala Ala Ala Ala Leu Glu Gln His Leu Ser Thr Pro Gln Tyr Gly Lys
    275                 280                 285

Phe Met Lys Leu Pro Pro Leu Glu His Val Ala Gly Gly Val Gly Leu
290                 295                 300

Leu Ala Ala Ala Gly Gly Gly Glu Tyr Cys Ser Ala Ala Asp Ala
305                 310                 315                 320

Ser Gly Ile Ala Asp Trp Asp Thr Leu Asp Arg Leu Ala Ala Ser Tyr
                325                 330                 335

Glu Leu Asn Gly Ala Leu Ser Asp Val Ala Ser Gly Lys Asn Met Ala
            340                 345                 350

Gly Phe Phe Asp Val Val Asp Gln Pro Ala Gly Ala Ala Phe Ser
                355                 360                 365

Ser Gly Asp Gly Asp Leu Trp Ser Leu Ala Arg Ser Val Ser Ser Ser
    370                 375                 380

Leu His Ala Asp Leu Thr Thr Met Asn Asn Val
385                 390                 395
```

<210> SEQ ID NO 12
<211> LENGTH: 419
<212> TYPE: PRT
<213> ORGANISM: Sorghum bicolor

<400> SEQUENCE: 12

| | | | | | | | | | | | | | | |
|---|---|---|---|---|---|---|---|---|---|---|---|---|---|---|
| Met | Ser | Ile | Ser | Val | Asn | Gly | Gln | Ser | Cys | Val | Pro | Pro | Gly | Phe | Arg |
| 1 | | | | 5 | | | | | 10 | | | | | 15 | |

| Phe | His | Pro | Thr | Glu | Glu | Leu | Leu | Asn | Tyr | Tyr | Leu | Arg | Lys | Lys |
|---|---|---|---|---|---|---|---|---|---|---|---|---|---|---|
| | | | 20 | | | | | 25 | | | | | 30 | |

| Val | Ala | Ser | Gln | Glu | Ile | Asp | Leu | Asp | Val | Ile | Arg | Asp | Val | Asp | Leu |
|---|---|---|---|---|---|---|---|---|---|---|---|---|---|---|---|
| | | | 35 | | | | | 40 | | | | | 45 | | |

| Asn | Lys | Leu | Glu | Pro | Trp | Asp | Ile | Gln | Glu | Lys | Cys | Lys | Ile | Gly | Ser |
|---|---|---|---|---|---|---|---|---|---|---|---|---|---|---|---|
| | 50 | | | | | 55 | | | | | 60 | | | | |

| Gly | Pro | Gln | Asn | Asp | Trp | Tyr | Phe | Phe | Ser | His | Lys | Asp | Lys | Lys | Tyr |
|---|---|---|---|---|---|---|---|---|---|---|---|---|---|---|---|
| 65 | | | | | 70 | | | | | 75 | | | | | 80 |

| Pro | Thr | Gly | Thr | Arg | Thr | Asn | Arg | Ala | Thr | Ala | Ala | Gly | Phe | Trp | Lys |
|---|---|---|---|---|---|---|---|---|---|---|---|---|---|---|---|
| | | | | 85 | | | | | 90 | | | | | 95 | |

| Ala | Thr | Gly | Arg | Asp | Lys | Ala | Ile | Tyr | Asn | Ala | Val | Lys | Arg | Ile | Gly |
|---|---|---|---|---|---|---|---|---|---|---|---|---|---|---|---|
| | | | | 100 | | | | | 105 | | | | | 110 | |

| Met | Arg | Lys | Thr | Leu | Val | Phe | Tyr | Lys | Gly | Arg | Ala | Pro | His | Gly | Gln |
|---|---|---|---|---|---|---|---|---|---|---|---|---|---|---|---|
| | | | | 115 | | | | | 120 | | | | | 125 | |

| Lys | Ser | Asp | Trp | Ile | Met | His | Glu | Tyr | Arg | Leu | Asp | Asp | Pro | Ala | Ala |
|---|---|---|---|---|---|---|---|---|---|---|---|---|---|---|---|
| | 130 | | | | | 135 | | | | | 140 | | | | |

| Ser | Gly | Asp | Ala | Ala | Ala | Ala | Thr | Ala | Ala | Ala | Ala | Ala | Thr | Val |
|---|---|---|---|---|---|---|---|---|---|---|---|---|---|---|
| 145 | | | | | 150 | | | | | 155 | | | | | 160 |

| Ala | Ala | Ala | Ala | Ala | Ser | Ser | Asp | Gly | Gly | Gln | Glu | Asp | Ala | Trp | Val |
|---|---|---|---|---|---|---|---|---|---|---|---|---|---|---|---|
| | | | | 165 | | | | | 170 | | | | | 175 | |

| Val | Tyr | Arg | Val | Phe | Lys | Lys | Lys | His | His | His | Lys | Glu | Ser | Ser | Gly |
|---|---|---|---|---|---|---|---|---|---|---|---|---|---|---|---|
| | | | 180 | | | | | 185 | | | | | 190 | | |

| Gly | Gly | Gly | Gly | Ser | Lys | His | Gly | Gly | Ser | Asn | Asn | Glu | His | Gly | His |
|---|---|---|---|---|---|---|---|---|---|---|---|---|---|---|---|
| | | | 195 | | | | | 200 | | | | | 205 | | |

| Gly | Gly | Gly | Lys | Ala | Ala | Ala | Ala | Ala | Ala | Ala | Ala | His | Gln | His |
|---|---|---|---|---|---|---|---|---|---|---|---|---|---|---|
| | 210 | | | | | 215 | | | | | 220 | | | | |

| His | Gly | Gly | Leu | Gln | Tyr | Ser | Ser | Ser | Asp | Asp | Ala | Leu | Asp | Gln | Ile |
|---|---|---|---|---|---|---|---|---|---|---|---|---|---|---|---|
| 225 | | | | | 230 | | | | | 235 | | | | | 240 |

| Leu | Gln | Tyr | Met | Gly | Arg | Ser | Cys | Lys | Gln | Glu | His | Glu | Leu | Leu | Ser |
|---|---|---|---|---|---|---|---|---|---|---|---|---|---|---|---|
| | | | | 245 | | | | | 250 | | | | | 255 | |

| Pro | Pro | Pro | Pro | Gly | Arg | Ala | Ala | Ser | Arg | Tyr | Leu | Arg | Pro | Ile | Glu |
|---|---|---|---|---|---|---|---|---|---|---|---|---|---|---|---|
| | | | 260 | | | | | 265 | | | | | 270 | | |

| Thr | Val | Leu | Gly | Gly | His | Gly | Phe | Met | Lys | Leu | Pro | Pro | Leu | Glu | Ser |
|---|---|---|---|---|---|---|---|---|---|---|---|---|---|---|---|
| | | | 275 | | | | | 280 | | | | | 285 | | |

| Pro | Ser | Ala | Ala | Ala | Ala | Met | Thr | Pro | Gln | Ala | Val | Ser | Gly | Asp | Ala |
|---|---|---|---|---|---|---|---|---|---|---|---|---|---|---|---|
| | 290 | | | | | 295 | | | | | 300 | | | | |

| Gly | Val | Val | Asp | Asp | Leu | Leu | Gly | Leu | His | Arg | Gly | Gly | Ile | Gly | Asn |
|---|---|---|---|---|---|---|---|---|---|---|---|---|---|---|---|
| | 305 | | | | | 310 | | | | | 315 | | | | 320 |

| Gly | Ile | Thr | Asp | Trp | Ala | Met | Met | Asp | Arg | Leu | Val | Ala | Ser | His | Leu |
|---|---|---|---|---|---|---|---|---|---|---|---|---|---|---|---|
| | | | | 325 | | | | | 330 | | | | | 335 | |

| Asn | Gly | Gln | Glu | Ala | Pro | Asp | Val | Ala | Pro | Ala | Ala | Asp | Gln | Leu | Gly |
|---|---|---|---|---|---|---|---|---|---|---|---|---|---|---|---|
| | | | 340 | | | | | 345 | | | | | 350 | | |

| Ser | Cys | Phe | Asp | Asp | Ala | Thr | Gly | Ala | Asp | Asp | Ala | Asp | Ala | Ala | Gly |
|---|---|---|---|---|---|---|---|---|---|---|---|---|---|---|---|
| | | | 355 | | | | | 360 | | | | | 365 | | |

| Leu | Ala | Phe | Tyr | Ser | Ala | Ala | Ala | Asn | Arg | Leu | Leu | Val | Gly | Ser | Ala |
|---|---|---|---|---|---|---|---|---|---|---|---|---|---|---|---|
| | 370 | | | | | 375 | | | | | 380 | | | | |

```
Gly Ser Ser Gly Ala Gly Ser Asp Asp Asp Leu Trp Ser Phe Thr Arg
385                 390                 395                 400

Ser Ser Ala Ala Ala Ala Ala Thr Ser Thr Glu Arg Leu Ser His
                405                 410                 415

Val Ser Leu

<210> SEQ ID NO 13
<211> LENGTH: 428
<212> TYPE: PRT
<213> ORGANISM: Sorghum bicolor

<400> SEQUENCE: 13

Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
                20                  25                  30

Val Ala Ser Glu Arg Ile Asp Leu Asp Val Ile Arg Asp Val Asp Leu
                35                  40                  45

Asn Lys Leu Glu Pro Trp Asp Ile Gln Glu Lys Cys Arg Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ala Ser Gly Ala Arg Arg Ile
                100                 105                 110

Gly Met Arg Lys Thr Leu Val Phe Tyr Lys Gly Arg Ala Pro His Gly
                115                 120                 125

Gln Lys Ser Asp Trp Ile Met His Glu Tyr Arg Leu Glu Pro Ala Leu
130                 135                 140

Asp Val Asp Ala Ala Gly Ser Ala Ser Ala His His Ala Ala
145                 150                 155                 160

Gly Ala Ala Ala Asp His His Pro Tyr Tyr Thr Ser Ser Pro Pro
                165                 170                 175

Ala Leu Pro Thr Ala Ile Arg Gly Ala Ala Gly Asp Gln Gln Ala Ala
                180                 185                 190

Gln Glu Gln Glu Gly Trp Val Ile Cys Arg Val Phe Lys Lys Lys Asn
                195                 200                 205

Leu Val His His Gly Gln Ser Ser Gly Gly Val Thr Ala Ala Gly
210                 215                 220

Ser Lys Met Ala Ser Ala Ala Pro Met Glu Gly Ser Pro Ser His
225                 230                 235                 240

Cys Ser Ser Val Thr Val Ile Ser Asp His Thr Met Asn Lys His Gln
                245                 250                 255

Ala Gln Ala Met Leu Gln His Ser Ala Ser Asp Asp Asp Ala Leu Asp
                260                 265                 270

His Ile Leu Gln Tyr Met Gly Gly Gly Gly Lys Gln Pro Asp Thr
                275                 280                 285

Lys Pro Val Leu Leu Asp His His His His His Leu Ala Ala Ala
                290                 295                 300

Ala Thr Thr Thr Thr Thr Ala Cys Ser Ala Gly Gly Ala Gly Leu Tyr
305                 310                 315                 320

Gly Lys Phe Met Lys Leu Pro Pro Leu Glu His Ala Gly Gly Gly Gly
                325                 330                 335
```

```
Gly Leu Leu Pro Ser Pro Ala Gly Ala Cys Asp Tyr Gly Ala Ala Asp
                340                 345                 350

Ala Ser Gly Ile Ala Asp Trp Asp Ala Leu Asp Arg Leu Ala Ala Tyr
            355                 360                 365

Glu Leu Asn Gly Leu Ser Asp Ala Ser Lys Asn Met Ser Ala Phe Phe
        370                 375                 380

Asp Glu Pro Ser Ala Thr Ala Ala Phe Ser Ser Ser Ser Ser Ser Val
385                 390                 395                 400

His Ala Ala Ala Val Asp Gly Asp Leu Trp Ser Leu Ala Arg Ser Val
                405                 410                 415

Ser Ala Leu His Ala Asp Leu Thr Met Asn Asn Val
                420                 425

<210> SEQ ID NO 14
<211> LENGTH: 388
<212> TYPE: PRT
<213> ORGANISM: Glycine max

<400> SEQUENCE: 14

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
            35                  40                  45

Asp Val Asp Leu Asn Lys Leu Glu Pro Trp Asp Ile Gln Glu Lys Cys
        50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
            115                 120                 125

Pro His Gly Gln Lys Ser Asp Trp Ile Met His Glu Tyr Arg Leu Asp
        130                 135                 140

Asp Asn Asn Thr Ser Asp Ile Asn Ile Val Ser Asn Val Met Gly Asp
145                 150                 155                 160

Ala Ala Gln Glu Glu Gly Trp Val Val Cys Arg Ile Phe Lys Lys Lys
                165                 170                 175

Asn His Leu Lys Thr Leu Asp Ser Pro Leu Ala Ser Gly Glu Gly Arg
            180                 185                 190

Arg Ser His Met Phe Asp Ser Cys Asp Glu Gly Ala Leu Glu Gln Ile
            195                 200                 205

Leu Gln Gln Met Gly Arg Gly Cys Lys Glu Glu Ser Ser Tyr Glu Gly
        210                 215                 220

Asn Tyr Asn Ser Tyr Gly Arg Phe Ala Met Gly Leu Asn Asn Gly Gly
225                 230                 235                 240

Gly Gly Gly Tyr Asn Asp Arg Phe Met Lys Leu Pro Ser Leu Glu Ser
                245                 250                 255

Pro Lys Ser Ala Ser Met Glu Asn His His Asn Thr Asn Asn Asn Cys
            260                 265                 270

Asn Asn Asn Met Lys Ser Gly Gly Gly Leu Thr Asn Trp Ala Ala Leu
            275                 280                 285
```

```
Asp Arg Leu Val Ala Ser Gln Leu Asn Gly Gln Thr Asp Ala Ser Arg
    290             295                 300

Gln Leu Gly Cys Ala Phe Asn Asp Pro Thr Met Tyr Cys Thr Ser Val
305                 310                 315                 320

Asp His His Asp Leu His His Gln Ile Pro Thr Leu Arg Ser Ser Ser
                325                 330                 335

Thr Ser Ala Asn Thr Arg Pro Ser Pro Ala Pro Ala Phe Ile Asn Pro
            340                 345                 350

Pro Thr Gln Asp Phe Thr Ser Glu Ile Asp Leu Trp Asn Phe Ser Arg
        355                 360                 365

Ser Thr Ser Ser Leu Leu Ala Ser Ser Glu Pro Leu Cys His Val Ser
370                 375                 380

Asn Thr Ser Val
385

<210> SEQ ID NO 15
<211> LENGTH: 419
<212> TYPE: PRT
<213> ORGANISM: Glycine max

<400> SEQUENCE: 15

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Asn Thr Ala Asp Thr Asn Ile Val Ser Asn Val Met Gly Asp
145                 150                 155                 160

Ala Ala Gln Glu Glu Gly Trp Val Val Cys Arg Ile Phe Lys Lys Lys
                165                 170                 175

Asn His Leu Lys Thr Leu Asp Ser Pro Leu Ala Ser Gly Glu Asp Arg
            180                 185                 190

Arg Ser His Leu Phe Asp Ser Cys Asp Glu Gly Ala Leu Glu Gln Ile
        195                 200                 205

Leu Glu Gln Met Gly Arg Ser Cys Lys Glu Glu Ser Ser Tyr Glu Gly
    210                 215                 220

Asn Tyr Arg Asn Tyr Gly Arg Phe Thr Arg Pro Tyr Glu Thr Thr Gly
225                 230                 235                 240

Leu Asn Asn Gly Gly Gly Tyr Asn Asp Arg Phe Met Lys Leu Pro Ser
                245                 250                 255

Leu Glu Ser Pro Lys Ser Ala Ser Met Glu Ser His His Asn Thr Asn
            260                 265                 270
```

-continued

Asn Asn Asn Met Asn Ser Asn Asn Asn Asn Gly Asp Asn Asn
            275                 280                 285

Glu Asn Asn Asn Asn Gly Tyr His Pro Met Ile Pro Val Glu Met
290                 295                 300

Gly Thr Asp Asn Glu Gly Ser Phe Thr Thr His Gln Val Ser Gly Gly
305                 310                 315                 320

Asp Pro Asn Asn Asn Asn Asn Met Val His Pro Leu Glu Val Gly
                325                 330                 335

Ser Gly Gly Gly Gly Leu Thr Asn Trp Ala Ala Leu Asp Arg Leu Val
            340                 345                 350

Ala Ser Gln Leu Asn Gly Gln Thr Asp Ala Ser Arg Gln Leu Ala Cys
            355                 360                 365

Ala Phe Asn Asp Pro Thr Met Tyr Cys Thr Thr Phe Ile Asn Pro Thr
370                 375                 380

Thr Gln Asp Phe Thr Ser Glu Ile Asp Leu Trp Asn Phe Thr Arg Ser
385                 390                 395                 400

Thr Ser Ser Leu Leu Ala Ser Ser Glu Pro Leu Cys His Val Ser Asn
            405                 410                 415

Thr Ser Val

<210> SEQ ID NO 16
<211> LENGTH: 365
<212> TYPE: PRT
<213> ORGANISM: Arabidopsis thaliana

<400> SEQUENCE: 16

Met Met Ser Lys Ser Met Ser Ile Ser Val Asn Gly Gln Ser Gln Val
1               5                   10                  15

Pro Pro Gly Phe Arg Phe His Pro Thr Glu Glu Glu Leu Leu Gln Tyr
            20                  25                  30

Tyr Leu Arg Lys Lys Val Asn Ser Ile Glu Ile Asp Leu Asp Val Ile
            35                  40                  45

Arg Asp Val Asp Leu Asn Lys Leu Glu Pro Trp Asp Ile Gln Glu Met
50                  55                  60

Cys Lys Ile Gly Thr Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Ala
                85                  90                  95

Ala Gly Phe Trp Lys Ala Thr Gly Arg Asp Lys Ile Ile Tyr Ser Asn
            100                 105                 110

Gly Arg Arg Ile Gly Met Arg Lys Thr Leu Val Phe Tyr Lys Gly Arg
        115                 120                 125

Ala Pro His Gly Gln Lys Ser Asp Trp Ile Met His Glu Tyr Arg Leu
130                 135                 140

Asp Asp Asn Ile Ile Ser Pro Glu Asp Val Thr Val His Glu Val Val
145                 150                 155                 160

Ser Ile Ile Gly Glu Ala Ser Gln Asp Glu Gly Trp Val Val Cys Arg
            165                 170                 175

Ile Phe Lys Lys Lys Asn Leu His Lys Thr Leu Asn Ser Pro Val Gly
            180                 185                 190

Gly Ala Ser Leu Ser Gly Gly Gly Asp Thr Pro Lys Thr Thr Ser Ser
        195                 200                 205

Gln Ile Phe Asn Glu Asp Thr Leu Asp Gln Phe Leu Glu Leu Met Gly
210                 215                 220

```
Arg Ser Cys Lys Glu Glu Leu Asn Leu Asp Pro Phe Met Lys Leu Pro
225                 230                 235                 240

Asn Leu Glu Ser Pro Asn Ser Gln Ala Ile Asn Asn Cys His Val Ser
            245                 250                 255

Ser Pro Asp Thr Asn His Asn Ile His Val Ser Asn Val Val Asp Thr
        260                 265                 270

Ser Phe Val Thr Ser Trp Ala Ala Leu Asp Arg Leu Val Ala Ser Gln
    275                 280                 285

Leu Asn Gly Pro Thr Ser Tyr Ser Ile Thr Ala Val Asn Glu Ser His
290                 295                 300

Val Gly His Asp His Leu Ala Leu Pro Ser Val Arg Ser Pro Tyr Pro
305                 310                 315                 320

Ser Leu Asn Arg Ser Ala Ser Tyr His Ala Gly Leu Thr Gln Glu Tyr
                325                 330                 335

Thr Pro Glu Met Glu Leu Trp Asn Thr Thr Ser Ser Leu Ser Ser
            340                 345                 350

Ser Pro Gly Pro Phe Cys His Val Ser Asn Gly Ser Gly
        355                 360                 365

<210> SEQ ID NO 17
<211> LENGTH: 358
<212> TYPE: PRT
<213> ORGANISM: Arabidopsis thaliana

<400> SEQUENCE: 17

Met Ala Asp Asn Lys Val Asn Leu Ser Ile Asn Gly Gln Ser Lys Val
1               5                   10                  15

Pro Pro Gly Phe Arg Phe His Pro Thr Glu Glu Leu Leu His Tyr
            20                  25                  30

Tyr Leu Arg Lys Lys Val Asn Ser Gln Lys Ile Asp Leu Asp Val Ile
            35                  40                  45

Arg Glu Val Asp Leu Asn Lys Leu Glu Pro Trp Asp Ile Gln Glu Glu
50                  55                  60

Cys Arg Ile Gly Ser Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Val
                85                  90                  95

Ala Gly Phe Trp Lys Ala Thr Gly Arg Asp Lys Ile Ile Cys Ser Cys
            100                 105                 110

Val Arg Arg Ile Gly Leu Arg Lys Thr Leu Val Phe Tyr Lys Gly Arg
        115                 120                 125

Ala Pro His Gly Gln Lys Ser Asp Trp Ile Met His Glu Tyr Arg Leu
130                 135                 140

Asp Asp Thr Pro Met Ser Asn Gly Tyr Ala Asp Val Val Thr Glu Asp
145                 150                 155                 160

Pro Met Ser Tyr Asn Glu Glu Gly Trp Val Val Cys Arg Val Phe Arg
                165                 170                 175

Lys Lys Asn Tyr Gln Lys Ile Asp Asp Cys Pro Lys Ile Thr Leu Ser
            180                 185                 190

Ser Leu Pro Asp Asp Thr Glu Glu Lys Gly Pro Thr Phe His Asn
        195                 200                 205

Thr Gln Asn Val Thr Gly Leu Asp His Val Leu Leu Tyr Met Asp Arg
210                 215                 220

Thr Gly Ser Asn Ile Cys Met Pro Glu Ser Gln Thr Thr Gln His
225                 230                 235                 240
```

Gln Asp Asp Val Leu Phe Met Gln Leu Pro Ser Leu Glu Thr Pro Lys
            245                 250                 255

Ser Glu Ser Pro Val Asp Gln Ser Phe Leu Thr Pro Ser Lys Leu Asp
        260                 265                 270

Phe Ser Pro Val Gln Glu Lys Ile Thr Glu Arg Pro Val Cys Ser Asn
        275                 280                 285

Trp Ala Ser Leu Asp Arg Leu Val Ala Trp Gln Leu Asn Asn Gly His
    290                 295                 300

His Asn Pro Cys His Arg Lys Ser Phe Asp Glu Glu Glu Asn Gly
305                 310                 315                 320

Asp Thr Met Met Gln Arg Trp Asp Leu His Trp Asn Asn Asp Asp Asn
                325                 330                 335

Val Asp Leu Trp Ser Ser Phe Thr Glu Ser Ser Ser Leu Asp Pro
            340                 345                 350

Leu Leu His Leu Ser Val
        355

<210> SEQ ID NO 18
<211> LENGTH: 334
<212> TYPE: PRT
<213> ORGANISM: Arabidopsis thaliana

<400> SEQUENCE: 18

Met Asn Ile Ser Val Asn Gly Gln Ser Gln Val Pro Pro Gly Phe Arg
1               5                   10                  15

Phe His Pro Thr Glu Glu Leu Leu Lys Tyr Tyr Leu Arg Lys Lys
            20                  25                  30

Ile Ser Asn Ile Lys Ile Asp Leu Asp Val Ile Pro Asp Ile Asp Leu
        35                  40                  45

Asn Lys Leu Glu Pro Trp Asp Ile Gln Glu Met Cys Lys Ile Gly Thr
    50                  55                  60

Thr Pro Gln Asn Asp Trp Tyr Phe Tyr Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Thr Ile Tyr Thr Asn Gly Asp Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Glu Ser Val Leu
    130                 135                 140

Ile Ser Ser Cys Gly Asp His Asp Val Asn Val Glu Thr Cys Asp Val
145                 150                 155                 160

Ile Gly Ser Asp Glu Gly Trp Val Val Cys Arg Val Phe Lys Lys Asn
                165                 170                 175

Asn Leu Cys Lys Asn Met Ile Ser Ser Pro Ala Ser Ser Val Lys
            180                 185                 190

Thr Pro Ser Phe Asn Glu Glu Thr Ile Glu Gln Leu Leu Glu Val Met
        195                 200                 205

Gly Gln Ser Cys Lys Gly Glu Ile Val Leu Asp Pro Phe Leu Lys Leu
    210                 215                 220

Pro Asn Leu Glu Cys His Asn Asn Thr Thr Ile Thr Ser Tyr Gln Trp
225                 230                 235                 240

Leu Ile Asp Asp Gln Val Asn Asn Cys His Val Ser Lys Val Met Asp
                245                 250                 255

```
Pro Ser Phe Ile Thr Ser Trp Ala Ala Leu Asp Arg Leu Val Ala Ser
            260                 265                 270

Gln Leu Asn Gly Pro Asn Ser Tyr Ser Ile Pro Ala Val Asn Glu Thr
        275                 280                 285

Ser Gln Ser Pro Tyr His Gly Leu Asn Arg Ser Gly Cys Asn Thr Gly
    290                 295                 300

Leu Thr Pro Asp Tyr Tyr Ile Pro Glu Ile Asp Leu Trp Asn Glu Ala
305                 310                 315                 320

Asp Phe Ala Arg Thr Thr Cys His Leu Leu Asn Gly Ser Gly
                325                 330

<210> SEQ ID NO 19
<211> LENGTH: 379
<212> TYPE: PRT
<213> ORGANISM: Zea mays

<400> SEQUENCE: 19

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Gln Ile Asp Leu Asp Val Ile Arg Asp Val Asp Leu
        35                  40                  45

Asn Lys Leu Glu Pro Trp Asp Ile Gln Glu Arg Cys Lys Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ser Ala Val Arg Arg Met Gly
            100                 105                 110

Met Arg Lys Thr Leu Val Phe Tyr Arg Gly Arg Ala Pro His Gly His
        115                 120                 125

Lys Ser Asp Trp Ile Met His Glu Tyr Arg Leu Asp Asp Pro Asp Ala
    130                 135                 140

Ala Ala Val Ala Ala Thr Val Ala Ala Ala Ala Ser Ser Asp Gly
145                 150                 155                 160

Gly Gln Glu Asp Gly Trp Val Val Cys Arg Val Phe Gln Lys Lys His
                165                 170                 175

His His Lys Glu Ser Ser Gly Arg Cys Arg Ser Lys Arg Gly Ser Lys
            180                 185                 190

Thr Glu His Gly His Gly Glu Ala Lys Thr Ala Ala His Gln Arg His
        195                 200                 205

Gly Cys Gly Leu Gln Tyr Ser Ser Asn Asp Asp Thr Leu Asp His Met
    210                 215                 220

Leu Gly Arg Arg Ser Cys Lys Gln Glu His Glu Leu Leu Pro Leu Pro
225                 230                 235                 240

Pro Pro Ala Ala Ala Arg Ala Ala Ser Arg Tyr Ile Arg Pro Ile Glu
                245                 250                 255

Thr Val Leu Gly Gly His Gly Phe Met Lys Leu Pro Pro Leu Glu Ser
            260                 265                 270

Pro Ala Ala Ala Glu Ala Leu Thr Thr Pro His Ala Val Ser Ala Gly
        275                 280                 285

Asp Ala Thr Ala Ala Gly Ala Leu Asp Gly Leu His Arg Ala Gly Asn
    290                 295                 300
```

Gly Ile Thr Asp Trp Val Met Met Asp Arg Met Val Ala Leu His Leu
305                 310                 315                 320

Asn Gly Gln Ala Pro Ala Ala Asp Gln Leu Gly Ser Cys Phe Asp Ala
            325                 330                 335

Ser Ala Asp Gly Gly Leu Ala Cys Phe Tyr Ser Ala Ala Ala Asn
            340                 345                 350

Arg Leu Leu Gly Gly Asp Asp Leu Trp Ser Phe Thr Arg Ser
            355                 360                 365

Ser Ser Thr Glu Arg Leu Gly His Val Ser Leu
        370                 375

<210> SEQ ID NO 20
<211> LENGTH: 435
<212> TYPE: PRT
<213> ORGANISM: Zea mays

<400> SEQUENCE: 20

Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
            20                  25                  30

Val Ala Ser Glu Arg Ile Asp Leu Asp Val Ile Arg Asp Val Asp Leu
        35                  40                  45

Asn Lys Leu Glu Pro Trp Asp Ile Gln Glu Lys Cys Arg Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ala Ser Pro Gly Ala Arg Arg
            100                 105                 110

Ile Gly Met Arg Lys Thr Leu Val Phe Tyr Lys Gly Arg Ala Pro His
            115                 120                 125

Gly Gln Lys Ser Asp Trp Ile Met His Glu Tyr Arg Leu Glu Ala Pro
130                 135                 140

Val Asp Ala Gly Ala Gly Ala Ala His His Leu Leu Leu Pro Ala Ala
145                 150                 155                 160

Glu His Pro Pro Tyr Tyr Thr Ser Pro Gln Ala Pro Ser Ser Thr
                165                 170                 175

Thr Thr Ala Thr Ile Arg Gly Ala Ala Gly Asp Gln Ala Ala Gln Glu
            180                 185                 190

Gln Glu Gly Trp Val Ile Cys Arg Val Phe Lys Lys Asn Leu Val
        195                 200                 205

His His Gly Gln Ser Ser Gly Val Lys Gln Gln Ala Gly Asp Asp
210                 215                 220

His Ala Ala Ser His Thr Ala Ala Ala Ala His Met Asp Glu Ser
225                 230                 235                 240

Ser Pro Ser Gln Cys Ser Ser Val Thr Val Ile Ser Asp His Val His
            245                 250                 255

Ala Asn Val Asn Asp Lys Gln Gln Gln Ala Gln Ala Ser Leu Leu Met
            260                 265                 270

Met His Thr His His Ser Ala Ser Ser Asp Asp Ala Leu Asp His
        275                 280                 285

Ile Leu Gln Gln Tyr Met Gly Gly Gly Arg Gln Ala Pro Ala Pro Asp
290                 295                 300

-continued

```
Thr Lys Pro Ala Leu Leu Glu Gln Leu Asp His Leu His His Leu
305                 310                 315                 320

Ala Ala Ala Pro Thr Thr Arg Ala Ala Gly Phe Tyr Tyr Gly Lys
            325                 330                 335

Phe Met Lys Leu Pro Pro Leu Glu His Ala Gly Leu Pro Ser Pro
            340                 345                 350

Pro Pro Pro Gly Ala Arg Glu Tyr Gly Ala Ala Ala Ala Gly Trp
            355                 360                 365

Asp Asp Asp Asp Asp Ala Leu Asp Arg Leu Ala Ala Tyr Asp His Leu
            370                 375                 380

Asn Gly Leu Ser Asn Asp Ala Ser Lys Asn Met Ala Ala Phe Phe Asp
385                 390                 395                 400

Val Glu Pro Ser Ala Ala Ala Ala Ala Val Asp Gly Asp Leu Trp
            405                 410                 415

Ser Leu Ala Arg Ser Val Ser Ala Leu His Ala Asp Leu Thr Met Asn
            420                 425                 430

Asn Asn Val
        435

<210> SEQ ID NO 21
<211> LENGTH: 408
<212> TYPE: PRT
<213> ORGANISM: Brachypodium distachyon

<400> SEQUENCE: 21

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Gln Ile Asp Leu Asp Val Ile Arg Asp Val Asp Leu
            35                  40                  45

Asn Lys Leu Glu Pro Trp Asp Ile Gln Glu Arg Cys Lys Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
            85                  90                  95

Ala Thr Gly Arg Asp Lys Ala Ile Tyr Asn Ala Val Ser Arg Ile Gly
            100                 105                 110

Met Arg Lys Thr Leu Val Phe Tyr Lys Gly Arg Ala Pro His Gly Leu
            115                 120                 125

Lys Ser Asp Trp Ile Met His Glu Tyr Arg Leu Leu Asp Ala Asp Asp
            130                 135                 140

Ser Ser Ser Ala Ala Thr Ala Ala Met Val Arg Val Ser Val Thr Ala
145                 150                 155                 160

Ser Ser Val Ala Ala Ser Glu Ala Ala Gly Gln Gln Gly Pro Glu Asp
            165                 170                 175

Gly Trp Val Val Cys Arg Val Phe Lys Lys His His Lys Asp
            180                 185                 190

Thr Asn Ser Gly Ser Gly Ser Gly Asn Lys Lys Ala Ala Ala
            195                 200                 205

Leu Arg Arg Ser Ser Ser Pro Leu Tyr Ser Ser Gly Asp Asp Ala
            210                 215                 220

Ala Leu Asp Gln Ile Leu His Tyr Met Gly Arg Ser Ser Ala Ala Cys
225                 230                 235                 240
```

```
Lys Gln Glu His Asp Ser Pro Arg Pro Ala Pro Gln Thr Gln Ala
            245                 250                 255

Gln Ala Arg Pro Thr Ser Arg Tyr Leu Arg Pro Ile Glu Thr Ala Leu
        260                 265                 270

Ala Gly Gly His Gly Phe Met Lys Leu Pro Pro Leu Glu Ser Pro Ser
        275                 280                 285

Ser Ala Ala Ala Ala Pro Pro Asn Thr Thr Pro Val Pro Glu Thr
290                 295                 300

Thr Met Asp Trp Ala Met Met Asp Arg Leu Val Ala Ser His Leu Asn
305                 310                 315                 320

Gly Gln Leu His Asp Asp His Ala Ser Thr Ala Val Val Asp Asp Asp
            325                 330                 335

His Arg Leu Cys Ser Ala Phe Asp Asp Gly Ala Gly Glu Asp Asn Asp
            340                 345                 350

Asp Gly Glu Met Ala Gly Pro Asp Val Glu Arg Pro Val Gly Glu Pro
        355                 360                 365

Ser Arg Gly Ser Ser Ala Ala Gln Leu Ala Val Asn Arg Pro Ser Trp
        370                 375                 380

Lys Lys Lys Val Ser Phe Arg Pro Arg Gly Gly Pro Pro Leu Val Pro
385                 390                 395                 400

Thr Val Pro Val Asp Gly Gly Gly
            405

<210> SEQ ID NO 22
<211> LENGTH: 405
<212> TYPE: PRT
<213> ORGANISM: Vitis vinifera

<400> SEQUENCE: 22

Met Ser Glu Asp Met Asn Leu Ser Val Asn Gly Gln Ser Gln Val Pro
1               5                   10                  15

Pro Gly Phe Arg Phe His Pro Thr Glu Glu Leu Leu His Tyr Tyr
        20                  25                  30

Leu Arg Lys Lys Val Ala Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Ser Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Ser Phe
        100                 105                 110

Arg Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Glu
    130                 135                 140

Glu Asn Thr Pro Val His Asp Thr Met Ala Ser Asn Ser Leu Gly Glu
145                 150                 155                 160

Ser Met Pro Glu Asp Gly Trp Val Val Cys Arg Val Phe Arg Lys Lys
                165                 170                 175

Asn Tyr Gln Lys Thr Leu Glu Ser Pro Lys Thr Ser Asn Ser Met
        180                 185                 190

Asp Ser Arg Thr Gln Met Leu Asn Ser Ser Asn Asp Gly Val Leu Asp
        195                 200                 205
```

```
Gln Ile Leu Ser Tyr Met Gly Arg Thr Cys Lys Gln Glu Asn Glu Ala
    210                 215                 220

Ile Ser Asn Val Asn Phe Ser Asp Ser Asn Asn Thr Met Arg Phe Leu
225                 230                 235                 240

Asn Gln Asn Asn Thr Gly Ile Ser Glu Gly Leu Gln Glu Arg Phe Met
                245                 250                 255

His Leu Pro Arg Leu Glu Ser Pro Thr Leu Pro Ser Leu Pro Asn Asn
            260                 265                 270

Ser Ser His Phe Asp Gln Glu Arg Cys Phe Asn Ile Ala Cys Leu Gln
        275                 280                 285

Ser Ile Asp Glu Met Leu Arg Gly Ser Glu Pro Ser Ser Glu Asn Gln
    290                 295                 300

Gly Ser Gly Cys Asn Thr Thr Pro Val His Asp Pro Lys Ala Gly Leu
305                 310                 315                 320

Asn Asp Trp Val Ala Phe Asp Arg Leu Val Ala Ser Gln Leu Asn Gly
                325                 330                 335

Gln Val Asp Thr Lys Gln Leu Ser Cys Phe Ser Thr Pro Asn Met
                340                 345                 350

Gly Phe Cys Leu Ser Pro Asp His Asp Val Glu Leu Ser His Leu Arg
            355                 360                 365

Ser Ser Arg Pro Asn Pro Asn Pro Gln Asn Tyr Asn Ser Glu Met Asp
370                 375                 380

Leu Trp Asn Phe Thr Arg Ser Ser Ser Ser Ser Ser Asp Pro Leu
385                 390                 395                 400

Gly His Leu Ser Val
                405

<210> SEQ ID NO 23
<211> LENGTH: 400
<212> TYPE: PRT
<213> ORGANISM: Glycine max

<400> SEQUENCE: 23

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
                20                  25                  30

Leu Arg Lys Lys Val Ser Tyr Glu Lys Ile Asp Leu Asp Val Ile Arg
            35                  40                  45

Asp Val Asp Leu Asn Lys Leu Glu Pro Trp Asp Ile Gln Glu Lys Cys
    50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Asn Thr Ala Asp Thr Asn Ile Val Ser Asn Val Met Gly Asp
145                 150                 155                 160

Ala Ala Gln Glu Glu Gly Trp Val Val Cys Arg Ile Phe Lys Lys Lys
                165                 170                 175
```

Asn His Leu Lys Thr Leu Asp Ser Pro Leu Ala Ser Gly Glu Asp Arg
            180                 185                 190

Arg Ser His Leu Phe Asp Ser Cys Asp Glu Gly Ala Leu Glu Gln Ile
        195                 200                 205

Leu Glu Gln Met Gly Arg Ser Cys Lys Glu Ser Ser Tyr Glu Gly
    210                 215                 220

Asn Tyr Arg Asn Tyr Gly Arg Phe Thr Arg Pro Tyr Glu Thr Thr Gly
225                 230                 235                 240

Leu Asn Asn Gly Gly Tyr Asn Asp Arg Phe Met Lys Leu Pro Ser
                245                 250                 255

Leu Glu Ser Pro Lys Ser Ala Ser Met Glu Ser His His Asn Thr Asn
            260                 265                 270

Asn Asn Asn Asn Met Asn Ser Asn Asn Asn Asn Gly Asp Asn Asn
            275                 280                 285

Glu Asn Asn Asn Asn Gly Tyr His Pro Met Ile Pro Val Glu Met
    290                 295                 300

Gly Thr Asp Asn Glu Gly Ser Phe Thr Thr His Gln Val Ser Gly Gly
305                 310                 315                 320

Asp Pro Asn Asn Asn Asn Asn Met Val His Pro Leu Glu Val Gly
                325                 330                 335

Ser Gly Gly Gly Leu Thr Asn Trp Ala Ala Leu Asp Arg Leu Val
            340                 345                 350

Ala Ser Gln Leu Asn Gly Gln Thr Asp Ala Ser Arg Gln Leu Ala Cys
            355                 360                 365

Ala Phe Asn Asp Pro Thr Met Tyr Cys Thr Ser Asp His His Asp Leu
370                 375                 380

His Gln Ile Pro Thr Leu Arg Ser Ser Thr Ser Ala Ala His Thr
385                 390                 395                 400

<210> SEQ ID NO 24
<211> LENGTH: 389
<212> TYPE: PRT
<213> ORGANISM: Gossypium hirsutum

<400> SEQUENCE: 24

Met Asn Leu Ser Ile Asn Gly Gln Ser Gln Val Pro Pro Gly Phe Arg
1               5                   10                  15

Phe His Pro Thr Glu Glu Leu Leu His Tyr Tyr Leu Arg Lys Lys
            20                  25                  30

Val Ala Tyr Glu Lys Ile Asp Leu Asp Val Ile Gln Glu Val Asp Leu
        35                  40                  45

Asn Lys Leu Glu Pro Trp Asp Ile Gln Glu Lys Cys Arg Ile Gly Ser
50                  55                  60

Thr Pro Gln Asn Glu Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ile Ile Tyr Ser Gly Phe Arg Arg Ile Gly
            100                 105                 110

Leu Arg Lys Thr Leu Val Phe Tyr Lys Gly Arg Ala Pro His Gly Gln
        115                 120                 125

Lys Ser Asp Trp Ile Met His Glu Tyr Arg Leu Asp Asp Asn Thr Thr
130                 135                 140

Thr His Asp Ser Asn Gly Ser Asn Pro Ile Gly Asp Ser Val Thr Glu
145                 150                 155                 160

```
Asp Gly Trp Val Val Cys Arg Val Phe Arg Lys Lys Asn Tyr Leu Lys
            165                 170                 175
Thr Leu Glu Ser Pro Lys Ser Asn Ser Ser Thr Gly His Asp Leu
        180                 185                 190
Lys Thr His Met Leu Ser Ser Gly Gly Asn Asp Gly Val Leu Asp Gln
            195                 200                 205
Ile Leu His Tyr Met Gly Arg Thr Cys Lys Met Glu Ser Asp Ser Leu
            210                 215                 220
Asn Asn Ile Asn Asn Ile Pro Ile Pro Asp Asn Asn Pro Arg Met Leu
225                 230                 235                 240
Val Gly Asn Asn Gly Gly Ile Asn Asp Gly Phe His Asp His Glu Arg
            245                 250                 255
Phe Met His Leu Pro Arg Leu Glu Ser Pro Thr Leu Pro Ser Leu Cys
            260                 265                 270
Tyr Gln Ser Ile Glu Asp Met Leu Thr Glu Thr Glu His Arg Gly Gly
            275                 280                 285
Cys Cys Gly Gly Gly Gly Asn Asn Glu Thr Lys Asn Gly Val Asn Asp
            290                 295                 300
Trp Val Thr Leu Asp Gln Leu Val Ala Ser Gln Leu Ser Gly Gln Val
305                 310                 315                 320
Glu Thr Ser Lys Gln Leu Ser Cys Phe Ser Asp Pro Asn Ala Val Phe
            325                 330                 335
Ser Leu Cys His Asp Asp Gly Ile Gln Leu Ser His Leu Asn Leu Gln
            340                 345                 350
Arg Ser Asn Gln Ser Ser Gln Val Tyr Ser Asn Asn Asp Asn Asp Leu
            355                 360                 365
Trp Ser Leu Thr Lys Ser Ser Phe Ser Pro Phe Ser Ser Asp Pro Leu
            370                 375                 380
Cys His Leu Ser Val
385

<210> SEQ ID NO 25
<211> LENGTH: 401
<212> TYPE: PRT
<213> ORGANISM: Pyrus malus

<400> SEQUENCE: 25

Met Ser Asp Asp His Met Ser Leu Ser Ile Asn Gly Gln Ser Gln Val
1               5                   10                  15
Pro Pro Gly Phe Arg Phe His Pro Thr Glu Glu Glu Leu Leu His Tyr
            20                  25                  30
Tyr Leu Arg Lys Lys Val Ala Phe Glu Arg Ile Asp Leu Asp Val Ile
            35                  40                  45
Arg Glu Val Asp Leu Asn Lys Leu Glu Pro Trp Asp Ile Gln Glu Lys
        50                  55                  60
Cys Lys Ile Gly Ser Thr Pro Gln Asn Asp Trp Tyr Phe Phe Ser His
65                  70                  75                  80
Lys Asp Lys Lys Tyr Pro Thr Gly Thr Arg Thr Asn Arg Ala Thr Thr
            85                  90                  95
Ala Gly Phe Trp Lys Ala Thr Gly Arg Asp Lys Ile Ile Tyr Ser Gly
            100                 105                 110
Phe Lys Arg Ile Gly Leu Arg Lys Thr Leu Val Phe Tyr Lys Gly Arg
        115                 120                 125
Ala Pro His Gly Gln Lys Ser Asp Trp Ile Met His Glu Tyr Arg Leu
        130                 135                 140
```

-continued

Glu Glu Ser Asn Ser Thr His Asp Thr Thr Val Ser Ser Ser Met Gly
145                 150                 155                 160

Glu Ser Met Thr Glu Glu Gly Trp Val Val Cys Arg Val Phe Lys Lys
                165                 170                 175

Lys Asn Tyr Gln Lys Ala Leu Glu Ser Pro Lys Ala Ser Phe Ser Met
            180                 185                 190

Asp Ser Ser Asn Asn Gln Ile His Gly Ser Arg Asn Asp Gly Val Leu
        195                 200                 205

Asp Gln Ile Leu Met Tyr Met Gly Arg Thr Cys Lys Leu Glu Asn His
    210                 215                 220

Asp Glu Pro Leu Thr Met Asn Asn Ile Ser Glu Arg Phe Met His Leu
225                 230                 235                 240

Pro Arg Leu Glu Ser Pro Thr Leu Pro Asn Leu Pro Ala Phe Asp Gln
                245                 250                 255

Asp Arg Ser Phe Lys Ala Cys Tyr Gln Ala Ile Asp Met Phe Ile
            260                 265                 270

Glu Thr Glu Pro Pro Ser Thr Asn Gln Gln Ser Asn Gly Cys Asp Asn
        275                 280                 285

Asn Glu Leu Val Asp Asp His Glu Asp Pro Lys Arg Arg Val Asn Asp
    290                 295                 300

Trp Val Thr Leu Asp Arg Leu Val Ala Ser Gln Leu Gly Gln Leu Asn
305                 310                 315                 320

Gly Gln Asp Gln Val Thr Pro Lys His Leu Ser Cys Phe Gly Asp Pro
                325                 330                 335

Asn Met Ala Phe Cys Ser Ser Pro Pro Arg Asn Asp His Asp His
            340                 345                 350

Asp Val Gln Leu Ser Tyr Pro Tyr Leu Arg Thr Ser Ser Ser Ser His
        355                 360                 365

His Gln Ser Asp Val Tyr Asn Asn Glu Asn Asp Leu Trp Asn Phe Thr
    370                 375                 380

Lys Ser Ser Ser Ser Pro Ser Ser Thr Asp Pro Leu Cys His Leu Ser
385                 390                 395                 400

Val

<210> SEQ ID NO 26
<211> LENGTH: 411
<212> TYPE: PRT
<213> ORGANISM: Hordeum vulgare

<400> SEQUENCE: 26

Met Ser Ile Ser Val Asn Gly Gln Ser Val Val Pro Pro Gly Phe Arg
1               5                   10                  15

Phe His Pro Thr Glu Glu Glu Leu Leu Thr Tyr Tyr Leu Ala Lys Lys
                20                  25                  30

Val Ala Ser Gln Arg Ile Asp Leu Asp Val Ile Pro Asp Val Asp Leu
            35                  40                  45

Asn Lys Leu Glu Pro Trp Asp Ile Gln Glu Cys Cys Arg Ile Gly Thr
        50                  55                  60

Gly Pro Gln Asn Asp Trp Tyr Leu Phe Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Ala Ile Tyr Pro Ala Ala Gly Tyr Gly His
            100                 105                 110

Ile Gly Met Arg Lys Thr Leu Val Phe Tyr Gln Gly Arg Ala Pro His
            115                 120                 125

Gly His Lys Ser Asp Trp Ile Met His Glu Tyr Arg Leu Asp Asp Ala
        130                 135                 140

Thr Thr Pro Gly Asn Asn Pro Ala Asn Gln Ala Ile Gly Asn Ala Pro
145                 150                 155                 160

Tyr Tyr Pro Gly Ser Ser Ser Ile Arg Ser Leu Val Gly Asp Gln
                165                 170                 175

Ser Ser Ala Gln Glu Asp Gly Trp Val Ile Cys Arg Val Phe Lys Lys
                180                 185                 190

Lys Asn Ile Val Val Gln Gln Ala Asp Gln Asn Gly Gly Arg
            195                 200                 205

Arg Thr Ala Ser Asn Asn Leu Val Ala Ala Gly Ala Ile Glu Leu Ser
        210                 215                 220

Arg Ser Asn Cys Ser Ser Thr Val Thr Thr Ala Ser Asp His Ala Lys
225                 230                 235                 240

Ala Thr His Met Gln Gln His Tyr Tyr Ser Ala Ser Asp Asp Ala Leu
                245                 250                 255

Asp His Ile Leu Asn Gln Tyr Met His Gly Arg Ser Ser Thr Thr Thr
            260                 265                 270

Thr Ser Cys Lys Lys Glu Thr Asn Ala Thr Asn Pro Ser Ser Ser Ala
        275                 280                 285

Leu Asp His Leu Ile Asn Ser Glu Cys His Asn Val Ser Ser Thr Leu
    290                 295                 300

Tyr Glu Lys Leu Pro Pro Leu Glu His Val Val Pro Gly Glu Leu Leu
305                 310                 315                 320

Pro Pro Thr Glu Tyr Ser Gly Asp Trp Asp Ala Leu Asp Arg Leu Ala
                325                 330                 335

Ala Tyr Glu Leu Asn Gly Leu Ser Asp Ala Ala Ser Ala Lys Thr Thr
            340                 345                 350

Asn Gly Met Pro Phe Ile Val Asp Glu Leu Gly Gly Ala Thr Ala Tyr
        355                 360                 365

Ser Gly Gly Gly Arg Leu His Val Ser Ser Ile Thr Gly Thr Gly Asp
    370                 375                 380

Gly Asp Leu Trp Ser Leu Gly Arg Ser Val Ser Ser Leu His Ala Asp
385                 390                 395                 400

Leu Thr Ile Asn Ser Phe Asn Ala Val Gly Cys
                405                 410

<210> SEQ ID NO 27
<211> LENGTH: 399
<212> TYPE: PRT
<213> ORGANISM: Arabidopsis thaliana

<400> SEQUENCE: 27

Met Ser Lys Ser Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Asn Ser Ile Glu Ile Asp Leu Asp Val Ile Arg
        35                  40                  45

Asp Val Asp Leu Asn Lys Leu Glu Pro Trp Asp Ile Gln Glu Met Cys
    50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Ile Ile Tyr Ser Asn Gly
            100                 105                 110

Arg Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Ile Ile Ser Pro Glu Asp Val Thr His Glu Val Val Ser
145                 150                 155                 160

Ile Ile Gly Glu Ala Ser Gln Asp Glu Gly Trp Val Val Cys Arg Ile
                165                 170                 175

Phe Lys Lys Lys Asn Leu His Lys Thr Leu Asn Ser Pro Val Gly Gly
            180                 185                 190

Ala Ser Leu Ser Gly Gly Gly Asp Thr Pro Lys Thr Thr Ser Ser Gln
        195                 200                 205

Ile Phe Asn Glu Asp Thr Leu Asp Gln Phe Leu Glu Leu Met Gly Arg
    210                 215                 220

Ser Cys Lys Glu Glu Leu Asn Leu Asp Pro Phe Met Lys Leu Pro Asn
225                 230                 235                 240

Leu Glu Ser Pro Asn Ser Gln Ala Ile Asn Asn Cys His Val Ser Ser
                245                 250                 255

Pro Asp Thr Asn His Asn Ile His Val Ser Asn Val Val Asp Thr Ser
            260                 265                 270

Phe Val Thr Ser Trp Ala Ala Leu Asp Arg Leu Val Ala Ser Gln Leu
        275                 280                 285

Asn Gly Pro Thr Ser Tyr Ser Ile Thr Ala Val Asn Glu Ser His Val
    290                 295                 300

Gly His Asp His Leu Ala Leu Pro Ser Val Arg Ser Pro Tyr Pro Ser
305                 310                 315                 320

Leu Asn Arg Ser Ala Ser Tyr His Ala Gly Leu Thr Gln Glu Tyr Thr
                325                 330                 335

Pro Glu Met Glu Leu Trp Asn Thr Thr Thr Ser Ser Leu Ser Ser Ser
            340                 345                 350

Pro Gly Pro Phe Cys His Val Ser Asn Val Leu Leu Leu Val Cys Leu
        355                 360                 365

Leu Arg Leu Gln Leu Gln Phe Trp Pro Phe Gln Pro Trp Gln Arg Gln
    370                 375                 380

Val His Phe Asp Leu Ser Ser Pro Gln Met Gln Ile Ser Leu His
385                 390                 395

<210> SEQ ID NO 28
<211> LENGTH: 1725
<212> TYPE: DNA
<213> ORGANISM: Zea mays

<400> SEQUENCE: 28
atgaagcagc cgaggggccg gcaggagccg cgccgggtgg gcaacgccgc catggtcgtc      60
accatggtcg tctccctctg cgtcctcacg tacatcaagg cgcgatactg ctccaaccct     120
ttccccaagg cggtggcgga ggtggaggtg acgaggact acgacagcac gcggtacaag     180
ctgacgggcc ccgtgggcga ggaggacttc gaccgtccc gccccacctg ctacaacacc     240
agcaagcggt cggagcggtg cgccgccgtg ggcgacatcc gcgtggacgg caaccactcg     300
cggatctaca tcagcccgct gtcccgcgag tggcggacca agccgtacgc gcggcggcac     360

```
gacgccgtgg ccatggacga cgtgcgcgag ttcacgctgg tccccttcgg cggccccaac      420
gacacggccg tgccgccgct ctgcacgcgc acccactccg tcccgggctt cctcttctcc      480
agcggcgggt tcgcgggcaa cctgtaccac gactacgccg acgtgctggt gccgctcttc      540
gccagcacca accacctggg cggggaggtc cagttcctgc tggccgacat caaggactgg      600
tgggccgaca agttccgccc gctcttccgc cagctctccc gctacgacgt catcgacgtg      660
aacaacgacc gcgaggtgca ctgcttcccg cggatcatca tcggctccac cttccaccgc      720
gccatgggca tcgacccctc gcgctcgccc ggcggcgtca cggtggccga cttcaagcgc      780
ctgctccgcc gcgcgttccg gctggagcgc ccgtcgcgt cgcggtcggg ggcgccccgg       840
cgccgggacc ggccccgcct cctcatcatc tcgcgcaaga gctcgcgccg cttcgtcaac      900
gagcgcgcca tggcgcgcgc cgcggcggcc gcccggttcg acgtgcggat cgccgagccc      960
gacaaccaca cggacatgcc caacttcgcg aggctggtga actcggcgga cgtgatgatg     1020
ggcgtgcacg cgccgggct caccaacatg gtgttcctgc ccagccgcgc cgtgctggtg      1080
caggtggtgc cgttcggcgg gctggagtgg ctcacccgcg tcaccttcaa ggaccccgca     1140
agggacatgg acgtcacgta catggagtac aacgtgtcgc tggaggagag ctcgctcagg     1200
gacctctacc cggaggacca cttctacctg aagcacccct acgacgtgca caagaagggg     1260
tgggacgcca tcaagacggt gtacctggac aagcagaacg tcaggctcaa cctcaccagg     1320
ttcaccagga cgctggagca ggcgcgagat ctcttgccga cgccatgact gatgatgacc     1380
tcccctctt tcctctgctc tgctgcaggt tcattcact tcagatcagc tgctcacctc       1440
acttcacgcc gtgtctctct ctctttttttt tttctgttgt tgttctatac atatacttgt    1500
ttcctcttct cctttcccct ctctctctag tctctccctc tccactcttg tggtggcaag     1560
attcatttct ttcattgttt tgttttttgt tgttgttgtt gaggaaggat aggaacaaaa     1620
acaaggtatt gtcgtgtcca aggttaatct acacaaacac acactgtaaa tgattgattg     1680
attgctgtca gtagaggcga acacaaggaa taggtaaaaa aaaaa                     1725
```

<210> SEQ ID NO 29
<211> LENGTH: 455
<212> TYPE: PRT
<213> ORGANISM: Zea mays

<400> SEQUENCE: 29

```
Met Lys Gln Pro Arg Gly Arg Gln Glu Pro Arg Val Gly Asn Ala
1               5                   10                  15

Ala Met Val Val Thr Met Val Val Ser Leu Cys Val Leu Thr Tyr Ile
            20                  25                  30

Lys Ala Arg Tyr Cys Ser Asn Pro Phe Pro Lys Ala Val Ala Glu Val
        35                  40                  45

Glu Val Asp Glu Asp Tyr Asp Ser Thr Arg Tyr Lys Leu Thr Gly Pro
    50                  55                  60

Val Gly Glu Glu Asp Phe Asp Pro Ser Arg Pro Thr Cys Tyr Asn Thr
65                  70                  75                  80

Ser Lys Arg Ser Glu Arg Cys Ala Ala Val Gly Asp Ile Arg Val Asp
                85                  90                  95

Gly Asn His Ser Arg Ile Tyr Ile Ser Pro Leu Ser Arg Glu Trp Arg
            100                 105                 110

Thr Lys Pro Tyr Ala Arg Arg His Asp Ala Val Ala Met Asp Asp Val
        115                 120                 125
```

```
Arg Glu Phe Thr Leu Val Pro Phe Gly Gly Pro Asn Asp Thr Ala Val
    130                 135                 140

Pro Pro Leu Cys Thr Arg Thr His Ser Val Pro Gly Phe Leu Phe Ser
145                 150                 155                 160

Ser Gly Gly Phe Ala Gly Asn Leu Tyr His Asp Tyr Ala Asp Val Leu
                165                 170                 175

Val Pro Leu Phe Ala Ser Thr Asn His Leu Gly Gly Glu Val Gln Phe
            180                 185                 190

Leu Leu Ala Asp Ile Lys Asp Trp Trp Ala Asp Lys Phe Arg Pro Val
        195                 200                 205

Phe Arg Gln Leu Ser Arg Tyr Asp Val Ile Asp Val Asn Asn Asp Arg
210                 215                 220

Glu Val His Cys Phe Pro Arg Thr Ile Ile Gly Ser Thr Phe His Arg
225                 230                 235                 240

Ala Met Gly Ile Asp Pro Ser Arg Ser Pro Gly Gly Val Thr Val Ala
                245                 250                 255

Asp Phe Lys Arg Leu Leu Arg Arg Ala Phe Arg Leu Glu Arg Ala Val
            260                 265                 270

Ala Ser Arg Ser Gly Ala Pro Arg Arg Asp Arg Pro Arg Leu Leu
        275                 280                 285

Ile Ile Ser Arg Lys Ser Ser Arg Arg Phe Val Asn Glu Arg Ala Met
290                 295                 300

Ala Arg Ala Ala Ala Ala Arg Phe Asp Val Arg Ile Ala Glu Pro
305                 310                 315                 320

Asp Asn His Thr Asp Met Pro Asn Phe Ala Arg Leu Val Asn Ser Ala
                325                 330                 335

Asp Val Met Met Gly Val His Gly Ala Gly Leu Thr Asn Met Val Phe
            340                 345                 350

Leu Pro Ser Arg Ala Val Leu Val Gln Val Val Pro Phe Gly Gly Leu
        355                 360                 365

Glu Trp Leu Thr Arg Val Thr Phe Lys Asp Pro Ala Arg Asp Met Asp
    370                 375                 380

Val Thr Tyr Met Glu Tyr Asn Val Ser Leu Glu Glu Ser Ser Leu Arg
385                 390                 395                 400

Asp Leu Tyr Pro Glu Asp His Phe Tyr Leu Lys His Pro Tyr Asp Val
                405                 410                 415

His Lys Lys Gly Trp Asp Ala Ile Lys Thr Val Tyr Leu Asp Lys Gln
            420                 425                 430

Asn Val Arg Leu Asn Leu Thr Arg Phe Thr Arg Thr Leu Glu Gln Ala
        435                 440                 445

Arg Asp Leu Leu Pro Thr Pro
450                 455

<210> SEQ ID NO 30
<211> LENGTH: 1870
<212> TYPE: DNA
<213> ORGANISM: Zea mays

<400> SEQUENCE: 30
atgaagcagc cgaggggccg gcaggagccg cgccgggtgg gcaacgccgc catggtcgtc     60
accatggtcg tctccctctg cgtcctcacg tacatcaagg cgcgatactg ctccaaccct    120
ttccccaagg cggtggcgga ggtggaggtg acgaggact  acgacagcac gcggtacaag    180
ctgacgggcc ccgtgggcga ggaggacttc gacccgtccc gccccacctg ctacaacacc    240
```

-continued

```
agcaagcggt cggagcggtg cgccgccgtg ggcgacatcc gcgtggacgg caaccactcg    300
cggatctaca tcagcccgct gtcccgcgag tggcggacca agccgtacgc gcggcggcac    360
gacgccgtgg ccatggacga cgtgcgcgag ttcacgctgg tccccttcgg cggccccaac    420
gacacggccg tgccgccgct ctgcacgcgc acccactccg tcccgggctt cctcttctcc    480
agcggcgggt cgcgggcaa cctgtaccac gactacgccg acgtgctggt gccgctcttc    540
gccagcacca accacctggg cggggaggtc cagttcctgc tggccgacat caaggactgg    600
tgggccgaca agttccgccc gctcttccgc cagctctccc gctacgacgt catcgacgtg    660
aacaacgacc gcgaggtgca ctgcttcccg cggatcatca tcggctccac cttccaccgc    720
gccatgggca tcgacccctc gcgctcgccc ggcggcgtca cggtggccga cttcaagcgc    780
ctgctccgcc gcgcgttccg gctggagcgc ccgtcgcgt cgcggtcggg ggcgccccgg    840
cgccgggacc ggccccgcct cctcatcatc tcgcgcaaga gctcgcgccg cttcgtcaac    900
gagcgcgcca tggcgcgcgc cgcggcggcc gcccggttcg acgtgcggat cgccgagccc    960
gacaaccaca cggacatgcc caacttcgcg aggctggtga actcggcgga cgtgatgatg   1020
ggcgtgcacg cgccgggct caccaacatg gtgttcctgc ccagccgcgc cgtgctggtg   1080
caggtggtgc cgttcggcgg gctggagtgg ctcacccgcg tcaccttcaa ggaccccgca   1140
agggacgaga taattgccat tatgacgaa gagggaaggg gattcgacga aatggaggcg   1200
ttggcgttgg cttctctgtt ttggagacgc acgcgacagc caaactccaa aacggatacg   1260
agacagctct tggggctgcg taaacaggga catggacgtc acgtacatgg agtacaacgt   1320
gtcgctggag gagagctcgc tcagggacct ctacccggag gaccacttct acctgaagca   1380
cccctacgac gtgcacaaga aggggtggga cgccatcaag acgtgtacc tggacaagca   1440 gaacgtcagg ctcaacctca ccaggttcac caggacgctg gagcaggcgc gagatctctt   1500
gccgacgcca tgactgatga tgacctcccc ctctttcctc tgctctgctg caggtttcat   1560
tcacttcaga tcagctgctc acctcacttc acgccgtgtc tctctctctt ttttttttct   1620
gttgttgttc tatacatata cttgtttcct cttctccttt cccctctctc tctagtctct   1680
ccctctccac tcttgtggtg gcaagattca tttctttcat tgtttttgttt tttgttgttg   1740 ttgttgagga aggataggaa caaaaacaag gtattgtcgt gtccaaggtt aatctacaca   1800
aacacacact gtaaatgatt gattgattgc tgtcagtaga ggcgaacaca aggaataggt   1860
aaaaaaaaaa                                                         1870
```

<210> SEQ ID NO 31
<211> LENGTH: 605
<212> TYPE: PRT
<213> ORGANISM: Zea mays

<400> SEQUENCE: 31

```
Met Lys Gln Pro Arg Gly Arg Gln Glu Pro Arg Val Gly Asn Ala
1               5                   10                  15

Ala Met Val Val Thr Met Val Val Ser Leu Cys Val Leu Thr Tyr Ile
            20                  25                  30

Lys Ala Arg Tyr Cys Ser Asn Pro Phe Pro Lys Ala Val Ala Glu Val
        35                  40                  45

Glu Val Asp Glu Asp Tyr Asp Ser Thr Arg Tyr Lys Leu Thr Gly Pro
    50                  55                  60

Val Gly Glu Glu Asp Phe Asp Pro Ser Arg Pro Thr Cys Tyr Asn Thr
65                  70                  75                  80
```

```
Ser Lys Arg Ser Glu Arg Cys Ala Ala Val Gly Asp Ile Arg Val Asp
                 85                  90                  95

Gly Asn His Ser Arg Ile Tyr Ile Ser Pro Leu Ser Arg Glu Trp Arg
            100                 105                 110

Thr Lys Pro Tyr Ala Arg Arg His Asp Ala Val Ala Met Asp Asp Val
        115                 120                 125

Arg Glu Phe Thr Leu Val Pro Phe Gly Gly Pro Asn Asp Thr Ala Val
    130                 135                 140

Pro Pro Leu Cys Thr Arg Thr His Ser Val Pro Gly Phe Leu Phe Ser
145                 150                 155                 160

Ser Gly Gly Phe Ala Gly Asn Leu Tyr His Asp Tyr Ala Asp Val Leu
                165                 170                 175

Val Pro Leu Phe Ala Ser Thr Asn His Leu Gly Gly Glu Val Gln Phe
            180                 185                 190

Leu Leu Ala Asp Ile Lys Asp Trp Trp Ala Asp Lys Phe Arg Pro Leu
        195                 200                 205

Phe Arg Gln Leu Ser Arg Tyr Asp Val Ile Asp Val Asn Asn Asp Arg
    210                 215                 220

Glu Val His Cys Phe Pro Arg Ile Ile Ile Gly Ser Thr Phe His Arg
225                 230                 235                 240

Ala Met Gly Ile Asp Pro Ser Arg Ser Pro Gly Gly Val Thr Val Ala
                245                 250                 255

Asp Phe Lys Arg Leu Leu Arg Arg Ala Phe Arg Leu Glu Arg Ala Val
            260                 265                 270

Ala Ser Arg Ser Gly Ala Pro Arg Arg Asp Arg Pro Arg Leu Leu
        275                 280                 285

Ile Ile Ser Arg Lys Ser Ser Arg Arg Phe Val Asn Glu Arg Ala Met
    290                 295                 300

Ala Arg Ala Ala Ala Ala Arg Phe Asp Val Arg Ile Ala Glu Pro
305                 310                 315                 320

Asp Asn His Thr Asp Met Pro Asn Phe Ala Arg Leu Val Asn Ser Ala
                325                 330                 335

Asp Val Met Met Gly Val His Gly Ala Gly Leu Thr Asn Met Val Phe
            340                 345                 350

Leu Pro Ser Arg Ala Val Leu Val Gln Val Val Pro Phe Gly Gly Leu
        355                 360                 365

Glu Trp Leu Thr Arg Val Thr Phe Lys Asp Pro Ala Arg Asp Glu Ile
    370                 375                 380

Ile Ala Ile Met Asp Glu Glu Gly Arg Gly Phe Asp Glu Met Glu Ala
385                 390                 395                 400

Leu Ala Leu Ala Ser Leu Phe Trp Arg Arg Thr Arg Gln Pro Asn Ser
                405                 410                 415

Lys Thr Asp Thr Arg Gln Leu Leu Gly Leu Arg Lys Gln Gly His Gly
            420                 425                 430

Arg His Val His Gly Val Gln Arg Val Ala Gly Gly Glu Leu Ala Gln
        435                 440                 445

Gly Pro Leu Pro Gly Gly Pro Leu Leu Pro Glu Ala Pro Leu Arg Arg
    450                 455                 460

Ala Gln Glu Gly Val Gly Arg His Gln Asp Gly Val Pro Gly Gln Ala
465                 470                 475                 480

Glu Arg Gln Ala Gln Pro His Gln Val His Gln Asp Ala Gly Ala Gly
                485                 490                 495
```

```
Ala Arg Ser Leu Ala Asp Ala Met Thr Asp Asp Leu Pro Leu Phe
            500                 505                 510

Pro Leu Leu Cys Cys Arg Phe His Ser Leu Gln Ile Ser Cys Ser Pro
        515                 520                 525

His Phe Thr Pro Cys Leu Ser Leu Phe Phe Phe Ser Val Val Val Leu
    530                 535                 540

Tyr Ile Tyr Leu Phe Pro Leu Leu Leu Ser Pro Leu Ser Leu Val Ser
545                 550                 555                 560

Pro Ser Pro Leu Leu Trp Trp Gln Asp Ser Phe Leu Ser Leu Phe Cys
                565                 570                 575

Phe Leu Leu Leu Leu Leu Arg Lys Asp Arg Asn Lys Asn Lys Val Leu
                580                 585                 590

Ser Cys Pro Arg Leu Ile Tyr Thr Asn Thr His Cys Lys
        595                 600                 605

<210> SEQ ID NO 32
<211> LENGTH: 1725
<212> TYPE: DNA
<213> ORGANISM: Zea mays

<400> SEQUENCE: 32
atgaagcagc cgaggggccg gcaggagccg cgccgggtgg gcaacgccgc catggtcgtc      60
accatggtcg tctccctctg cgtcctcacg tacatcaagg cgcgatactg ctccaaccct    120
ttccccaagg cggtggcgga ggtggaggtg acgaggact acgacagcac gcggtacaag     180
ctgacgggcc ccgtgggcga ggaggacttc gacccgtccc gccccacctg ctacaacacc    240
agcaagcggt cggagcggtg cgccgccgtg gcgacatcc gcgtggacgg caaccactcg     300
cggatctaca tcagcccgct gtcccgcgag tggcggacca gccgtacgc gcggcggcac     360 gacgccgtgg ccatggacga cgtgcgcgag ttcacgctgg tccccttcgg cggccccaac    420 gacacgccg tgccgccgct ctgcacgcgc acccactccg tcccgggctt cctcttctcc     480
agcggcgggt cgcgggcaa cctgtaccac gactacgccg acgtgctggt gccgctcttc    540
gccagcacca accacctggg cggggaggtc cagttcctgc tggccgacat caaggactgg    600
tgggccgaca agttccgccc gctcttccgc cagctctccc gctacgacgt catcgacgtg    660
aacaacgacc gcgaggtgca cctgcttccg cggatcatca tcggctccac cttccaccgc    720
gccatgggca tcgaccctc gcgctcgccc ggcggcgtca cggtggccga cttcaagcgc    780
ctgctccgcc gcgcgttccg gctggagcgc gccgtcgcgt cgcggtcggg ggcgccccgg   840
cgccgggacc ggccccgcct cctcatcatc tcgtgcaaga gctcgcgccg cttcgtcaac   900
gagcgcgcca tggcgcgcgc gcggcggcc gcccggttcg acgtgcggat cgccgagccc   960
gacaaccaca cggacatgcc caacttcgcg aggctggtga actcggcgga cgtgatgatg  1020
ggcgtgcacg cgccgggct caccaacatg gtgttcctgc ccagccgcgc cgtgctggtg   1080
caggtggtgc cgttcggcgg gctggagtgg ctcacccgcg tcaccttcaa ggaccccgca   1140
agggacatgg acgtcacgta catggagtac aacgtgtcgc tggaggagag ctcgctcagg   1200
gacctctacc ggaggaccca cttctacctg aagcacccct acgacgtgca caagaagggg   1260
tgggacgcca tcaagacggt gtacctggac aagcagaacg tcaggctcaa cctcaccagg   1320
ttcaccagga cgctggagca ggcgcgagat ctcttgccga cgccatgact gatgatgacc  1380
tccccctctt tcctctgctc tgctgcaggt tcattcact tcagatcagc tgctcacctc    1440
acttcacgcc gtgtctctct ctcttttttt tttctgttgt tgttctatac atatacttgt   1500
```

```
ttcctcttct cctttcccct ctctctctag tctctccctc tccactcttg tggtggcaag    1560
attcatttct ttcattgttt tgttttttgt tgttgttgtt gaggaaggat aggaacaaaa    1620
acaaggtatt gtcgtgtcca aggttaatct acacaaacac acactgtaaa tgattgattg    1680
attgctgtca gtagaggcga acacaaggaa taggtaaaaa aaaaa                    1725
```

<210> SEQ ID NO 33
<211> LENGTH: 455
<212> TYPE: PRT
<213> ORGANISM: Zea mays

<400> SEQUENCE: 33

```
Met Lys Gln Pro Arg Gly Arg Gln Glu Pro Arg Val Gly Asn Ala
1               5                   10                  15

Ala Met Val Val Thr Met Val Val Ser Leu Cys Val Leu Thr Tyr Ile
                20                  25                  30

Lys Ala Arg Tyr Cys Ser Asn Pro Phe Pro Lys Ala Val Ala Glu Val
                35                  40                  45

Glu Val Asp Glu Asp Tyr Asp Ser Thr Arg Tyr Lys Leu Thr Gly Pro
50                  55                  60

Val Gly Glu Glu Asp Phe Asp Pro Ser Arg Pro Thr Cys Tyr Asn Thr
65                  70                  75                  80

Ser Lys Arg Ser Glu Arg Cys Ala Ala Val Gly Asp Ile Arg Val Asp
                85                  90                  95

Gly Asn His Ser Arg Ile Tyr Ile Ser Pro Leu Ser Arg Glu Trp Arg
                100                 105                 110

Thr Lys Pro Tyr Ala Arg Arg His Asp Ala Val Ala Met Asp Asp Val
                115                 120                 125

Arg Glu Phe Thr Leu Val Pro Phe Gly Gly Pro Asn Asp Thr Ala Val
130                 135                 140

Pro Pro Leu Cys Thr Arg Thr His Ser Val Pro Gly Phe Leu Phe Ser
145                 150                 155                 160

Ser Gly Gly Phe Ala Gly Asn Leu Tyr His Asp Tyr Ala Asp Val Leu
                165                 170                 175

Val Pro Leu Phe Ala Ser Thr Asn His Leu Gly Gly Glu Val Gln Phe
                180                 185                 190

Leu Leu Ala Asp Ile Lys Asp Trp Trp Ala Asp Lys Phe Arg Pro Val
                195                 200                 205

Phe Arg Gln Leu Ser Arg Tyr Asp Val Ile Asp Val Asn Asn Asp Arg
210                 215                 220

Glu Val His Cys Phe Pro Arg Thr Ile Ile Gly Ser Thr Phe His Arg
225                 230                 235                 240

Ala Met Gly Ile Asp Pro Ser Arg Ser Pro Gly Gly Val Thr Val Ala
                245                 250                 255

Asp Phe Lys Arg Leu Leu Arg Arg Ala Phe Arg Leu Glu Arg Ala Val
                260                 265                 270

Ala Ser Arg Ser Gly Ala Pro Arg Arg Asp Arg Pro Arg Leu Leu
                275                 280                 285

Ile Ile Ser Cys Lys Ser Ser Arg Phe Val Asn Glu Arg Ala Met
                290                 295                 300

Ala Arg Ala Ala Ala Ala Arg Phe Asp Val Arg Ile Ala Glu Pro
305                 310                 315                 320

Asp Asn His Thr Asp Met Pro Asn Phe Ala Arg Leu Val Asn Ser Ala
                325                 330                 335
```

```
Asp Val Met Met Gly Val His Gly Ala Gly Leu Thr Asn Met Val Phe
                340                 345                 350

Leu Pro Ser Arg Ala Val Leu Val Gln Val Val Pro Phe Gly Gly Leu
        355                 360                 365

Glu Trp Leu Thr Arg Val Thr Phe Lys Asp Pro Ala Arg Asp Met Asp
    370                 375                 380

Val Thr Tyr Met Glu Tyr Asn Val Ser Leu Glu Glu Ser Ser Leu Arg
385                 390                 395                 400

Asp Leu Tyr Pro Glu Asp His Phe Tyr Leu Lys His Pro Tyr Asp Val
                405                 410                 415

His Lys Lys Gly Trp Asp Ala Ile Lys Thr Val Tyr Leu Asp Lys Gln
                420                 425                 430

Asn Val Arg Leu Asn Leu Thr Arg Phe Thr Arg Thr Leu Glu Gln Ala
                435                 440                 445

Arg Asp Leu Leu Pro Thr Pro
        450                 455

<210> SEQ ID NO 34
<211> LENGTH: 488
<212> TYPE: PRT
<213> ORGANISM: Zea mays

<400> SEQUENCE: 34

Met Lys Ser Ser Leu Arg Ser Arg Gln Glu Pro Arg Arg Val Ser Asn
1               5                   10                  15

Gly Val Ile Ile Gly Ala Met Leu Leu Ser Leu Cys Val Leu Ser Ile
                20                  25                  30

Val Lys Ala Arg Tyr Cys Ala Thr Pro Phe Gly Lys Ala Glu Asp Gln
                35                  40                  45

Leu Gln Glu Gln Met Asn Ser Ser Ile Arg Met Glu Pro Glu Glu Ser
        50                  55                  60

Ser Pro Ala Arg Thr Pro Gly Glu Glu Glu Glu Asp Asp Gly Glu
65                  70                  75                  80

Asn Gly Ala Ser Ala Thr Thr Thr Thr Ala Pro Ala Val Thr Lys Thr
                85                  90                  95

Pro Ala Ala Val Ala Ala Gly Gly Asn Arg Gly Lys Gly Lys Pro Thr
                100                 105                 110

Cys Tyr Met Thr Ser Lys Arg Ser Glu Arg Cys Asp Ala Ser Gly Asp
                115                 120                 125

Ile Arg Val Asp Gly Asn Arg Ser Thr Ile Tyr Val Ser Gly Ile Asp
        130                 135                 140

Arg Glu Trp Lys Thr Lys Pro Tyr Ala Arg Tyr His Asp Pro Val Ala
145                 150                 155                 160

Met Ala His Val Arg Glu Tyr Thr Leu Lys Pro Leu Pro Glu Ala Ala
                165                 170                 175

Pro Ala Pro Ala Cys Thr Arg Asn His Ser Val Pro Gly Phe Leu Phe
                180                 185                 190

Ser Asn Gly Gly Phe Ser Gly Asn Leu Tyr His Asp Tyr Thr Asp Val
        195                 200                 205

Leu Val Pro Leu Phe Ile Ser Thr His Gln Phe Arg Gly Arg Val Gln
    210                 215                 220

Phe Leu Leu Ser Gly Met Lys Pro Trp Trp Val Ala Lys Phe Thr Pro
225                 230                 235                 240

Phe Phe Arg Gln Leu Thr Arg Tyr Asp Val Ile Asp Val Asp Asn Asp
                245                 250                 255
```

Gln Glu Val His Cys Phe Pro Arg Ile Val Val Gly Ala Thr Phe His
            260                 265                 270

Lys Asp Met Gly Val Asp Pro Arg Arg Ser Pro Gly His Val Ser Val
            275                 280                 285

Val Asp Phe Lys Arg Ala Leu Arg Arg Ala Phe Gly Leu Pro Arg Glu
            290                 295                 300

Ala Ala Ser Arg Gly Gly Ala Thr Gly Arg Gly Lys Pro Arg Leu Leu
305                 310                 315                 320

Ile Ile Ser Arg Arg Gly Ser Arg Arg Phe Leu Asn Glu Arg Glu Met
                325                 330                 335

Ala Arg Ala Ala Ala Gly Ala Gly Phe Glu Val Arg Val Ala Glu Pro
            340                 345                 350

Asp Gln His Thr Asp Thr Ala Ala Phe Ala Ala Leu Val Asn Ser Ala
            355                 360                 365

Asp Val Met Val Gly Val His Gly Ala Gly Leu Thr Asn Met Val Phe
            370                 375                 380

Leu Pro Arg Gly Ala Val Leu Val Gln Val Val Pro Phe Gly Gly Leu
385                 390                 395                 400

Glu Trp Leu Thr Gly Val Thr Phe Lys Asp Pro Ala Ala Asp Met Glu
                405                 410                 415

Val Ser Tyr Met Gly Tyr Asp Val Thr Leu Glu Glu Ser Ser Leu Ile
            420                 425                 430

Asp Gln Tyr Pro Arg Asn His Gln Val Leu Thr Asp Pro Tyr Ala Val
            435                 440                 445

His Lys Gln Gly Trp Asp Ala Leu Lys Ala Ala Tyr Leu Asp Lys Gln
450                 455                 460

Asn Ile Arg Met Asp Leu Asp Arg Phe Arg Ala Thr Leu Arg Glu Ala
465                 470                 475                 480

Met Ser Arg Leu Pro Pro Ala Pro
                485

<210> SEQ ID NO 35
<211> LENGTH: 491
<212> TYPE: PRT
<213> ORGANISM: Zea mays

<400> SEQUENCE: 35

Met Lys Ser Ser Leu Arg Ser Arg Gln Glu Ser Arg Arg Val Ser Asn
1               5                   10                  15

Gly Val Ile Ile Gly Ala Met Leu Leu Ser Leu Cys Val Leu Ser Phe
            20                  25                  30

Val Lys Ala Arg Tyr Cys Ala Thr Pro Leu Gly Lys Ala Glu Asp Gln
            35                  40                  45

Leu Glu Glu Gln Met Asn Ala Ser Ile Arg Met Glu Pro Glu Glu Ser
        50                  55                  60

Ser Pro Ala Arg Thr Pro Gly Glu Glu Asp Glu Gln Glu Ala Glu
65                  70                  75                  80

Glu Glu Asn Val Val Thr Lys Pro Pro Pro Pro Pro Ala Val Thr
                85                  90                  95

Ala Asn Arg Gly Ser Lys Lys Lys Gly Lys Gly Lys Pro Thr Cys
            100                 105                 110

Tyr Met Thr Ser Lys Arg Ser Glu Arg Cys Asp Ala Ser Gly Asp Ile
            115                 120                 125

Arg Val Asp Gly Asn Arg Ser Thr Ile Tyr Val Gly Gly Ile Glu Arg
130                 135                 140

```
Glu Trp Arg Thr Lys Pro Tyr Ala Arg Tyr His Asp Pro Val Ala Met
145                 150                 155                 160

Ala His Val Arg Glu Tyr Thr Leu Lys Ala Leu Pro Glu Pro Gly Ala
            165                 170                 175

Ala Ala Ala Pro Ala Cys Thr Arg Asn His Ser Val Pro Gly Phe Leu
        180                 185                 190

Phe Ser Asn Gly Gly Phe Ser Gly Asn Leu Tyr His Asp Tyr Thr Asp
    195                 200                 205

Val Leu Val Pro Leu Phe Ile Ser Thr His Gln Phe Arg Gly Arg Val
210                 215                 220

Gln Phe Leu Val Ser Gly Met Lys Pro Trp Trp Val Gly Lys Phe Thr
225                 230                 235                 240

Pro Phe Phe Arg Gln Leu Thr Arg His Asp Val Ile Asp Val Asp Lys
            245                 250                 255

Asp Gly Glu Val His Cys Phe Pro Arg Ile Val Gly Ala Thr Phe
        260                 265                 270

His Arg Asp Met Gly Val Asp Pro Arg Ala Pro Gly His Val Ser
    275                 280                 285

Ala Val Asp Phe Lys Arg Ala Leu Arg Ala Ala Phe Gly Leu Lys Arg
290                 295                 300

Glu Ala Ala Ser Arg Gly Gly Gly Gly Ala Thr Gly Asp Gly Lys
305                 310                 315                 320

Pro Arg Leu Leu Ile Ile Ser Arg Arg Gly Ser Arg Phe Leu Asn
            325                 330                 335

Ser Arg Glu Met Ala Val Ala Ala Gly Asp Ala Gly Phe Glu Val Arg
        340                 345                 350

Val Ala Glu Pro Asp Gln Arg Thr Asp Met Ala Ala Phe Ala Ala Leu
            355                 360                 365

Val Asn Ser Ala Asp Ala Met Val Gly Val His Gly Ala Gly Leu Thr
370                 375                 380

Asn Met Val Phe Leu Pro Arg Gly Ala Val Leu Val Gln Val Val Pro
385                 390                 395                 400

Phe Gly Gly Leu Glu Trp Leu Thr Gly Val Thr Phe Lys Glu Pro Ala
            405                 410                 415

Ala Asp Met Glu Val Ser Tyr Met Asp Tyr His Val Arg Leu Glu Glu
        420                 425                 430

Ser Ser Leu Val Asp Gln Tyr Pro Arg Gly His Gln Val Leu Thr Asp
            435                 440                 445

Pro Tyr Ala Val His Arg Gln Gly Trp Asp Ala Leu Lys Thr Ala Tyr
450                 455                 460

Leu Asp Lys Gln Asn Ile Arg Met Asp Leu Asp Arg Phe Arg Ala Thr
465                 470                 475                 480

Leu Arg Glu Val Met Ala Arg Leu Pro Ser Pro
            485                 490

<210> SEQ ID NO 36
<211> LENGTH: 460
<212> TYPE: PRT
<213> ORGANISM: Oryza sativa

<400> SEQUENCE: 36

Met Lys His His His Val Ala Arg Gly Arg Ala Glu Pro Arg Arg Met
1               5                   10                  15

Gly Asn Ala Ala Met Val Ile Thr Met Leu Leu Ser Leu Cys Val Leu
            20                  25                  30
```

```
Thr Tyr Ile Lys Ala Arg Tyr Cys Ser Thr Pro Phe Pro Lys Ala Ala
            35                  40                  45

Glu Glu Met Glu Val Val Glu Ile Asp Glu Asp Tyr Asp Ser Thr Arg
 50                  55                  60

Tyr Lys Met Thr Gly Pro Ile Gly Glu Glu Asp Phe Asp Pro Thr Arg
 65                  70                  75                  80

Pro Thr Cys Tyr Val Thr Ser Lys Arg Ser Glu Arg Cys Ala Ala Val
                85                  90                  95

Gly Asp Ile Arg Val Asp Gly Asn His Ser Lys Ile Tyr Ile Asn Pro
                100                 105                 110

Leu Asp Lys Glu Trp Arg Thr Lys Pro Tyr Ala Arg Leu His Asp Ala
            115                 120                 125

Val Ala Met Asp Asp Val Arg Glu Phe Thr Leu Val Pro Phe Gly Gly
        130                 135                 140

Ala Asn His Thr Ala Val Pro Pro Leu Cys Thr Arg Asn His Ser Val
145                 150                 155                 160

Pro Ala Phe Leu Phe Ser Ser Gly Gly Phe Ala Gly Asn Leu Tyr His
                165                 170                 175

Asp Tyr Thr Asp Val Leu Val Pro Leu Phe Thr Ser Thr Asn His Phe
                180                 185                 190

Gly Gly Glu Val Gln Phe Leu Leu Ser Gly Ile Lys Asp Trp Trp Leu
            195                 200                 205

Asp Lys Phe Thr Pro Leu Phe Arg Gln Leu Ser Arg Tyr Asp Val Ile
        210                 215                 220

Asp Val Asp Asn Asp Gln Glu Val His Cys Phe Pro Arg Ile Phe Ile
225                 230                 235                 240

Gly Ala Thr Phe His Arg Ala Met Gly Ile Asp Pro Ala Arg Ser Pro
                245                 250                 255

Gly Gly Val Thr Val Ala Asp Phe Lys Arg Leu Leu Arg Arg Thr Phe
                260                 265                 270

Arg Leu Glu Arg Ala Val Ala Ser Arg Thr Gly Ala Pro Arg Arg Asp
            275                 280                 285

Lys Pro Arg Leu Leu Ile Ile Ser Arg Lys Ser Ser Arg Arg Phe Leu
        290                 295                 300

Asn Glu Arg Ala Met Ala His Ala Ala Leu Ala Arg Phe Asp Val
305                 310                 315                 320

Arg Ile Ala Glu Pro Asp Asn His Thr Asp Met Pro Asn Phe Ala Arg
                325                 330                 335

Leu Val Asn Ser Ala Asp Val Met Met Gly Val His Gly Ala Gly Leu
            340                 345                 350

Thr Asn Met Val Phe Leu Pro Ser Arg Ala Val Leu Ile Gln Val Val
        355                 360                 365

Pro Phe Gly Gly Leu Glu Trp Leu Thr Arg Val Thr Phe Lys Asp Pro
    370                 375                 380

Ala Lys Asp Met Asp Val Asn Tyr Met Glu Tyr Asn Val Ser Phe Asp
385                 390                 395                 400

Glu Ser Ser Leu Arg Glu Leu Tyr Pro Arg Asp His Phe Tyr Ile Gln
                405                 410                 415

His Pro Tyr Asp Val His Lys Lys Gly Trp Asp Ala Ile Lys Thr Val
                420                 425                 430
```

Tyr Leu Asp Lys Gln Asn Val Glu Leu Asn Leu Thr Lys Leu Thr Asn
            435                 440                 445

Thr Leu Glu Arg Ala Arg Asp Phe Leu Pro Glu Pro
    450                 455                 460

<210> SEQ ID NO 37
<211> LENGTH: 485
<212> TYPE: PRT
<213> ORGANISM: Oryza sativa

<400> SEQUENCE: 37

Met Lys Gln Ser Met Arg Ser Arg Gln Glu Pro Arg Arg Val Ser Asn
1               5                   10                  15

Gly Val Ile Ile Ala Ala Met Leu Leu Ser Leu Cys Val Leu Ser Ile
            20                  25                  30

Val Lys Ala Arg Tyr Cys Ser Thr Pro Phe Val Lys Pro Asp Asp Gln
        35                  40                  45

Leu Gln Glu Gln Met Asn Ser Ser Ile Arg Met Glu Thr Asp Glu Pro
    50                  55                  60

Ala Thr Met Ala Ala Gly Glu Gln Glu Asp Glu Glu Glu Glu Glu Ser
65              70                  75                  80

Ser Gly Gly Gly Ala Glu Pro Glu Val Ser Ala Thr Pro Ala Val
                85                  90                  95

Val Val Thr Ala Ala Gly Gly Gly Gly Lys Arg Lys Pro Thr
            100                 105                 110

Cys Arg Met Thr Ser Lys Arg Ser Glu Arg Cys Glu Ala Arg Gly Asp
            115                 120                 125

Ile Arg Val Glu Gly Asn Ala Ser Thr Ile Tyr Ile Gly Gly Ile Asp
    130                 135                 140

Lys Glu Trp Lys Thr Lys Pro Tyr Ala Arg Tyr His Asp Pro Val Ala
145                 150                 155                 160

Met Ala Val Val Arg Glu Phe Thr Leu Lys Pro Val Thr Glu Ser Ser
                165                 170                 175

Pro Ala Cys Thr Arg Asn His Ser Val Pro Ala Phe Val Phe Ser Asn
            180                 185                 190

Gly Gly Phe Ser Gly Asn Leu Tyr His Asp Tyr Thr Asp Val Leu Val
        195                 200                 205

Pro Leu Phe Leu Ser Thr His Gln Phe Lys Gly Gln Val Gln Phe Leu
    210                 215                 220

Leu Ser Gly Leu Lys Pro Trp Trp Val Asn Lys Phe Asn Leu Phe Phe
225                 230                 235                 240

Arg Gln Leu Thr Lys Tyr Asp Ile Leu Asp Ile Asp Asn Asp Lys Asp
                245                 250                 255

Val His Cys Phe Pro Arg Ile Val Val Gly Ala Thr Phe His Lys Asp
            260                 265                 270

Met Gly Val Asp Pro Lys Arg Ser Pro Gly His Val Ser Val Val Asp
        275                 280                 285

Phe Lys Arg Ala Leu Arg Arg Ala Phe Gly Leu Glu Arg Val Ala Ala
    290                 295                 300

Ser Arg Gly Gly Ala Thr Gly Asn Gly Lys Pro Arg Leu Leu Ile Ile
305                 310                 315                 320

Ser Arg Lys Asn Ser Arg Phe Leu Asn Glu Arg Glu Met Ala Gln
                325                 330                 335

Ala Ala Ala Ala Val Gly Phe Glu Val Arg Ile Ala Glu Pro Asp Gln
            340                 345                 350

```
His Thr Asp Met Ser Thr Phe Ala Gln Leu Val Asn Ser Ala Asp Val
            355                 360                 365

Met Ile Gly Val His Gly Ala Gly Leu Thr Asn Met Val Phe Leu Pro
    370                 375                 380

Arg Gly Ala Val Leu Ile Gln Val Val Pro Phe Gly Gly Leu Glu Trp
385                 390                 395                 400

Leu Thr Thr Val Thr Phe Lys Asn Pro Ala Lys Asp Met Glu Val Thr
                405                 410                 415

Tyr Met Asp Tyr Asn Val Gln Leu Glu Ser Ser Leu Ile Asp Gln
            420                 425                 430

Tyr Pro Arg Asn His Gln Val Leu Thr Asp Pro Tyr Ala Val His Lys
        435                 440                 445

Gln Gly Trp Asp Ala Leu Lys Thr Ala Tyr Leu Asp Lys Gln Asn Ile
    450                 455                 460

Lys Met Asp Met Asp Arg Phe Lys Lys Thr Leu Gln Glu Ala Leu Asp
465                 470                 475                 480

Arg Leu Pro Pro Ala
            485

<210> SEQ ID NO 38
<211> LENGTH: 462
<212> TYPE: PRT
<213> ORGANISM: Sorghum bicolor

<400> SEQUENCE: 38

Met Thr Met Lys Gln Pro Arg Gly Arg Gln Glu Pro Arg Arg Met Gly
1               5                   10                  15

Asn Ala Ala Met Val Val Thr Met Leu Val Ser Leu Cys Val Leu Thr
                20                  25                  30

Tyr Ile Lys Ala Arg Tyr Cys Ser Asn Pro Phe Pro Lys Pro Ala Glu
            35                  40                  45

Glu Leu Glu Val Val Glu Val Asp Glu Asp Tyr Asp Ser Thr Arg Tyr
    50                  55                  60

Lys Leu Ser Gly Pro Ile Gly Glu Glu Asp Phe Asp Pro Ser Arg Pro
65                  70                  75                  80

Thr Cys Tyr Asn Thr Ser Lys Arg Ser Glu Arg Cys Ala Ala Val Gly
                85                  90                  95

Asp Ile Arg Val Asp Gly Asn His Ser Arg Ile Tyr Ile Ser Pro Leu
            100                 105                 110

Ser Arg Glu Trp Lys Thr Lys Pro Tyr Ala Arg Leu His Asp Pro Val
        115                 120                 125

Ala Met Asp Asp Val Arg Glu Phe Thr Leu Val Pro Phe Gly Pro Gly
    130                 135                 140

Ser Pro Asn Gly Thr Val Val Pro Pro Leu Cys Thr Arg Asn His Ser
145                 150                 155                 160

Val Pro Gly Phe Leu Phe Ser Ser Gly Gly Phe Ala Gly Asn Leu Tyr
                165                 170                 175

His Asp Tyr Ala Asp Val Leu Val Pro Leu Phe Ala Ser Thr His His
            180                 185                 190

Phe Gly Gly Glu Val Gln Phe Leu Leu Ala Asp Ile Lys Asp Trp Trp
        195                 200                 205

Ala Asp Lys Phe Lys Pro Leu Phe Arg Gln Leu Ser Arg Tyr Asp Val
    210                 215                 220

Ile Asp Val Asn Asn Asp Arg Glu Val His Cys Phe Pro Arg Ile Val
225                 230                 235                 240
```

```
Ile Gly Ser Thr Phe His Arg Ala Met Gly Ile Asp Ala Ser Arg Ser
            245                 250                 255

Pro Gly Gly Glu Thr Val Ala Asp Phe Lys Arg Val Leu Arg Arg Ala
        260                 265                 270

Phe Lys Leu Glu Arg Ala Val Ala Ser Arg Ser Gly Ala Pro Arg Arg
        275                 280                 285

Lys Asp Arg Pro Arg Leu Leu Ile Ile Ser Arg Lys Ser Ser Arg Arg
290                 295                 300

Phe Val Asn Glu Arg Ala Met Ala Arg Ala Ala Ala Ala Ala Lys Phe
305                 310                 315                 320

Asp Val Arg Ile Ala Glu Pro Asp Asn His Thr Asp Met Pro Asn Phe
                325                 330                 335

Ala Arg Leu Val Asn Ser Ala Asp Val Met Met Gly Val His Gly Ala
                340                 345                 350

Gly Leu Thr Asn Met Val Phe Leu Pro Ser Arg Ala Val Leu Val Gln
                355                 360                 365

Val Val Pro Phe Gly Gly Leu Glu Trp Leu Thr Arg Val Thr Phe Lys
        370                 375                 380

Asp Pro Ala Arg Asp Met Asp Val Thr Tyr Met Glu Tyr Asn Val Ser
385                 390                 395                 400

Leu Glu Glu Ser Ser Leu Arg Asp Leu Tyr Pro Glu Asp His Phe Tyr
                405                 410                 415

Leu Lys His Pro Tyr Asp Val His Lys Lys Gly Trp Asp Ala Ile Lys
                420                 425                 430

Thr Val Tyr Leu Asp Lys Gln Asn Val Arg Leu Asn Leu Thr Arg Phe
                435                 440                 445

Thr Arg Thr Leu Glu Gln Ala Arg Asp Leu Leu Pro Ser Pro
        450                 455                 460

<210> SEQ ID NO 39
<211> LENGTH: 499
<212> TYPE: PRT
<213> ORGANISM: Sorghum bicolor

<400> SEQUENCE: 39

Met Lys Ser Ser Leu Arg Thr Arg Gln Glu Pro Arg Arg Val Ser Asn
1               5                   10                  15

Gly Val Ile Ile Gly Ala Met Leu Leu Ser Leu Cys Val Leu Ser Ile
                20                  25                  30

Val Lys Ala Arg Tyr Cys Ala Thr Pro Phe Gly Lys Ala Glu Asp Gln
        35                  40                  45

Leu Gln Glu Gln Met Asn Ser Ser Ile Arg Met Glu Pro Glu Glu Ser
    50                  55                  60

Ser Pro Ala Arg Thr Pro Gly Glu Glu Glu Asp Glu Gln Glu Glu Glu
65                  70                  75                  80

Glu Glu Glu Asn Gly Ala Ser Ala Thr Pro Ala Thr Thr Thr Ala Pro
                85                  90                  95

Ala Val Thr Lys Thr Thr Pro Thr Ala Val Pro Ala Thr Ala Gly Asn
                100                 105                 110

Arg Gly Lys Val Ser Lys Gly Gly Lys Gly Lys Pro Thr Cys Tyr Met
        115                 120                 125

Thr Ser Lys Arg Ser Glu Arg Cys Asp Ala Ser Gly Asp Ile Arg Val
    130                 135                 140

Asp Gly Asn Arg Ser Ala Ile Tyr Val Ser Gly Ile Asp Lys Glu Trp
145                 150                 155                 160
```

```
Lys Thr Lys Pro Tyr Ala Arg Tyr His Asp Pro Val Ala Met Ala His
            165                 170                 175

Val Arg Glu Tyr Thr Leu Lys Pro Leu Pro Ala Ala Glu Ala Pro Ala
            180                 185                 190

Cys Thr Arg Asn His Ser Val Pro Gly Phe Leu Phe Ser Asn Gly Gly
            195                 200                 205

Phe Ser Gly Asn Leu Tyr His Asp Tyr Thr Asp Val Leu Val Pro Leu
210                 215                 220

Phe Ile Ser Thr His Gln Phe Arg Gly Arg Val Gln Phe Leu Leu Ser
225                 230                 235                 240

Gly Met Lys Pro Trp Trp Val Ala Lys Phe Thr Pro Phe Phe Arg Gln
            245                 250                 255

Leu Thr Lys Tyr Asp Val Ile Asp Val Asp Asn Asp Gln Glu Val His
            260                 265                 270

Cys Phe Pro Arg Ile Val Ala Gly Ala Thr Phe His Lys Asp Met Gly
            275                 280                 285

Val Asp Pro Arg Arg Ser Pro Gly His Val Ser Val Asp Phe Lys
            290                 295                 300

Arg Ala Leu Arg Arg Ala Phe Gly Leu Glu Arg Glu Ala Ala Ser Arg
305                 310                 315                 320

Gly Gly Ala Thr Gly His Gly Lys Pro Arg Leu Leu Ile Ile Ser Arg
            325                 330                 335

Arg Gly Ser Arg Arg Phe Leu Asn Glu Arg Glu Met Ala Arg Ala Ala
            340                 345                 350

Ala Asp Ala Gly Phe Glu Val Arg Val Ala Glu Pro Asp Gln His Thr
            355                 360                 365

Asp Met Ala Thr Phe Ala Ala Leu Val Asn Ser Ala Asp Val Met Val
370                 375                 380

Gly Val His Gly Ala Gly Leu Thr Asn Met Val Phe Leu Pro Arg Gly
385                 390                 395                 400

Ala Val Leu Ile Gln Val Val Pro Phe Gly Gly Leu Glu Trp Leu Thr
            405                 410                 415

Ser Val Thr Phe Lys Asp Pro Ala Ala Asp Met Glu Val Asn Tyr Met
            420                 425                 430

Asp Tyr Asn Val Lys Leu Glu Glu Ser Ser Leu Leu Asp Gln Tyr Pro
            435                 440                 445

Arg Asn His Gln Val Leu Thr Asp Pro Tyr Ala Val His Lys Gln Gly
            450                 455                 460

Trp Asp Ala Leu Lys Thr Ala Tyr Leu Asp Lys Gln Asn Ile Arg Met
465                 470                 475                 480

Asp Leu Asp Arg Phe Arg Ala Thr Leu Arg Glu Ala Met Ser Arg Leu
            485                 490                 495

Pro Ser Pro

<210> SEQ ID NO 40
<211> LENGTH: 452
<212> TYPE: PRT
<213> ORGANISM: Glycine max

<400> SEQUENCE: 40

Met Ile Tyr Asp Thr Val Leu Ala Lys Ser Phe Ser Arg Tyr Asp Gln
1               5                   10                  15

Lys Arg Leu Gly Tyr Gly Ala Phe Val Ser Cys Leu Leu Ile Val Leu
            20                  25                  30
```

```
Met Leu Leu His Pro Leu Ala Leu Ile Thr Tyr Phe His Asn Pro Arg
             35                  40                  45

Pro Ser Thr Ser Ile His Cys Ala Leu Val Ile Gly Ile Lys Cys Arg
 50                  55                  60

Tyr Ile Phe His His Phe Glu Leu Leu Cys Thr Ser Glu Glu Arg Thr
 65                  70                  75                  80

Lys Phe Cys Gln Ala Arg Gly Asp Ile Arg Val His Gly Lys Ser Ser
                 85                  90                  95

Thr Val Tyr Ile Val Ser Ser Lys Thr Thr Met Ser Glu Lys Asn Met
            100                 105                 110

Ser Trp Asn Leu Lys Pro Tyr Ala Arg Arg Asp Val Asp Ala Met
            115                 120                 125

Ile Arg Val Arg Glu Trp Ser Val Lys Ala Val Asn Val Ser Gln Lys
            130                 135                 140

Ala Pro Gln Cys Thr Gln Tyr His Asn Ile Pro Ala Val Leu Phe Ser
145                 150                 155                 160

Thr Gly Gly Tyr Ala Gly Asn His Phe His Glu Phe Thr Asp Ile Val
                165                 170                 175

Ile Pro Leu Phe Leu Thr Ala Arg Gln Phe Asn Gly Glu Val Gln Phe
            180                 185                 190

Ile Ile Thr Asp Lys Arg Pro Trp Trp Ile Ser Lys His Lys Pro Leu
            195                 200                 205

Leu Lys Lys Leu Ser Asn Tyr Glu Thr Met Asp Ile Asp Gly Asp Asp
210                 215                 220

Glu Val His Cys Phe Pro Arg Val Thr Val Gly Leu Lys Arg Tyr Gln
225                 230                 235                 240

Lys Glu Leu Ser Ile Glu Pro Gln Lys Tyr Ser Tyr Ser Met Lys Asp
                245                 250                 255

Phe Arg Asp Leu Leu Arg Ser Ser Tyr Ala Leu Lys Arg Val Glu Ala
            260                 265                 270

Ile Lys Thr Arg Asp Gly Leu Arg Gly Lys Pro Arg Leu Met Ile Leu
            275                 280                 285

Ser Arg Lys Arg Ser Arg Phe Phe Thr Asn Thr Asp Glu Ile Ala Lys
290                 295                 300

Met Ala Glu Ser Leu Gly Phe Asp Val Ile Lys Glu Ala Gly Trp
305                 310                 315                 320

Ser Met Trp Gly Phe Ala Asn Val Val Asn Ser Cys Asp Val Leu Leu
                325                 330                 335

Gly Val His Gly Ala Gly Leu Thr Asn Ile Leu Phe Leu Pro Glu Asn
            340                 345                 350

Ala Val Phe Val Gln Val Val Pro Tyr Gly Gly Val Thr Leu Asp Trp
            355                 360                 365

Leu Ala Thr Asn Asp Phe Gly Asn Pro Ser Lys Asp Met Asn Ile Lys
370                 375                 380

Tyr Leu Glu Tyr Lys Ile Ser Leu Glu Glu Ser Thr Leu Ile Gln Gln
385                 390                 395                 400

Tyr Pro Leu Asp His Met Phe Ile Lys Asp Pro Pro Leu Ile Glu Lys
                405                 410                 415

Ile Gly Trp Glu Glu Phe Lys Ser Val Tyr Leu Asp Lys Gln Asn Val
            420                 425                 430
```

```
Lys Leu Asp Val Asp Arg Phe Arg Pro Thr Leu Gln Lys Ala Leu Glu
            435                 440                 445

Leu Leu His Gln
    450

<210> SEQ ID NO 41
<211> LENGTH: 462
<212> TYPE: PRT
<213> ORGANISM: Glycine max

<400> SEQUENCE: 41

Met Ile Tyr Asp Thr Val Leu Ala Lys Ser Phe Ser Arg Tyr Asp Gln
1               5                   10                  15

Lys Arg Leu Gly Tyr Gly Ala Phe Val Ser Cys Leu Phe Ile Ile Leu
            20                  25                  30

Ser Leu Cys Thr Val Phe Lys Pro Tyr Leu Gly Pro Val His Val Leu
        35                  40                  45

Ser Leu Lys Leu Phe Ile Asp Val Asp Thr Lys Met Leu Ile Thr Ser
    50                  55                  60

Ser Ser Leu Gln Ile Ala Lys Val Lys Gly Lys Glu Thr Lys Lys Glu
65                  70                  75                  80

Glu Leu Leu Cys Thr Ser Glu Glu Arg Thr Glu Phe Cys Gln Ala Arg
                85                  90                  95

Gly Asp Ile Arg Val His Gly Lys Ser Ser Thr Val Ser Ile Val Ser
            100                 105                 110

Ser Lys Thr Thr Met Leu Glu Lys Thr Met Ser Arg Ser Leu Lys Pro
        115                 120                 125

Tyr Ala Arg Arg Gly Asp Ile Asp Ala Met Asn Arg Val Arg Glu Trp
    130                 135                 140

Ser Val Lys Ala Val Asn Ala Ser Gln Lys Ala Pro Gln Cys Thr Gln
145                 150                 155                 160

Ser His Asn Ile Thr Ala Val Leu Phe Ser Thr Gly Gly Tyr Ser Gly
                165                 170                 175

Asn His Phe His Glu Phe Thr Asp Ile Val Ile Pro Leu Phe Leu Thr
            180                 185                 190

Ala Arg Gln Phe Asn Gly Glu Val Gln Phe Ile Ile Thr Asp Lys Arg
        195                 200                 205

Pro Trp Trp Ile Ser Lys His Lys Pro Leu Leu Lys Lys Leu Ser Asn
    210                 215                 220

Tyr Glu Thr Met Asp Ile Asp Gly Asp Asp Gln Val His Cys Phe Pro
225                 230                 235                 240

Ser Val Thr Val Gly Leu Lys Arg Tyr Gln Lys Glu Leu Ser Ile Asp
                245                 250                 255

Pro Gln Lys Tyr Ser Tyr Ser Met Lys Asp Phe Arg Asp Leu Leu Arg
            260                 265                 270

Ser Ser Tyr Ala Leu Lys Arg Val Glu Ala Met Lys Ile Arg Asp Gly
        275                 280                 285

Leu Arg Gly Lys Pro Arg Leu Met Ile Leu Ser Arg Lys Arg Ser Arg
    290                 295                 300

Ser Phe Thr Asn Thr Asp Glu Ile Ala Lys Met Ala Ala Ser Leu Gly
305                 310                 315                 320

Phe Asp Val Ile Val Lys Glu Ala Gly Trp Ser Met Trp Gly Phe Ala
                325                 330                 335

Asn Val Val Asn Ser Cys Asp Val Leu Leu Gly Val His Gly Ala Gly
            340                 345                 350
```

```
Leu Thr Asn Ile Leu Phe Leu Pro Glu Asn Ala Val Phe Ile Gln Val
            355                 360                 365

Val Pro Tyr Gly Gly Phe Thr Leu Asp Trp Leu Ala Thr Asn Asp Phe
370                 375                 380

Gly Lys Pro Ser Lys Asp Met Asn Leu Lys Tyr Leu Glu Tyr Lys Ile
385                 390                 395                 400

Gly Leu Lys Glu Ser Thr Leu Ile Gln Gln Tyr Pro Leu Asp His Ile
            405                 410                 415

Phe Ile Lys Asp Pro Pro Leu Val Glu Lys Ile Gly Trp Glu Phe
            420                 425                 430

Lys Ser Val Tyr Leu Asp Lys Gln Asn Val Lys Leu Asp Val Asp Arg
            435                 440                 445

Phe Arg Pro Thr Leu Gln Lys Ala Phe Glu Leu Leu His Gln
450                 455                 460

<210> SEQ ID NO 42
<211> LENGTH: 384
<212> TYPE: PRT
<213> ORGANISM: Arabidopsis thaliana

<400> SEQUENCE: 42

Met Lys Pro Ile Cys Thr Lys Leu Ala Arg Thr Glu Phe Cys Glu Leu
1               5                   10                  15

Asn Gly Asp Val Arg Val His Gly Lys Ser Ala Thr Val Ser Ala Ala
            20                  25                  30

Ile Thr Phe Ala Phe Ser Gly Asn Ser Thr Trp His Ile Arg Pro Tyr
        35                  40                  45

Ala Arg Lys Gly Asp Thr Val Ala Met Lys Arg Val Arg Glu Trp Thr
    50                  55                  60

Val Lys Leu Glu Gln Asn Ala Asp Gln Leu Glu Asn Ala Asn Phe Ser
65                  70                  75                  80

Arg Cys Val Arg Asn His Ser Val Pro Ala Met Ile Phe Ser Leu Gly
                85                  90                  95

Gly Tyr Ser Met Asn Asn Phe His Asp Phe Thr Asp Ile Val Ile Pro
            100                 105                 110

Leu Tyr Thr Thr Ala Arg Arg Phe Asn Gly Glu Val Gln Phe Leu Val
        115                 120                 125

Thr Asn Lys Ser Pro Ser Trp Ile Asn Lys Phe Lys Glu Leu Val Arg
    130                 135                 140

Lys Leu Ser Asn Tyr Glu Val Ile Tyr Ile Asp Glu Glu Asp Glu Thr
145                 150                 155                 160

His Cys Phe Ser Ser Val Thr Val Gly Leu Thr Arg His Arg Glu Tyr
                165                 170                 175

Phe Lys Glu Leu Thr Ile Asp Pro Ser Asn Ser Glu Tyr Ser Met Ser
            180                 185                 190

Asp Phe Arg Ser Phe Leu Arg Asp Thr Tyr Ser Leu Arg Asn Asp Ala
        195                 200                 205

Val Ala Thr Arg Gln Ile Arg Arg Arg Pro Arg Ile Leu Ile Leu
    210                 215                 220

Ala Arg Gly Arg Ser Arg Ala Phe Val Asn Thr Gly Glu Ile Ala Arg
225                 230                 235                 240

Ala Ala Arg Gln Ile Gly Phe Lys Val Val Ala Glu Ala Asn Ile
                245                 250                 255

Gly Ile Ala Lys Phe Ala Gln Thr Val Asn Ser Cys Asp Val Met Leu
            260                 265                 270
```

```
Gly Val His Gly Ala Gly Leu Thr Asn Met Val Phe Leu Pro Glu Asn
            275                 280                 285

Ala Val Val Ile Gln Val Leu Pro Ile Gly Gly Phe Glu Trp Leu Ala
    290                 295                 300

Lys Thr Asp Phe Glu Lys Pro Ser Glu Gly Met Asn Leu Arg Tyr Leu
305                 310                 315                 320

Glu Tyr Lys Ile Ala Val Glu Ser Thr Leu Val Lys Lys Tyr Gly
                325                 330                 335

Arg Asp His Glu Ile Val Arg Asp Pro Ser Ala Val Ala Lys His Gly
            340                 345                 350

Trp Glu Met Phe Lys Ser Val Tyr Leu Val Gln Gln Asn Val Ser Ile
            355                 360                 365

Asp Ile Asn Arg Phe Lys Pro Val Leu Val Lys Ala Leu Glu Leu Leu
            370                 375                 380

<210> SEQ ID NO 43
<211> LENGTH: 470
<212> TYPE: PRT
<213> ORGANISM: Arabidopsis thaliana

<400> SEQUENCE: 43

Met Thr Lys Lys Asp Ile Leu Tyr Asp Thr Val Leu Ala Arg Ser Phe
1               5                   10                  15

Ser Lys Thr Asp Gln Lys Arg Leu Cys Cys Gly Ala Phe Ile Ala Ser
            20                  25                  30

Leu Leu Leu Val Leu Thr Leu Cys Thr Val Val Lys Pro Tyr Leu Ser
            35                  40                  45

Pro Leu Pro Ile Val Glu Leu Gln Leu Ser Val Gly Thr Gly Leu Arg
50                  55                  60

Met Leu Ser Ile Thr Glu Leu Thr Thr Asn Thr Thr Ile Ser Lys Glu
65                  70                  75                  80

Glu Val Ile Ser Glu Cys Asn Lys Met Glu Lys Pro Ile Cys His Cys
                85                  90                  95

Asn Thr Leu Gly Ser Lys Glu Phe Cys Asp Val Ser Gly Asp Val Arg
            100                 105                 110

Ile His Gly Lys Ser Ala Thr Val Leu Ala Ala Val Thr Phe Ala Phe
        115                 120                 125

Ser Gly Asn Ser Thr Trp Tyr Met Arg Pro Tyr Ala Arg Lys Asp Gln
    130                 135                 140

Val Pro Ala Met Lys Arg Val Arg Glu Trp Thr Val Lys Leu Val Gln
145                 150                 155                 160

Asn Ala Ser Leu Ser Arg Cys Val Arg Asn His Ser Val Pro Ala Ile
                165                 170                 175

Leu Phe Ser Leu Gly Gly Phe Ser Leu Asn Asn Phe His Asp Phe Thr
            180                 185                 190

Asp Ile Val Ile Pro Leu Tyr Thr Thr Ala Arg Arg Phe Ser Gly Glu
        195                 200                 205

Val Gln Phe Leu Val Thr Asn Lys Asn Leu Leu Trp Ile Asn Lys Phe
    210                 215                 220

Lys Glu Leu Val Arg Lys Leu Ser Asn Tyr Glu Val Ile Tyr Ile Asp
225                 230                 235                 240

Glu Glu Asp Glu Thr His Cys Phe Ser Ser Val Ile Val Gly Leu Asn
                245                 250                 255

Arg His Arg Asp Tyr Asp Lys Glu Leu Thr Thr Asp Pro Ser Asn Ser
            260                 265                 270
```

-continued

```
Glu Tyr Ser Met Ser Asp Phe Arg Lys Phe Leu Arg Asp Thr Tyr Ser
            275                 280                 285

Leu Arg Asn Ser Ala Val Thr Thr Arg Lys Pro Arg Ile Leu Ile
290                 295                 300

Leu Ser Arg Ser Arg Ser Arg Ala Phe Val Asn Ala Gly Glu Ile Ala
305                 310                 315                 320

Arg Ala Ala Arg Gln Ile Gly Phe Lys Val Val Ala Glu Ala Asn
                325                 330                 335

Thr Glu Ile Ala Ser Phe Ala Ile Thr Val Asn Ser Cys Asp Val Met
                340                 345                 350

Leu Gly Val His Gly Ala Gly Met Thr Asn Met Val Phe Leu Pro Asp
            355                 360                 365

Asn Ala Ile Val Ile Gln Ile Leu Pro Ile Gly Gly Phe Glu Trp Leu
            370                 375                 380

Ala Lys Met Asp Phe Glu Tyr Pro Ser Lys Gly Met Asn Leu Arg Tyr
385                 390                 395                 400

Leu Glu Tyr Lys Ile Thr Ala Glu Glu Ser Thr Leu Val Lys Gln Tyr
                405                 410                 415

Gly Arg Asp His Glu Phe Val Arg Asp Pro Leu Ala Val Ala Lys Arg
                420                 425                 430

Gly Trp Gly Thr Phe Lys Ser Val Tyr Leu Val Gln Gln Asn Val Ser
            435                 440                 445

Val Asp Ile Asn Arg Phe Lys Leu Val Leu Val Lys Ala Leu Glu Leu
450                 455                 460

Leu His Asn Gln Ser Val
465                 470

<210> SEQ ID NO 44
<211> LENGTH: 462
<212> TYPE: PRT
<213> ORGANISM: Hordeum vulgare

<400> SEQUENCE: 44

Met Lys Gln Pro Arg Ser Arg Gln Glu Pro Arg Arg Met Gly Asn Ser
1               5                   10                  15

Ala Met Val Val Thr Met Leu Leu Ser Leu Cys Val Leu Thr Phe Ile
                20                  25                  30

Lys Ala Arg Tyr Cys Ser Thr Pro Tyr Pro Asn Lys Pro Ala Pro Leu
            35                  40                  45

Leu Asp Leu Glu Ala Gly Ile Asp Glu Asp Tyr Asp Ser Ser Arg Tyr
50                  55                  60

Lys Ile Ser Gly Pro Ile Gly Glu Glu Glu Phe Asp Pro Ser Arg Pro
65                  70                  75                  80

Thr Cys Tyr Asn Thr Ser Lys Arg Ser Glu Arg Cys Ala Ala Val Gly
                85                  90                  95

Asp Ile Arg Val Asp Gly Asn His Ser Lys Ile Tyr Ile Ser Pro Leu
            100                 105                 110

Asp Arg Val Trp Arg Thr Lys Pro Tyr Ala Arg Arg His Asp Ala Val
            115                 120                 125

Ala Met Asp Asp Val Arg Glu Phe Ala Leu Leu Pro Phe Gly Gly Gly
130                 135                 140

Asn Asp Ser Ala Val Pro Pro Leu Cys Thr Arg Asn His Ser Val Pro
145                 150                 155                 160

Ala Phe Leu Phe Ser Ser Gly Gly Phe Ala Gly Asn Leu Tyr His Asp
                165                 170                 175
```

Tyr Thr Asp Val Leu Val Pro Leu Phe Thr Ser His His Phe Gly
            180                 185                 190

Gly Glu Val Gln Phe Leu Leu Thr Asp Ile Lys Asp Trp Trp Leu Asp
        195                 200                 205

Lys Phe Thr Pro Leu Phe Arg Gln Leu Ser Asn Tyr Asp Val Ile Asp
    210                 215                 220

Val Asp Asn Asp Gln Glu Val His Cys Phe Pro Arg Ile Val Ile Gly
225                 230                 235                 240

Ser Thr Phe His Arg Pro Met Gly Ile Asp Gly Thr Arg Ser Pro Gly
                245                 250                 255

Gly Glu Thr Val Ala Asp Phe Lys Arg Leu Leu Arg Arg Ala Phe Arg
            260                 265                 270

Leu Asp Arg Val Val Ala Ser His Asp Gly Ser Ala Ser Leu Gly Lys
        275                 280                 285

Pro Arg Leu Leu Ile Ile Ser Arg Lys Ser Ser Arg Arg Phe Leu Asn
    290                 295                 300

Glu Arg Ala Met Ala His Ala Ala Ala Leu Ala Gln Phe Asp Val Arg
305                 310                 315                 320

Ile Ala Glu Pro Asp Asn His Thr Asp Met Pro Asn Phe Ala Arg Leu
                325                 330                 335

Val Asn Ser Ala Asp Val Met Met Gly Val His Gly Ala Gly Leu Thr
            340                 345                 350

Asn Met Val Phe Leu Pro Ser Arg Ala Val Leu Leu Gln Val Val Pro
        355                 360                 365

Phe Gly Gly Leu Glu Trp Leu Ser Arg Val Thr Phe Lys Asp Pro Ala
    370                 375                 380

Lys Asp Phe Asp Val Thr Tyr Met Glu Tyr Asn Val Ser Leu Glu Glu
385                 390                 395                 400

Ser Ser Leu Lys Asn Leu Tyr Pro Lys Asp His Phe Tyr Leu Gln His
                405                 410                 415

Pro Tyr Asp Val His Lys Lys Gly Trp Asn Ala Ile Lys Thr Val Tyr
            420                 425                 430

Leu Asp Lys Gln Ser Val Arg Leu Asp Leu Ala Lys Leu Thr Arg Thr
        435                 440                 445

Leu Glu His Ala Arg Ser Leu Leu Pro Ser Ser Ser His
    450                 455                 460

<210> SEQ ID NO 45
<211> LENGTH: 455
<212> TYPE: PRT
<213> ORGANISM: Brachypodium distachyon

<400> SEQUENCE: 45

Met Met Lys Ala Gln Gln Gln Gly Arg Ser Arg Gln Glu Pro Arg Arg
1               5                   10                  15

Met Gly Asn Ser Ala Met Val Ile Thr Met Leu Leu Ser Leu Cys Val
            20                  25                  30

Leu Thr Phe Ile Lys Ala Arg Tyr Cys Ser Thr Pro Phe Pro Lys Ala
        35                  40                  45

Ala Pro Val Leu Glu Val Glu Asp Glu Asp Tyr Asp Gly Ser Arg
    50                  55                  60

Tyr Arg Ile Asp Gly Pro Ile Gly Glu Glu Asp Phe Asp Pro His Arg
65                  70                  75                  80

Pro Thr Cys Tyr Asn Thr Ser Lys Arg Ser Glu Arg Cys Ala Ala Val
                85                  90                  95

```
Gly Asp Ile Arg Phe Asp Gly Asn His Ser Lys Ile Tyr Ile Asn Pro
                100                 105                 110

Leu Asp Lys Glu Trp Arg Thr Lys Pro Tyr Ala Arg Arg His Asp Ala
            115                 120                 125

Val Ala Met Asp Asp Val Arg Glu Phe Thr Leu Leu Pro Phe Asp Thr
130                 135                 140

Glu Ser Ser Asn Thr Thr Val Val Pro Leu Cys Thr Arg Asn His
145                 150                 155                 160

Ser Val Pro Ala Phe Leu Phe Ser Ser Gly Gly Phe Ala Gly Asn Leu
                165                 170                 175

Tyr His Asp Tyr Thr Asp Val Leu Val Pro Leu Phe Thr Ser Thr His
            180                 185                 190

His Phe Arg Gly Glu Val Gln Phe Leu Leu Thr Asp Ile Lys Asp Trp
            195                 200                 205

Trp Leu Asp Lys Phe Thr Pro Leu Phe Arg Gln Leu Ser Asn Tyr Asp
        210                 215                 220

Val Ile Asp Ala Asp Asn Asp Gln Gln Val His Cys Phe Arg Arg Ile
225                 230                 235                 240

Ile Ile Gly Ala Thr Phe His Arg Ala Met Gly Ile Asp Pro Lys Arg
                245                 250                 255

Ser Pro Gly Gly Glu Thr Val Ala Asp Phe Lys Arg Leu Leu Arg His
            260                 265                 270

Ala Phe His Leu Thr Arg Pro Val Ala Ser Arg Asp Asn Pro Arg Leu
        275                 280                 285

Leu Ile Ile Ser Arg Lys Ser Ser Arg Arg Phe Leu Asn Glu Arg Ala
        290                 295                 300

Met Ala His Ala Ala Ala Leu Ala Lys Phe Asp Val Arg Ile Ala Glu
305                 310                 315                 320

Pro Asp Asn His Thr Asp Met Pro Asn Phe Ala Arg Leu Val Asn Ser
                325                 330                 335

Ala Asp Ile Met Met Gly Val His Gly Ala Gly Leu Thr Asn Met Val
            340                 345                 350

Phe Leu Pro Ser Arg Ala Val Leu Leu Gln Val Val Pro Phe Gly Gly
        355                 360                 365

Leu Glu Trp Leu Ser Arg Val Thr Phe Lys Asp Pro Ala Lys Asp Met
        370                 375                 380

Asp Val Asn Tyr Met Glu Tyr Asn Val Ser Leu Glu Glu Ser Ser Leu
385                 390                 395                 400

Arg Asn Leu Tyr Pro Glu Gly His Phe Tyr Leu Lys His Pro Tyr Asp
                405                 410                 415

Val His Lys Lys Gly Trp Asp Ala Ile Lys Thr Val Tyr Leu Asp Lys
            420                 425                 430

Gln Ser Val Arg Leu Asn Leu Thr Lys Phe Val Gln Thr Leu Glu Leu
        435                 440                 445

Ala Arg Ser Arg Leu Pro Ala
        450                 455

<210> SEQ ID NO 46
<211> LENGTH: 1536
<212> TYPE: DNA
<213> ORGANISM: Paspalum notatum
```

<400> SEQUENCE: 46

```
gccatccagc gctccaacca gctccagcaa gctccagatc cagcggaaac cgaccggcga       60
tgaagcagcc taggggggcgg caggagccgc ggcgggtggg caacgccgcc atggtcgtca      120
ccatgctcat ctccctctgc gtcctcacct acatcaaggc gcgatactgc tccaacccct      180
tccccaagkc gccggagccg ctggagccag cggcggtgga tgtggacgag gactacgaca      240
gcacgcggta caagctctcg ggccccatcg gcgaggaaga cttcgacccg acgcgcccca      300
cgtgctacaa cacgagcaag cgctccgagc ggtgcgcggc ggtgggcgac atccgcgtcg      360
acggcaacca ctccaagatc tacatcagcc cactctcccg cgagtggcgc accaaaccct      420
acgcgcgcct gcacgacgcc gtggccatgg acgacgtgcg cgagtacacg ctcgtccccT      480
tcggcggcgc caacgacacc gccgtgccgc cgctctgcac gcgcaaccac tccgccccgg      540
ccttcctctt ctccaacggc ggcttcgcgg gcaacctcta ccacgactac gccgacgtcc      600
tcgtgccgct cttcaccagc acgcaccatt tcggtgggga ggtggtgttc ctgctcagcg      660
ggatgaagga ctggtggaac gagaagttca cgccgctgtt ccgccagctc tcgcgctacg      720
acgtcgtcga cgtcgacaac gacctcgagg tgcactgctt ccatcggatc gtcatcgggg      780
ccaccttcca ccgcgccatg ggcatcgacc ccacgcggtc gccgggcggg atcacggtgg      840
ccgacttcaa gcggacgctg cgscgcgcgt tcaggctgga gcgcgccgtc gcgtcgcgga      900
cgggggcgcc gaggagggac cgcccgcggc tactcatcat ctcgcgcagg agctcgcgcc      960
ggttcctcaa cgagcgcgcc atggcgcacg ccgccgcggc ggccaggttc gacgtgcgca     1020
tcgccgagcc cgacaaccac acggacatgc ccaacttcgc gcggctcgtc aactcggcgg     1080
acgtgatgat gggcgtgcac ggcgccgggc tcaccaacat ggtgttcctg cccagccgcg     1140
ccgtgctcat ccaggtggtg cccttcgggg gkctcgagtg gctctcgcgc gtcaccttca     1200
aggaccccgc caggacatg gacgtcaact acatggagta caacgtgtcg ctggaggaga     1260
gctcgctcag ggacctctac ccggagggc atttctacct caagcaccca tacgacgtgc     1320
acaagaaggg atgggacgcc atcaagaccg tctacctcga caagcagaac gtcaggctca     1380
acctcaccag gttcactgag acgctggagc aggcaaggga cctcttgcca ctgccctgac     1440
gtccattgca tgctctcagg atggatttgc gcgccttaat tggtagctag gcaggcagtg     1500
aagcagatgc aggcaggctc atcaccatga ccatgc                              1536
```

<210> SEQ ID NO 47
<211> LENGTH: 459
<212> TYPE: PRT
<213> ORGANISM: Paspalum notatum
<220> FEATURE:
<221> NAME/KEY: misc_feature
<222> LOCATION: (44)..(44)
<223> OTHER INFORMATION: Xaa can be any naturally occurring amino acid

<400> SEQUENCE: 47

```
Met Lys Gln Pro Arg Gly Arg Gln Glu Pro Arg Arg Val Gly Asn Ala
 1               5                  10                  15

Ala Met Val Val Thr Met Leu Ile Ser Leu Cys Val Leu Thr Tyr Ile
                20                  25                  30

Lys Ala Arg Tyr Cys Ser Asn Pro Phe Pro Lys Xaa Pro Glu Pro Leu
            35                  40                  45
```

Glu Pro Ala Ala Val Asp Val Asp Glu Asp Tyr Asp Ser Thr Arg Tyr
 50                  55                  60

Lys Leu Ser Gly Pro Ile Gly Glu Glu Asp Phe Asp Pro Thr Arg Pro
 65                  70                  75                  80

Thr Cys Tyr Asn Thr Ser Lys Arg Ser Glu Arg Cys Ala Ala Val Gly
                 85                  90                  95

Asp Ile Arg Val Asp Gly Asn His Ser Lys Ile Tyr Ile Ser Pro Leu
                100                 105                 110

Ser Arg Glu Trp Arg Thr Lys Pro Tyr Ala Arg Leu His Asp Ala Val
            115                 120                 125

Ala Met Asp Asp Val Arg Glu Tyr Thr Leu Val Pro Phe Gly Gly Ala
130                 135                 140

Asn Asp Thr Ala Val Pro Pro Leu Cys Thr Arg Asn His Ser Ala Pro
145                 150                 155                 160

Ala Phe Leu Phe Ser Asn Gly Gly Phe Ala Gly Asn Leu Tyr His Asp
                165                 170                 175

Tyr Ala Asp Val Leu Val Pro Leu Phe Thr Ser Thr His His Phe Gly
                180                 185                 190

Gly Glu Val Val Phe Leu Leu Ser Gly Met Lys Asp Trp Trp Asn Glu
            195                 200                 205

Lys Phe Thr Pro Leu Phe Arg Gln Leu Ser Arg Tyr Asp Val Val Asp
210                 215                 220

Val Asp Asn Asp Leu Glu Val His Cys Phe His Arg Ile Val Ile Gly
225                 230                 235                 240

Ala Thr Phe His Arg Ala Met Gly Ile Asp Pro Thr Arg Ser Pro Gly
                245                 250                 255

Gly Ile Thr Val Ala Asp Phe Lys Arg Thr Leu Arg Arg Ala Phe Arg
                260                 265                 270

Leu Glu Arg Ala Val Ala Ser Arg Thr Gly Ala Pro Arg Arg Asp Arg
            275                 280                 285

Pro Arg Leu Leu Ile Ile Ser Arg Arg Ser Ser Arg Arg Phe Leu Asn
290                 295                 300

Glu Arg Ala Met Ala His Ala Ala Ala Ala Arg Phe Asp Val Arg
305                 310                 315                 320

Ile Ala Glu Pro Asp Asn His Thr Asp Met Pro Asn Phe Ala Arg Leu
                325                 330                 335

Val Asn Ser Ala Asp Val Met Met Gly Val His Gly Ala Gly Leu Thr
                340                 345                 350

Asn Met Val Phe Leu Pro Ser Arg Ala Val Leu Ile Gln Val Val Pro
            355                 360                 365

Phe Gly Gly Leu Glu Trp Leu Ser Arg Val Thr Phe Lys Asp Pro Ala
370                 375                 380

Arg Asp Met Asp Val Asn Tyr Met Glu Tyr Asn Val Ser Leu Glu Glu
385                 390                 395                 400

Ser Ser Leu Arg Asp Leu Tyr Pro Glu Gly His Phe Tyr Leu Lys His
                405                 410                 415

Pro Tyr Asp Val His Lys Lys Gly Trp Asp Ala Ile Lys Thr Val Tyr
                420                 425                 430

Leu Asp Lys Gln Asn Val Arg Leu Asn Leu Thr Arg Phe Thr Glu Thr
            435                 440                 445

Leu Glu Gln Ala Arg Asp Leu Leu Pro Leu Pro
450                 455

<210> SEQ ID NO 48
<211> LENGTH: 1498
<212> TYPE: DNA
<213> ORGANISM: Eragrostis nindensis

<400> SEQUENCE: 48

```
gcttgctctg cagtctcggg cggtgggggga tccagccaga cccggagcga tgaagcatcc    60
gaggagccgg caggagccgc ggcggatggg caacggcgcc atggtcgtca ccatgctgct   120
ctcgctctgc gtcctcacct acatcaaggc gcgatactgc tccaacccat tccccaaggc   180
ggcggatgag atggaggtgg tggagatcga cgaggactac gacagcacgc ggtacaagat   240
ggacggcccg atcggggagg aggacttcga cccttcccgg ccgacttgct acaacaccag   300
caagcgctcg gagcggtgcg cggccgtggg cgacatccgc gtcgacggca accactccaa   360
aatctacatc agcccgctga gcaaggagtg gaagacgaag ccgtacgcgc ggcggcacga   420
cgccgtggcc atggacgacg tgcgggagtt cacgctcctc cccttcggcg ggccaacga   480
cacggccgtg ccgccgctct gcacccggaa ccactccgtc ccgggcttcc tcttctccat   540
cggcgggttc gccggcaacc tgtaccacga ctacaccgac gtgctggtgc cgctcttcac   600
cagcacccac cacttcggcg gggaggtgca gttgatgatc agcgacatat ggggcaagga   660
ggacaaggac tggtgggtcg acaagttcac gccgctgttc cgccagctct ccaagtacga   720
cgtcatcgac gccgacaacg accaggaggt gcactgcttc ccgcgcatcg tcatcggccc   780
caccttccac cgcgccatgg catcgaccc cacgcgctcg ccgggggca tcaacatcgc   840
cgacttcaag cgcctcctcc gccgcacctt ccgcctcgag cgcgccgtcg cgtcgcgcac   900
gggggcgccg cgacgcgaca agccgcgcct gctcatcatc tcccgcaaga gctcccggcg   960
attcctcaac gagcgcgccg tggcgcacgc cgccgcgctg gccaagttcg acgtgcgcat  1020
cgccgagccg gacaaccaca cggacatgcc caacttcgcg cggctcgtca actcagcgga  1080
cgtgatgatg ggcgtgcacg gcgccgggct caccaacatg gtgttcctcc gagccgcgc  1140
cgtgctcatc caggtggtgc ccttcggcgg actcgagtgg ctcagccgcg tcaccttcaa  1200
ggacccggcc aaggactacg acgtcaacta catggagtac aacgtgtcgc tggaggagag  1260
ctcgctcagg gacctctacc ggaggaccat tttctacctc aagcatccct acgacgtgca  1320
caagaaggga tgggacgcca tcaagaccac ctatctcgac aagcagaacg tcaggctcaa  1380
cctcaccagg ttcaccaaaa cgctgcaaca ggcgcgggac ctgttgcctt cacccctgaca  1440
tcatcactgg gaggagctgc gacggtcaag ggatagatag gttcatcatg tgaagctt    1498
```

<210> SEQ ID NO 49
<211> LENGTH: 462
<212> TYPE: PRT
<213> ORGANISM: Eragrostis nindensis

<400> SEQUENCE: 49

```
Met Lys His Pro Arg Ser Arg Gln Glu Pro Arg Met Gly Asn Gly
1               5                   10                  15

Ala Met Val Val Thr Met Leu Leu Ser Leu Cys Val Leu Thr Tyr Ile
            20                  25                  30

Lys Ala Arg Tyr Cys Ser Asn Pro Phe Pro Lys Ala Ala Asp Glu Met
        35                  40                  45

Glu Val Val Glu Ile Asp Glu Asp Tyr Asp Ser Thr Arg Tyr Lys Met
    50                  55                  60

Asp Gly Pro Ile Gly Glu Glu Asp Phe Asp Pro Ser Arg Pro Thr Cys
65                  70                  75                  80
```

```
Tyr Asn Thr Ser Lys Arg Ser Glu Arg Cys Ala Ala Val Gly Asp Ile
             85                  90                  95

Arg Val Asp Gly Asn His Ser Lys Ile Tyr Ile Ser Pro Leu Ser Lys
            100                 105                 110

Glu Trp Lys Thr Lys Pro Tyr Ala Arg Arg His Asp Ala Val Ala Met
            115                 120                 125

Asp Asp Val Arg Glu Phe Thr Leu Leu Pro Phe Gly Gly Ala Asn Asp
130                 135                 140

Thr Ala Val Pro Pro Leu Cys Thr Arg Asn His Ser Val Pro Gly Phe
145                 150                 155                 160

Leu Phe Ser Ile Gly Gly Phe Ala Gly Asn Leu Tyr His Asp Tyr Thr
                165                 170                 175

Asp Val Leu Val Pro Leu Phe Thr Ser Thr His His Phe Gly Gly Glu
            180                 185                 190

Val Gln Leu Met Ile Ser Asp Ile Trp Gly Lys Glu Asp Lys Asp Trp
            195                 200                 205

Trp Val Asp Lys Phe Thr Pro Leu Phe Arg Gln Leu Ser Lys Tyr Asp
210                 215                 220

Val Ile Asp Ala Asp Asn Asp Gln Glu Val His Cys Phe Pro Arg Ile
225                 230                 235                 240

Val Ile Gly Pro Thr Phe His Arg Ala Met Gly Ile Asp Pro Thr Arg
                245                 250                 255

Ser Pro Gly Gly Ile Asn Ile Ala Asp Phe Lys Arg Leu Leu Arg Arg
            260                 265                 270

Thr Phe Arg Leu Glu Arg Ala Val Ala Ser Arg Thr Gly Ala Pro Arg
            275                 280                 285

Arg Asp Lys Pro Arg Leu Leu Ile Ile Ser Arg Lys Ser Ser Arg Arg
290                 295                 300

Phe Leu Asn Glu Arg Ala Val Ala His Ala Ala Ala Leu Ala Lys Phe
305                 310                 315                 320

Asp Val Arg Ile Ala Glu Pro Asp Asn His Thr Asp Met Pro Asn Phe
                325                 330                 335

Ala Arg Leu Val Asn Ser Ala Asp Val Met Met Gly Val His Gly Ala
            340                 345                 350

Gly Leu Thr Asn Met Val Phe Leu Pro Ser Arg Ala Val Leu Ile Gln
            355                 360                 365

Val Val Pro Phe Gly Gly Leu Glu Trp Leu Ser Arg Val Thr Phe Lys
            370                 375                 380

Asp Pro Ala Lys Asp Tyr Asp Val Asn Tyr Met Glu Tyr Asn Val Ser
385                 390                 395                 400

Leu Glu Glu Ser Ser Leu Arg Asp Leu Tyr Pro Glu Asp His Phe Tyr
                405                 410                 415

Leu Lys His Pro Tyr Asp Val His Lys Lys Gly Trp Asp Ala Ile Lys
            420                 425                 430

Thr Thr Tyr Leu Asp Lys Gln Asn Val Arg Leu Asn Leu Thr Arg Phe
            435                 440                 445

Thr Lys Thr Leu Gln Gln Ala Arg Asp Leu Leu Pro Ser Pro
450                 455                 460

<210> SEQ ID NO 50
<211> LENGTH: 462
<212> TYPE: PRT
<213> ORGANISM: Glycine max
```

<400> SEQUENCE: 50

```
Met Ile Tyr Asp Thr Val Leu Ala Lys Ser Phe Ser Arg Tyr Asp Gln
1               5                   10                  15

Lys Arg Leu Gly Tyr Gly Ala Phe Val Ser Cys Leu Leu Ile Val Leu
            20                  25                  30

Ser Leu Cys Thr Val Phe Lys Pro Tyr Leu Gly Pro Val His Val Leu
        35                  40                  45

Asn Leu Lys Leu Phe Ile Asp Val Asp Thr Lys Met Leu Ile Thr Arg
    50                  55                  60

Ser Ser Ser Gln Ile Ala Lys Val Glu Gly Lys Glu Thr Lys Lys Glu
65                  70                  75                  80

Glu Leu Leu Cys Thr Ser Glu Glu Arg Thr Lys Phe Cys Gln Ala Arg
                85                  90                  95

Gly Asp Ile Arg Val His Gly Lys Ser Ser Thr Val Tyr Ile Val Ser
            100                 105                 110

Ser Lys Thr Thr Met Ser Glu Lys Asn Met Ser Trp Asn Leu Lys Pro
        115                 120                 125

Tyr Ala Arg Arg Asp Asp Val Asp Ala Met Ile Arg Val Arg Glu Trp
    130                 135                 140

Ser Val Lys Ala Val Asn Val Ser Gln Lys Ala Pro Gln Cys Thr Gln
145                 150                 155                 160

Tyr His Asn Ile Pro Ala Val Leu Phe Ser Thr Gly Gly Tyr Ala Gly
                165                 170                 175

Asn His Phe His Glu Phe Thr Asp Ile Val Ile Pro Leu Phe Leu Thr
            180                 185                 190

Ala Arg Gln Phe Asn Gly Glu Val Gln Phe Ile Ile Thr Asp Lys Arg
        195                 200                 205

Pro Trp Trp Ile Ser Lys His Lys Pro Leu Leu Lys Lys Leu Ser Asn
    210                 215                 220

Tyr Glu Thr Met Asp Ile Asp Gly Asp Glu Val His Cys Phe Pro
225                 230                 235                 240

Arg Val Thr Val Gly Leu Lys Arg Tyr Gln Lys Glu Leu Ser Ile Glu
                245                 250                 255

Pro Gln Lys Tyr Ser Tyr Ser Met Lys Asp Phe Arg Asp Leu Leu Arg
            260                 265                 270

Ser Ser Tyr Ala Leu Lys Arg Val Glu Ala Ile Lys Thr Arg Asp Gly
        275                 280                 285

Leu Arg Gly Lys Pro Arg Leu Met Ile Leu Ser Arg Lys Arg Ser Arg
    290                 295                 300

Phe Phe Thr Asn Thr Asp Glu Ile Ala Lys Met Ala Glu Ser Leu Gly
305                 310                 315                 320

Phe Asp Val Ile Ile Lys Glu Ala Gly Trp Ser Met Trp Gly Phe Ala
                325                 330                 335

Asn Val Val Asn Ser Cys Asp Val Leu Leu Gly Val His Gly Ala Gly
            340                 345                 350

Leu Thr Asn Ile Leu Phe Leu Pro Glu Asn Ala Val Phe Val Gln Val
        355                 360                 365

Val Pro Tyr Gly Gly Val Thr Leu Asp Trp Leu Ala Thr Asn Asp Phe
    370                 375                 380

Gly Asn Pro Ser Lys Asp Met Asn Ile Lys Tyr Leu Glu Tyr Lys Ile
385                 390                 395                 400

Ser Leu Glu Glu Ser Thr Leu Ile Gln Gln Tyr Pro Leu Asp His Met
                405                 410                 415
```

-continued

```
Phe Ile Lys Asp Pro Pro Leu Ile Glu Lys Ile Gly Trp Glu Glu Phe
            420                 425                 430

Lys Ser Val Tyr Leu Asp Lys Gln Asn Val Lys Leu Asp Val Asp Arg
        435                 440                 445

Phe Arg Pro Thr Leu Gln Lys Ala Leu Glu Leu Leu His Gln
    450                 455                 460
```